(12) United States Patent
Gordon et al.

(10) Patent No.: US 10,222,349 B2
(45) Date of Patent: *Mar. 5, 2019

(54) METHODS AND DEVICES FOR SEQUENCING NUCLEIC ACIDS IN SMALLER BATCHES

(71) Applicant: Intelligent BioSystems, Inc., Waltham, MA (US)

(72) Inventors: Steven Gordon, Weston, MA (US); Thomas Hagerott, Needham, MA (US); Edmund Golaski, Cambridge, MA (US); Jerzy Olejnik, Brookline, MA (US)

(73) Assignee: QIAGEN SCIENCES, LLC, Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/656,307

(22) Filed: Jul. 21, 2017

(65) Prior Publication Data

US 2018/0017525 A1    Jan. 18, 2018

Related U.S. Application Data

(63) Continuation of application No. 14/708,675, filed on May 11, 2015, now Pat. No. 9,791,409, which is a continuation of application No. 14/463,211, filed on Aug. 19, 2014, now Pat. No. 9,145,589, which is a continuation of application No. 13/786,895, filed on Mar. 6, 2013, now Pat. No. 8,900,810, which is a continuation of application No. 12/719,469, filed on Mar. 8, 2010, now Pat. No. 8,481,259, which is a continuation-in-part of application No. 12/405,694, filed on Mar. 17, 2009, now Pat. No. 8,612,161, which is a continuation-in-part of application No. 12/020,284, filed on Jan. 25, 2008, now abandoned.

(60) Provisional application No. 61/037,845, filed on Mar. 19, 2008, provisional application No. 60/899,454, filed on Feb. 5, 2007.

(51) Int. Cl.
```
G01N 27/447      (2006.01)
B01L 3/00        (2006.01)
C12Q 1/68        (2018.01)
C12Q 1/6869      (2018.01)
```

(52) U.S. Cl.
CPC .. G01N 27/44791 (2013.01); B01L 3/502761 (2013.01); C12Q 1/6869 (2013.01); G01N 27/44726 (2013.01); B01L 3/502715 (2013.01); B01L 2200/0668 (2013.01); B01L 2300/0877 (2013.01); B01L 2400/0487 (2013.01)

(58) Field of Classification Search
CPC ....... G10N 27/44726; G01N 27/44791; C12Q 1/6869
See application file for complete search history.

(56) References Cited

U.S. PATENT DOCUMENTS

| | | | |
|---|---|---|---|
| 5,143,854 A | 9/1992 | Pirrung et al. | 436/518 |
| 5,302,509 A | 4/1994 | Cheeseman | 435/6.11 |
| 5,313,264 A | 5/1994 | Iavarsson et al. | 356/73 |
| 5,547,839 A | 8/1996 | Dower et al. | 435/6.11 |
| 5,571,639 A | 11/1996 | Hubbell et al. | 430/5 |
| 5,733,729 A | 3/1998 | Lipshutz et al. | 435/6.11 |
| 5,795,716 A | 8/1998 | Chee | 435/6.11 |
| 6,066,454 A | 5/2000 | Lipshutz et al. | 506/8 |
| 6,097,025 A | 8/2000 | Modlin et al. | 250/227.22 |
| 6,107,061 A | 8/2000 | Johnson | 435/91.1 |
| 6,228,593 B1 | 5/2001 | Lipshutz et al. | 506/8 |
| 6,309,836 B1 | 10/2001 | Kwiatkowski | 435/6.12 |
| 6,355,420 B1 | 3/2002 | Chan | 435/6.12 |
| 6,485,944 B1 | 11/2002 | Church et al. | 435/91.2 |
| 6,545,758 B1 | 4/2003 | Sandstrom | 356/317 |
| 6,546,340 B2 | 4/2003 | Lipshutz et al. | 702/20 |
| 6,586,750 B2 | 7/2003 | Montagu | 250/458.1 |
| 6,598,013 B1 | 7/2003 | Domnisoru et al. | 702/191 |
| 6,613,513 B1 | 9/2003 | Parce et al. | 435/6.11 |
| 6,664,079 B2 | 12/2003 | Ju et al. | 435/91.1 |
| 6,856,390 B2 | 2/2005 | Nordman et al. | 356/344 |
| 6,957,149 B2 | 10/2005 | Lipshutz et al. | 702/20 |
| 7,057,031 B2 | 6/2006 | Olejnik et al. | 536/25.3 |
| 7,147,362 B2 | 12/2006 | Caren et al. | 366/135 |
| 7,209,836 B1 | 4/2007 | Schermer et al. | 702/19 |
| 7,279,563 B2 | 10/2007 | Kwiatkowski | 536/23.1 |
| 7,883,869 B2 | 3/2011 | Ju et al. | 435/91.1 |
| 8,481,259 B2 * | 7/2013 | Gordon | B01L 3/502761 435/6.1 |

(Continued)

FOREIGN PATENT DOCUMENTS

| | | |
|---|---|---|
| DE | 69511903 T2 | 4/2000 |
| DE | 69634490 T2 | 3/2006 |

(Continued)

OTHER PUBLICATIONS

U.S. Appl. No. 61/171,975, filed Apr. 23, 2009, Olejnik.

(Continued)

*Primary Examiner* — David C Thomas

(74) *Attorney, Agent, or Firm* — Medlen & Carroll, LLP

(57) ABSTRACT

The invention provides methods and compositions, including, without limitation, algorithms, computer readable media, computer programs, apparatus, and systems for determining the identity of nucleic acids in nucleotide sequences using, for example, data obtained from sequencing by synthesis methods. A plurality of smaller flow cells is employed, each with a relatively small area to be imaged, in order to provide greater flexibility and efficiency.

6 Claims, 89 Drawing Sheets

Specification includes a Sequence Listing.

(56) References Cited

U.S. PATENT DOCUMENTS

| | | | |
|---|---|---|---|
| 8,900,810 B2* | 12/2014 | Gordon | B01L 3/502761 435/6.1 |
| 9,145,589 B2 | 9/2015 | Gordon et al. | 435/6.1 |
| 2003/0105195 A1 | 6/2003 | Holcomb et al. | 524/102 |
| 2003/0120471 A1 | 6/2003 | Izmailov et al. | 703/11 |
| 2004/0137604 A1 | 7/2004 | Goodman et al. | 435/287.2 |
| 2005/0202400 A1 | 9/2005 | Tsuji et al. | 435/4 |
| 2006/0012793 A1 | 1/2006 | Harris | 356/436 |
| 2006/0029267 A1 | 2/2006 | Frost et al. | 382/129 |
| 2006/0160075 A1 | 7/2006 | Balasubramanian et al. | 435/6.11 |
| 2006/0228708 A1 | 10/2006 | Smilansky | 435/6.11 |
| 2006/0240439 A1 | 10/2006 | Smith et al. | 435/6.12 |
| 2006/0257993 A1 | 11/2006 | McDevitt et al. | 435/287.2 |
| 2006/0275893 A1 | 12/2006 | Ishii et al. | 435/288.7 |
| 2007/0117104 A1 | 5/2007 | Buzby | 435/6.11 |
| 2007/0131870 A1 | 6/2007 | Pang et al. | 250/373 |
| 2007/0194249 A1 | 8/2007 | Gavrilov et al. | 250/459.1 |
| 2008/0262747 A1* | 10/2008 | Kain | C12Q 1/686 702/20 |
| 2011/0220775 A1* | 9/2011 | Triener | G01N 21/6428 250/201.1 |
| 2014/0234832 A1 | 8/2014 | Olejnik et al. | 435/6.1 |

FOREIGN PATENT DOCUMENTS

| | | |
|---|---|---|
| DE | 102006058575 A1 | 6/2007 |
| DE | 602005002773 T2 | 7/2008 |
| DE | 102007021544 A1 | 11/2008 |
| EP | 0769159 | 4/1997 |
| EP | 1584692 | 10/2005 |
| EP | 1529213 | 12/2006 |
| WO | WO 1997/021090 | 6/1997 |
| WO | WO 1998/13683 | 2/1998 |
| WO | WO 1999/057321 | 11/1999 |
| WO | WO 2000/053812 | 9/2000 |
| WO | WO 2001/092284 | 6/2001 |
| WO | WO 2003/100474 | 4/2003 |
| WO | WO 2003078978 | 9/2003 |
| WO | WO 2004/018493 | 4/2004 |
| WO | WO 2005/024010 | 3/2005 |
| WO | WO 2008135566 | 11/2008 |
| WO | WO 2009/054922 | 4/2009 |

OTHER PUBLICATIONS

Aitken, et al., "An Oxygen Scavenging System for Improvement of Dye Stability in Single-Molecule Fluorescence Experiments." 6*Biophys J.* 94(5):1826-1835 (2008).

Azoulay et al., A New Drug-release Method Using the Staudinger Ligation, *Bioorganic & Medicinal Chemistry Letters* 16(12):3147-3149 (2006).

Bi et al., Design and Synthesis of a Chemically Cleavable Fluorescent Nucleotide, 3'-O-Allyl-dGTP-allyl-Bodipy-FL-510, as a Reversible Terminator for DNA Sequencing by Synthesis, *J. Am. Chem Soc.* 128(8):2542-3 (2006).

Borchardt and Cohen, Stereopopulation Control. II. Rate Enhancement of Intramolecular Nucleophilic Displacement, *J. Am. Chem. Soc.* 94(26): 9166-9174 (1972).

Bruchez, et al. "Semiconductor Nanocrystals as Fluorescent Biological Labels." *Science*, 281: 2013-2016 (1998).

Carl et al., A Novel Connector Linkage Applicable in Prodrug Design, *J. Med. Chem.* 24(5):479-480 (1981).

Chan and Nie, "Quantum Dot Bioconjugates for Ultrasensitive Nonisotopic Detection." *Science*, 281: 2016-2018 (1998).

Chang, et al., "Sequencing of novel protein from *Bacillus pumilus* PH-01 using a high-resolution hybrid quadrupole-time-of-flight mass spectrometer." *Int. J. of Mass Spectrometry*, 209(1):47-55 (2001).

Chaput DNA Polymerase-Mediated DNA Synthesis on a TNA Template. *J. Am. Chem. Soc* 125:856-857 (2003).

Duimstra et al., A Gadolinium Chelate for Detection of B-Glucuronidase: A Self-Immolative Approach, *J. Am. Chem. Soc* 127(37): 12847-12855) (2005).

Eltoukhy et al., Modeling and Base-Calling for DNA Sequencing-By-Synthesis, *IEEE International Conference on Acoustics, Speech and signal processing* 2:1032-1035 (2006).

Gardner and Jack, "Acyclic and dideoxy terminator preferences denote divergent sugar recognition by archaeon and TAQ DNA polymerases." *Nucl. Acids Res.*, 30:605-613 (2002).

Gardner and Jack, "Determinants of nucleotide sugar recognition in an archaeon DNA polymerase." *Nucl. Acids Res.*, 27:2545-2555 (1999).

Giddings, et al., "An adaptive, object oriented strategy for base calling in DNA sequence analysis." *Nucleic Acids Res.* 21(19):4530-40 (1993).

Horhota, et al., "Glycerol Nucleoside Triphosphates: Synthesis and Polymerase Substrate Activities." *Organic Letters*, vol. 8, No. 23:5345-5347(2006).

Hovinen, et al., "Novel solid supports for the preparation of 3'-derivatized oligonucleotides: Introduction of 3'-alkylphosphate tether groups bearing amino, carboxy, carboxamido, and mercapto functionalities." *Tetrahedron* 50(24):7203-7218 (1994).

International Search Report (ISR) for PCT/US09/01730 published Sep. 24, 2009 as WO/2009/117119, dated Jul. 24, 2009.

International Search Report (ISR) for PCT/US2008/01208 published Aug. 14, 2008 as WO 2008/097455, dated Jun. 25, 2008.

Izamilov, et al., "A general approach to the analysis of errors and failure modes in the base-calling function in automated fluorescent DNA sequencing." *Electrophoresis* 23(16):2720-8 (2002).

Landry, et al., "Characterization of photoactivated singlet oxygen damage in single-molecule optical trap experiments." *Biophys. J.*, 97(8):2128-213 (2009).

Landry, et al., "Characterization of photoactivated singlet oxygen damage in single-molecule optical trap experiments." *Biophys. J.*, 97(8):2128-2136, Supplemental Data (2009).

Lee, et al., "Reactivity of acetylenyl-terminated self-assembled monolayers on gold: triazole formation." *Langmuir* 20(10):3844-7 (2004).

Longin, et al., "Comparison of anti-fading agents used in fluorescence microscopy: image analysis and laser confocal microscopy study." *J. Histochem. Cytochem.* 41:1833-1840 (1993).

Margulies, et al., "Genome Sequencing in Microfabricated High-Density Picolotre Reactors." *Nature*, 437:376-380 (2005).

McDonnell, et al., "Zinc ejection as a new rationale for the use of cystamine and related disulfide-containing antiviral agents in the treatment of AIDS." *J Med Chem.* 40(13):1969-76 (1997).

Meena, et al., "2',3'-Dideoxy-3'-thionueleoside Triphosphates: Syntheses and Polymerase Substrate Activities." *Organic Letters*, 9(6):1161-1163 (2007).

Metzker, "Emerging Technologies in DNA Sequencing." *Genome Res.*, 15(12): 1767-1776 (2005).

Mitra, et al., "Fluorescent in situ sequencing on polymerase colonies." *Anal Biochem.* 320(1):55-65 (2003).

Murata, et al., "A Novel Linker for Solid-Phase Synthesis Cleavable Under Neutral Conditions." *Tetrahedron Letters* 47(13):2147-2150 (2006).

Olejnik, et al., "Photocleavable Biotin derivatives: A Versatile Approach for the Isolation of Biomolecules." *Proceedings of the National Academy of Science (USA)* 92:7590-7594 (1995).

Ono, et al., "Quantitative comparison of anti-fading mounting media for confocal laser scanning microscopy." *J. Histochem. Cytochem.*, 49:305-312 (2001).

Rasnik, et al., "Nonblinking and long-lasting single-molecule fluorescence imaging." *Nat. Methods.* 3(11):891-3 (2006).

Ruparel et al., Design and Synthesis of a 3'-O-allyl Photocleavable Fluorescent Nucleotide as a Reversible Terminator for DNA Sequencing by Synthesis. *Proc. Natl. Acad. Sci.* 102(17) 5932-7 (2005).

Scriven and Turnbull, "Azides: their preparation and synthetic uses." *Chem Rev.* 88:297 (1988).

Seo, et al., "Four-color DNA sequencing by synthesis on a chip using photocleavable fluorescent nucleotides." *PNAS* 102 5926-5931 (2005).

(56) References Cited

OTHER PUBLICATIONS

Shendure, et al., "Advanced Sequencing Technologies: Methods and Goals." *Nature Reviews Genetics*, 5:335-344 (2004).
Sies and Menck, "Singlet oxygen induced DNA damage." *Mutat. Res.* 275:367-375 (1992).
Turcatti, et al., "A new class of cleavable fluorescent nucleotides: synthesis and optimization as reversible terminators for DNA sequencing by synthesis." *Nucleic Acids Res.*, 36(4):e25 (2008).
Turcatti, et al., "A new class of cleavable fluorescent nucleotides: synthesis and optimization as reversible terminators for DNA sequencing by synthesis." *Nucleic Acids Res.*, 36(4):e25, Supplemental Data (2008).
Wada, et al., "2-(Azidomethyl)benzoyl as a New Protecting Group in Nucleosides." *Tetrahedron Letters* 42(6):1069-1072 (2001).
Wang, et al., "Development of a Novel Redox-Sensitive Protecting Group for Amines Which Utilizes a Facilitated Lactonization Reaction." *J. Org. Chem.* 60(3): 539-543 (1995).
Wang, et al., "Structural Analysis of a Facile Lactonization System Facilitated by a Trimethyl Lock", *Bioorg. Chem.* 24: 39-49 (1996).
Wang, et al., "Synthesis of a Novel Esterase-Sensitive Cyclic Prodrug System for Peptides That Utilizes a "Trimethyl Lock"—Facilitated Lactonization Reaction." *J. Org. Chem.* 62(5):1363-1367 (1997).
Xu, et al., "(2-Azidomethyl)phenylacetyl as a New, Reductively Cleavable Protecting Group for Hydroxyl Groups in Carbohydrate Synthesis." *Carbohydrate Research* 337(2): 87-91 (2002).
Zavgorodny, et al., "S,X-acetals in nucleoside chemistry. III. Synthesis of 2'- and 3'-O-azidomethyl derivatives of ribonucleosides." *Nucleosides, Nucleotides and Nucleic Acids* 19(10-12):1977-91 (2000).

\* cited by examiner

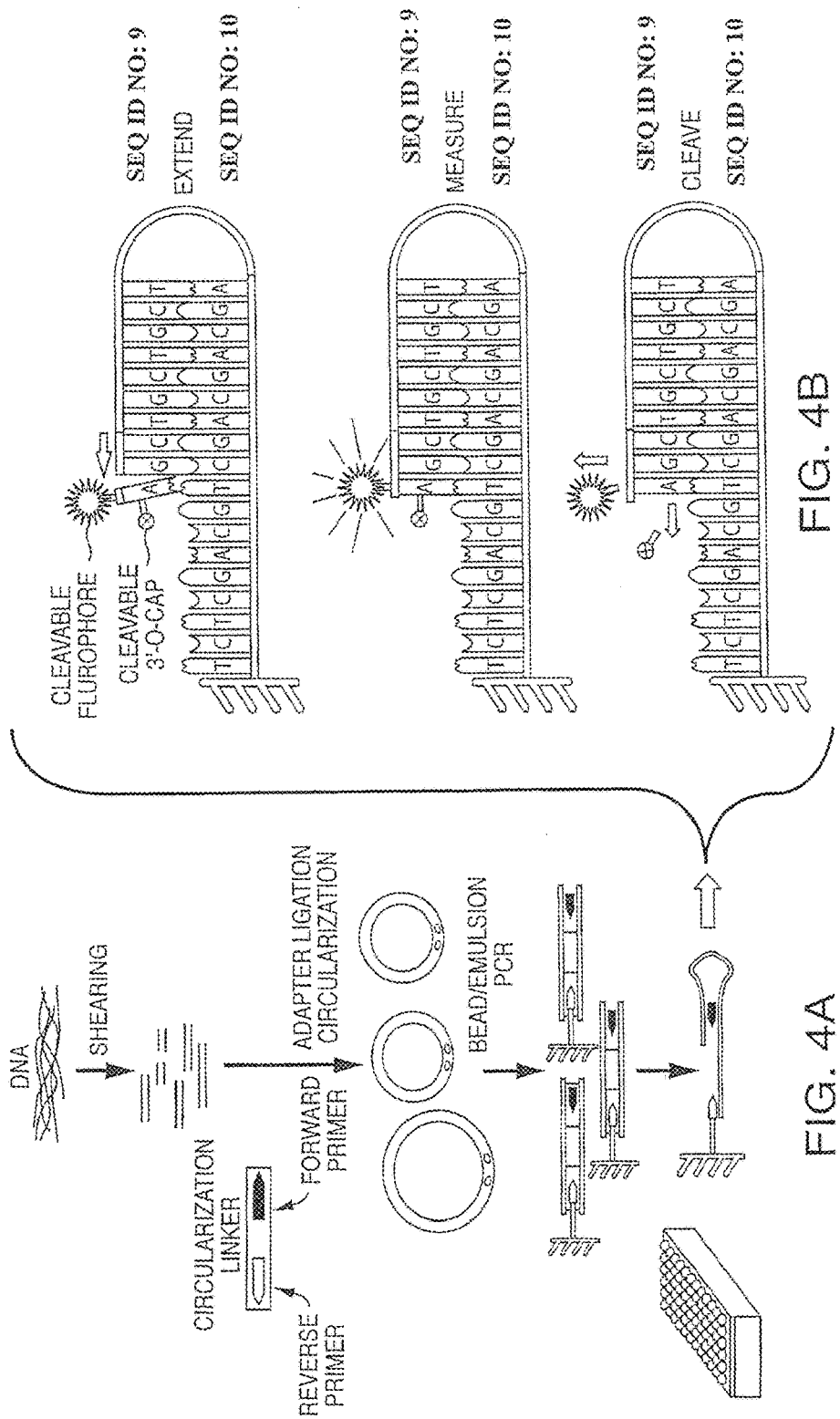

FIG. 11

SIMULATED INSTRUMENT DATA

DE-PHASED DATA FOR 35 BASE READ

SEQ ID NO: 1   5'-NH2-CAT CAC TCT CAC ATG TCA GAC TCG AGC TGA ATT CCG CGT TCG CGG AAT TCA GC-3'

TEMPLATE 20

SEQ ID NO: 2   5'-NH2-GCG AAA AAG AAG AGA TGG GGT GAA GGC TGA ATT CCG CGT TCG CGG AAT TCA GC-3'

TEMPLATE 21

SEQ ID NO: 3   5'-NH2-TGA TTT CGC TTT TAC CCT ACA CTC TGC TGA ATT CCG CGT TCG CGG AAT TCA GC-3'
TEMPLATE 22

SEQ ID NO: 4   5'-NH2-ATC GCC CTA TAT TCT AAC TTG ACT CGC TGA ATT CCG CGT TCG CGG AAT TCA GC-3'
TEMPLATE 23

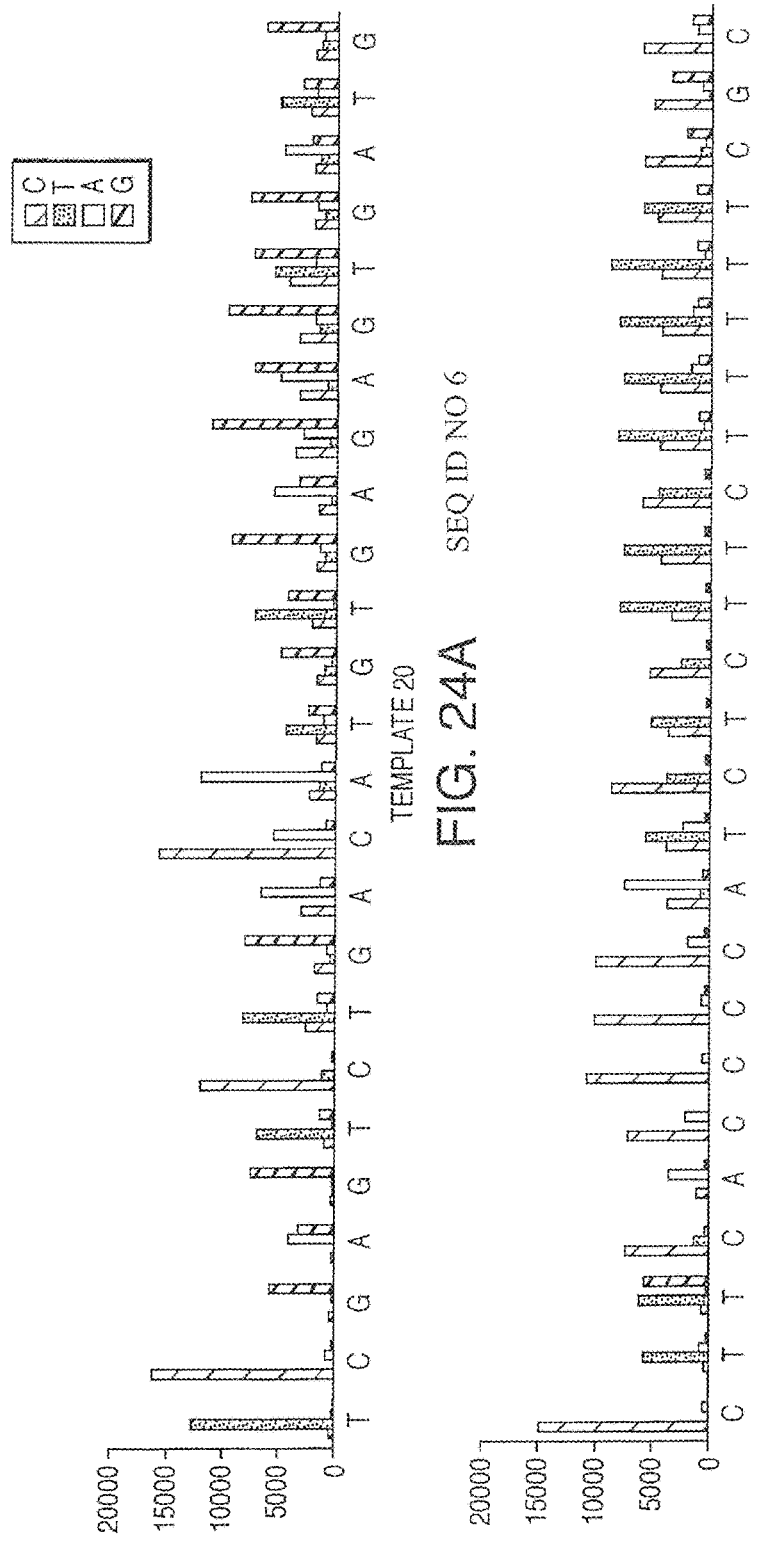

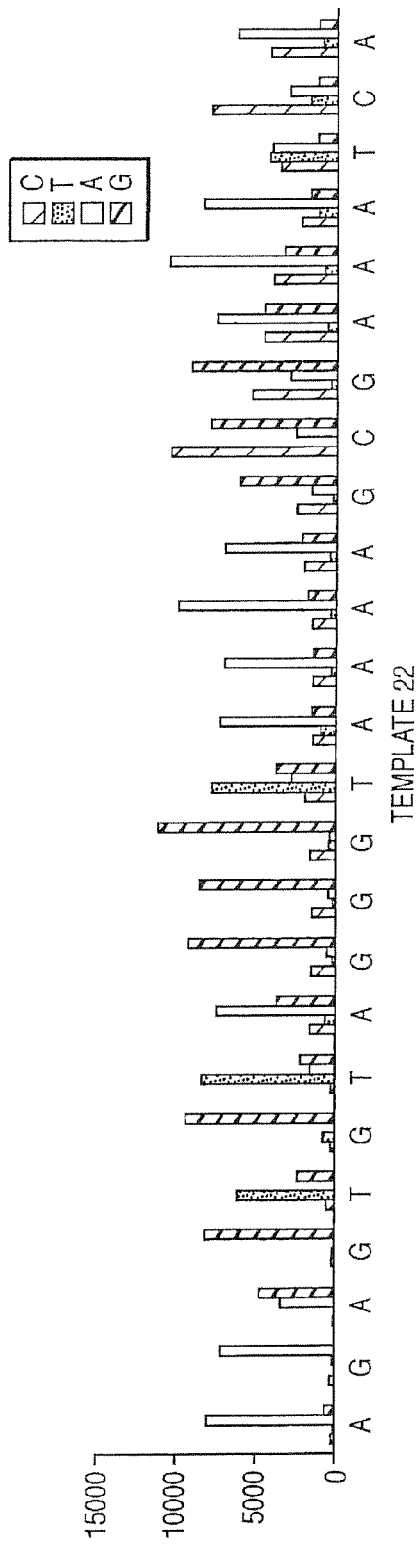
FIG. 24C TEMPLATE 22 SEQ ID NO 8
FIG. 24D TEMPLATE 23 SEQ ID NO 9

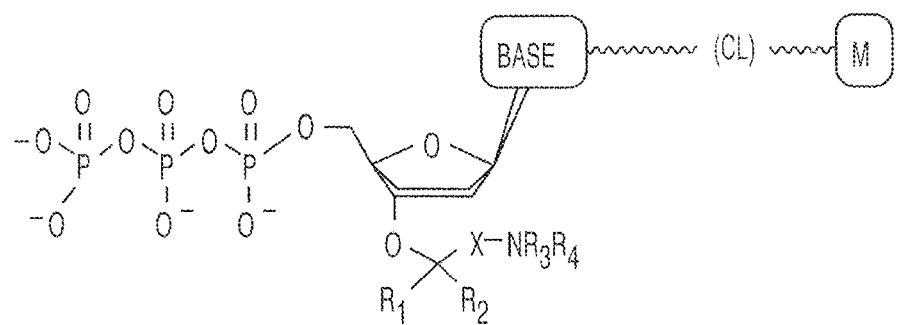
X = O, NH; $R_1, R_2, R_3, R_4$ = H, ALKYL GROUP
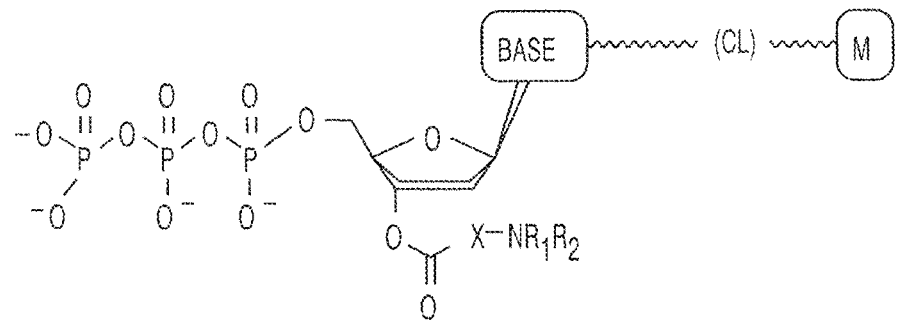
X = O, NH; $R_1, R_2$ = H, ALKYL GROUP
FIG. 27

INSTRUMENT DATA TEMPL 22

RE-PHASED DATA TEMPLE 22

SBS-DNA

FIGURE 46
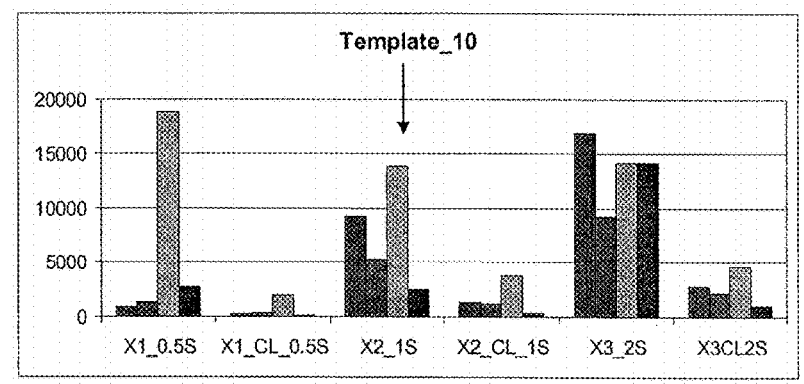
100% labeled
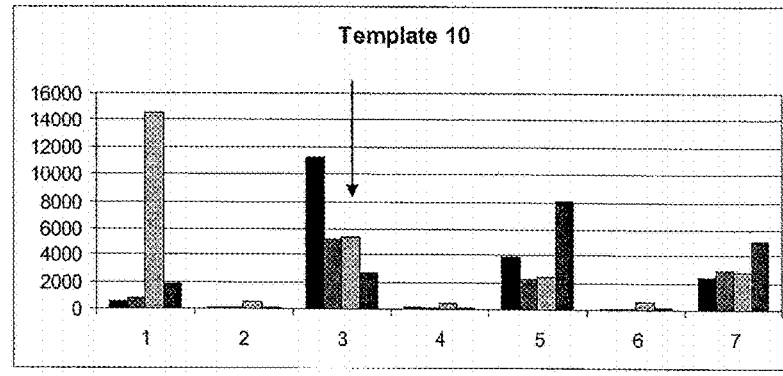
50% labeled
50% unlabeled

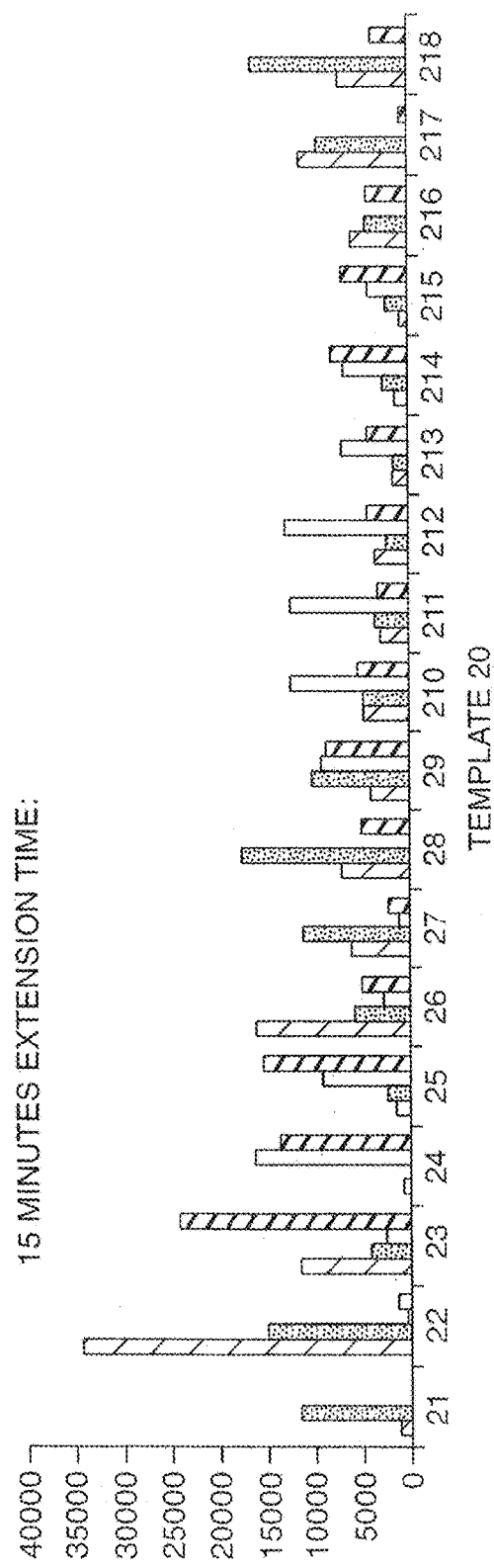
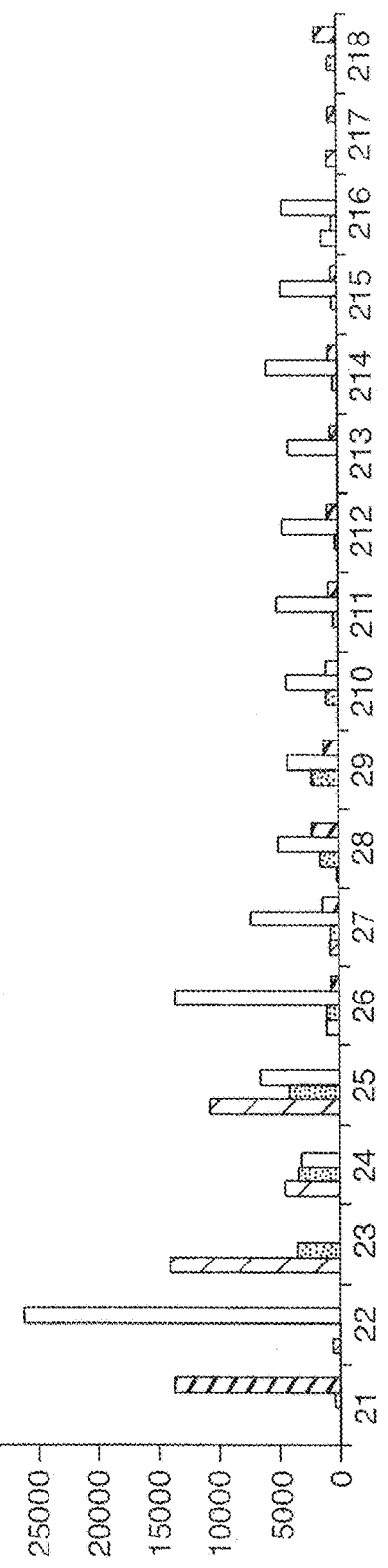
FIG. 48A
FIG. 48B

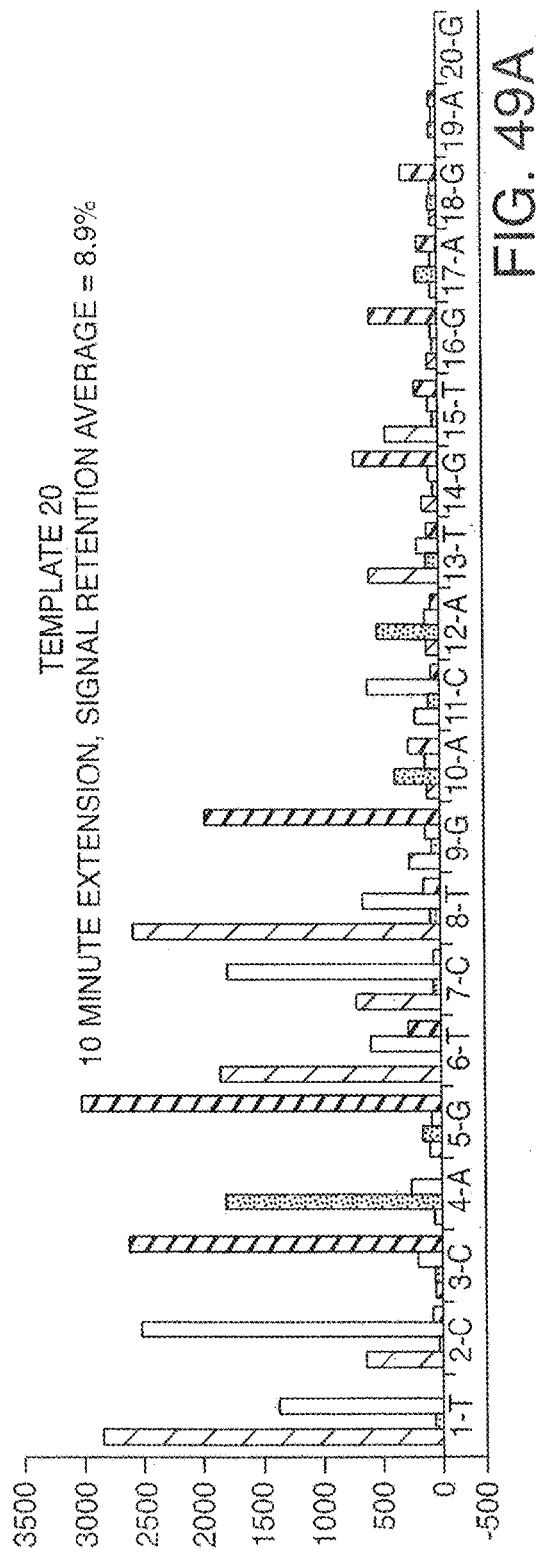

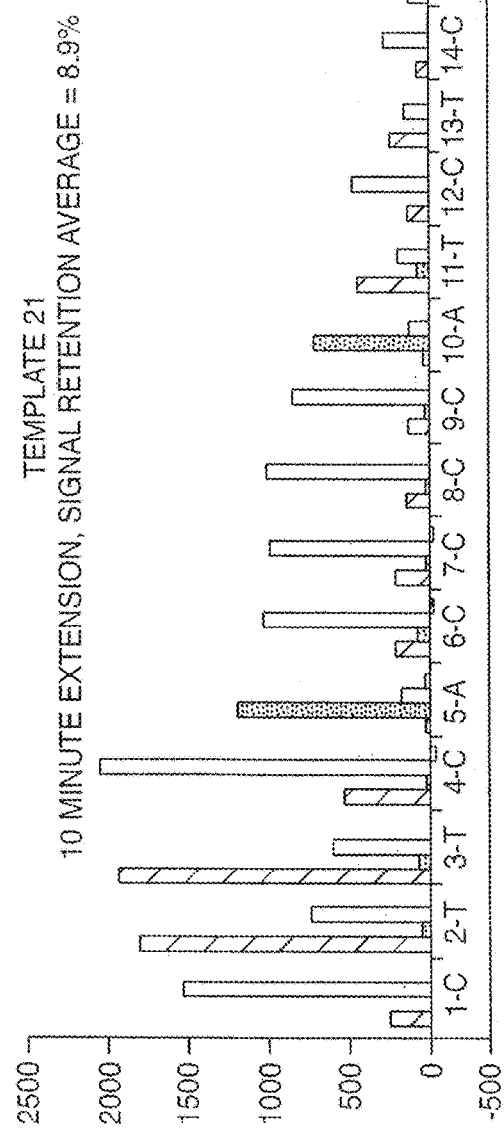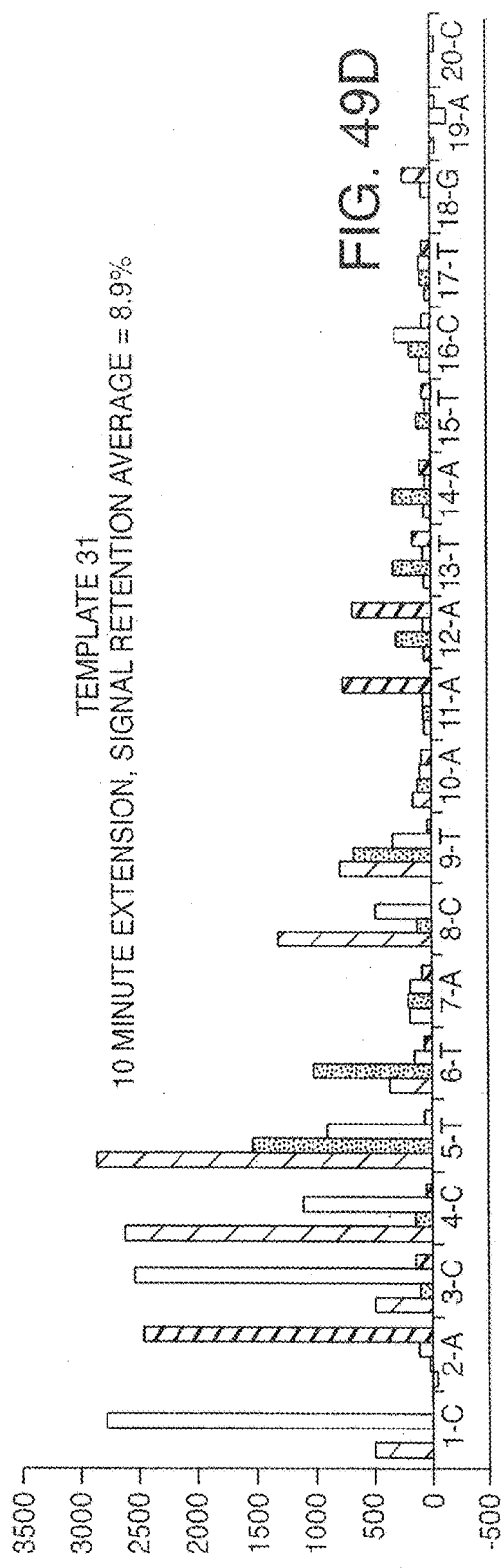

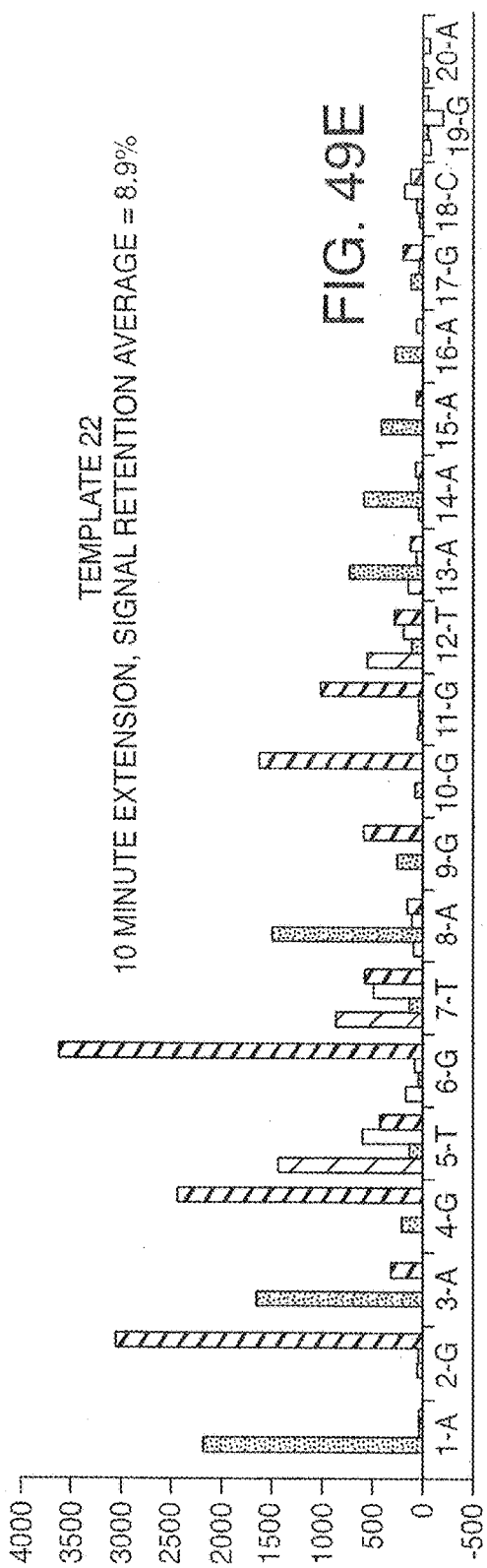
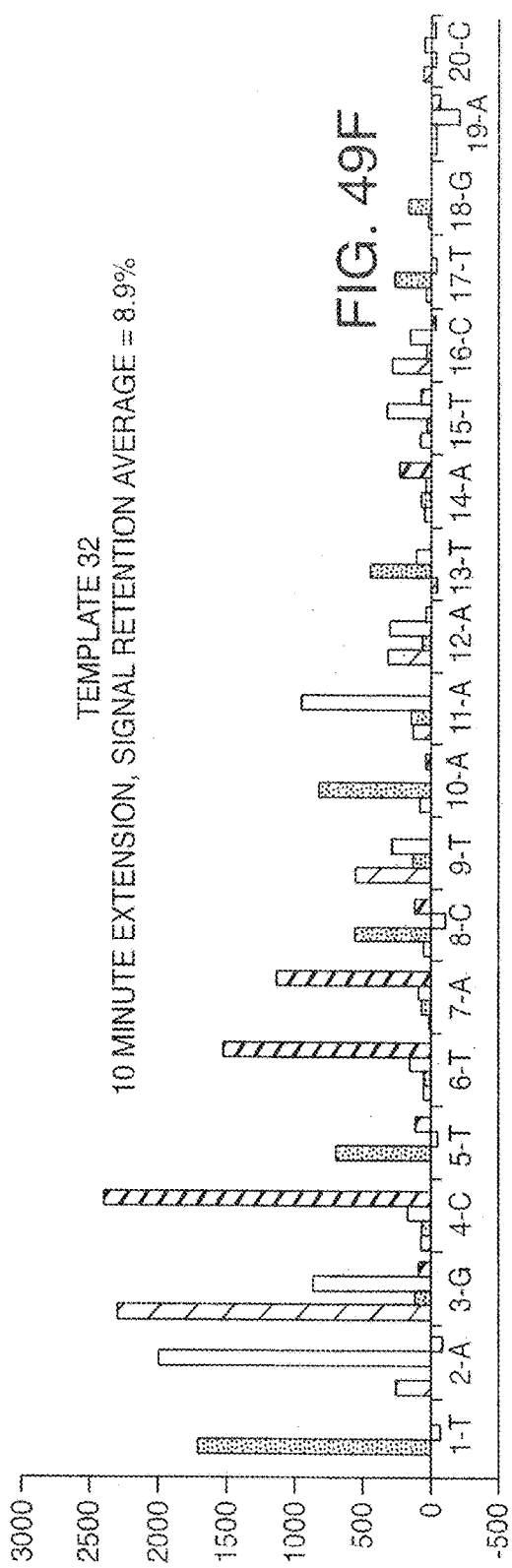

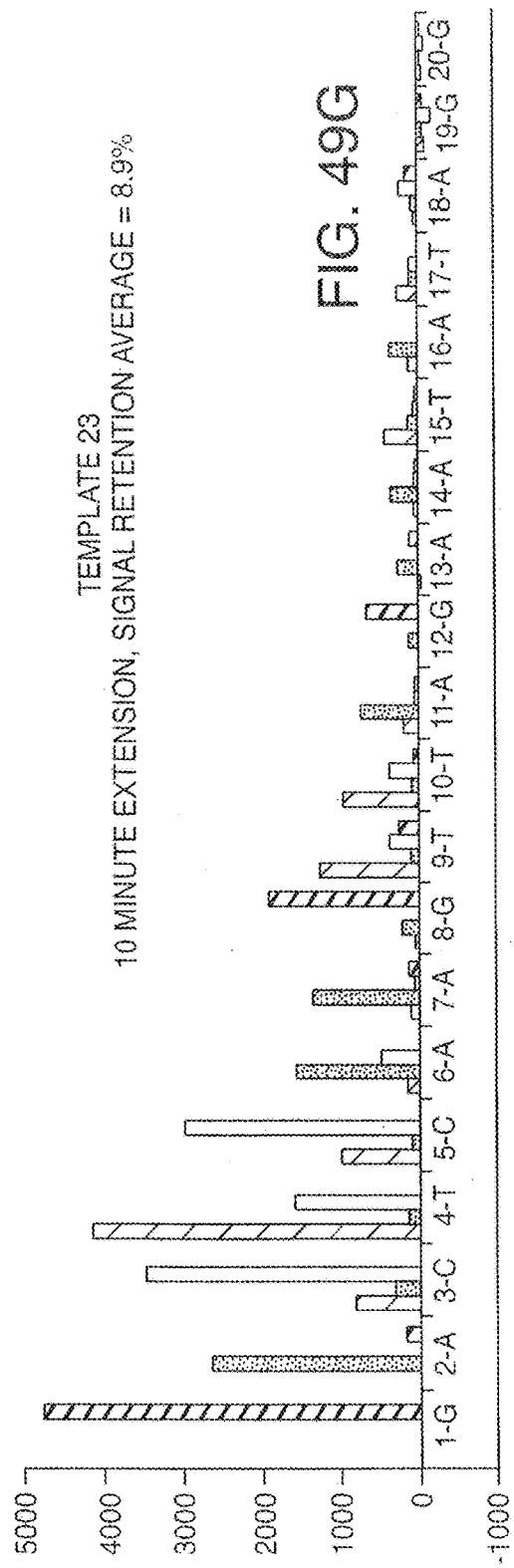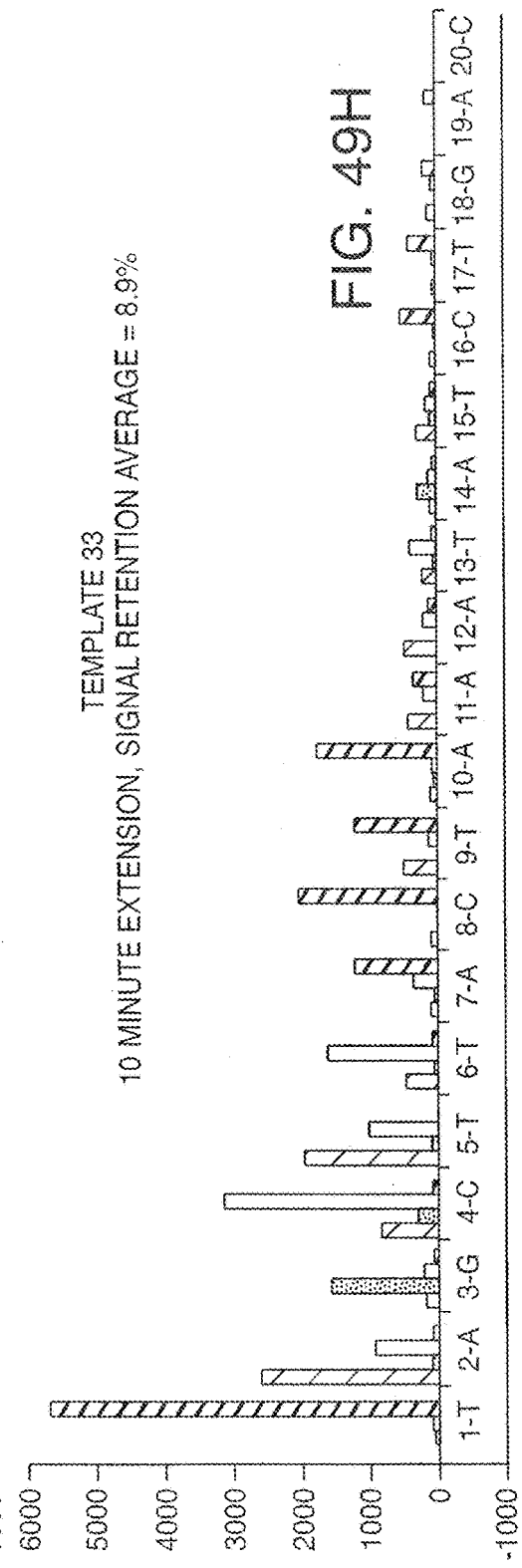

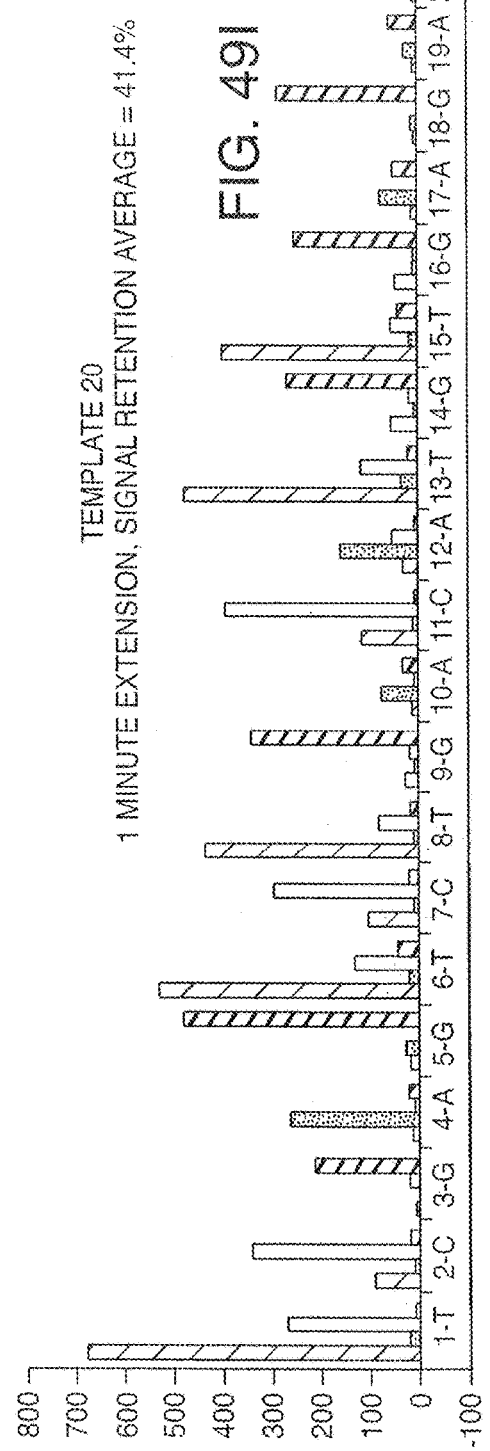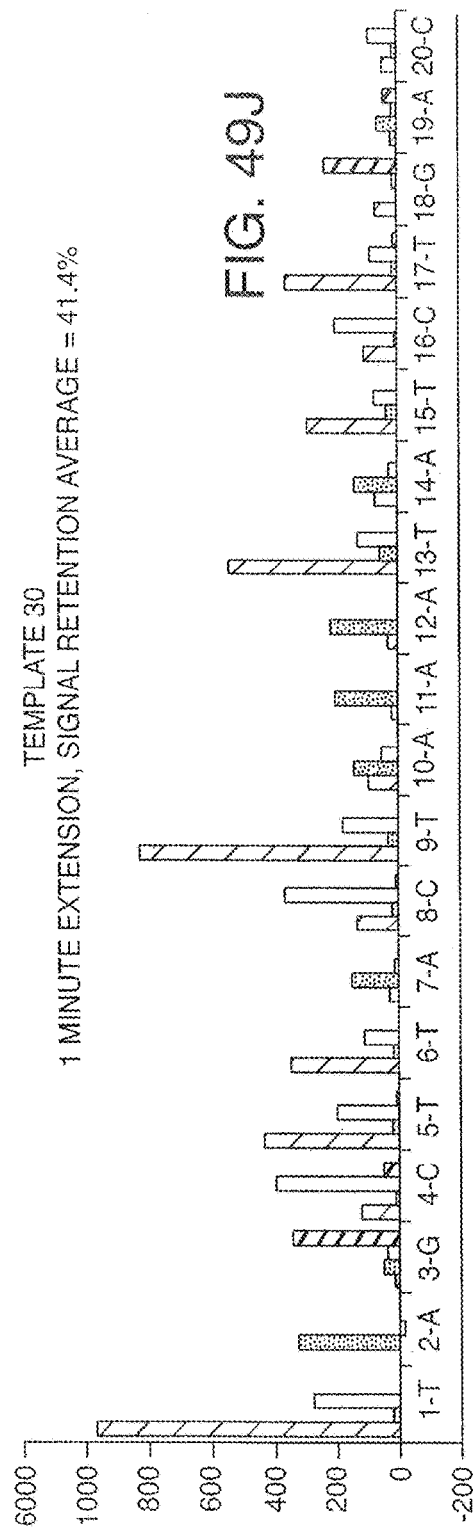

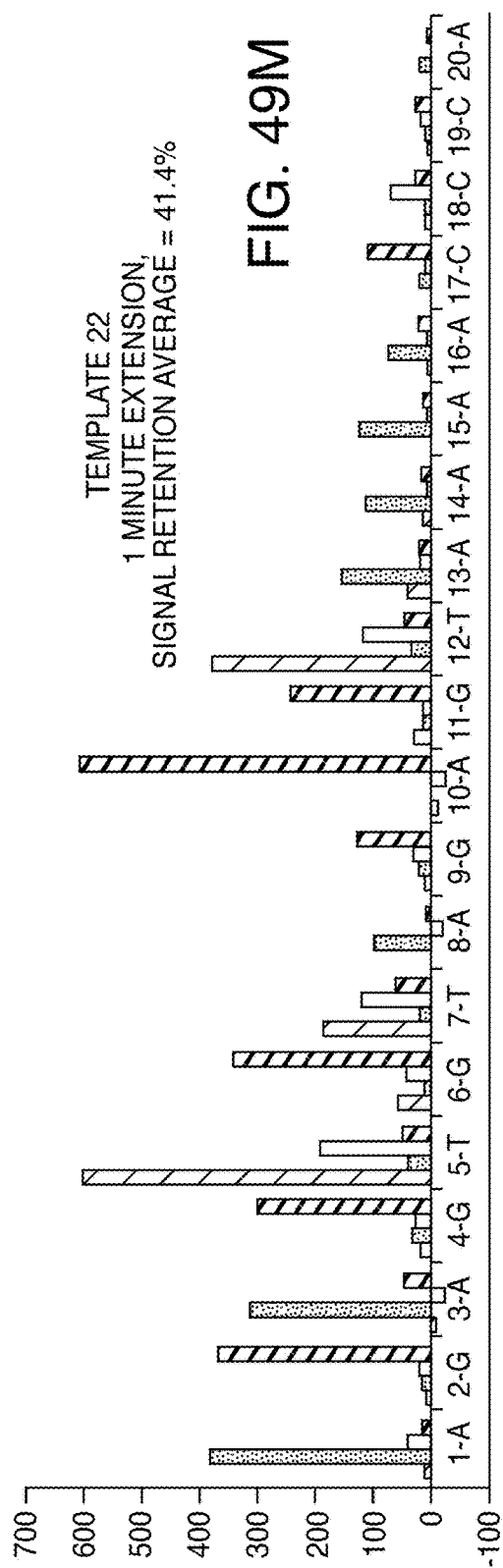
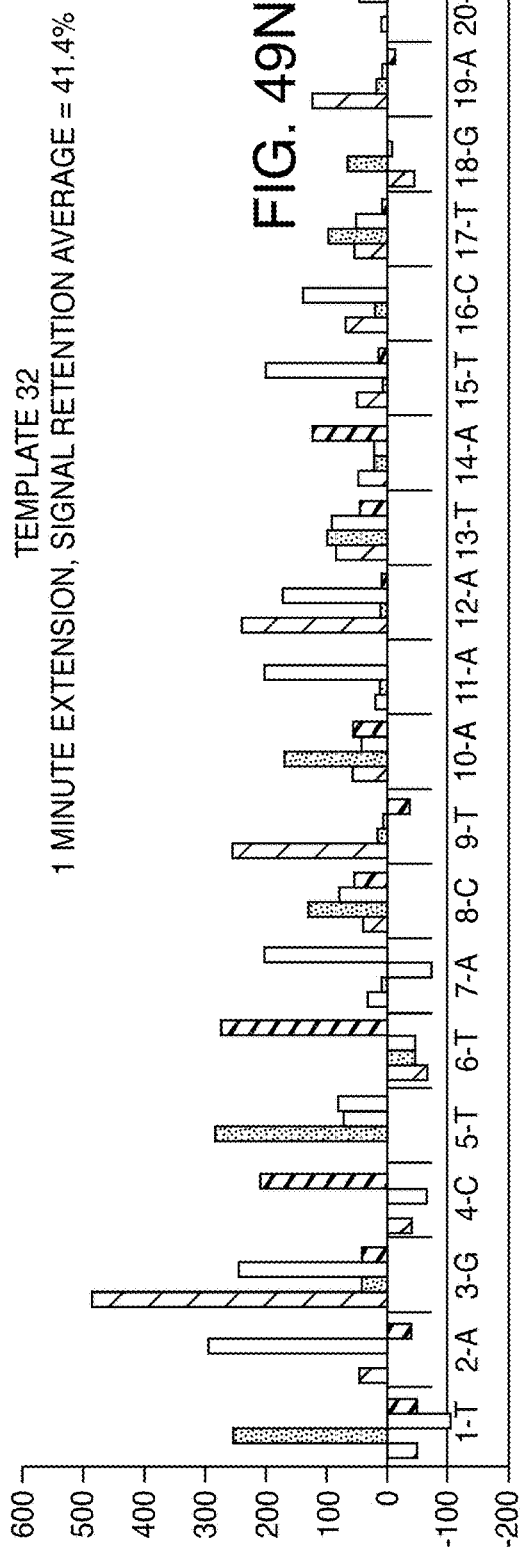

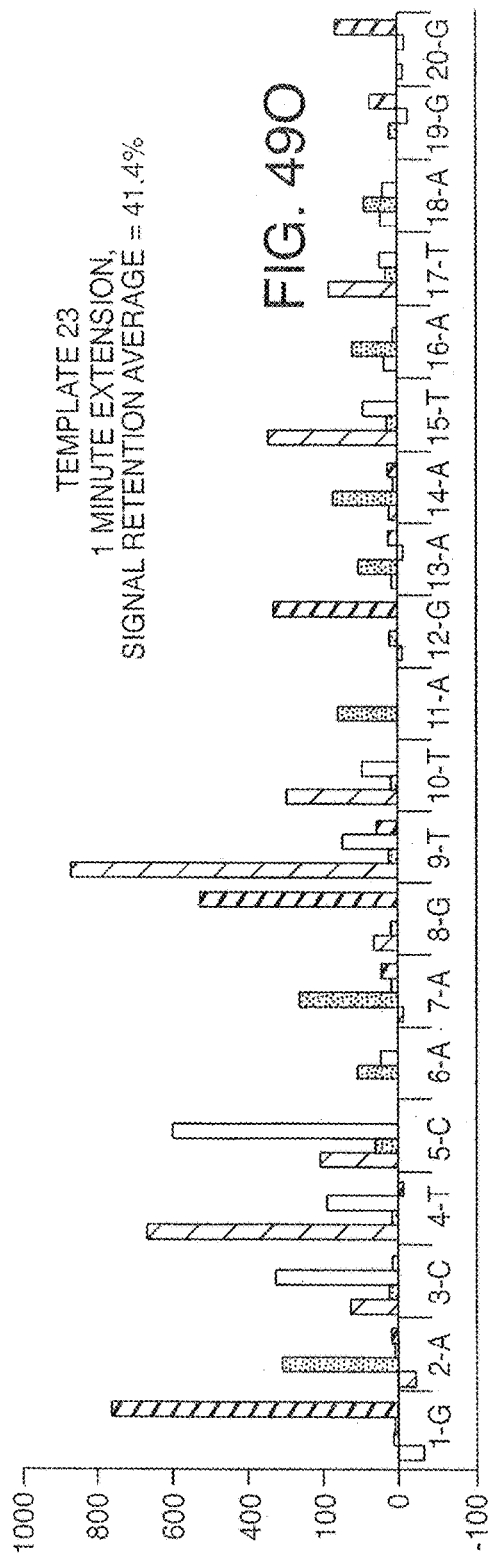
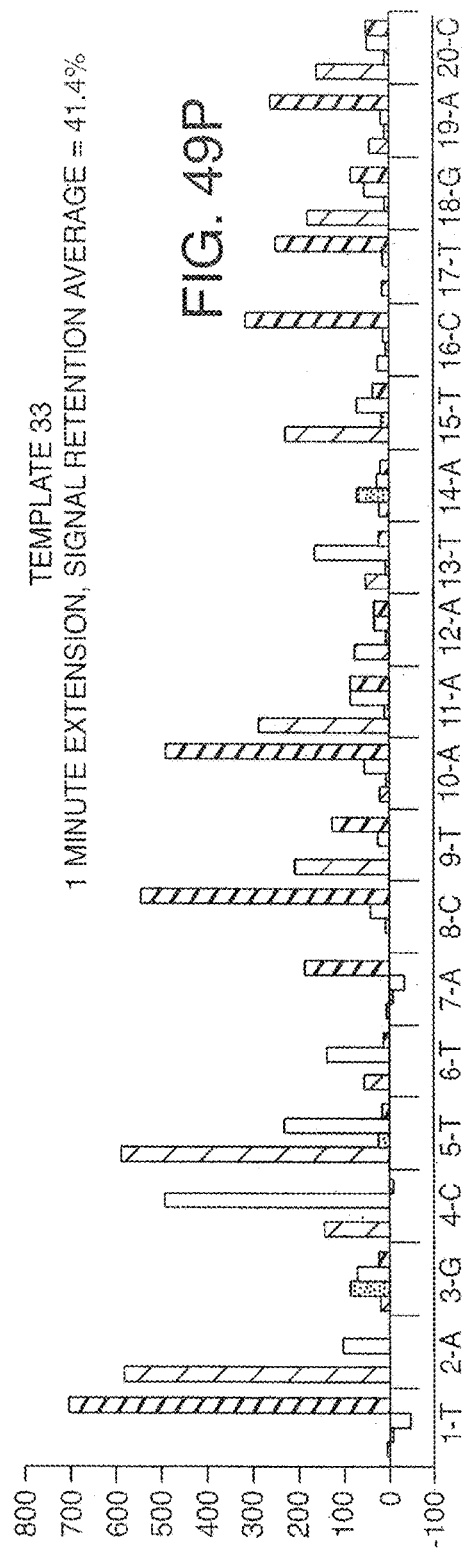

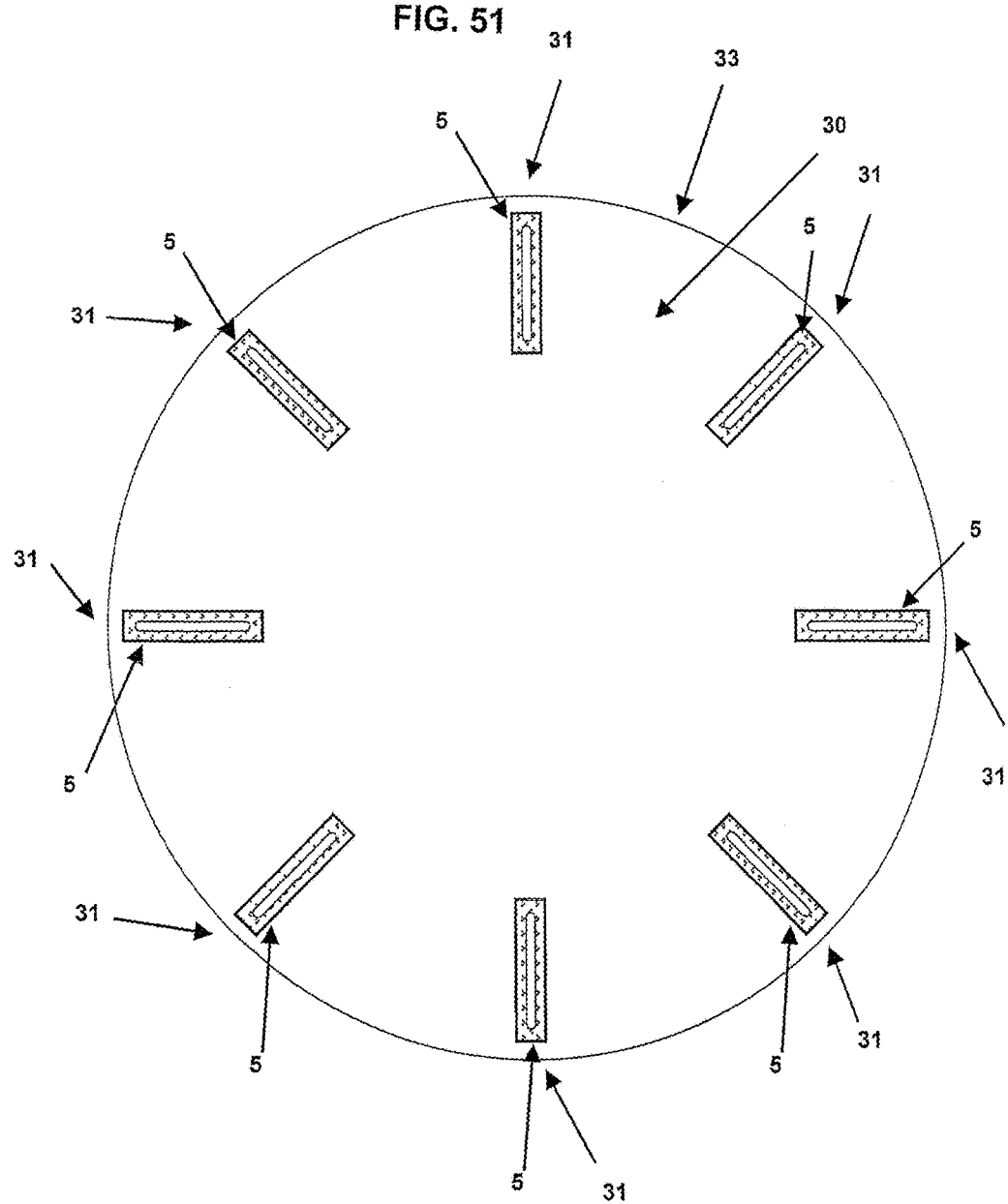

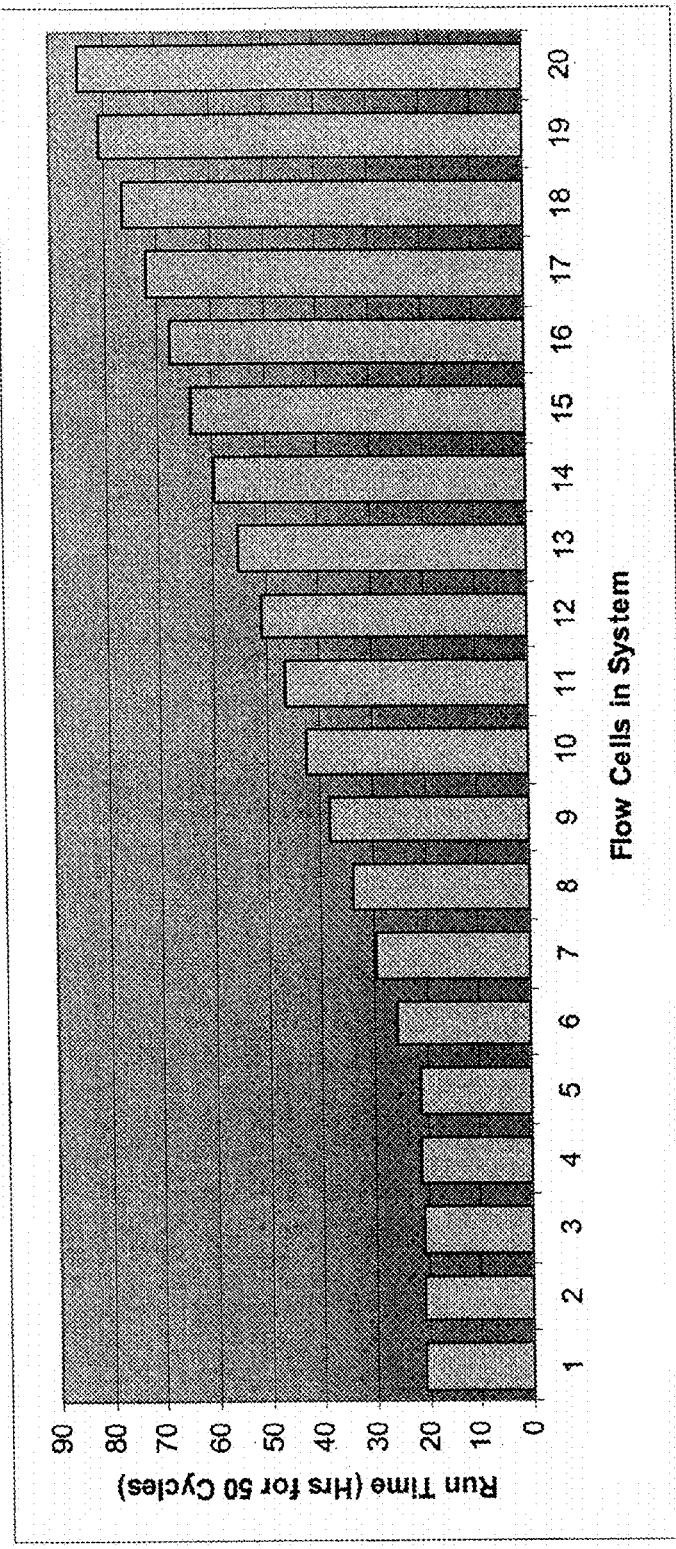
Figure 63 – Run Times for Large Chips

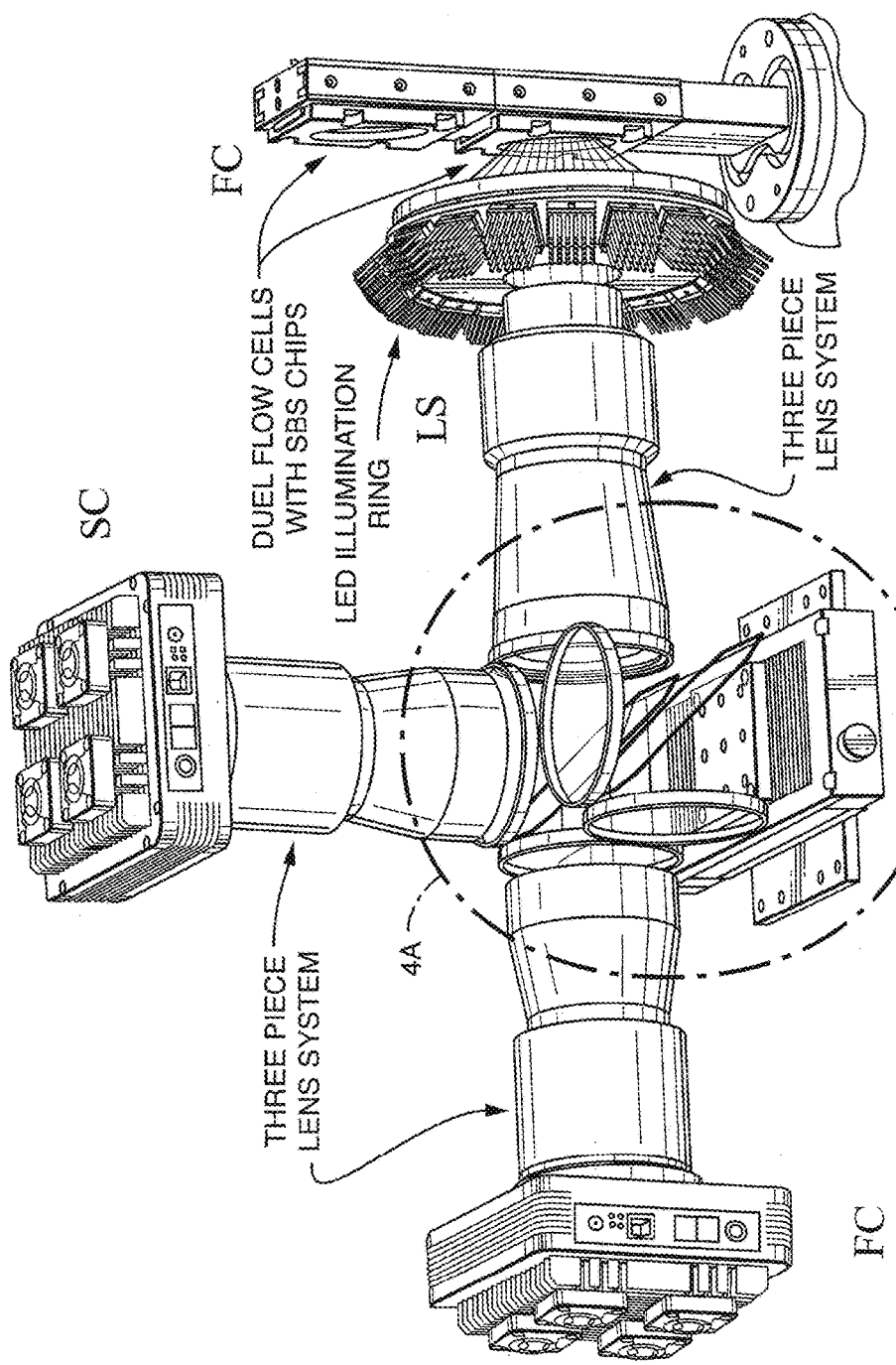
Figure 64-A

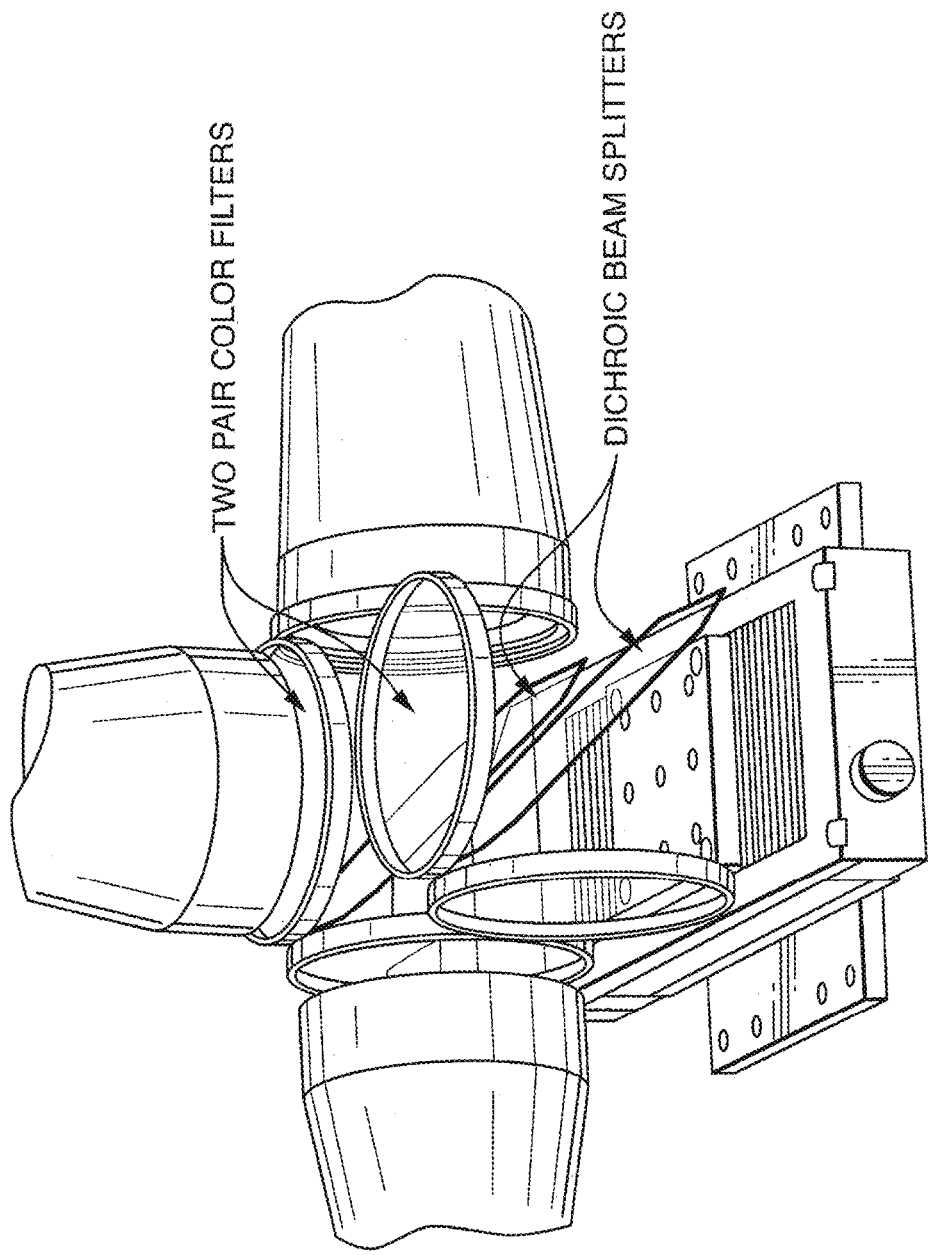
Figure 64-B

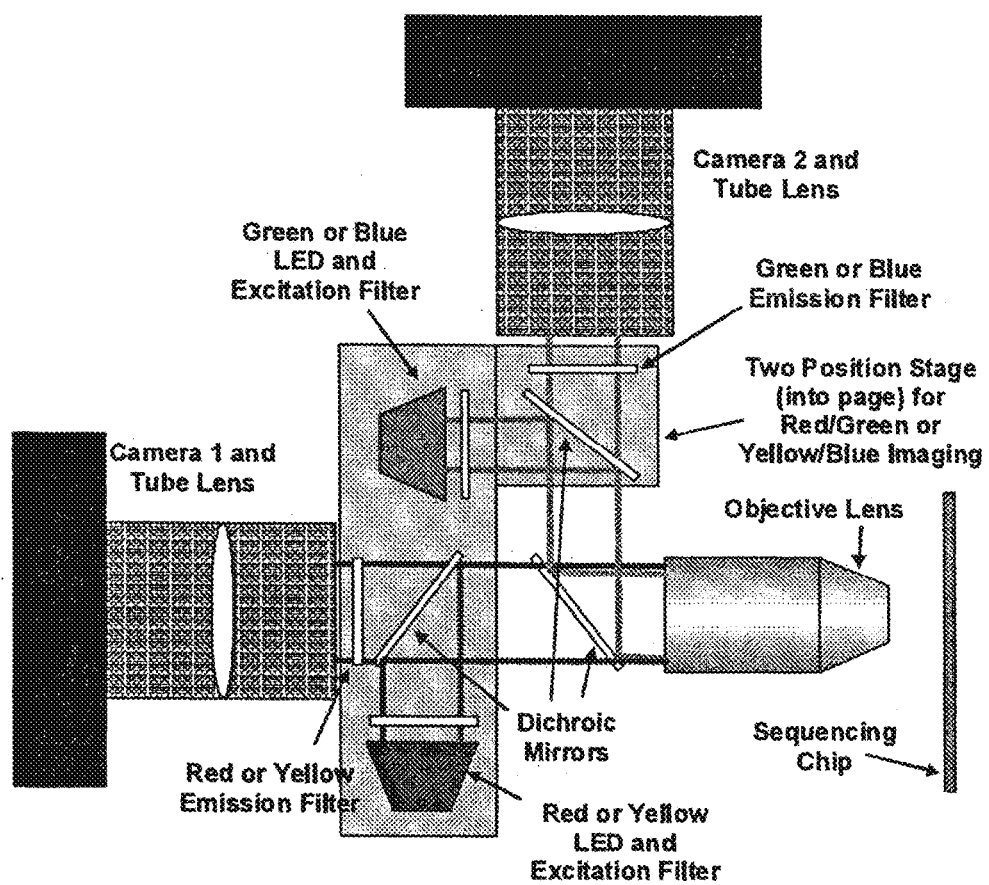
Figure 64-C

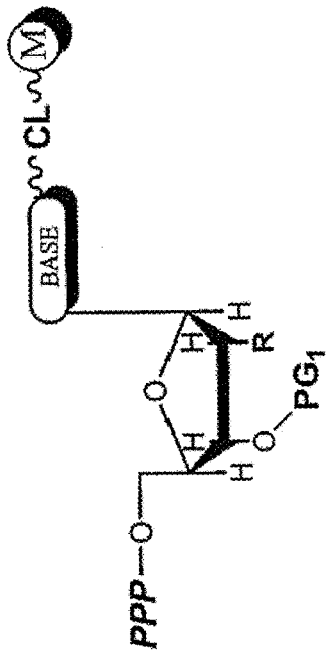
FIG 66A
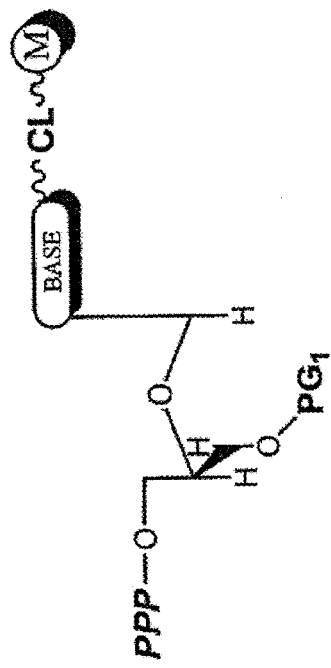
FIG 66B
CL = Cleavable linker
PG₁ = Protective Group
Ⓜ = Detectable Marker
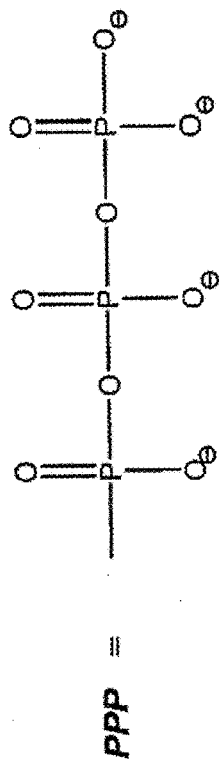
PPP =

SEQUENCE LISTING

```
<160> NUMBER OF SEQ ID NOS: 10

<210> SEQ ID NO 1
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 1
catcactctc acatgtcaga ctcgagctga attccgcgtt cgcggaattc agc        53

<210> SEQ ID NO 2
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 2
gcgaaaaaga agagatgggg tgaaggctga attccgcgtt cgcggaattc agc        53

<210> SEQ ID NO 3
<211> LENGTH: 53
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 3
tgatttcgct tttaccctac actctgctga attccgcgtt cgcggaattc agc        53

<210> SEQ ID NO 4
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 4
atcgccctat attctaactt gactcgctga attccgcgtt cgcggaattc agc        53

<210> SEQ ID NO 5
<211> LENGTH: 12
<212> TYPE: DNA
<213> ORGANISM: Artificial Sequence
<220> FEATURE:
<223> OTHER INFORMATION: Synthetic

<400> SEQUENCE: 5
actgactgac tg                                                     12

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
tcgagtctga catgtgagag tgatg                                       25

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
cttcacccca tctcttcttt ttcgc                                       25

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
agagtgtagg gtaaaagcga aatca                                       25
```

```
<210> SEQ ID NO 9
<211> LENGTH: 25
<212> TYPE: DNA
<213> ORGANISM: Artificial Sequence
<220> FEATURE:
<223> OTHER INFORMATION: Synthetic

<400> SEQUENCE: 9
gagtcaagtt agaatatagg gcgat                                              25

<210> SEQ ID NO 10
<211> LENGTH: 12
<212> TYPE: DNA
<213> ORGANISM: Artificial Sequence
<220> FEATURE:
<223> OTHER INFORMATION: Synthetic

<400> SEQUENCE: 10
agctagctag ct                                                            12
```

METHODS AND DEVICES FOR SEQUENCING NUCLEIC ACIDS IN SMALLER BATCHES

FIELD OF THE INVENTION

The invention relates to methods, compositions, devices, systems and kits including, without limitation, reagents, mixtures, data processing steps, algorithms, computer readable media, and computer programs, for determining the identity of nucleic acids in nucleotide sequences using, for example, data obtained from sequencing by synthesis, sequencing by ligation and other nucleic acid sequencing methods. In one embodiment, the present invention provides methods and devices for smaller sequencing projects, i.e. sequencing nucleic acids in smaller batches.

BACKGROUND OF THE INVENTION

Over the past 25 years, the amount of DNA sequence information that has been generated and deposited into Genbank has grown exponentially. Many of the next-generation sequencing technologies use a form of sequencing by synthesis (SBS), wherein specially designed nucleotides and DNA polymerases are used to read the sequence of chip-bound, single-stranded DNA templates in a controlled manner. Other next-generation sequencing technologies may use native nucleotides and/or polymerases or labeled oligonucleotides and ligation enzymes to determine nucleic acid sequences. To attain high throughput, many millions of such template spots, each being either single or multiple molecules, are arrayed across a sequencing chip and their sequence is independently read out and recorded. The desire to perform high throughput sequencing stems from the need for faster processing and reduced costs. However, commercial high throughput systems, while reducing the cost of large scale sequencing (e.g. 10-100 gigabases), make smaller scale sequencing (e.g. 100 megabases to 1 gigabases) costly and inconvenient. There is, therefore, a continued need for improved methods and devices for sequencing nucleic acid in order to address the practical day-to-day sequencing work of the average scientist.

SUMMARY OF THE INVENTION

At present, all highly parallel commercial sequencers require the user to run an entire, large flow cell, no matter what size the study or how many (or few) separate samples one might need. This is due to current designs which employ a single flow cell or dual flow cells, wherein all reagents and washes occur at a single station for each flow cell and valving is used to change the reagent delivered to the flow cell. This lack of flexibility has a number of unfavorable consequences. First, it means that one must either tolerate the waste and higher costs of smaller sequencing jobs (e.g. 100 megabases to 1 gigabases), or wait until a number of smaller sequencing jobs can be combined into a larger run. Second, it means that large sequencing projects will be favored (e.g. at a core facility) since they are more cost-effective, causing the average researcher with the smaller project to be excluded or (at best) forced to wait days to weeks before getting access to a shared machine.

In one embodiment, the present invention provides important features in a sequencing system that result in greater flexibility. That is to say, researchers who want to run a relatively small sequencing study on a single sample, or parallel studies on multiple samples (say sequence the same five genes from 10 individuals), can do so without waiting days to weeks to be "fit" into a larger run. Indeed, researchers can choose the size of their projects and scale their reagent usage accordingly, resulting in cost-effective smaller runs.

In one embodiment, this flexibility is provided by a) scaling down the size of the reaction chamber or flow cell to where the dimensions of the chip or the area to be imaged are less than the size of a standard microscope slide (i.e. less than 75 mm×25 mm) and preferably considerably less (e.g. 35 mm×2.5 mm, or smaller), and/or b) providing a plurality of these smaller flow cells (typically, 2, 4, 8, 10, 16 or even 20 flow cells) that are (preferably) both moveable and removeable. By scaling down the size of the flow cell, reagent volumes are reduced (e.g. to between 10 and 40 microliters, and more typically to approximately 20 microliters) in order to reduce costs. In addition, the amount of area that is imaged is reduced (allowing for faster imaging times and less expensive imaging equipment). Thus, rather than continuing to scale up sequencing, the present invention, in one embodiment, takes the approach of sequencing in smaller batches.

These changes also provide advantages in the context of genomic analysis and diagnostic testing, including but not limited to, sequencing of polymorphic areas in the genome that are linked to disease. Rather than using a relatively large single array or chip in a single flow cell, wherein the nucleic acid of a plurality of subjects, including but not limited to human patients, are combined, the present invention contemplates, in one embodiment, using a plurality of smaller arrays or chips in smaller flow cells, wherein any one chip contains the nucleic acid of but a single subject, including but not limited to a single human patient. In another embodiment, multiple subjects are sequenced on a single flow cell, but the sequencing may be completed faster and more cost effectively as compared to larger flow cell systems. Of course, it is not intended that the present invention be limited to sequencing using arrays or chips. Nucleic acid to be sequenced can be housed in the flow cell in a number of ways, including but not limited to, immobilized on beads where the beads are in fixed positions or are not in fixed positions (e.g. free to move about) within the flow cell.

In one embodiment, the present invention contemplates a method for carrying out steps of a nucleic acid sequencing protocol (e.g. where the protocol involves numerous cycles, each cycle having a number of steps), at least one step performed first in a cycle, some steps performed later in said cycle, said method comprising: a) providing: i) a camera; ii) a plurality of reservoirs, at least one of which comprising nucleic acid sequencing reagents, and at least one of which comprising wash buffer; iii) first nucleic acids in a first flow cell and second nucleic acids in a second flow cell, said first and second nucleic acids comprising templates to be sequenced in an area to be imaged, said flow cells mounted on iv) a moveable support, said support configured to move said flow cells to v) a plurality of stations, at least some of which are reagent delivery stations, each reagent delivery station in fluidic communication with at least one of said reservoirs and associated with at least one step, or portion thereof, of said nucleic acid sequencing protocol, at least one of said steps comprising positioning a flow cell such that said area to be imaged can be imaged by said camera; b) moving said moveable support under conditions such that said first flow cell is aligned with and connected to the reagent delivery station associated with a first step in said sequencing protocol, whereby said first flow cell is in fluid communication with at least a first reservoir of said plurality of reservoirs; c) introducing reagent via one of said reservoirs into said first flow cell under conditions such that said reagent contacts said first nucleic acids; and d) moving said moveable support under conditions such that i) said first flow cell is disconnected with said reagent delivery station associated with said first step and aligned with a station associated with a later step in said sequencing protocol, and ii) said second flow cell is aligned with and connected to said reagent delivery station associated with said first step in said sequencing protocol, whereby said second flow cell is in fluid communication with at least said first reservoir of said plurality of reservoirs. In one embodiment, the method further comprises performing a plurality of cycles, wherein steps b, c and d are repeated. In one embodiment, said later step comprises the second step in said sequencing protocol and said first flow cell is aligned with and connected to reagent delivery station associated with said second step in said sequencing protocol, whereby said first flow cell is in fluid communication with at least said second reservoir of said plurality of reservoirs. In one embodiment, said reagent delivery station associated with a first step in said sequencing protocol also performs the second step in said sequencing protocol. In one embodiment, said later step comprises the third step in said sequencing protocol. In one embodiment, said second step is a wash step wherein said first nucleic acids of said first flow cell is contacted with wash buffer. In one embodiment, said at least one station is a dwell station and not a reagent delivery station. In one embodiment, said later step comprises pausing at said dwell station. In one embodiment, one of said reservoirs comprises labeled nucleotide analogues comprising a base and a sugar. In one embodiment, said sugar is an acyclic sugar. In one embodiment, the labeled nucleotide analogues comprise a label attached to the base of said nucleotide analogues via a cleavable linker. In one embodiment, said labeled nucleotide analogues further comprising a cleavable blocking group on the sugar. In one embodiment, said labeled nucleotides are introduced at step c). In one embodiment, the labeled nucleotide analogues produce the signals required for imaging and sequencing. In one embodiment, said reagent is introduced into said first flow cell at step c) in a volume that is less than 50 microliters. In one embodiment, said reagent is introduced into said first flow cell at step c) in a volume of approximately 20 microliters or less (but not less than 5 microliters). In one embodiment, the method further comprises the step e) introducing reagent via said first reservoir into said second flow cell under conditions such that said reagent contacts said second nucleic acids. In one embodiment, the method further comprises the step f) moving said moveable support under conditions that i) said first flow cell is disconnected with said reagent delivery station associated with said second step and aligned with and connected to the reagent delivery station associated with a third step in said sequencing protocol, whereby said first flow cell is in fluid communication with at least a third reservoir of said plurality of reservoirs, and ii) said second flow cell is disconnected with said reagent delivery station associated with said first step and aligned with and connected to the reagent delivery station associated with a second step in said sequencing protocol, whereby said second flow cell is in fluid communication with at least a second reservoir of said plurality of reservoirs. In one embodiment said third step in said sequencing protocol is a wash step wherein said first nucleic acids of said first flow cell are contacted with wash buffer. In one embodiment, said first nucleic acids in said first flow cell, are scanned and imaged with said camera after step 1).

In one embodiment, said first flow cell is removed from said moveable support prior to said imaging. In one embodiment, an oxygen scavenger is introduced into said first flow cell before, during or after said first nuclei acids are scanned and imaged. In one embodiment, the method further comprises moving said carousel under conditions that said first flow cell is aligned with and connected to the reagent delivery station associated with a fourth step in said sequencing protocol, whereby said first flow cell is in fluid communication with at least a fourth reservoir of said plurality of reservoirs. In one embodiment, said fourth step in said sequencing protocol is a cleavage step wherein said first chip of said first flow cell is contacted with buffer comprising a cleaving agent (which can be an agent that cleaves chemically or an agent that cleaves enzymatically) which cleaves said cleavable linker under first conditions. In one embodiment, said cleavable blocking group is thereafter cleaved under second conditions. In one embodiment, said first conditions and second conditions are different. In one embodiment, the method further comprises moving said carousel under conditions that said first flow cell is disconnected with said reagent delivery station associated with said fourth step and aligned with and connected to the reagent delivery station associated with a fifth step in said sequencing protocol, whereby said first flow cell is in fluid communication with at least a fifth reservoir of said plurality of reservoirs. In one embodiment, said fifth step in said sequencing protocol comprising introducing a cleaving agent scavenger to address (e.g. neutralize, bind, or otherwise render inactive) leftover cleaving agent, which might prematurely cleave in the next cycle (e.g. cause an unintended and undesired cleavage of a label from a nucleotide, before the nucleotide is incorporated, or before the label can be detected). In one embodiment, said first nucleic acids are on a first chip in said first flow cell, and said chip is scanned and imaged with said camera after step f). In one embodiment, said first flow cell is removed from said moveable support prior to said imaging. In one embodiment, said first flow cell is aligned with aid connected to the reagent delivery station associated with a fourth step in said sequencing protocol prior to said imaging with said camera. In one embodiment, said second nucleic acids are on a second chip in said second flow cell, and said second chip is scanned and imaged after said first chip in said first flow cell is scanned and imaged. In one embodiment, said instrument comprises a second camera, and said second chip in said second flow cell is scanned and imaged with said second camera at the same time said first chip in said first flow cell is scanned and imaged with said first camera. In one embodiment, said instrument comprises a second camera (FIG. 64A), and said first chip in said first flow cell is simultaneously scanned and imaged with said first and second cameras. In one embodiment, a third flow cell comprising third nucleic acids is added to said moveable support before said first flow cell is scanned and imaged with said camera. In one embodiment, a third flow cell comprising third nucleic acids is present on said moveable support when said first flow cell is scanned and imaged with said camera. In one embodiment, said third flow cell was not present on said moveable support prior to step b). In one embodiment, a third flow cell comprising third nucleic acids is added to said moveable support after said first flow cell is scanned and imaged with said camera. In one embodiment, said area to be imaged on said first and second chips is (on each) approximately 35 mm×2.5 mm, or less (but not less than 10% of this area). In one embodiment, said first chip remains in said first flow cell while it is imaged at least a portion of said first and second flow cells is transparent. In one embodiment, said first flow cell is in a first position on said moveable support and said second flow cell is in a second position on said moveable support said first ad first and second positions being in a fixed relationship on said moveable support. In one embodiment, said first flow cell is removed from said first position on said moveable support and repositioned in a new position on said moveable support, said new position being different from said first or second position. In one embodiment, said first flow cell is removed from said first position before or after a first cycle of steps is completed. In one embodiment, said moveable support is a carousel. In one embodiment, said carousel is under the control of (e.g. in electronic communication with) a processor. In one embodiment, said processor can be programmed to change the movement of said carousel. In one embodiment, said first nucleic acids are immobilized on a plurality of beads in said first flow cell, and said beads are scanned and imaged with said camera after step f). In one embodiment, said first nucleic acids are from a first subject and said second nucleic acids are from a second subject. In one embodiment, said first nucleic acids are from a first subject, said second nucleic acids are from a second subject, and said third nucleic acids are from a third subject.

In one embodiment, the present invention contemplates a system comprising i) a plurality of reservoirs, at least one of which comprises nucleic acid sequencing reagents; ii) first nucleic acids in a first flow cell and iii) second nucleic acids in a second flow cell, said first and second nucleic acids comprising templates to be sequenced in an area to be imaged, said flow cells mounted on iv) a moveable support, said support configured to move said flow cells to v) a plurality of reagent delivery stations, each station in fluidic communication with at least one of said reservoirs and associated with at least one step, or portion thereof, of said nucleic acid sequencing protocol, said steps of said protocol carried out by vi) a programmable processor. In one embodiment, said first nucleic acids are from a first subject and said second nucleic acids are from a second subject. In one embodiment, the system further comprises a camera for imaging one or more flow cells. In one embodiment, at least one of said stations is positioned such that said area to be imaged can be imaged by said camera. In one embodiment, said system is contained within the housing of an instrument, said instrument comprising a user interface, said user interface in (electronic) communication with said programmable processor. In one embodiment, said system further comprises an imaging platform capable of x/y movement, said imaging platform positioned under said camera further comprising a transfer means capable of moving at least one of said flow cells from said moveable support said moveable support to said imaging platform. In one embodiment, said area to be imaged in said first and second flow cells is (on each) approximately 35 mm×2.5 mm, or less (but not less than 10% of this area). In one embodiment, said templates to be sequenced are on chips in said flow cells. In one embodiment, said templates are on beads in said flow cells. In one embodiment, said beads are immobilized. In one embodiment, said beads are immobilized by attachment of each bead to a solid support or to the flow cell itself.

In one embodiment, the present invention contemplates a method for carrying out steps of a nucleic acid sequencing protocol (e.g. where the protocol involves numerous cycles, each cycle having a number of steps), at least one step performed first in a cycle, some steps performed later in said cycle, said method comprising: a) providing: i) an imaging platform capable of x/y movement; ii) a camera position above said imaging platform; iii) a plurality of reservoirs, at least one of which comprising nucleic acid sequencing reagents, and at least one of which comprising wash buffer; iv) a first chip (or solid support) in a first flow cell and a second chip (or solid support) in a second flow cell, said first and second chips comprising nucleic acid templates to be sequenced in an area to be imaged, said flow cells mounted on v) a carousel, said carousel configured to move said flow cells to vi) a plurality of stations, at least some stations comprising reagent delivery stations in fluidic communication with at least one of said reservoirs and associated with at least one step, or portion thereof, of said nucleic acid sequencing protocol; and vii) a transfer means capable of moving at least one of said flow cells from said carousel to said imaging platform, and from said imaging platform to said carousel; b) moving said carousel under conditions such that said first flow cell is aligned with and connected to the reagent delivery station associated with a first step in said sequencing protocol, whereby said first flow cell is in fluid communication with at least a first reservoir of said plurality of reservoirs; c) introducing reagent via one of said reservoirs into said first flow cell under conditions such that said reagent contacts said nucleic acid templates of said first chip; and d) moving said carousel under conditions such that i) said first flow cell is disconnected with said reagent delivery station associated with said first step and aligned with a station associated with a later step in said sequencing protocol, and ii) said second flow cell is aligned with and connected to said reagent delivery station associated with said first step in said sequencing protocol, whereby said second flow cell is in fluid communication with at least said first reservoir of said plurality of reservoirs. In one embodiment, the method further comprises performing a plurality of cycles, wherein steps b, c and d are repeated. In one embodiment, said later step comprises the second step in said sequencing protocol and said first flow cell is aligned with and connected to said reagent delivery station associated with said second step in said sequencing protocol, whereby said first flow cell is in fluid communication with at least said second reservoir of said plurality of reservoirs. In one embodiment, said reagent delivery station associated with a first step in said sequencing protocol also performs the second step in said sequencing protocol. In one embodiment, said later step comprises the third step in said sequencing protocol. In one embodiment, said second step is a wash step wherein said first chip of said first flow cell is contacted with wash buffer. In one embodiment, at least one station is a dwell station and not a reagent delivery station. In one embodiment, said later step comprises pausing at said dwell station. In one embodiment, one of said reservoirs comprises labeled nucleotide analogues comprising a base and a sugar. In one embodiment, said sugar is an acyclic sugar. In one embodiment, labeled nucleotide analogues comprise a label attached to the base of said nucleotide analogues via a cleavable linker. In one embodiment, said labeled nucleotide analogues further comprising a cleavable blocking group on the sugar. In one embodiment, said labeled nucleotides are introduced at step c). In one embodiment, the labeled nucleotide analogues produce the signals required for imaging and sequencing. In one embodiment, the method further comprises the step e) introducing reagent via said first reservoir into said second flow cell under conditions such that said reagent contacts said nucleic acid templates of said second chip further comprising the step f) moving said carousel under conditions that i) said first flow cell is disconnected with said reagent delivery station associated with said second step and aligned with and connected to the reagent delivery station associated with a third step in said sequencing protocol, whereby said first flow cell is in fluid communication with at least a third reservoir of said plurality of reservoirs, and ii) said second flow cell is disconnected with said reagent delivery station associated with said first step and aligned with and connected to the reagent delivery station associated with a second step in said sequencing protocol, whereby said second flow cell is in fluid communication with at least a second reservoir of said plurality of reservoirs said third step in said sequencing protocol is a wash step wherein said first chip of said first flow cell is contacted with wash buffer. In one embodiment, after step f), said first chip in said first flow cell is moved to a station that is not in fluid communication with a reservoir. In one embodiment, said first flow cell is transferred from said station not in fluid communication with a reservoir to said imaging platform via said transfer means. In one embodiment, said flow cell transferred to said imaging platform is scanned and imaged with said camera. In one embodiment, an oxygen scavenger is introduced into said first flow cell before, during or after said flow cell is scanned and imaged. In one embodiment, after said flow cell is imaged, said flow cell is transferred back to said carousel via said transfer means. In one embodiment, said flow cell is transferred back to the same station from which it was transferred. In one embodiment, said flow cell is transferred back to a different station. In one embodiment, the method further comprises moving said carousel under conditions that said first flow cell is aligned with and connected to the reagent delivery station associated with a fourth step in said sequencing protocol, whereby said first flow cell is in fluid communication with at least a fourth reservoir of said plurality of reservoirs said fourth step in said sequencing protocol is a cleavage step wherein said first chip of said first flow cell is contacted with buffer comprising a cleaving agent (which can cleave chemically or, alternatively, enzymatically) which cleaves said cleavable linker under first conditions. In one embodiment, said cleavable blocking group is thereafter cleaved under second conditions. In one embodiment, said first conditions and second conditions are different. In one embodiment, the method further comprises moving said carousel under conditions that said first flow cell is disconnected with said reagent delivery station associated with said fourth step and aligned with and connected to the reagent delivery station associated with a fifth step in said sequencing protocol, whereby said first flow cell is in fluid communication with at least a fifth reservoir of said plurality of reservoirs. In one embodiment, said fifth step in said sequencing protocol comprises introducing a cleaving agent scavenger to address (e.g. neutralize, bind to, or otherwise render inactive) leftover cleaving agent which might prematurely cleave in the next cycle. In one embodiment, said different station is adjacent a reagent delivery station associated with a later step in the same cycle of said sequencing protocol. In one embodiment, said different station is the reagent delivery station associated with a later step in the same cycle of said sequencing protocol. In one embodiment, said different station is adjacent a reagent delivery station associated with a first step in a later cycle of said sequencing protocol. In one embodiment, said different station is the reagent delivery station associated with a first step in a later cycle of said sequencing protocol. In one embodiment, the method further comprises moving said carousel under conditions such that said first flow cell is aligned with and connected to said reagent delivery station associated with a first step in said sequencing protocol, whereby said first flow cell is in fluid communication with at least a first reservoir of said plurality of reservoirs, such that a second cycle of said sequencing protocol can commence. In one embodiment, there is at least one dwell station between the station from which the flow cell was transferred and the station adjacent a reagent delivery station associated with a first step in said sequencing protocol. In one embodiment, said first flow cell is in a first position on said moveable support and said second flow cell is in a second position on said moveable support, said first and second positions being in a fixed relationship on said moveable support. In one embodiment, said first flow cell is removed from said first position on said moveable support and repositioned in a new position on said moveable support, said new position being different from said first or second position. In one embodiment, said first flow cell is removed from said first position before or after a first cycle of steps is completed. In one embodiment, said nucleic acid templates in said first flow cell are from a first human patient and said nucleic acid templates in said second flow cell are from a second human patient. In one embodiment, there is a third flow cell. In one embodiment, said nucleic acid templates in said first flow cell are from a first human patient, said nucleic acid templates in said second flow cell are from a second human patient, and said nucleic acid templates in said third flow cell are from a third human patient (i.e. each flow cell is limited to the nucleic acid from at most one patient). In other embodiments, each flow cell comprises the nucleic acid from at least two patients. In one embodiment, said area to be imaged in said first and second flow cells is (on each) approximately 35 mm×2.5 mm, or less (but not less than 10% of this area).

In yet another embodiment, the present invention contemplates a method for carrying out steps of a nucleic acid sequencing protocol (e.g. where a plurality of cycles are performed), at least one step performed first in a cycle, some steps performed later in said cycle, said method comprising: a) providing: i) a plurality of flow cells, the number of flow cells corresponding approximately to (or corresponding exactly to) the number of steps in one cycle, said flow cells comprising nucleic acid templates to be sequenced in an area to be imaged, said flow cells mounted on ii) a moveable support, said support configured to move said flow cells to iii) a plurality of stations, at least some of which are reagent delivery stations, each reagent delivery station in fluidic communication with at least one reservoir of a plurality of reservoirs and associated with at least one step, or portion thereof, of said nucleic acid sequencing protocol, some of said reservoirs comprising reagent; b) moving said moveable support under conditions such that a first flow cell of said plurality of flow cells is aligned with and connected to the reagent delivery station associated with a first step in said sequencing protocol, whereby said first flow cell is in fluid communication with at least a first reservoir of said plurality of reservoirs; c) introducing reagent via one of said reservoirs into said first flow cell under conditions such that said reagent contacts said nucleic acid templates in said first flow cell; and d) moving said moveable support under conditions such that said first flow cell is disconnected with said reagent delivery station associated with said first step and aligned with a station associated with a later step in said sequencing protocol. In one embodiment, each cycle comprises five steps and the number of flow cells is between five and seven. In one embodiment, each cycle comprises six steps and the number of flow cells is between four and eight. In one embodiment, each cycle comprises seven steps and the number of flow cells is between five and nine. In one embodiment, the number of flow cells is equal to the number of steps in one cycle. In one embodiment, said nucleic acid templates are on a first chip in said first flow cell. In one embodiment, said nucleic acid templates are immobilized on a plurality of beads in said first flow cell. In one embodiment, said area to be imaged is approximately 35 mm×2.5 mm, or less. In one embodiment, said area to be imaged is not less than 10% of the area defined by 35 mm×2.5 mm. In one embodiment, said reagent of step c) comprises labeled nucleotide analogues, said analogues comprising i) a label attached to the base of said nucleotide analogues via a cleavable linker and ii) a cleavable blocking group on the sugar. In one embodiment, the method farther comprises performing a plurality of cycles, wherein steps b, c and d are repeated.

In yet another embodiment, the present invention contemplates a method for carrying out steps of a nucleic acid sequencing protocol (e.g. where a plurality of cycles are performed), at least one step performed first in a cycle, some steps performed later in said cycle, said method comprising: a) providing: i) a plurality of flow cells, said flow cells comprising nucleic acid templates to be sequenced in an area to be imaged, said flow cells mounted on ii) a moveable support, said support configured to move said flow cells to iii) a plurality of stations, at least some of which are reagent delivery stations, each reagent delivery station in fluidic communication with at least one reservoir of a plurality of reservoirs and associated with at least one step, or portion thereof, of said nucleic acid sequencing protocol, some of said reservoirs comprising reagent; b) positioning (or placing) a first flow cell of said plurality of flow cells on said moveable support such that it is aligned with and connected to a reagent delivery station associated with a first step in said sequencing protocol, whereby said first flow cell is in fluid communication with at least a first reservoir of said plurality of reservoirs; c) introducing reagent via one of said reservoirs into said first flow cell under conditions such that said reagent contacts said nucleic acid templates in said first flow cell; and d) moving said moveable support under conditions such that said first flow cell is disconnected with said reagent delivery station associated with said first step and aligned with a station associated with a later step in said sequencing protocol. In one embodiment, the method further comprises removing said first flow cell from said moveable support. In one embodiment, the method further comprises adding one or more additional flow cells to said moveable support.

While the preferred mode of sequencing is sequencing by synthesis, many of the features and advantages described herein can be applied to other sequencing approaches. For example, a plurality of smaller flow cells can be used with the pyrosequencing approach that employs four natural (native) nucleotides (comprising a base of adenine (A), cytosine (C), guanine (G), or thymine (T)) and several other enzymes for sequencing DNA. In this approach, the detection is based on the pyrophosphate (PPi) released during the DNA polymerase reaction, the quantitative conversion of pyrophosphate to adenosine triphosphate (ATP) by sulfurylase, and the subsequent production of visible light by firefly luciferase. Similarly, a plurality of smaller flow cells can be used with either sequencing by hybridization or sequencing by ligation. Sequencing by hybridization is widely used in several different forms, including dynamic hybridization, and is the primary method currently used in all microarray detection formats. Sequencing by ligation is based on the ability of DNA ligase to join the ends of two oligonucleotides annealed next to each other on a template. For example, two oligonucleotides can be designed to anneal to both sides of a SNP site, and by detecting the formation of ligation product, the genotype of a target can be inferred. Finally, still other approaches to sequencing are contemplated, such as sequencing by degradation, single molecule sequencing, and nanopore (luminescent, fluorescent, FRET or current/voltage readout or combinations thereof).

In one embodiment, the flow cells do not move, but "stations" with the requisite reagent (or wash) delivery connections and controls (e.g. tubing, channels, inlets, ports, pumps, valving, etc.) move to the flow cells. However, in a preferred embodiment, the flow cells are in positions on a moving support and the support moves the flow cells to discrete locations, some locations having stations, some stations comprising the requisite reagent delivery connections and controls (in this embodiment, imaging can be done where the flow cells are moved to the camera, or the camera is moved to the flow cells, or both flow cells and camera move). In a preferred embodiment, a plurality of smaller flow cells are mounted on a moving plate (or other support) that brings each flow cell to a "station" associated with at least one step (or partial step) in the sequencing protocol (e.g. reagent introduction, washing, etc.). In some embodiments, two or more steps are done at a single station. In some embodiments, a portion of a step is done at one station and the remaining portion of the step is done at another station. Movement from station to station requires, in many cases, disconnecting from one set of ports and connecting to another set of ports (described more fully below with regard to the figures).

Thus, in one embodiment, the present invention contemplates a method for carrying out steps of a nucleic acid sequencing protocol, comprising: a) providing a first chip in a first flow cell, a second chip in a second flow cell, nucleic acid to be sequenced, nucleic acid sequencing reagents, and a first camera; and b) introducing said nucleic acid to be sequenced and said nucleic acid sequencing reagents into said first and second flow cells under conditions such that, while said first chip in said first flow cell is undergoing one or more reaction steps, said second chip in a second flow cell is being scanned and imaged with said first camera. In one embodiment, the method further comprises the step c) wherein said first chip in said first flow cell is scanned and imaged with said first camera after step b). In one embodiment, the method further comprises the step c) wherein said first chip in said first flow cell is scanned and imaged with a second camera after step b). In one embodiment, said nucleic acid sequencing reagents comprise labeled nucleotide analogues and polymerase. In one embodiment, said nucleic acid sequencing reagents are introduced into said flow cells in a volume that is less than 50 microliters. In a preferred embodiment, said nucleic acid sequencing reagents are introduced into said flow cells in a volume of approximately 20 microliters or less. The first and second chips typically contain nucleic acid templates derived from genomic DNA (either self-priming hairpins or single-stranded to which oligonucleotide primers can be hybridized and extended). In one embodiment, said first and second chips comprise arrays of such nucleic acid in the form of "spots." In one embodiment, the nucleic acid sequencing reagents pass the spots and produce the signals required for sequencing. In a preferred embodiment, the second chip remains in the flow cell while it is imaged, ha a particularly preferred embodiment, said first and second flow cells are positioned on a moving support (such as a rotary stage or carousel). In a preferred embodiment, said first and second flow cells are transparent (or at least a portion thereof is transparent). In a preferred embodiment, said flow cells are incorporated within an instrument (having a housing, within which is the camera and reservoirs for the various reagents).

The advantages of associating each station with at least one step (or partial step) in the sequencing protocol are significant. In current large systems, where all steps are done using a single flow cell, one particular step may be the "rate limiter." For example, in current large systems, the area to be imaged may be so great that the imaging step takes twice as long (or more) as any other step in the sequencing protocol. In these systems, subsequent steps are "held up" or delayed until the longer step of imaging is complete. By contrast, using a plurality of smaller flow cells at stations associated with a step (or partial step) in the sequencing protocol, allows one to a) reduce the time necessary for imaging, and thereby b) reduce the overall processing time. For example, a simplified sequencing protocol might employ five steps (after which the cycle begins again): 1) incorporating nucleotide analogues with a polymerase; 2) washing; 3) detecting the label of the incorporated nucleotide analogues (imaging); 4) removing the chemical moiety of the incorporated nucleotide analogue capping the 3'-OH group with a cleaving agent; and 5) washing. If each step (other than the imaging step) takes seven minutes, and the imaging step takes fifteen minutes, using current approaches results in an overall processing time of forty-three minutes. Using the approach of the present invention, the smaller flow cell may require only seven minutes to image, reducing the overall processing time to thirty-five minutes, and—most importantly—allowing other flow cells to move to the next station to be processed (including moving the next flow cell to the imaging station). Another approach to handling a "rate limiting" step in the sequencing protocol is to utilize two stations to complete the single step (i.e. each station does a part of the step).

Scaling down the flow cell into multiple flow cells with smaller imaging areas in the manner described herein, while not necessarily resulting in more throughput (i.e. bases sequenced per day), can increase the speed of each cycle of the sequencing protocol. This is particularly true where the number of flow cells corresponds to (or corresponds approximately to) the number of steps in the sequencing protocol, e.g. the number of steps in one cycle (as contemplated in preferred embodiments) where the protocol typically involves numerous cycles (eg. 20 to 100 or more). FIG. 60 and the associated table illustrate the interesting and subtle dynamics of this scaling down process by quantitatively comparing a single flow cell system, a dual flow cell system and an eight flow-cell system (each flow cell containing nucleic acid to be sequenced). In this comparison, the sequencing protocol involves seven chemistry steps, approximately equal in time, required for sequencing, followed by the imaging step (for a total of eight steps in a "cycle"). Each flow cell has a "chip" comprising nucleic acid to be sequenced, which is preferably arrayed so that sequencing goes on in parallel in each flow cell—each cycle resulting in a single nucleotide being incorporated and detected at each position in the array, the total number of bases being proportional to the imaging area, depending on the array density.

In the case of a single flow cell, the imaging step involves scanning across the entire area of the flow cell, such area equal to A. During the imaging, all other steps must wait. Similarly, during the other steps (i.e. the chemistry steps), there is no imaging. Thus, the imaging system is intermittently idle (in this case for seven chemistry steps) and not fully utilized. FIG. 61 shows 4 cycles are completed in a representative time period or "T." Since each cycle results in the sequencing of a single nucleotide at each position in the array, 4 cycles translates into 4 bases sequenced per T multiplied by the number of positions on the array (for shorthand, 4 cycles translates to "4A" bases sequenced). Thus, the time required to sequence 80 bases at each position on the array within the single flow cell would be 20T (see associated table).

By contrast, in the dual flow cell system, the imaging portion is more fully utilized since the second flow cell may be imaged while the first is undergoing the seven chemistry steps and vice versa. Interestingly, Table 1 shows that, during the time period (T), the number of total bases sequenced increases almost two-fold (expressed in the associated table as 7A). And yet, the time needed to sequence 80 bases at each position in the arrays of both flow cells is not decreased. This illustrates that just adding flow cells, particularly flow cells of the same size, will not maximize efficiency (e.g. will not minimize cycle time). Furthermore, it should be stressed that, in this example, the number of flow cells (two) does not correspond (even approximately) to the number of sequencing steps (8 steps total). By corresponding or approximately corresponding (i.e. plus or minus two) to the number of steps, the maximum or near maximum efficiencies can be obtained.

In the eight flow cell configuration, each of the flow cells is $1/7$A in area and therefore takes $1/7^{th}$ the time to image. Moreover, the eight flow cells correspond to the number of sequencing steps (which is a preferred embodiment). In this configuration, the imaging station is still fully utilized and therefore produces the same amount of sequence information over a given time period as the dual flow cell configuration (expressed in the table 1 as 7A); however, since it has a greater number of fluid delivery stations, it can complete more cycles in a given time than either the single or dual flow cell configurations (see associated table). Thus, the time required to sequence 80 bases at each position on the array within the eight flow cells would be approximately 11T (see associated table). In sum, by increasing the number of flow cells (to reflect the number of sequencing steps or at least approximate the number of sequencing steps) and reducing the area to be imaged per flow cell, the number of cycles per unit time is increased such that reaching a desired sequence read length can be reduced by almost one half.

Further advantages (discussed in more detail below) are achieved by being able to move flow cells in a manner that they need not return to their prior position. For example, in one embodiment, flow cells are off-loaded (e.g. for imaging) from the moving support at a first position (e.g. the last position in the cycle), and loaded back onto the moving support at a second position (preferably the second position allows the flow cell to either return to the same cycle, or start a new sequencing cycle, without passing through non-functional stations or dwell stations).

It is not intended that the present invention be limited by the nature of the plate or support (e.g. glass, metal, etc.) for the flow cells or the nature of the movement (e.g. x/y, up/down or circular) of the plate or support which comprises the plurality of smaller flow cells; however, a circular support (in the manner of a carousel) is preferred and provides certain advantages described herein.

In one embodiment, a first flow cell is moved to a first station for the first step of the sequencing protocol. When the first step is complete, the first flow cell is moved to a second station in order to carry out the second step of the sequencing protocol. At the same time, a second flow cell is moved to the first station for the first step of the sequencing protocol. In this embodiment, multiple flow cells are run in parallel at different stages in the protocol. In this sequential approach, the first flow cell will complete the sequencing protocol prior to the second flow cell, allowing replacement of the first flow cell with a new flow cell for processing, even though the other flow cells require additional processing. Using "removeable" flow cells in this manner, a researcher can gain access to a shared machine (e.g. in a core facility) without waiting for the completion of processing for all flow cells. Furthermore, not all flow cells need to be processed in every run; some "slots" can be "open" for the introduction of a new flow cell (e.g. only two flow cells might be "running" on a carousel which has a capacity for eight or more flow cells).

Alternatively, in another embodiment, a plurality of smaller flow cells are processed simultaneously, not sequentially. This has the disadvantage that a researcher cannot gain access to the shared machine until the processing is complete for all flow cells.

Connections, controls, seals and fluidics at each station are designed with due concern for the potential for contamination (i.e. possible carryover of reagent in a later step from an earlier step in the protocol). For example, in one embodiment, seal areas between the flow cell and the inlet and outlet to the flow cell at the wash station are larger than the seal areas at the reagent stations in order to clean the surface at the seal interface so as to not contaminate the flow cell with reagents from previous steps.

Each station can have a pump or there can be fewer pumps than stations. Preferably, a single pump can be employed with valving for the different stations (e.g. commercially available syringe pumps have such valving). Reagent sources are preferably positioned below the flow cells, with tubing coming up to the flow cell through inlet ports (described more fully in connection with the drawings below).

In one embodiment of the system and method, there are 5 chemistry (reagent delivery) stations, 1 imaging station, 1 load/unload station and 12-14 dwell stations. This system can accommodate from 1 to 20 flow cells and it will run with any number of flow cells up to 20. One could configure the system to have a max number of flow cells of almost anything independent of the number of steps. In one embodiment of the system and method, there are 4-7 chemistry stations, 1-2 imaging station, 1-2 load/unload stations and 12-14 dwell stations. This system can accommodate from 1 to 20 flow cells and it will run with any number of flow cells up to 20. Again, one could configure the system to have a max number of flow cells of almost anything independent of the number of steps. Thus, in one embodiment, the number of flow cells exceeds the number of steps in any one cycle of a sequencing protocol, e.g. where the number of flow cells is twice the number of steps, or three times the number of steps, or even four times the number of steps or more.

FIG. 61 shows one embodiment of the system and method with twenty equally spaced locations, numbered 1 to 20, around a circular carousel that represent positions where the flow cells on the carousel may stop. Only ten flow cells are shown in every other location for clarity; however, as many as twenty fixtures can be on the carousel to locate from one to twenty flow cells. These flow cells are sequenced through the set of extension, washing, imaging, cleaving, and washing steps which cover ten locations around the system. An additional ten non-functional locations are provided to expand the diameter of the carousel and, therefore, the number of samples (flow cells) that may be run at one time. If the carousel is not fully populated with twenty flow cells, then some or all of the non-functional locations may be skipped, making the system a semi-synchronous one rather than a fully synchronous one. In this embodiment, the imaging station removes the flow cells from the carousel for scanning. The station may also replace the flow cell at a different (empty) position on the carousel from where the flow cell originally resided in order to skip over certain non-functional locations. Thus, even when the system is populated with fewer than ten flow cells, no extra time is required to allow flow cells to index though the non-functional locations.

FIG. 61 shows an embodiment wherein a plurality of locations in the system are heated (e.g. to between 37° C. and 70° C., and preferably 55° C.) to facilitate various steps in the sequencing reaction. FIG. 61 shows that a subset of the locations have a fluidics station that can flow reagents or washes thorough the flow cells located at those stations. Some stations are dwell stations where flow cells that were filled in previous stations are continued to be maintained at the appropriate temperature to allow the reactions to complete should reactions times be more than the indexing time.

FIG. 62 shows that additional flow cells beyond five will increase the cycle time. The run times for 1 through 10 flow cells are shown in a MINI system that indexes every 2.5 minutes and 50 cycles (rotations) for every flow cell. One rotation equals one additional base in read length. It should be noted that up to five flow cells may be run in the system with the shortest possible cycle times (about 25 minutes) and any additional flow cells above five will slow the overall cycle time of the system, since additional indexes and dwells are required. FIG. 62 shows the run times for a 50-base read with varying numbers of relatively small flow cells (e.g. flow cells with areas that can support 20 million reads). Thus, 50 bases long reads for five flow cells generates 5 gigabases of sequence in less than a day and 50-base reads for a fully populated run of 20 flow cells will generate 20 Gigabases of sequence in 3.5 days.

If the system is run with larger format flow cells (e.g. flow cells that have 100 million reads), then the throughput for a 50-base run is shown in FIG. 63. In this configuration, the run time is primarily dependent on the time is takes to image a chip and the advantage of breaking up the chemistry steps is less important in determining the run time. Twenty flow cells of this configuration will generate 100 Gigabases of sequence in a 50-base run; however it will take about 17 days to complete. As a practical matter, a lab that has large projects requiring such ultra-high-throughput runs would likely have a system designed specifically for such runs.

The invention provides methods, compositions, devices, systems and kits are described including, without limitation, reagents, mixtures, data processing steps, algorithms, computer readable media, and computer programs, for determining the identity of nucleic acids in nucleotide sequences using, for example, data obtained from sequencing by synthesis methods. The methods of the invention include reducing and/or correcting one or more phenomena that are encountered during nucleotide sequencing, such as using sequencing by synthesis methods. These phenomena include, without limitation, sequence lead, sequence lag, spectral crosstalk, light from neighboring spots, and noise resulting from variations in illumination and/or filter responses.

In one embodiment, the present invention contemplates a set of data processing steps that may be used to analyze images of a hexagonal array of spots or beads on a surface. In one embodiment, the steps comprise a) field flattening and background subtraction, b) spot location in the array, c) image sharpening, d) spot brightness determination, e)

neighbor influence elimination, and f) color crosstalk elimination. Each of these steps is described in more detail below. Of course, in one embodiment, the present invention contemplates using a subset of these steps (in the same order or in a different order) as well as additional processing steps. The result of the analysis may be used to make measurements of the output of four different fluorescent dyes for each spot in the array. The methods described may also be generalized for a rectangular or other shaped arrays rather than a hexagonal array.

In one embodiment, the invention provides a method for determining an identity of a nucleic acid at an interrogation position in a nucleotide sequence from data acquired from one or more channels, comprising a) obtaining a data set for one or more probe intensities at one or more nucleic acid positions in the sequence, wherein each probe corresponds to a nucleic acid, b) determining the ratio contribution to probe intensity at the interrogation position from probe intensities at the interrogation position and at one or both of i) at least one subsequent nucleic acid positions in the sequence, and ii) at least one preceding nucleic acid positions in the sequence, and c) applying the ratio contribution to probe intensity to the data set to arrive at an identity for a nucleic acid at the interrogation position in the nucleotide sequence. In a particular embodiment, the step of determining the ratio contribution to probe intensity comprises measuring the rate (that is, the fraction of template molecules in an ensemble of identical template molecules) at which a lag, such as Gi, occurs at one or more nucleotide position in the nucleotide sequence, such as at each nucleotide position in the nucleotide sequence. In another embodiment, the step of determining the ratio contribution to probe intensity comprises measuring the rate (fraction) at which a lead, such as Di, occurs at one or more nucleotide positions in the nucleotide sequence. In yet another embodiment, the method further comprises calling a nucleic acid at the interrogation position in the nucleotide sequence. In a further embodiment, the method comprises repeating steps b) and c) to arrive at an identity for a nucleic acid at more than one interrogation position in the nucleotide sequence.

While not intending to limit the invention's method to particular steps, in one embodiment, the method further comprises a) applying a sequence lead-lag compensation equation to determine the ratio contribution to probe intensity from probe at i) the interrogation position, ii) each position preceding the interrogation position, and iii) each position subsequent to the interrogation position, and b) summing up the ratio contribution to probe intensity. In an alternative embodiment, the step of applying of the ratio contribution to probe intensity comprises a) comparing probe intensities from the one or more channels at the interrogation position, b) selecting the highest probe intensity of the compared probe intensities, and c) calling a nucleic acid, which corresponds to the selected probe, at the interrogation position.

It is not intended to limit the invention to a particular mathematical formula. Nonetheless, in one embodiment, the method comprises applying a sequence lead-lag compensation equation to the ratio contribution to probe intensity at a plurality of positions in the sequence. In one particular embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}$$

where $I_{M1}$ is a probe intensity measured at position 1 in the sequence, $I_{M2}$ is a probe intensity measured at position 2 in the sequence, $I_{MN}$ is a probe intensity measured at position N in the sequence, $I_{A1}$ is the actual probe intensity at position 1 in the sequence, $I_{A2}$ is the actual probe intensity at position 2 in the sequence, $I_{AN}$ is the actual probe intensity at position N in the sequence, where $$K_{Lead/Lag} = \begin{bmatrix} R_{Lag/Lead,1} & R_{+1Lead,1} & R_{+2Lead,1} & R_{+3Lead,1} & \cdots & R_{+(N-1)Lead,1} \\ R_{-1Lag,2} & R_{Lag/Lead,2} & R_{+1Lead,2} & R_{+2Lead,2} & \cdots & R_{+(N-2)Lead,2} \\ R_{-2Lag,3} & R_{-1Lag,3} & R_{Lag/Lead,3} & R_{+1Lead,3} & \cdots & R_{+(N-3)Lead,3} \\ R_{-3Lag,4} & R_{-2Lag,4} & R_{-1Lag,4} & R_{Lag/Lead,4} & \cdots & R_{+(N-4)Lead,4} \\ \vdots & \vdots & \vdots & \vdots & \ddots & \vdots \\ R_{-(N-1)Lag,N} & R_{-(N-2)Lag,N} & R_{-(N-3)Lag,N} & R_{-(N-4)Lag,N} & \cdots & R_{Lag/Lead,N} \end{bmatrix}$$

where $R_{lag/Lead,1}$ is the ratio between reduced probe intensity for nucleic acid at position 1 to actual probe intensity at the nucleic acid at position 1, $R_{+1Lead,1}$ is the ratio contribution to probe intensity at nucleic acid position 1 from probe at nucleic acid position 2, $R_{+2Lead,1}$ is the ratio contribution to probe intensity at nucleic acid position 1 from probe at nucleic acid position 3, $R_{+3Lead,1}$ is the ratio contribution to probe intensity at nucleic acid position 1 from probe at nucleic acid position 4, $R_{+(N-1)Lead,1}$ is the ratio contribution to probe intensity at nucleic acid position 1 from probe at nucleic acid position 1+(N−1), $R_{-1Lag,2}$ is the ratio contribution to probe intensity at nucleic acid position 2 from probe at nucleic acid position 1, $R_{Lag/Lead,2}$ is the ratio between reduced probe intensity for nucleic acid at position 2 to actual probe intensity at the nucleic acid at position 2, $R_{+1Lead,2}$ is the ratio contribution to probe intensity at nucleic acid position 2 from probe at nucleic acid position 3, $R_{+2Lead,2}$ is the ratio contribution to probe intensity at nucleic acid position 2 from probe at nucleic acid position 4, $R_{+(N-2)Lead,2}$ is the ratio contribution to probe intensity at nucleic acid position 2 from probe at nucleic acid position 2+(N−2), $R_{-2Lag,3}$ is the ratio contribution to probe intensity at nucleic acid position 3 from probe at nucleic acid position 1, $R_{-1Lag,3}$ is the ratio contribution to probe intensity at nucleic acid position 3 from probe at nucleic acid position 2, $R_{Lag/Lead,3}$ is the ratio between reduced probe intensity for nucleic acid at position 3 to actual probe intensity at the nucleic acid at position 3, $R_{+1Lead,3}$ is the ratio contribution to probe intensity at nucleic acid position 3 from probe at nucleic acid position 4, $R_{+(N-3)Lead,3}$ is the ratio contribution to probe intensity at nucleic acid position 3 from probe at nucleic acid position 3+(N−3), $R_{-3Lag,4}$ is the ratio contribution to probe intensity at nucleic acid position 4 from probe at nucleic acid position 1, $R_{-2Lag,4}$ is the ratio contribution to probe intensity at nucleic acid position 4 from probe at nucleic acid position 2, $R_{-1Lag,4}$ is the ratio contribution to probe intensity at nucleic acid position 4 from probe at nucleic acid position 3, $R_{Lag/Lead,4}$ is the ratio between reduced probe intensity for nucleic acid at position 4 to actual probe intensity at the nucleic acid at position 4, $R_{+(N-4)Lead,4}$ is the ratio contribution to probe intensity at nucleic acid position 4 from probe at nucleic acid position 4+(N−4), $R_{-(N-1)Lag,N}$ is the ratio contribution to probe intensity at nucleic acid position N from probe at nucleic acid position N−(N−1), $R_{-(N-2)Lag,N}$ is the ratio contribution to probe intensity at nucleic acid position N from probe at nucleic acid position N−(N−2), $R_{-(N-4)Lag,N}$ is the ratio contribution to probe intensity at nucleic acid position N from probe at nucleic acid position N−(N−3), $R_{-(N-4)Lag,N}$ is the ratio contribution to probe intensity at nucleic acid position N from probe at nucleic acid position N−(N−4), and $R_{Lag/Lead,N}$ is the ratio between reduced probe intensity for nucleic acid at position N to actual probe intensity at the nucleic acid at position N.

In a further embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}.$$

In a particular embodiment, the nucleic acid comprises a base selected from the group of adenine (A), guanine (G), cytosine (C), thymine (T), and uracil (U), and the probe is detectable using any means such as color in the visible spectrum (e.g., fluorescence), radioactivity, and the like.

While not intending to limit the invention's methods to particular steps, in one embodiment, the methods further comprise field flattening of background data for the data set. This may be accomplished by, for example, a) obtaining a first data set for a plurality of pixel intensities of a first raw image of a probe at a first concentration on a solid support, wherein the first raw image is produced using a first spectral filter for detecting a first probe, b) obtaining a second data set for a plurality of pixel intensities of a second smoothed image of the probe uniformly spread on the solid support or other uniformly radiating substrate, wherein the second smoothed image is produced using a low pass filter, c) determining a field flattening intensity value for a plurality of pixels of the first raw image, and d) generating a third field flattened image of the probe on the solid support using the field flattening intensity of the plurality of pixels, wherein the correlation of intensity of a plurality of pixels to their spatial location on the third field flattened image is reduced compared to the intensity of a plurality of pixels at a corresponding location on the first raw image. In a particular embodiment, the background intensities are removed from both the first and second data sets so that the lowest intensity data point is at 0.

Although the field flattening methods are not intended to be limited to any particular equation, in one embodiment, the field flattening intensity value of a pixel is determined by equation $$F_{x,y} = R_{x,y} M_{x0,y0} / M_{x,y}$$

where $F_{x,y}$ is a field flattening intensity value, $R_{x,y}$ is the intensity of a pixel of the plurality of pixels on the first raw image, $M_{x,y}$ is the intensity of a pixel of the plurality of pixels on the second smoothed image at a corresponding spatial location to the pixel on the first raw image, and $M_{x0,y0}$ is the intensity of a reference pixel on the second smoothed image or is an arbitrary scale factor.

In one embodiment, the scale factor $M_{x0,y0}$ may also include a factor accounting for different exposure times or lighting intensities. In another embodiment, such as where a camera system has a proportional response to changes in exposure times or lighting conditions, the following equation may be used $$M_{x0,y0} = M_0 E_{(second\ image)} / E_{(first\ image)}$$

where $E_{(first\ image)}$ is the exposure or lighting level used during measurement of the first image, $E_{(second\ image)}$ is the exposure or lighting level used for the second image and $M_0$ is an arbitrary constant. In a further embodiment, the method further comprises repeating steps a) to d), using a second spectral filter for detecting a second probe. In an alternative embodiment, the method further comprises repeating steps a) to d), using the probe at a second concentration on the solid support. The solid support is exemplified, but not limited to, a microscope slide and silicon chip.

Also without limiting the invention's methods to particular steps, in one embodiment, the methods further comprise reducing spectral crosstalk in the one or more channels, by a) determining spectral crosstalk factors for each of the one or more probes in its corresponding channel from one or more adjacent channels, b) applying the spectral crosstalk factors to determine a spectral crosstalk matrix, and c) applying the spectral crosstalk matrix to the data set for the one or more probe intensities. In a particular embodiment, the step of reducing spectral crosstalk comprises a) determining probe intensity for one or more probes from one or more channels, wherein each channel corresponds to a probe, b) determining the ratios of the probe intensities in the one or more channels to arrive at signature ratios for the probe intensity in the channels, c) applying the signature ratios in a matrix equation, and d) inverting the matrix equation to arrive at an inverted matrix. In one embodiment, the method further comprises e) applying the inverted matrix to data from the one or more channels.

While not intending to limit reducing spectral crosstalk to any particular equation, in one embodiment, the step of determining spectral crosstalk matrix comprises using equation $$\begin{bmatrix} M_A \\ M_B \\ M_C \\ M_D \end{bmatrix} = K \begin{bmatrix} A \\ B \\ C \\ D \end{bmatrix}$$

where $$K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix},$$

and where $M_A$ is the observed intensity in the channel for probe A,
$M_B$ is the observed intensity in the channel for probe B,
$M_C$ is the observed intensity in the channel for probe C,
$M_D$ is the observed intensity in the channel for probe D,
A is the actual probe intensity of probe A,
B is the actual probe intensity of probe B,
C is the actual probe intensity of probe C,
D is the actual probe intensity of probe D,
$R_{AB}$ is the ratio between (a) the portion of intensity in the channel for probe A that is contributed by probe B, and (b) the actual probe intensity of probe B,
$R_{BA}$ is the ratio between (a) the portion of intensity in the channel for probe B that is contributed by probe A, and (b) the actual probe intensity of probe A,
$R_{BC}$ is the ratio between (a) the portion of intensity in the channel for probe B that is contributed by probe C, and (b) the actual probe intensity of probe C,
$R_{CB}$ is the ratio between (a) the portion of intensity in a channel for probe C that is contributed by probe B, and (b) the actual probe intensity of probe B,
$R_{CD}$ is the ratio between (a) the portion of intensity in a channel for probe C that is contributed by probe D, and (b) the actual probe intensity of probe D, and
$R_{DC}$ is the ratio between (a) the portion of intensity in a channel for probe D that is contributed by probe C, and (b) the actual probe intensity of probe C.

The above equation is solved to determine spectral crosstalk matrix $K^{-1}$ and an estimate of the actual intensities of the probes (A, B, C and D) using equation $$\begin{bmatrix} A \\ B \\ C \\ D \\ \vdots \end{bmatrix} = K^{-1} \begin{bmatrix} M_A \\ M_B \\ M_C \\ M_D \\ \vdots \end{bmatrix}$$

In alternative embodiment, the equation is solved to determine and/or estimate for actual probe intensities A, B, C and D.

The invention further provides an algorithm for processing data for nucleic acids in a nucleotide sequence, wherein the data is acquired from one or more channels, the algorithm comprising a) determining the ratio contribution to probe intensity in the one or more channels for one or more interrogation positions, from probe intensities at the interrogation position and at one or both of i) at least one subsequent nucleic acid positions in the sequence, and ii) at least one preceding nucleic acid positions in the sequence, b) processing data from the one or more channels to correct for sequence lead and sequence lag, and c) reconstructing the data in the one or more channels. In one embodiment, the step of processing data comprises applying the ratio contribution to probe intensity to determine, for the probe at the one or more interrogation positions, a sequence lead-lag compensation equation. Without limiting the invention to any particular equation, in one embodiment, the sequence lead-lag compensation equation is determined by applying equation $$\begin{bmatrix} I_{M1} \\ I_{M2} \\ \vdots \\ I_{MM} \end{bmatrix} = K_{Lead/Lag} \begin{bmatrix} I_{A1} \\ I_{A2} \\ \vdots \\ I_{AN} \end{bmatrix}$$

where $I_{M1}$ is a probe intensity measured at position 1 in the sequence,
$I_{M2}$ is a probe intensity measured at position 2 in the sequence,
$I_{MN}$ is a probe intensity measured at position N in the sequence,
$I_{A1}$ is the actual probe intensity at position 1 in the sequence,
$I_{A2}$ is the actual probe intensity at position 2 in the sequence,
$I_{AN}$ is the actual probe intensity at position N in the sequence, In an alternative embodiment, the sequence lead-lag compensation equation is determined by applying equation $$K_{Lead/Lag} = \begin{bmatrix} R_{Lag/Lead,1} & R_{+1Lead,1} & R_{+2Lead,1} & R_{+3Lead,1} & \cdots & R_{+(N-1)Lead,1} \\ R_{-1Lag,2} & R_{Lag/Lead,2} & R_{+1Lead,2} & R_{+2Lead,2} & \cdots & R_{+(N-2)Lead,2} \\ R_{-2Lag,3} & R_{-1Lag,3} & R_{Lag/Lead,3} & R_{+1Lead,3} & \cdots & R_{+(N-3)Lead,3} \\ R_{-3Lag,4} & R_{-2Lag,4} & R_{-1Lag,4} & R_{Lag/Lead,4} & \cdots & R_{+(N-4)Lead,4} \\ \vdots & \vdots & \vdots & \vdots & \ddots & \vdots \\ R_{-(N-1)Lag,N} & R_{-(N-2)Lag,N} & R_{-(N-3)Lag,N} & R_{-(N-4)Lag,N} & \cdots & R_{Lag/Lead,N} \end{bmatrix}$$

where
- $R_{Lag/Lead,1}$ is the ratio between reduced probe intensity for nucleic acid at position 1 to actual probe intensity at the nucleic acid at position 1,
- $R_{+1Lead,1}$ is the ratio contribution to probe intensity at nucleic acid position 1 from probe at nucleic acid position 2,
- $R_{+2Lead,1}$ is the ratio contribution to probe intensity at nucleic acid position 1 from probe at nucleic acid position 3,
- $R_{+3Lead,1}$ is the ratio contribution to probe intensity at nucleic acid position 1 from probe at nucleic acid position 4,
- $R_{+(N-1)Lead,1}$ is the ratio contribution to probe intensity at nucleic acid position 1 from probe at nucleic acid position 1+(N−1),
- $R_{-1Lag,2}$ is the ratio contribution to probe intensity at nucleic acid position 2 from probe at nucleic acid position 1,
- $R_{Lag/Lead,2}$ is the ratio between reduced probe intensity for nucleic acid at position 2 to actual probe intensity at the nucleic acid at position 2,
- $R_{+1Lead,2}$ is the ratio contribution to probe intensity at nucleic acid position 2 from probe at nucleic acid position 3,
- $R_{+2Lead,2}$ is the ratio contribution to probe intensity at nucleic acid position 2 from probe at nucleic acid position 4,
- $R_{+(N-2)Lead,2}$ is the ratio contribution to probe intensity at nucleic acid position 2 from probe at nucleic acid position 2+(N−2),
- $R_{-2Lag,3}$ is the ratio contribution to probe intensity at nucleic acid position 3 from probe at nucleic acid position 1,
- $R_{-1Lag,3}$ is the ratio contribution to probe intensity at nucleic acid position 3 from probe at nucleic acid position 2,
- $R_{Lag/Lead,3}$ is the ratio between reduced probe intensity for nucleic acid at position 3 to actual probe intensity at the nucleic acid at position 3,
- $R_{+1Lead,3}$ is the ratio contribution to probe intensity at nucleic acid position 3 from probe at nucleic acid position 4,
- $R_{+(N-3)Lead,3}$ is the ratio contribution to probe intensity at nucleic acid position 3 from probe at nucleic acid position 3+(N−3),
- $R_{-3Lag,4}$ is the ratio contribution to probe intensity at nucleic acid position 4 from probe at nucleic acid position 1,
- $R_{-2Lag,4}$ is the ratio contribution to probe intensity at nucleic acid position 4 from probe at nucleic acid position 2,
- $R_{-1Lag,4}$ is the ratio contribution to probe intensity at nucleic acid position 4 from probe at nucleic acid position 3,
- $R_{Lag/Lead,4}$ is the ratio between reduced probe intensity for nucleic acid at position 4 to actual probe intensity at the nucleic acid at position 4,
- $R_{+(N-4)Lead,4}$ is the ratio contribution to probe intensity at nucleic acid position 4 from probe at nucleic acid position 4+(N−4),
- $R_{-(N-1)Lag,N}$ is the ratio contribution to probe intensity at nucleic acid position N from probe at nucleic acid position N−(N−1),
- $R_{-(N-2)Lag,N}$ is the ratio contribution to probe intensity at nucleic acid position N from probe at nucleic acid position N−(N−2),
- $R_{-(N-3)Lag,N}$ is the ratio contribution to probe intensity at nucleic acid position N from probe at nucleic acid position N−(N−3),
- $R_{-(N-4)Lag,N}$ is the ratio contribution to probe intensity at nucleic acid position N from probe at nucleic acid position N−(N−4), and
- $R_{Lag/Lead,N}$ is the ratio between reduced probe intensity for nucleic acid at position N to actual probe intensity at the nucleic acid at position N.

In another alternative embodiment, the sequence lead-lag compensation equation is determined by applying equation $$\begin{bmatrix} I_{M1} \\ I_{M2} \\ \vdots \\ I_{MM} \end{bmatrix} = K_{Lead/Lag} \begin{bmatrix} I_{A1} \\ I_{A2} \\ \vdots \\ I_{AN} \end{bmatrix}.$$

While not necessary, it may be desirable to also include field flattening of background data in the algorithm and/or reducing spectral crosstalk between the data comprised in a plurality of channels. Dephasing correction (i.e., correction for lead-lag effects), field flattening and spectral crosstalk correction may be carried out in any order. Thus, in one embodiment, the field flattening is carried out before spectral crosstalk correction. In an alternative embodiment, spectral crosstalk correction is carried out before dephasing correction.

The invention also provides a computer readable medium containing a computer program for performing one or more of the method steps disclosed herein.

Also provided by the invention is a computer program product for processing data for nucleic acids in a nucleotide sequence to determine an identity of a nucleic acid at an interrogation position in the nucleotide sequence, the computer program product comprising a) computer code that inputs data from one or more channels for one or more probe intensities, wherein each channel corresponds to a probe, and each probe corresponds to a nucleic acid, b) computer code that applies to the input data a sequence lend-lag compensation equation to correct for sequence lead and sequence lag, c) computer code that compares probe intensities in the one or more channels that have been corrected for sequence lead and sequence lag, d) computer code that determines the highest probe intensity of the compared probe intensities, and e) computer code that identifies a nucleic acid at the interrogation position according to the highest probe intensity. Optionally, the computer program product may further comprise computer code that applies field flattening of background data and/or that reduces spectral crosstalk between data comprised in the one or more channels.

The invention also provides an apparatus that processes data for nucleic acids in a nucleotide sequence to determine an identity of a nucleic acid at an interrogation position in the nucleotide sequence, the apparatus comprising a) means for inputting data from one or more channels for one or more probe intensities, wherein each channel corresponds to a probe, and each probe corresponds to a nucleic acid, b) means for applying to the input data a sequence lead-lag compensation equation to correct for sequence lead and sequence lag, c) means for comparing probe intensities in the one or more channels that have been corrected for sequence lead and sequence lag, d) means for determining the highest probe intensity of the compared probe intensities, and e) means for identifying a nucleic acid at the interrogation position according to the highest probe intensity. Though not necessary, it may be desirable to also include means for applying field flattening of background data and/or for reducing spectral crosstalk between data comprised in the one or more channels.

Additionally provided herein is a system for processing data to determine an identity of a nucleic acid at an interrogation position in the nucleotide sequence, the system comprising a) a processor, and b) a computer readable medium readable by the processor, the computer readable medium storing a computer program that comprises i) code that receives as input a plurality of probe intensities at various positions in a nucleotide sequence, ii) code that applies to the input data a sequence lead-lag compensation equation to correct for sequence lead and sequence lag, and iii) code that identifies a nucleic acid at one or more interrogation position according to the corrected data. While not necessary, it may be desirable to additionally include in the computer readable medium code that applies field flattening of background data and/or that reduces spectral crosstalk between data comprised in the one ore more channels.

The invention also provides a method for field flattening an image of a probe on a solid support, comprising a) obtaining a first data set for a plurality of pixel intensities of a first raw image of a probe at a first concentration on a solid support, wherein the first raw image is produced using a first spectral filter for detecting a first probe, b) obtaining a second data set for a plurality of pixel intensities of a second smoothed image of the probe on the solid support, wherein the second smoothed image is produced using a low-pass filter, c) determining a field flattening intensity value for a plurality of pixels of the first raw image, and d) generating a third field flattened image of the probe on the solid support using the field flattening intensity of the plurality of pixels, wherein the correlation of intensity of a plurality of pixels to their spatial location on the third flattened image is reduced compared to the intensity of a plurality of pixels at a corresponding location on the first raw image. Without intending to limit the invention to any particular equation, in one embodiment, the field flattening intensity value of a pixel is determined by equation $$F_{x,y} = R_{x,y} M_{x0,y0} / M_{x,y}$$

where
$F_{x,y}$ is a field flattening intensity value,
$R_{x,y}$ is the intensity of a pixel of the plurality of pixels on the first raw image,
$M_{x,y}$ is the intensity of a pixel of the plurality of pixels on the second smoothed image at a corresponding spatial location to the pixel on the first raw image, and
$M_{x0,y0}$ is the intensity of a reference pixel on the second smoothed image, or is any other scale factor of interest.

In one embodiment, it may be desirable to repeat steps a) to d), using a second spectral filter for detecting a second probe. Alternatively, or in addition, it may be desirable to repeat steps a) to d), using the probe at a second concentration on the solid support. In one embodiment, the probe is fluorescent and corresponds to a nucleic acid that comprises a base selected from the group of adenine (A), guanine (G), cytosine (C), thymine (T), and uracil (U). The solid support may comprise a microscope slide, silicon chip, and the like.

The invention also provides a method for reducing spectral crosstalk in one or more channels that deliver data for determining the identity of a nucleic acid at an interrogation position in a nucleotide sequence, comprising a) obtaining a data set for one or more probe intensities at one or more nucleic acid positions in the sequence, wherein each probe corresponds to a nucleic acid, b) determining spectral crosstalk factors for each of the one or more probes in its corresponding channel from one or more adjacent channels, c) applying the spectral crosstalk factors to determine a spectral crosstalk matrix, and d) applying the spectral crosstalk matrix to the data set to arrive at an identity for a nucleic acid at the interrogation position in the nucleotide sequence. In one embodiment, the step of determining spectral crosstalk factors comprises determining a ratio between (a) the portion of probe intensity in a first channel of a first probe that is contributed by a second probe in a second channel adjacent to the first channel, and (b) the actual probe intensity of the second probe in the second channel. In a particular embodiment the method further comprises determining the ratio between (a) the portion of probe intensity in the first channel of the first probe that is contributed by a third probe in a third channel adjacent to the first channel, and (b) the actual probe intensity of the third probe in the third channel. Without limiting the type of equation used, in one embodiment, the step of determining spectral crosstalk matrix comprises using equation $$\begin{bmatrix} M_A \\ M_B \\ M_C \\ M_D \end{bmatrix} = K \begin{bmatrix} A \\ B \\ C \\ D \end{bmatrix}$$

where $$K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix},$$

and where
$M_A$ is the observed probe intensity of probe A,
$M_B$ is the observed probe intensity of probe B,
$M_C$ is the observed probe intensity of probe C,
$M_D$ is the observed probe intensity of probe D,
A is the actual probe intensity of probe A,
B is the actual probe intensity of probe B,
C is the actual probe intensity of probe C,
D is the actual probe intensity of probe D,
$R_{AB}$ is the ratio between (a) the portion of intensity in the channel for probe A that is contributed by probe B, and (b) the actual probe intensity of probe B,
$R_{BA}$ is the ratio between (a) the portion of intensity in the channel for probe B that is contributed by probe A, and (b) the actual probe intensity of probe A,
$R_{BC}$ is the ratio between (a) the portion of intensity in the channel for probe B that is contributed by probe C, and (b) the actual probe intensity of probe C,
$R_{CB}$ is the ratio between (a) the portion of intensity in a channel for probe C that is contributed by probe B, and (b) the actual probe intensity of probe B,
$R_{CD}$ is the ratio between (a) the portion of intensity in a channel for probe C that is contributed by probe D, and (b) the actual probe intensity of probe D, and
$R_{DC}$ is the ratio between (a) the portion of intensity in a channel for probe D that is contributed by probe C, and (b) the actual probe intensity of probe C.

In a further embodiment, the equation is solved to determine spectral crosstalk matrix $K^{-1}$ and an estimate of the actual intensity or probes (A, B, C and D) using equation $$\begin{bmatrix} A \\ B \\ C \\ D \\ \cdots \end{bmatrix} = K^{-1} \begin{bmatrix} M_A \\ M_B \\ M_C \\ M_D \\ \cdots \end{bmatrix}$$

In a particular embodiment, the order of the data correction methods described herein is 1) field flattening, 2) color crosstalk correction and 3) dephasing correction. When field flattening precedes color crosstalk correction, then the same crosstalk parameters may be used for the entire image. When color crosstalk correction precedes dephasing correction, the dephasing correction will be more accurate as the intensity data from the different channels will more precisely represent actual probe intensities.

As noted above, the present invention contemplates reducing some of these phenomenon that make accurate base calling difficult. One problem addressed in one embodiment of the present invention is the problem created by using a cleaving agent. In one embodiment, a cleaving agent scavenger is employed to address (e.g. neutralize or otherwise render inactive) leftover cleaving agent which might prematurely cleave in the next cycle. Thus, the present invention contemplates in one embodiment a method of incorporating labeled nucleotides into nucleic acid, comprising: a) providing a plurality of nucleic acid template molecules, a polymerase, a cleaving agent, a cleaving agent scavenger, and a plurality of nucleotide analogues wherein each nucleotide analogue is labeled with a unique label and contains a removable chemical moiety capping the 3'-OH group; b) incorporating a first nucleotide analogue with said polymerase; c) detecting the label of the incorporated nucleotide analogue; d) removing the chemical moiety of the incorporated nucleotide analogue capping the 3'-OH group with said cleaving agent; and f) incorporating a second nucleotide analogue in the presence of said cleaving agent scavenger. With regard to step f), the scavenger can, by way of example, be put into the solution used to incorporate nucleotides in the next round (indeed, in one embodiment, the present invention contemplates compositions comprising 1) the scavenger(s) and one or more labeled or unlabeled nucleotides, 2) the scavenger(s) and polymerase, 3) the scavenger(s) and one or more nucleotides with or without 3'-OH capping groups). Alternatively, the scavenger can be in a separate solution that is used prior to the incorporation solution (with residual scavenger present at the time of incorporation). In one embodiment, the present invention contemplates wash steps after step b) and after step d). In one embodiment, the nucleotide analogues comprise acyclic sugars.

It is not intended that the present invention be limited by the nature of the chemistry of the removable chemical moiety. A variety of chemistries are contemplated (and described below in more detail). In one embodiment, said removable chemical moiety comprises a disulfide bond. In another embodiment, said removable chemical moiety comprises an azido group (e.g. an azidomethyl ether). It is preferred that said moiety capping the 3'-OH is not a fluorescent moiety.

It is also not intended that the present invention be limited by the nature of the cleaving agent. In the case of azido-group-containing nucleotides (e.g. 3'-O-azidomethyl ether nucleotides), several types of cleaving agents can be used. In principle, any reducing agent capable of converting the azido group into an amine is suitable for this purpose. The amine undergoes spontaneous conversion to hydroxyl group to enable next nucleotide incorporation. Examples of cleaving agents include: a) Catalytic hydrogenation over $PtO2$ or Pd/C; b) Reduction with $LiAlH4$, $HCO_2NH_4$~10% Pd/C, $NaBS_4/CoCl_2.6H_2O$, $Zn/NH_4Cl$, $Fe/NH_4Cl$; and c) Reduction with phosphines; e.g. tri-n-butyl-phosphine, triphenyl phosphine and its sulfonated versions (i.e., tris(3-sulfophenyl)-phosphine, TPPTS), and tri(carboxyethyl)phosphine (TCEP) and its salts. Most preferred cleaving reagents are soluble in water and are highly selective reducing agents. Water soluble phosphines are particularly preferred. In one embodiment, said cleaving agent is a phosphine Tris(2-carboxy-ethyl)phosphine.

It is also not intended that the present invention be limited by the nature of the cleaving agent scavenger. A variety of chemistries are contemplated (and are described below and in the figures) and more than one type of chemistry can be used together (e.g. two different scavengers). In a preferred embodiment, said cleaving agent scavenger does not contain a nucleic acid base. In one embodiment, said cleaving agent scavenger comprises a disulfide bond (e.g. cystamine or one of the other disulfide-containing compounds shown in FIG. 37). Cystamine is also known as 2,2'-Dithiobisethanamine, 2-Aminoethyl disulfide, or Decarboxycystine, and is available commercially from Sigma-Aldrich. Alternatively, the present invention contemplates in one embodiment that said cleaving agent scavenger comprises an azido group (e.g. an azidomethyl group, an azidoethyl ether group, etc.). In a preferred embodiment, said scavenger is 11-Azido-3,6,9-trioxaundecan-1-amine (which is also known as: 1-Amino-11-azido-3,6,9-trioxaundecane, 2-{2-[2-(2-Azidoethoxy)ethoxy]ethoxy}ethylamine, or O-(2-Aminoethyl)-O'-(2-azidoethyl)-diethylene glycol, and which is available commercially from Sigma-Aldrich).

It is not intended that the present invention be limited by where the first and second nucleotides are incorporated. In one embodiment, they are incorporate incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self priming hairpin, such that said first nucleotide analogue is incorporated into said template molecules at step b)].

In some embodiments, two cites of cleavage are contemplated, i.e. cleavage occurs at two locations on the nucleotide analogue. Thus, in one embodiment, the present invention contemplates a method of incorporating labeled nucleotides into nucleic acid, comprising: a) providing a plurality of nucleic acid template molecules, a polymerase, a cleaving agent, a cleaving agent scavenger, and a plurality of nucleotide analogues selected from the group consisting of cytosine, thymine, deaza-adenine and deaza-guanine, wherein each nucleotide analogue comprises a unique label attached through a cleavable linker to a 5-position of cytosine or thymine or to a 7-position of deaza-adenine or deaza-guanine, and wherein each nucleotide analogue contains a removable chemical moiety capping the 3'-OH group; b) incorporating a first nucleotide analogue with said polymerase; c) detecting the label of the incorporated nucleotide analogue; d) removing the chemical moiety of the incorporated nucleotide analogue capping the 3'-OH group and cleaving the cleavable linker with said cleaving agent; and e) incorporating a second nucleotide analogue in the presence of said cleaving agent scavenger.

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecule s [e.g. said nucleic acid template molecules comprise a self-priming hairpin, such that said first nucleotide analogue is incorporated into said template molecules at step b)].

Again, it is not intended that the present invention be limited by the nature of the chemistry of the removable chemical moiety. A variety of chemistries are contemplated (and described below in more detail) and the chemistry need not be the same chemistry as used in the cleavable linker attaching the label. In one embodiment, said removable chemical moiety comprises a disulfide bond. In another embodiment, said removable chemical moiety comprises an azido group (e.g. an azidomethyl ether). It is preferred that said moiety capping the 3'-OH is not a fluorescent moiety.

Similarly, a variety of chemistries are contemplated for the cleavable linker attaching the label to the nucleotide analogue (and these are described in more detail below). In one embodiment, said cleavable linker comprises a disulfide bond. As noted above, the present invention contemplates embodiments wherein the chemistries for the cleavage at the two sites is the same, as well as embodiments where it is different. For example, in one embodiment, said removable chemical moiety comprises an azido group (e.g. an azidomethyl ether) and said cleavable linker (which attaches the label) comprises a disulfide bond. In another embodiment, the cleavable linker comprises an azido group and the removable chemical moiety comprises a disulfide bond. In another embodiment, the 3'-aminoxy (3'-ONH2) is used as a reversibly terminating moiety and in yet another one comprise hydrocarbyldithiomethyl groups as described in the U.S. Pat. No. 7,279,563, hereby incorporated by reference. Yet another embodiment comprises 3'-O—CH2-SSSS—R (3'-O-(Alkyl-tetrasulfanyl-methyloxy) group). In general, a variety of cleavable linkers can be used for this purpose and are described in the literature. The linkers may be cleavable chemically, cleavable by light or by other physical means. WO99/57321 describes the use of nucleotides comprising fluorophores linked to the nucleotide by chemically or photochemically cleavable linker moieties (Olejnik et al., Proc. Natl. Acad. Sci., 92:7590-7594 (1995). For example, the linkers could contain disulfide bonds (Mitra, R. D., Shendure, J., Olejnik, J., Edyta-Krzymanska-Olejnik, and Church, G. M. (2003) Anal Biochem. 320(1):55-65) cleavable under reducing conditions (or contain cis-diol linkages cleavable by periodate (WO/53812). The linkers could also be cleavable by enzymes (WO 01/92284). Other types of acid or base, oxidative or reducing agent cleavable linkers are also contemplated as will be recognized by the skilled in the art. Examples of such linkers are described in the literature (Greene et al., Protective Groups In Organic Synthesis, Second Edition, John Wiley & Sons, (1991).

Again, it is also not intended that the present invention be limited by the nature of the cleaving agent. However, in one embodiment, said cleaving agent is a phosphine (e.g. Tris (2-carboxy-ethyl)phosphine). Again, a variety of cleaving agent scavengers is contemplated (discussed above). In a preferred embodiment, said cleaving agent scavenger does not contain a nucleic acid base.

In one embodiment, the present invention contemplates incorporating nucleotides having only one location for cleavage (e.g. the cleavable linker attaching the label). Thus, in one embodiment, the present invention contemplates a method of incorporating labeled nucleotides into nucleic acid, comprising: a) providing a plurality of nucleic acid template molecules, a polymerase, a cleaving agent, a cleaving agent scavenger, and a plurality of nucleotide analogues wherein each nucleotide analogue is labeled with a unique label, said label attached by a cleavable linker, b) incorporating a first nucleotide analogue with said polymerase; c) detecting the label of the incorporated nucleotide analogue; d) removing the label of the incorporated nucleotide analogue by cleaving the cleavable linker with said cleaving agent; and e) incorporating a second nucleotide analogue in the presence of said cleaving agent scavenger.

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, a variety of chemistries is contemplated for the cleavable linker (e.g. wherein said cleavable linker comprises a disulfide bond, azido group, or some other chemical group). However, in a preferred embodiment, the chemistry of the cleavable linker dictates the chemistry of the scavenger (e.g. wherein wherein said cleaving agent scavenger comprises a disulfide bond, it is preferred that the scavenger also comprise a disulfide bond, such as where said scavenger is cystamine or other similar compound).

In one embodiment, the present invention contemplates carrying out nucleotide incorporation in a device, including automated devices. Solutions comprising various combinations of biomolecules are contemplated; such solutions can be, in one embodiment, conveniently stored in reservoirs which are in fluid communication with a reaction chamber (e.g. flow cells, microchannels, etc.). A series of steps can be carried out to introduce these solutions (and the reagents they contain) into the reaction chamber (e.g. by valving) to carry out the reaction(s). Thus, in one embodiment, the present invention contemplates a method of incorporating labeled nucleotides into nucleic acid, comprising: a) providing i) a reaction chamber (e.g. a flow cell) comprising plurality of nucleic acid template molecules bound to a solid support, ii) a first solution comprising polymerase and a plurality of nucleotide analogues wherein each nucleotide analogue is labeled with a unique label and contains a removable chemical moiety capping the 3'-OH group, iii) a second solution comprising a cleaving agent, and iv) a cleaving agent scavenger; b) introducing said first solution into said reaction chamber under conditions wherein a first nucleotide analogue is incorporated by said polymerase; c) detecting the label of the incorporated nucleotide analogue; d) introducing said second solution into said reaction change under conditions such that the chemical moiety of the incorporated nucleotide analogue capping the 3'-OH group is removed by said cleaving agent; and e) introducing said cleaving agent scavenger into said reaction chamber.

It is not intended that the present invention be limited by the way in which the cleaving agent scavenger is stored or introduced into the reaction chamber. In one embodiment, said cleaving agent scavenger is in a third solution and said scavenger is introduced into said reaction chamber in step e) by introducing said third solution. In another embodiment, the above-indicated method further comprises the step f) re-introducing said first solution into said reaction chamber under conditions such that a second nucleotide analogue is incorporated by said polymerase (and this first solution may contain the scavenger if desired). In another embodiment, separate steps [i.e. step e) and step f)] are not required; rather, a single step is contemplated wherein said cleaving agent scavenger is in said first solution and said introducing of step e) comprises introducing said first solution comprising said scavenger (in this embodiment, a second nucleotide analogue is incorporated in the presence of said cleaving agent scavenger). In some embodiments, additional wash steps are employed to remove reagents between steps [e.g. wash steps after step b), and step d)], although the usefulness of the scavenger has been discovered empirically, since residual cleaving agent is difficult to remove with a practical number of washes (discussed more below).

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, it is not intended that the present invention be limited by the nature of the chemical moiety capping the 3'-OH on the nucleotide analogue. In one embodiment, said removable chemical moiety comprises a disulfide bond. In one embodiment, said removable chemical moiety comprises an azido group (e.g. an azidomethyl ether). It is preferred that said moiety capping the 3'-OH is not a fluorescent moiety. Where the protective group residing on the 3'-OH groups of the nucleotides is a 3'-O-azidomethyl group, this group can be removed using mild reducing agents such as tri(carboethoxy)phosphine (TCEP). However, the present invention contemplates other protective groups. In another embodiment, the protective groups contemplated by the present invention are 3'-O—NH2 groups. These groups can be removed using in situ generated nitrous acid (such as from sodium nitrite). Similarly to the 3'-O-aminoxy group, the 3'-O-methylaminoxy (3'-O—CH2-NH2) group can be removed under mild oxidative conditions, for example using in situ generated nitrous acid (such as from sodium nitrite). 3'-O-allyl protective groups can be removed using variety of reducing agents, including transition metal complexes (Pd, Rh). In yet another embodiment, the present invention contemplates that the 3'-capping group is the 3'-O—CH2-SSSS—R (3'-O-(Alkyl-tetrasulfanyl-methyloxy) group). These protective groups can be removed using variety of reducing agents and cleaved into the corresponding 3'-OH derivative, for example by using tris(carboxyethyl)phosphine (TCEP). In yet another embodiment, the 3'-capping group is enzymatically cleavable.

Again, it is also not intended that the present invention be limited by the nature of the cleaving agent. However, in one embodiment, said cleaving agent is a phosphine (e.g. Tris(2-carboxy-ethyl)phosphine). Again, a variety of cleaving agent scavengers is contemplated (discussed above). In a preferred embodiment, said cleaving agent scavenger does not contain a nucleic acid base.

In some embodiments, the reaction in the device is directed at cleavage at two locations on the nucleotide analogue(s). Thus, in one embodiment, the present invention contemplates a method of incorporating labeled nucleotides into nucleic acid, comprising: a) providing i) a reaction chamber comprising plurality of nucleic acid template molecules bound to a solid support, ii) a first solution comprising polymerase and a plurality of nucleotide analogues selected from the group consisting of cytosine, thymine, deaza-adenine and deaza-guanine, wherein each nucleotide analogue comprises a unique label attached through a cleavable linker to a 5-position of cytosine or thymine or to a 7-position of deaza-adenine or deaza-guanine, and wherein each nucleotide analogue is labeled with a unique label and contains a removable chemical moiety capping the 3'-OH group, iii) a second solution comprising a cleaving agent (or a second and third solution incorporating different cleaving solutions), and iv) a cleaving agent scavenger, b) introducing said first solution into said reaction chamber under conditions wherein a first nucleotide analogue is incorporated by said polymerase; c) detecting the label of the incorporated nucleotide analogue; d) introducing said second solution (and then possibly the third solution) into said reaction change under conditions such that the chemical moiety of the incorporated nucleotide analogue capping the 3'-OH group is removed and said cleavable linker is cleaved by said cleaving agent; and e) introducing said cleaving agent scavenger into said reaction chamber (e.g. flow cell or the like).

Again, it is not intended that the present invention be limited by the way in which the cleaving agent scavenger is stored or introduced into the reaction chamber. In one embodiment, said cleaving agent scavenger is in a third solution and said scavenger is introduced into said reaction chamber in step e) by introducing said third solution. In another embodiment, the above-indicated method further comprises the step f) re-introducing said first solution into said reaction chamber under conditions such that a second nucleotide analogue is incorporated by said polymerase (and this first solution may contain the scavenger if desired). In another embodiment, separate steps [i.e. step e) and step f)] are not required; rather, a single step is contemplated wherein said cleaving agent scavenger is in said first solution and said introducing of step e) comprises introducing said first solution comprising said scavenger (in this embodiment, a second nucleotide analogue is incorporated in the presence of said cleaving agent scavenger). In some embodiments, additional wash steps are employed to remove reagents between steps [e.g. wash steps after step b), and step d)].

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, it is not intended that the present invention be limited by the nature of the chemical moiety capping the 3'-OH on the nucleotide analogue. In one embodiment, said removable chemical moiety comprises a disulfide bond. In one embodiment, said removable chemical moiety comprises an azido group (e.g. an azidomethyl ether). It is preferred that said moiety capping the 3'-OH is not a fluorescent moiety. Where the protective group residing on the 3'-OH groups of the nucleotides is a 3'-O-azidomethyl group, this group can be removed using mild reducing agents such as tri(carboethoxy)phosphine (TCEP). However, the present invention contemplates other protective groups. In another embodiment, the protective groups contemplated by the present invention are 3'-O—NH2 groups. These groups can be removed using in situ generated nitrous acid (such as from sodium nitrite). Similarly to the 3'-O-aminoxy group, the 3'-O-methylaminoxy (3'-O—CH2-NH2) group can be removed under mild oxidative conditions, for example using in situ generated nitrous acid (such as from sodium nitrite). 3'-O-allyl protective groups can be removed using variety of reducing agents, including transition metal complexes (Pd, Rh). In yet another embodiment, the present invention contemplates that the 3'-capping group is the 3'-O—CH2-SSSS—R (3'-O-(Alkyl-tetrasulfanyl-methyloxy) group). These protective groups can be removed using variety of reducing agents and cleaved into the corresponding 3'-OH derivative, for example by using tris (carboxyethyl)phosphine (TCEP). In yet another embodiment, the 3'-capping group is enzymatically cleavable.

Again, the chemistry of the cleavable linker (which attaches the label) may be the same or different vis-à-vis the removable chemical capping moiety. Thus, in one embodiment, the linker and the capping group comprise a disulfide bond. Yet, in another embodiment, said removable chemical moiety comprises a azido group and said cleavable linker comprises a disulfide bond (or the reverse, i.e. the capping group comprises a disulfide bond and the cleavable linker comprises an azido group).

Again, it is also not intended that the present invention be limited by the nature of the cleaving agent. However, in one embodiment, said cleaving agent is a phosphine (e.g. Tris (2-carboxy-ethyl)phosphine). Again, a variety of cleaving agent scavengers is contemplated (discussed above). In a preferred embodiment, said cleaving agent scavenger does not contain a nucleic acid base.

In some embodiments, the present invention contemplates a reaction in the device wherein only a single site of cleavage on the nucleotide analogue is targeted (e.g. a cleavable linker attaching the label). Thus, in one embodiment, the present invention contemplates a method of incorporating labeled nucleotides into nucleic acid, comprising: a) providing i) a reaction chamber comprising plurality of nucleic acid template molecules bound to a solid support, ii) a first solution comprising polymerase and a plurality of nucleotide analogues wherein each nucleotide analogue is labeled with a unique label, said label attached via a cleavable linker, iii) a second solution comprising a cleaving agent, and iv) a cleaving agent scavenger; b) introducing said first solution into said reaction chamber under conditions wherein a first nucleotide analogue is incorporated by said polymerase; c) detecting the label of the incorporated nucleotide analogue; d) introducing said second solution into said reaction change under conditions such that the label of the incorporated nucleotide analogue is removed by cleaving said cleavable linker with said cleaving agent; and e) introducing said cleaving agent scavenger into said reaction chamber.

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

A variety of chemistries for the cleavable linker is contemplated. In one embodiment, said cleavable linker comprises a disulfide bond.

In one embodiment, the chemistry used in the cleavable linker controls the chemistry of the scavenger. For example, in one embodiment, where the linker comprises a disulfide bond, said cleaving agent scavenger comprises a disulfide bond. In one embodiment, where the linker comprises an azido group, said cleaving agent scavenger comprises an azido group. In a preferred embodiment, said cleaving agent scavenger does not contain a nucleic acid base.

The present invention contemplates methods, kits, devices, systems and compositions. In one embodiment, the present invention contemplates a composition comprising cleaving agent scavenger and one or more nucleotide analogues (unlabeled or labeled as herein described). In one embodiment, said composition further comprises polymerase. In one embodiment, the present invention contemplates a composition comprising cleaving agent scavenger and polymerase, and (optionally) one or more nucleotide analogues (unlabeled or labeled as herein described).

In one embodiment, the present invention contemplates a reaction chamber (e.g. a flow cell, flow channels, etc.) comprising a solution, said solution comprising cleaving agent scavenger and one or more nucleotide analogues (labeled or unlabeled as herein described). In one embodiment, said solution further comprises polymerase. In one embodiment, said solution comprises cleaving agent scavenger and polymerase, and (optionally) one or more nucleotide analogues (unlabeled or labeled as herein described).

In one embodiment, the present invention contemplates kits, said kits comprising a solution comprising cleaving agent scavenger and one or more nucleotide analogues (labeled or unlabeled as herein described) and (optionally) polymerase. Alternatively, said kits comprise a solution comprising cleaving agent scavenger and polymerase, and (optionally) one or more nucleotide analogues (unlabeled or labeled as herein described). Preferably, such kits also provide instructions for carrying out incorporation reactions, as well as wash buffers and the like.

In one embodiment, the present invention contemplates a system comprising reservoirs in fluid communication with a reaction chamber, at least one of said reservoirs comprising a solution comprising cleaving agent scavenger and one or more nucleotide analogues (labeled or unlabeled as herein described) and (optionally) polymerase. Alternatively, at least one of said reservoirs comprises a solution comprising cleaving agent scavenger and polymerase, and (optionally) one or more nucleotide analogues (unlabeled or labeled as herein described). Preferably, such solutions can be introduced by automated means (e.g. valving).

As described herein, the present invention contemplates embodiments wherein nucleotides used in extension reactions contain linkers, spacers and chemical groups. The presence of these spacers and groups may affect the ability of the sequencing polymerases to incorporate the subsequent nucleotide. The present invention contemplates a number of ways to minimize or eliminate this undesirable effect, including but not limited to: a) reducing the amount of labeled nucleotides incorporated in the template; b) reducing the size of the spacer arm or eliminate it completely by carefully designing nucleotide analogs; and c) change the reactivity of the spacer arm groups or their charge by performing a chemical "capping" step, where specific reagent is added to react only with groups on the spacer arm.

Reducing the amount of labeled nucleotides that are incorporated can be accomplished by reducing the concentration of labeled nucleotides in the extension solution, and/or by mixing labeled nucleotides (reversible terminators) with non-labeled reversibly terminating nucleotides (e.g. where the non-labeled nucleotides are employed in ratios between 1:1 and 1000:1 relative to the labeled nucleotides, but more preferably in ratios between 10:1 and 100:1). In contrast to labeled nucleotides, non-labeled reversible terminator nucleotides after cleavage convert to native nucleotide (and therefore do not present problems for polymerases). Thus, in one embodiment, the present invention contemplates a composition comprising i) a first plurality of nucleotide analogues wherein each nucleotide analogue is labeled with a unique label and contains a removable chemical moiety capping the 3'-OH group; and ii) a second plurality of nucleotide analogues wherein each nucleotide analogue is unlabeled and contains a removable chemical moiety capping the 3'-OH group. In one embodiment, the composition further comprises polymerase. In a preferred embodiment, said nucleotide analogues are in solution. In one embodiment, the second plurality of nucleotide analogues is present in said solution at a high concentration than said first plurality of nucleotide analogues. In one embodiment, said second plurality of nucleotide analogues is present at a concentration between 1 uM and 100 uM. In one embodiment, said first plurality of nucleotide analogues is present at a concentration between 1 nM and 1 uM.

It is not intended that the composition be limited by the number or nature of nucleotide analogues in said composition. However, in a preferred embodiment, said first plurality of nucleotide analogues comprises four different nucleotide analogues (for example, in one embodiment, the four nucleotodes are either (i) aA, aC, aG, and aT, or (ii) aA, aC, a, aG and aU). In a preferred embodiment, said second plurality of (unlabeled) nucleotide analogues comprises four different nucleotide analogues (for example, either (i) aA, aC, aG, and aT, or (ii) aA, aC, aG, and aU).

It is also not intended that the composition be limited by the nature of the label. However, in one embodiment, each of said four different nucleotide analogues comprises a unique (preferably cleavable) label, said label selected from the group consisting of BODIPY, Rhodamine, Carboxyrhodamine, and Cyanine (see FIG. 36, which shows these labels in the context of a cleavable disulfide bond).

It is also not intended that the composition be limited by the chemistry of the removable chemical moiety, which may, by way of example, comprise a disulfide bond or an azido group (e.g. an azidomethyl ether). The chemistry may be the same or different vis-à-vis the cleavable linker. For example, said removable chemical moiety comprises an azido group and said cleavable linker comprises a disulfide bond.

In one embodiment, the present invention contemplates a composition comprising i) a first plurality of nucleotide analogues comprising four different (for example, in one embodiment, the four nucleotodes are either (i) aA, aC, aG, and aT, or (ii) aA, aC, aG, and aU) nucleotide analogues, wherein each different nucleotide analogue is labeled with a unique (preferably cleavable) label and contains a removable chemical moiety capping the 3'-OH group; and ii) a second plurality of nucleotide analogues comprising four different (for example, in one embodiment, the four nucleotodes are either (i) aA, aC, aG, and aT, or (ii) aA, aC, aG, and aU) nucleotide analogues, wherein each nucleotide analogue is unlabeled and contains a removable chemical moiety capping the 3'-OH group. Again, this composition may further comprise a polymerase and it is preferred that the reagents (e.g. said nucleotide analogues and optionally said polymerase) are in solution.

It is not intended that the composition be limited by the particular linkages. However, in a preferred embodiment, the nucleotide analogues selected from the group consisting of cytosine, thymine, deaza-adenine and deaza-quanine and each comprising a unique (preferably) label attached through a cleavable linker to a 5-position of cytosine or thymine or to a 7-position of deaza-adenine or deaza-guanine.

In one embodiment, the second plurality of nucleotide analogues is present in said solution at a high concentration than said first plurality of nucleotide analogues. In one embodiment, said second plurality of nucleotide analogues is present at a concentration between 1 uM and 100 uM. In one embodiment, said first plurality of nucleotide analogues is present at a concentration between 1 nM and 1 uM.

In one embodiment, the present invention contemplates kits, said kits comprising a mixture of labeled and unlabeled nucleotide analogues (preferably both containing groups capping the 3'-OH—such as an azido group) and (optionally) polymerase. Where the protective group residing on the 3'-OH groups of the nucleotides is a 3'-O-azidomethyl group, this group can be removed using mild reducing agents such as tri(carboethoxy)phosphine (TCEP). However, the present invention contemplates other protective groups. In another embodiment, the protective groups contemplated by the present invention are 3'-O—NH2 groups. These groups can be removed using in situ generated nitrous acid (such as from sodium nitrite). Similarly to the 3'-O-aminoxy group, the 3'-O-methylaminoxy (3'-O—CH2-NH2) group can be removed under mild oxidative conditions, for example using in situ generated nitrous acid (such as from sodium nitrite). 3'-O-allyl protective groups can be removed using variety of reducing agents, including transition metal complexes (Pd, Rh). In yet another embodiment, the present invention contemplates that the 3'-capping group is the 3'-O—CH2-SSSS—R (3'-O-(Alkyl-tetrasulfanyl-methyloxy) group). These protective groups can be removed using variety of reducing agents and cleaved into the corresponding 3'-OH derivative, for example by using tris(carboxyethyl)phosphine (TCEP). In yet another embodiment, the 3'-capping group is enzymatically cleavable.

In one embodiment, the present invention contemplates a mixture of 4 labeled and 4 unlabeled nucleotide analogues as herein described) and (optionally) polymerase. The mixture can be provided dry or in solution in the kit (along with appropriate instructions for extension reactions). Preferably, the unlabeled nucleotide analogues are present in the mixture in a greater amount than the labeled nucleotide analogues.

The above-indicated solutions provide advantages in incorporation reactions. Thus, in one embodiment, the present invention contemplates a method of incorporating labeled nucleotides into nucleic acid, comprising: a) providing i) a reaction chamber comprising plurality of nucleic acid template molecules bound to a solid support, ii) a solution comprising a first plurality of nucleotide analogues wherein each nucleotide analogue is labeled with a unique (preferably cleavable) label and contains a removable chemical moiety capping the 3'-OH group, and a second plurality of nucleotide analogues wherein each nucleotide analogue is unlabeled and contains a removable chemical moiety capping the 3'-OH group; and iii) polymerase; b) introducing said solution into said reaction chamber under conditions wherein a nucleotide analogue of said first plurality of nucleotide analogues is incorporated by said polymerase (e.g. the polymerase can be added separately or together with other reagents; regardless, it is preferred that said polymerase is in said solution prior to step b); and c) detecting the label of the incorporated nucleotide analogue. The method may comprise additional steps (cleavage of the capping group, washing, etc.) and may repeat steps (e.g. in order to incorporate subsequent, e.g. a second, third, third, fourth, etc., nucleotide analogues).

It is not intended that the present invention be limited by where the first (or subsequent) nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

In one embodiment, the second plurality of nucleotide analogues is present in said solution at a high concentration than said first plurality of nucleotide analogues. In one embodiment, said second plurality of nucleotide analogues is present at a concentration between 1 uM and 100 uM.

In one embodiment, said first plurality of nucleotide analogues is present at a concentration between 1 nM and 1 uM.

In a preferred embodiment, said first plurality of nucleotide analogues comprises four different nucleotide analogues and said second plurality of nucleotide analogues comprises four different nucleotide analogues. In one embodiment, each of said four different nucleotide analogues of said first plurality of labeled analogues comprises a unique label, said label selected from the group consisting of Alexa, BODIPY, Rhodamine, Carboxyrhodamie, and Cyanine. It is not intended that the present invention be limited by the nature of the label or fluorophore used and many other combinations are contemplated.

Again, it is not intended that the present invention be limited by the nature of the chemical moiety capping the 3'-OH on the nucleotide analogue or the (preferably cleavable) linker attaching the label. In one embodiment, said removable chemical moiety comprises a disulfide bond. In one embodiment, said removable chemical moiety comprises an azido group (e.g. an azidomethyl ether). In one embodiment, said removable chemical moiety comprises an azido group and said cleavable linker comprises a disulfide bond. In another embodiment, these chemistries are reversed. Again, it is preferred that said moiety capping the 3'-OH is not a fluorescent moiety. Where the protective group residing on the 3'-OH groups of the nucleotides is a 3'-O-azidomethyl group, this group can be removed using mild reducing agents such as tri(carboethoxy)phosphine (TCEP). However, the present invention contemplates other protective groups. In another embodiment, the protective groups contemplated by the present invention are 3'-O—NH2 groups. These groups can be removed using in situ generated nitrous acid (such as from sodium nitrite). Similarly to the 3'-O-aminoxy group, the 3'-O-methylaminoxy (3'-O—CH2-NH2) group can be removed under mild oxidative conditions, for example using in situ generated nitrous acid (such as from sodium nitrite). 3'-O-allyl protective groups can be removed using variety of reducing agents, including transition metal complexes (Pd, Rh). In yet another embodiment, the present invention contemplates that the 3'-capping group is the 3'-O—CH2-SSSS—R (3'-O-(Alkyl-tetrasulfanyl-methyloxy) group). These protective groups can be removed using variety of reducing agents and cleaved into the corresponding 3'-OH derivative, for example by using tris(carboxyethyl)phosphine (TCEP). In yet another embodiment, the 3'-capping group is enzymatically cleavable.

Increasing the number of bases that can be sequenced, i.e. increasing read lengths is desirable. However, as one proceeds to larger and larger read lengths, one often encounters a reduction in signal. In one embodiment, the present invention contemplates reducing extension times (e.g. extension times of 5-15 minutes are reduced to 1-2 minutes, or less) in order to maintain signal strength at longer read lengths (greater than 20 bases, more preferably greater than 30 bases, etc.). This reduction in extension times can be combined with other methods herein described (e.g. the use of mixtures of labeled and unlabeled nucleotides) to improve performance and increase the retention in signal. Signal retention is defined as the ratio of signals at the end of the run to the signals at the beginning of the run.

Another approach to increasing read lengths involves the use of one or more oxygen scavengers. In one embodiment, the oxygen scavenger is utilized in an imaging buffer, i.e. a buffer used before, during or after, and more preferably just prior (with no additional steps in between), during, or just after imaging (with no additional steps in between). While not intended to limit the invention to any particular mechanism, it is believed that the imaging process generates singlet state oxygen species, e.g. from the exposure of the dyes or labels to the light, and such species react rapidly with available exposed reactive groups in fluorescent dyes (rendering them non-fluorescent) and with biomolecules including nucleic acids (causing damage). See Sies, H., and C. F. Menck, "Singlet oxygen induced DNA damage," *Mutat. Res.* 275:367-375 (1992). Using an oxygen scavenger during the imaging process is believed to reduce this damage. Dyes species in their triplet excited state are non-fluorescent, and therefore non-desirable. Furthermore, the triplet excited state can convert dye molecules into permanent non-fluorescent state. Therefore, triplet state scavengers can also be introduced into the sequencing system imaging buffer. Oxygen scavengers include compounds that are oxidizable and react with dissolved oxygen. Preferred oxygen scavengers and triplet state quenchers include, but are not limited to: ascorbic acid and sodium ascorbate, beta mercaptoethanol, n-propyl gallate, p-phenylenediamine, 1,4-diazabicyclo[2.2.2]octane (DABCO), 6-hydroxy-2,5,7,8-tetramethyl-chroman-2-carboxylic acid (TROLOX), polyphenol antioxidants, polyvinyl alcohol, butylated hydroxy anisole (BHA), butylated hydroxy toluene (BHT), mercaptoethylamine (MEA), cyclo-octatetraene (COT). See Ono et. Al., J Histochem, Cytochem., Vol. 49, 305-312 (2001); see also Longin, A., C. Souchier, M. Ffrench, and P. A. Bryon, "Comparison of anti-fading agents used in fluorescence microscopy: image analysis and laser confocal microscopy study," *J. Histochem. Cytochem.* 41:1833-1840 (1993). Another approach to reducing oxygen availability is to use an enzyme-based, oxygen scavenging system. Preferred enzymatic oxygen scavenging systems include, but are not limited to, the glucose oxidase and catalase system. See M.

Landry, P. McCall, Z. Qi, Y. Chemla, Biophys. J., Vol. 97, Issue 8, Pages 2128-2136. Alternatively, a protocatechuic acid/protocatechuate-3,4-dioxygenase can be used. See Aitken et. Al., Biophys J. March 1; 94(5): 1826-1835 (2008). Other suitable enzymatic oxygen scavenging systems are also contemplated alone or in combination with quenchers. Finally, a combination of triplet state quenchers and oxygen scavengers can be used (Rasnik et. Al., Nat Methods. 2006 November; 3(11):891-3). In yet another embodiment, one uses an environment which is oxygen depleted by using an imaging buffer (which has been deoxygenated by purging with helium, argon or nitrogen or through exposure to vacuum) under a neutral gas blanket.

Yet another approach to increasing read lengths comprises balancing the amount of nucleotide analogue with the incorporation rate. For example, where a particular nucleotide analogue is incorporated quickly by the polymerase, the concentration of that particular nucleotide in the mixture of nucleotides can be reduced. Similarly, where a particular nucleotide analogue is incorporated slowly, the concentration of that particular nucleotide in the mixture can be increased. Importantly, under balanced nucleotide concentration conditions, the misincorporation rate is reduced. After a misincorporation event, the nucleic acid strand is no longer a substrate for the DNA polymerase due to the mismatch and this contributes to the decline of signal. The balancing can be done by first testing solution kinetics of each analog separately. This is best done by pre-forming a nucleic acid duplex in solution wherein the primer is labeled with a fluorescent dye on its 5'-end. Alter incorporation the reaction mixture is then subject to separation using denaturing capillary electrophoresis with laser-induced fluorescence. Then, kinetic parameters of the reaction are calculated and incorporation rates are compared for the same polymerase and same analog family. The rates are then normalized to the rate of one of the analogs, the concentrations adjusted based on the observed rates and then the kinetic studies (time course) are repeated and the concentrations refined and matched such that the extension reactions for all analogs are complete (100% incorporation) within the same time.

Yet another approach to increasing read lengths comprises purifying the nucleotide analogues to a higher degree of purity (e.g. than typically obtained from a commercial supplier) to reduce the amount of non-terminating nucleotides present. The presence of non-terminating nucleotides leads to fast signal dephasing and decline, and therefore may limit achievable read lengths in SBS. In one embodiment, the nucleotides are purified by orthogonal dual HPLC purification according to the following protocol. First, the nucleotides are purified using ion-exchange separation (for example Phenomenex Optisil SAX, anion exchange column) using a salt gradient. In one example separation conditions are as follows: a gradient of 0-50% of B in A over 45 minutes, where A=10 mM TEAB, 10% acetonitrile, B=0.85M TEAB, 20% acetonitrile. After this purification, a second purification is performed using reverse phase column and using a gradient of 0-50% acetonitrile in 50 mM TEAB, pH=8.0 on a reverse phase (e.g., NovaPak C18, reverse phase) column. A variety of other ion exchange columns and reverse phase columns and separation conditions are suitable to perform these purifications. In addition, other separation modes could also be used, such as hydrophobic interaction or size exclusion and combination modes. Finally, an enzymatic scavenging system can be used to eliminate any non-terminating nucleotide present after the chromatographic purification. For example, a reversibly terminating nucleotide preparation can be pretreated with an extendable DNA duplex and a polymerase that will efficiently utilize non-terminating (native) nucleotides (such as Klenow fragment, exo-) but is not capable of incorporating reversibly terminating nucleotides. After the treatment the nucleotide preparation would be essentially devoid of any native nucleotides. The scavenging duplex could be designed in such a way that it would not interfere with the sequencing reaction. An example of useful embodiment like this comprises mesophilic scavenging polymerase, low melting temperature scavenging duplex and thermophilic sequencing polymerase. If sequencing is performed at 55 deg C. for example, then the scavenging duplex with low melting point and mesophilic polymerase would be inactivated. The polymerase can also be immobilized on a column, such that the removal of native nucleotides is performed as affinity chromatography and the nucleotide preps are devoid of the scavenger polymerase.

Yet another approach to increasing read length (e.g. by reducing misincorporation) is by optimizing the reaction conditions. As noted above, after a misincorporation event, the nucleic acid strand is no longer a substrate for the DNA polymerase due to the mismatch and this contributes to the decline of signal and reduced read length. The optimization of reaction conditions may include, but are not limited to: nucleotide and polymerase concentrations, reaction temperature, pH, monovalent and divalent cation concentrations, ionic strength, cofactor concentrations, detergents and additives. This approach may also use various polymerase mutants and fusion constructs to improve fidelity.

The above approaches can be used separately. However, larger read lengths are achieved when such approaches are combined. Thus, in one embodiment, the present invention contemplates a) HPLC and/or enzymatically purifying the nucleotide analogues, b) balancing the concentration of the nucleotide analogues with their incorporation rate, c) utilizing an oxygen scavenger (chemical or enzymatic) and triplet quenching system, e.g. in an imaging buffer used just before, during and/or after imaging, and d) optimizing reaction conditions. Such a combined approach can improve the signal and thereby improve read lengths significantly.

BRIEF DESCRIPTION OF THE DRAWINGS

FIG. 2A shows a three dimensional translucent view of a flow cell, comprising fluid tubing connections, cartridge heaters, and O-ring seal, FIG. 2B is a two dimensional drawing of a side view of a flow cell (200), showing an array or slide (201) with spaced spots on the surface (representing positions for biomolecules and/or anchoring molecules), said array positioned (e.g. inverted) in a fluid channel (202) such that solutions of buffers and/or reagents can be introduced over the surface under conditions whereby reactions and/or washing can be achieved. The arrows show one particular direction of fluid flow, with entrance (204) and exit ports (205), as well as one particular method of sealing (O-ring seal 203). FIG. 2C is a drawing depicting beads (206) in the wells (207) of the slide (or chip 208), which preferably comprises nucleic acid to be sequenced (not shown), said slide positioned in a flow cell for contact with reagents in the solution traveling through the flow cell. The single dark arrow shows reagent flow in the flow cell. The many light arrow heads represent detection (e.g. light imaging) from the back of the slide (or chip).

FIGS. 4A-B show a schematic for steps involved in sample preparation FIG. 4 (A) and highly parallel sequencing steps FIG. 4 (B) for embodiments of the invention.

FIG. 9A shows actual fluorescent levels, FIG. 9B shows measured fluorescent levels.

FIG. 11 is a chart of an exemplary sequence of extension events using an exemplary 4 templates positions and 3 cycles.

FIGS. 24A-D show sequencing results using four different 25 nt DNA templates (FIGS. 24A, 24B, 24C, 24D).

FIG. 27 shows exemplary nucleotide structures with 3'-OH group protection that can be cleaved by mild oxidation reactions.

FIG. 32A is raw data, and FIG. 32B is data with the color crosstalk removed.

FIG. 46 shows that improvements in sequencing performance can be achieved with a mixture of labeled/unlabeled nucleotides. Using such a nucleotide mixture results in correct base calls.

FIGS. 48A-D shows that using a mixture of labeled and unlabeled nucleotides (e.g. a mixture of labeled and non-labeled reversible terminators) and controlling extension time can improve performance (e.g. increase retention of signal) on an automated sequencing device. With additional control provided (e.g. by reducing extension time from 15 minutes to 2 minutes), the incorporation rate of labeled nucleotides can be controlled and results in improved fidelity and performance. FIGS. 48A and 48B show the results for 15 minutes. FIGS. 48C and 48D show the results for 2 minutes.

FIGS. 49A-P shows that using a mixture of labeled and unlabeled nucleotides (e.g. a mixture of labeled and non-labeled reversible terminators) and controlling extension time can improve performance (e.g. increase retention of signal) on an automated sequencing device. FIGS. 49A, 49B, 49C, 49D, 49E, 49F, 49G and 49H show the results with 10 minute extension (for templates 20, 30, 21, 31, 22, 32, 23 and 33, respectively). FIGS. 49I, 49J, 49K, 49L, 49M, 49N, 49O and 49P show the results with 1 minute extension (for templates 20, 30, 21, 31, 23 and 33, respectively). With additional control provided (e.g. by reducing extension time from 10 minutes to 1 minute), the incorporation rate of labeled nucleotides can be controlled and results in improved fidelity and performance. Signal retention is defined as the ratio of signals at the end of the run to the signals at the beginning of the run.

FIG. 51 is a top view of one embodiment of a moving support or carousel, comprising a plurality of small flow cells (in this embodiment, eight flow cells are shown, but there is clearly room for more if desired).

FIG. 63 is a bar graph showing the relationship of the number of flow cells to cycle time where the flow cells are large.

FIGS. 64A, 64B and 64C show one embodiment of a dual camera arrangement for imaging nucleic acid during the sequencing protocol. FIG. 64A shows first (FC) and second (SC) cameras in relationship to the LED light source (LS) and flow cells (FC). FIG. 64B more clearly shows the color filters and dichroic beam splitters. FIG. 64C shows the relationship of the filters, mirrors and lenses in more detail.

FIGS. 65A and 64B show one embodiment of a user interface. More specifically, FIG. 65A is a picture of the control board (CB) for the instrument with the computer screen (CS) in the foreground (in electronic communication therewith).

FIG. 66A shows one embodiment of a modified nucleotide comprising an acyclic structure (e.g. acyclic sugar) lacking the (deoxy)ribose furanose ring. FIG. 66B shows a modified nucleotide comprising the furanose ring.

DEFINITIONS

Figure 1:
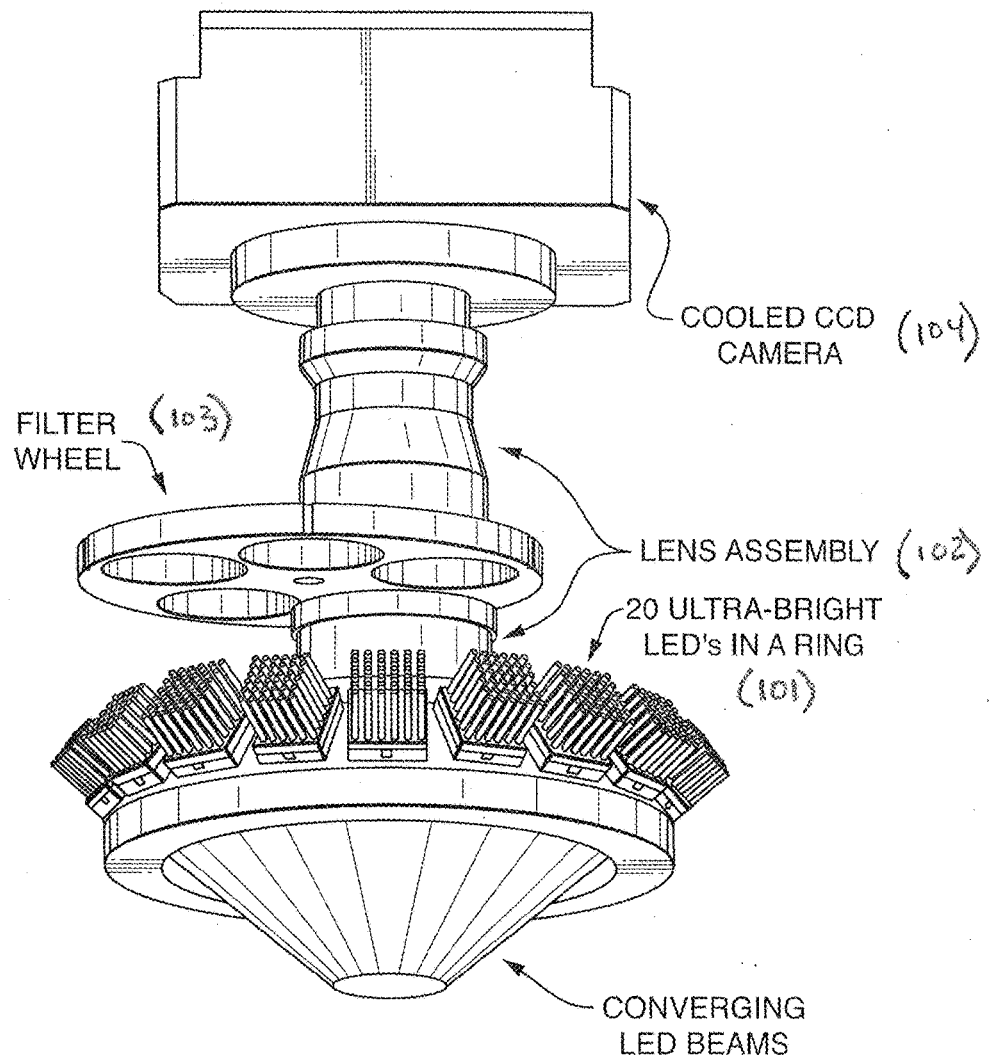
FIG. 1 schematically shows one embodiment of the imaging system of the present invention, said embodiment comprising a) a circular array of LEDs configured such that the emitted light converges on a region or platform (e.g. a position for a sample, flow cell, etc.) so as to excite fluorescence of fluorescent material, b) a lens assembly positioned above the region so as to capture at least a portion of said fluorescence, c) a filter wheel comprising bandpass filters, and d) light collection means (in this case a cooled CCD camera), wherein said filter wheel is positioned between the region where the light converges and the light collection means.

To facilitate understanding of the invention, a number of terms are defined below, and others are found elsewhere in the specification.

In one embodiment, the present invention contemplates nucleic acid samples or template "arrayed" on a "chip" or other surface or solid support. A "chip" is not limited to a silicon chip, but includes supports made of metal, plastic and glass. A "chip" need not be square and can take a number of shapes. A "chip" may have features (e.g. indentations and the like) or may be smooth. A "chip" is preferably smaller in dimensions than a conventional microscope slide.

In another embodiment, the nucleic acid to be sequenced is immobilized on particles or beads and the beads are either in a fixed position or not in a fixed position in said flow cell. In one embodiment, said beads are magnetic beads.

In yet another embodiment, nucleic acid to be sequenced is immobilized on beads that fit into holes or depressions in a "chip" surface.

The term "array" refers to a random or ordered plurality of molecules on a support. Devices, equations, and computer systems for forming and using arrays of material on a substrate for DNA sequencing are known (e.g., Ju et al., U.S. Pat. No. 6,664,079; Pirrung et al, U.S. Pat. No. 5,143,854; Hubbell et al., U.S. Pat. No. 571,639; Lipshutz et al., U.S. Pat. Nos. 6,957,149, 5,733,729, 6,066,454, 6,228,593 and 6,546,340; Chee et al, U.S. Pat. No. 5,795,716; Domnisoru et al., U.S. Pat. No. 6,598,013; Schermer et al., U.S. Pat. No. 7,209,836; Gavrilov et al., U.S. Pat. Application No. 2007/0194249; Eltoukhy et al. In: IEEE International Conference on Acoustics, Speech and signal processing, (2006) 2:1032-1035; Margulies et al. (2005) Nature 437:376-380; and Gerardo et al. (2008) Nucleic Acids Res. (2008) 36(4):e25).

The term "plurality" means two or more.

A "subject" can be a human or animal. It is not intended that the present invention be limited by the nature or status of the subject, e.g. the human may be disease-free or may have symptoms of a disease.

The term "nucleotide sequence" refers to a polymer comprising deoxyribonucleotides (in DNA) or ribonucleotides (in RNA).

The term "interrogation position" when made in reference to a nucleotide sequence refers to a location of interest in the sequence, such as the location at which the identity of a nucleic acid is sought to be determined.

The term "preceding nucleic acid" when made in reference to a first nucleic acid in relation to a second nucleic acid that is located at an interrogation position in a nucleotide sequence refers to a nucleic acid that is inserted during synthesis into the nucleotide sequence before the insertion of the second nucleic acid at the interrogation position. The term "subsequent nucleic acid" when made in reference to a third nucleic acid in relation to the second nucleic acid at the interrogation position refers to a nucleic acid that is inserted during synthesis into the nucleotide sequence after the insertion of the second nucleic acid at the interrogation position.

The terms "probe" and "label" are interchangeably used to describe a chemical moiety that, when attached to a composition of interest, acts as a marker for the presence of the composition of interest. Probes are exemplified by fluorescent moieties such as 5-carboxyfluorescein, 6-carboxyrhodamine-6G, N,N,N,N'-tetramethyl-6-carboxyrhodamine, and 6-carboxy-X-rhodamine. Probes also include a fluorescence energy transfer tag that comprises an energy transfer donor and an energy transfer acceptor. The energy transfer donor is exemplified by 5-carboxyfluorescein and cyanine, and the energy transfer acceptor is exemplified by dichlorocarboxyfluorescein, dichloro-6-carboxyrhodamine-6G, dichloro-N,N,N',N'-tetramethyl-6-carboxyrhodamine, and dichloro-6-carboxy-X-rhodamine. The mass tag is exemplified by a 2-nitro-a-methyl-benzyl group, 2-nitro-a-methyl-3-fluorobenzyl group, 2-nitro-a-methyl-3,4-difluorobenzyl group, and 2-nitro-a-methyl-3,4-dimethoxybenzyl group.

The term "probe corresponds to a nucleotide" means that the probe serves as a marker for the presence of the nucleotide. Thus, detecting the presence of the probe also detects the presence of the nucleotide.

The term "field flattening" when in reference to pixel intensity of an image refers to reducing differences in pixel intensity between two or more pixels at different spatial locations on the image of a uniformly radiating surface.

The terms "reducing," "decreasing" and grammatical equivalents when in reference to the level of a molecule and/or phenomenon (e.g., light intensity, chemical concentration, correlation between two event, etc.) in a first sample relative to a second sample, mean that the quantity of molecule and/or phenomenon in the first sample is lower than in the second sample by any amount that is statistically significant using any art-accepted statistical method of analysis. In some embodiments, the quantity of molecule and/or phenomenon in the first sample is at least 10% lower than, at least 25% lower than, at least 50% lower than, at least 75% lower than, and/or at least 90% lower than the quantity of the same molecule and/or phenomenon in a second sample. The term "reducing" includes, but does not require, a 100% lowering in the quantity of the molecule and/or phenomenon in the first sample compared to the second sample.

The terms "increasing," "elevating" and grammatical equivalents when in reference to the level of a molecule and/or phenomenon (e.g., light intensity, chemical concentration, correlation between two event, etc.) in a first sample relative to a second sample, mean that the quantity of molecule and/or phenomenon in the first sample is higher than in the second sample by any amount that is statistically significant using any art-accepted statistical method of analysis. In some embodiments, the quantity of the molecule and/or phenomenon in the first sample is at least 10% greater than, at least 25% greater than, at least 50% greater than, at least 75% greater than, and/or at least 90% greater than the quantity of the same molecule and/or phenomenon in a second sample.

"Spectral" is a term that refers to electromagnetic radiation. In one embodiment, the electromagnetic radiation is in the visible light region (wavelength of approximately 400-700 nanometers), such as that emitted by fluorescent moieties.

The terms "spectral filter" and "color filter" are interchangeably used to refer to a filter for detection of a particular range of electromagnetic wavelengths, such as in the visible region, thereb The terms "spectral crosstalk" and "color crosstalk" refer to any phenomenon by which a spectral signal, or a digital signal that corresponds to a spectral signal, that is transmitted and measured in one channel of transmission creates an undesired effect in another channel. For example, spectral crosstalk may occur when exciting only a green dye, resulting in a signal that is visible in the yellow channel as well as in the green channel. Using methods disclosed herein, if this spectral crosstalk is calibrated, it may be removed from subsequent measurements even if the dyes are mixed in unknown quantities.

The term "low pass filter" refers to a filter that passes slowly spatially varying intensity signals but reduces signals with higher spatial variation than a desired cutoff value. Exemplary software for carrying out these steps is shown Appendix C, which is a source code for creating a flat map calibration image.

The term "computer readable medium" refers to a medium, such as a compact optical disc, that is used to store and retrieve digital data.

One element is in "fluid communication" or "fluidic communication" with another element when it is attached through a channel, tube or other conduit that permits the passage of liquid, gas, vapor and the like. "Tubing" can be made of a variety of materials, including put not limited to various plastics, metals and composites. Tubing can be rigid or flexible. Tubing can be "attached" in a detachable mode or a fixed mode. Tubing is typically attached by sliding into or over (both of which are examples of "slidably engaging") other tubing or connectors.

In some embodiments, certain elements are in electronic communication with other elements (and thereby "communicate electronically"). For example, the user interface is in electronic communication with the processor. "Electronic communication" can be implemented in a hard-wired electrical connection, e.g., a shielded cable, or an optical connection, e.g., an optical fiber, a wireless communication, e.g., infrared or radiowaves, a combination thereof, and the like.

Sequencing typically involves a number of steps (e.g. steps a through e) that are repeated. For this reason, each repeat of the collection of steps is often called a "cycle." The steps in a cycle typically have a temporal order, with a first step and a last step, and some steps performed after said first step and before said last step. Not all steps in a cycle need be reaction steps. In one embodiment, one or more steps may comprise pausing at a "dwell" station (e.g. where a flow cell is moved to a position where no new reagents are added). The "cycle time" is the time needed to complete one cycle. In sequencing by synthesis, each cycle identifies or "reads" one base at all or some of the various spots on the chip.

In one embodiment, the present invention contemplates positions being in a "fixed relationship" on a moveable support, in the sense that the markings on a wall clock are in a fixed relationship. Thus, flow cells may be put in positions such that a first and second flow cell are in a fixed relationship (e.g. the first flow cell at 1 o'clock and the second flow cell at 2 o'clock); but this fixed relationship may be changed by moving the first and/or second flow cell to new positions, thereby creating a new fixed relationship.

DESCRIPTION OF THE INVENTION

For further clarity, the invention is described below under the following headings
A. Sequencing By Synthesis; B. Device Embodiments and Elements; C. Nucleotides; D. Reducing Lead And Lag; E. Dephasing; F. Field Flattening; G. Spot Location in the Array; H. Image Sharpening; I. Spot Brightness Determination; J. Neighbor Influence Elimination; K. Spectral Crosstalk Calibration; L. Base Calls; and M. Software Appendices A-C
A. Sequencing by Synthesis The invention relates to methods and compositions for determining the identity of nucleic acids in nucleotide sequences using, for example, data obtained from sequencing by synthesis methods. Methods of DNA sequencing are generally described in Metzker, Genome Res. (2005) 15(12): 1767-1776 and Shendure et al. (2004) Nature Reviews Genetics 5: 335-344. The Sanger sequencing method or chain termination or dideoxy method is a technique that uses an enzymatic procedure to synthesize DNA chains of varying length in different reactions that contain diluted concentrations of individual dideoxy nucleotides mixed in with normal nucleotides. DNA replication is stopped at positions that are occupied by one of the dideoxy nucleotide bases resulting in a distribution of nucleotide fragments since the normal nucleotides will properly incorporate. Unnatural ddNTP terminators replace the OH with an H at the 3'-position of the deoxyribose molecule and irreversibly terminate DNA polymerase activity. The activity. The resulting fragment lengths are determined to decipher the ultimate sequence. Electrophoretic separation of the deoxyribonucleotide triphosphate (dNTP) fragments may be accomplished with single-base resolution.

In sequencing by synthesis, nucleotides conjugated with fluorescent markers that incorporate into a growing double-stranded nucleic acid from the single strand are detected. For example, one may immobilize template DNA on a solid surface by its 5'end. One may accomplish this by annealing a sequencing primer to a consensus sequence and introducing DNA polymerase and fluorescent nucleotide conjugates (alternatively, a self-priming hairpin can be introduced by PCR or ligation to the template). One detects nucleotide incorporation using a laser microarray scanner or fluorescent microscope by correlating a particular fluorescent marker to a specific nucleotide. After each nucleotide is incorporated and the fluorescent signal is detected, one bleaches or removes the fluorescent moiety from the nucleotide conjugate so as to prevent the accumulation of a background signal.

In one embodiment, the present invention contemplate DNA sequencing by synthesis using an automated instrument, as well as methods and compositions useful for sequencing using such an instrument. In one embodiment, the instrument comprises a flow cell (FIGS. 2A and 2B) with at least two fluidics ports, a substrate with sequenceable nucleic acid molecules attached to the substrate, reagent and waste reservoirs and fluidic system connecting the reservoirs to the flowcell (FIG. 3A-B). The flowcell is interfaced with a detection system to monitor the incorporation of the nucleotides.

As noted above, in a preferred embodiment, the present invention employs a plurality of smaller flow cells (with an area for imaging of approximately 35 mm×2.5 mm, or less) mounted on a support, in the manner of a carousel. FIG. 51 shows such one embodiment of such a carousel (33) comprising eight such flow cells (5) mounted on the surface (30), each flow cell associated with a station (31), each station associated with a step (or partial step) in the sequencing protocol. The carousel (33) can rotate clockwise or counterclockwise in order to bring each flow cell (5) to the next station (31) for processing. In a preferred embodiment, the carousel (30) transports one or more flow cells (5) to station blocks (FIG. 50A, element 15), at various station locations (31) is shown. Generally, the transport occurs in short indexing motions, so that the flow cells spend most of the time at station locations rather than in motion. While a plurality of flow cells is preferred, the processor of the system is programmable, such that a user may run from one to the maximum number of flow cells.

Figure 50A:
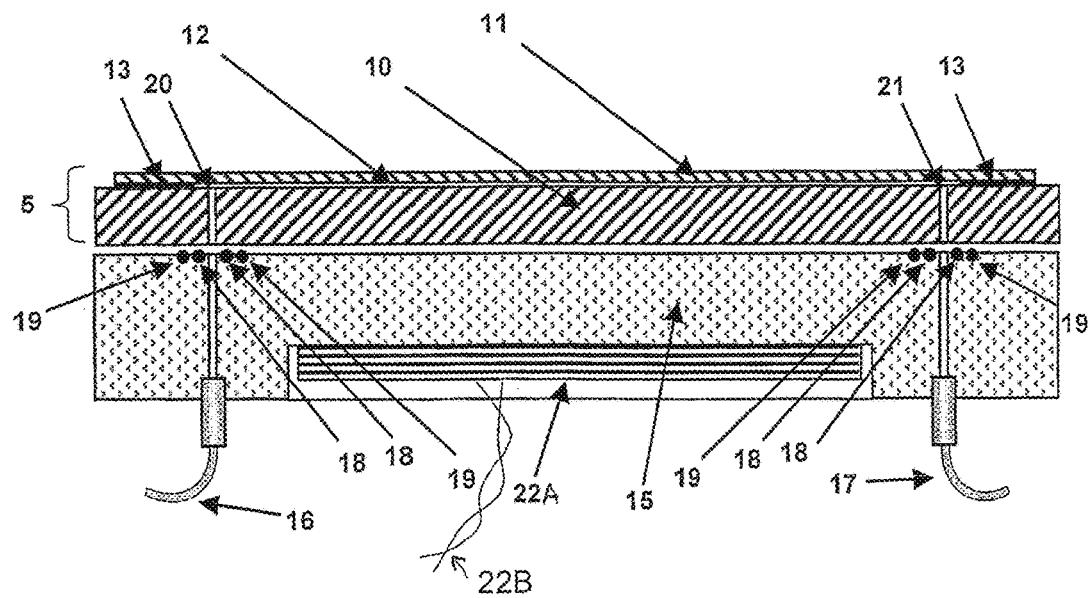
FIG. 50A shows a cross section view of one embodiment of a flow cell positioned at a station in fluidic communication with reagent or wash solutions via tubing and inlet/outlet ports.
Figure 52:
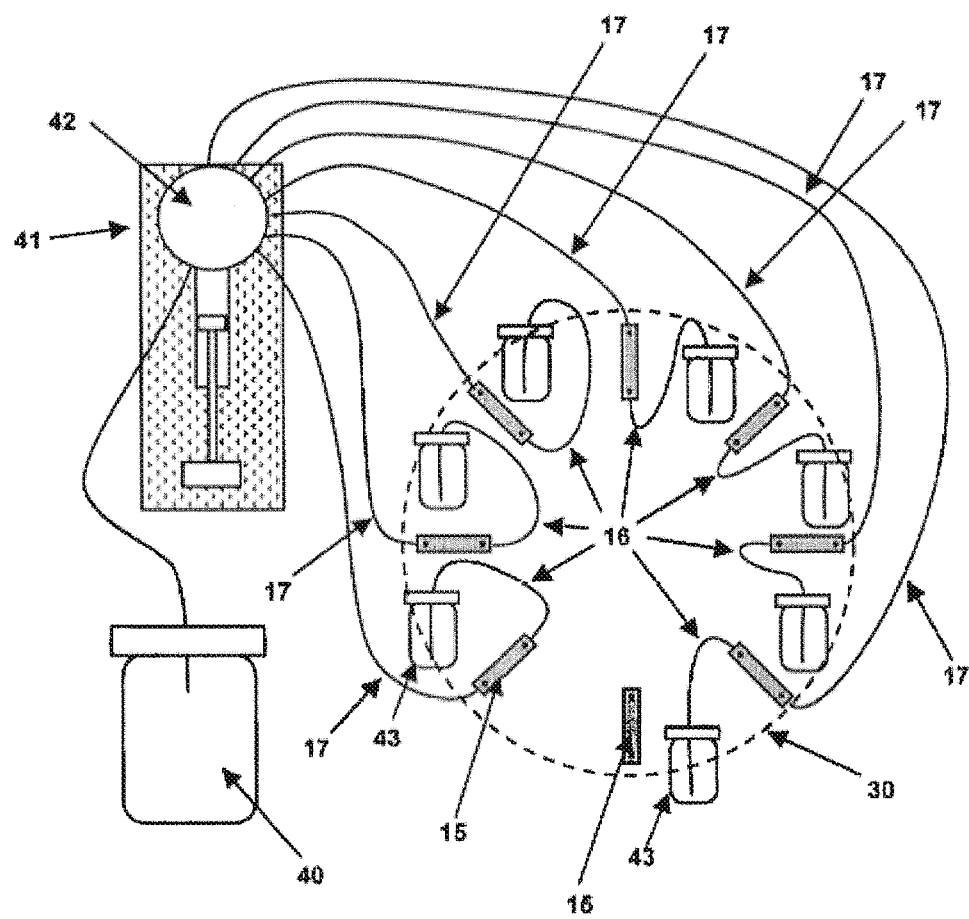
FIG. 52 is a schematic showing a top view off one embodiment of flow cells on a moveable support, in the context of the fluidics provided at each station.
Figure 53:
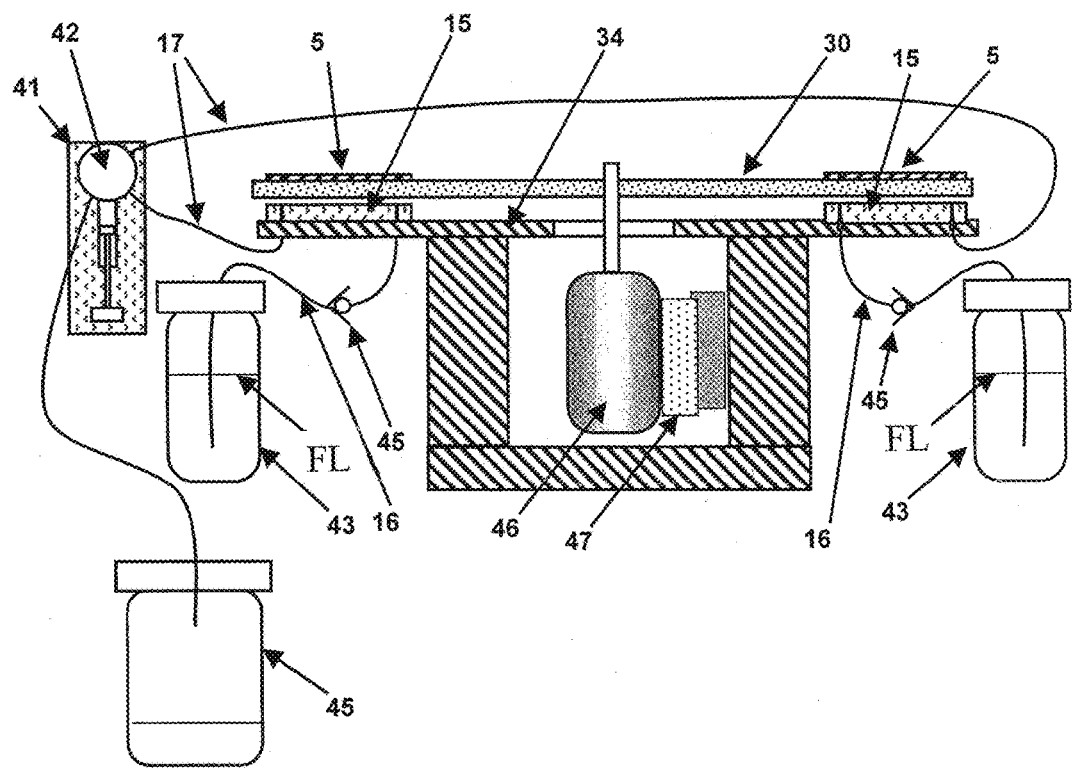
FIG. 53 is a schematic showing a side view of one embodiment of the moveable support, in the context of both the fluidics and the mechanics for moving the support.

FIG. 50A shows (in cross section) a single, removeable flow cell (5) positioned at a station (and aligned with a station block 15) in fluidic communication with reagent or wash solutions via tubing (16) associated with an inlet port (20) and tubing (17) associated with an outlet port (21). In one embodiment, the flow cell is constructed of at least three pieces including a base plate (10), a spacer film (13) mid a top cover (11). The samples to be sequenced may either be located on a separate chip affixed to the base plate, the base plate itself, or the bottom surface of the top cover. An "array," "slide" or "chip" refers to any of the aforementioned locations where the samples to be sequenced are located. The top cover (11) is preferably transparent so that a chip positioned inside the flow cell can be imaged. The flow path (12) is a narrow space between the base plate (10) and the top cover (11) and forms the area where the reagents and wash fluids may flow across the samples on the chip from the flow cell inlet (20) to the flow cell outlet (21). The station block (15) also has ports that approximately line up with the flow cell inlet (20) and outlet (21). Elastomeric seals, such as O-ring seals, seal the interface of the two sets of ports so that fluids may flow between the flow cell and station block without leaking. In stations which deliver reagents, the seals (18) have a smaller open area where the fluids may flow than the seals (19) in station where wash fluids flow. Thus, any reagents trapped in sealing areas at reagent stations are more efficiently washed from the bottom surface of the flow cell bottom plates (10) at the wash stations so as to not contaminate the flow cell with reagents from previous steps. Reagents or wash fluids are drawn through the station blocks (15) and flow cells (5) by fluid in tubing (17) drawn by a pump, such as a syringe pump (FIGS. 52 and 53, element 41). Reagents are supplied through tubing (16) from reagent vessels or reservoirs (FIG. 52, element 43). Stations block may be temperature controlled by resistive heating or thermoelectric heating/cooling elements (22A) that are in communication with a power source (not shown) via wires (22B) or other connections. Since the flow cell connection to reagents and washes is, in a preferred embodiment, right at (i.e. in the immediate vicinity of) the flow cell rather than through a few feet of tubing back to a valve, there is less reagent waste and less washing necessary to clean out the wetted materials between steps.

Figure 50B:
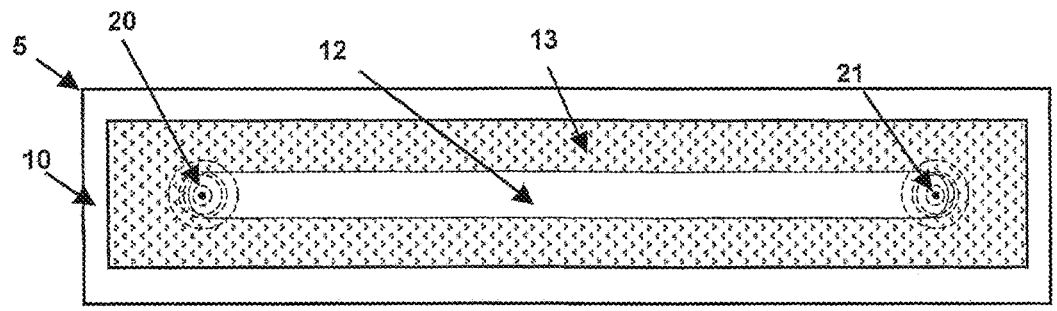
FIG. 50B is a top view of one embodiment of a flow cell positioned at a station in fluidic communication with reagent or wash solutions via tubing and inlet/outlet ports, the inlet port introducing such solutions into the flow cell and the outlet port removing such solutions from the flow cell.

FIG. 50B is a top view of one embodiment of a removeable flow cell (5) positioned at a station in fluidic communication with reagent or wash solutions via tubing and inlet (20) and outlet (21) ports, the inlet port (20) introducing such solutions into the enclosed flow chamber (12) defining the flow path of the flow cell (5) and the outlet port (21) removing such solutions from the flow cell (5). The shape of the spacer film (13) which forms the periphery of the flow path (12) may be seen. The base plate (10) may extend beyond the bounds of the spacer film (13) and the top cover (11), or it may be flush with the edges. An extended dimension may be used to clamp the flow cell to the station block (15), without putting pressure on the more delicate and thin material that makes up the top cover (11). In this manner, the flow cell (5) is held in position by fastening means (13) which can be a clamping device or an adhesive, including sticky tape (preferably double sticky tape).

FIG. 52 shows one embodiment of a fluidics configuration for the station blocks (15) positioned around and under a carousel (30). In this embodiment, seven station blocks (15) are connected (although more or fewer can be used in other embodiments) to one or more source bottles or reservoirs (43) through tubing (16) and at least one waste container (40) through tubing (17) connected to a syringe pump (41). One station block is shown with no fluid connections, since in certain embodiments, one or more stations may not require fluids (for example, at an imaging station, at a dwell station, or at a load/unload station). All of the stations with fluid connections are shown to be in fluid communication via tubing (17) with at least one syringe pump (41) through a multiplexing valve (42). In other embodiments, more than a single syringe pump may be used. In one embodiment, at least one waste receptacle (40) is also connected to the syringe pump to receive used reagents and wash fluids from the stations. In some embodiment, different waste bottles are used for different used reagents, in order to permit certain reagents to be collected and used again.

In one embodiment, the carousel (30) carries/transports the flow cells (5) to different locations, some of these locations being associated with stations, at least some of these stations being reagent delivery stations. In one embodiment (FIG. 53), the flow cells (5) are moved between the station blocks (15) using a rotary actuator (46). In the case where the flow cells are positioned at a reagent delivery station, the flow cells (5), prior to movement, must be separated/disconnected from the station blocks (15). In one embodiment, this is done by raising the carousel (30). In another embodiment, this is done by lowering the station blocks (15). In yet another embodiment, a combination of raising and lower is performed. A linear actuator (47) is shown and may be used to raise the rotary actuator (46), which in turn raises the flow cells (5) on the carousel (30) by raising the carousel. In one embodiment, check valves (45) are used in the supply lines (16) between the reagent vessel (e.g reservoir) (43) and the station blocks (15), so that when the continuous fluid column is broken by raising the flow cells (5) from the station blocks (15), the fluid does not flow back into the reagent bottles (43). The fluid level (FL) in the reagent bottles (43) is preferably kept below the vertical level of the station blocks (15), so that in the case of a valve failure, fluid does not continuously flow out of the reagent bottles (43), and flood the system when the flow cells (5) are raised from the station blocks (15). The actuators (46 and 47) are in electronic communication with a programmable processor, which is in turn connected to a user interface (see FIGS. 65A and 65B). The system thereby permits multiple flow cells run in parallel at different stages in the sequencing protocol.

Figure 54:
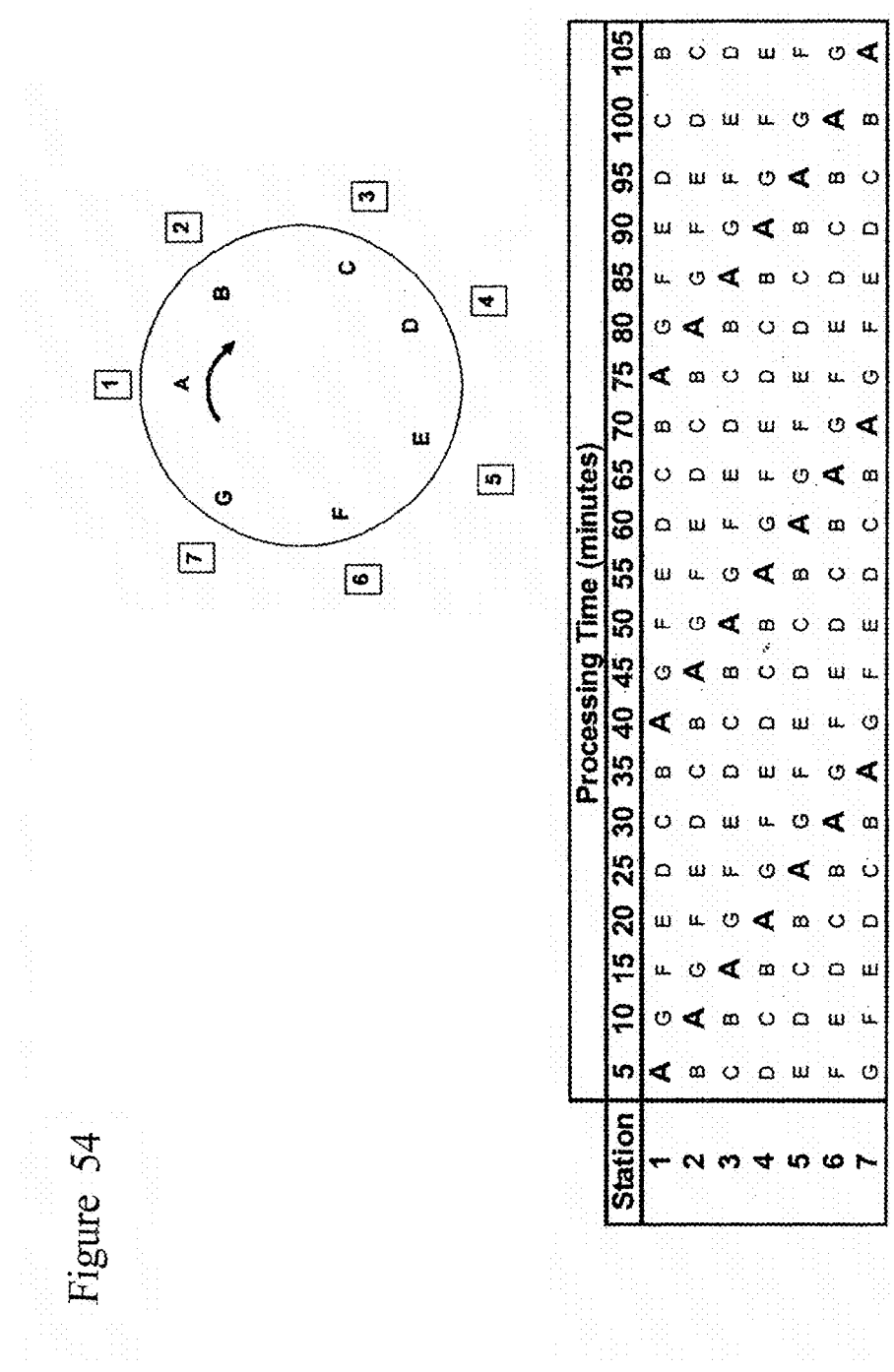
FIG. 54 shows a system with no open slots or non-functional positions, wherein the number of flow cells is equal to the number of functional stations. An associated Table provides the overall time to complete sequencing cycles using this system.
Figure 55:
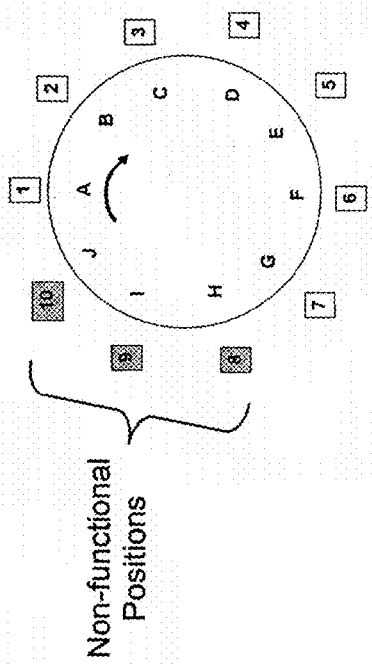
FIG. 55 shows a system with no open slots, but non-functional stations, wherein the number of flow cells is greater than the number of functional stations. An associated Table provides the overall time to complete sequencing cycles using this system.
Figure 56:
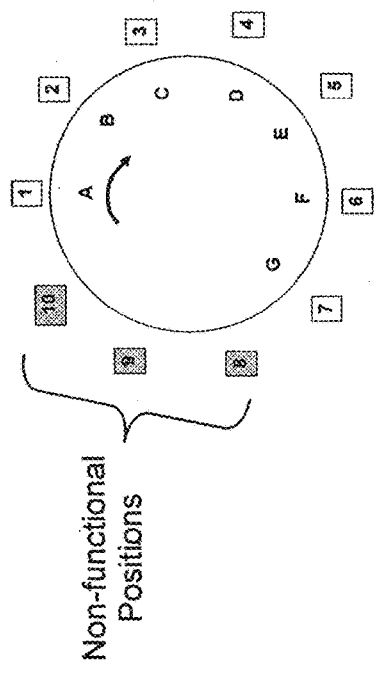
FIG. 56 shows a system with both open slots and non-functional stations. An associated Table provides the overall time to complete sequencing cycles using this system.

In one embodiment, flow cells are moved from their position on the carousel to a different position. This can have advantages, particularly where there are "open" slots on the carousel (i.e. the position lacks a flow cell) and/or non-functional stations (or dwell stations). To understand this advantage clearly, it is helpful to first consider the situation where there are no open slots or non-functional stations. FIG. 54 shows a system with seven functional stations, numbered one through seven, equally positioned around a carousel with seven positions for detachable flow cells, numbered A through G. The associated table shows the progression of flow cells through the seven stations for a system that indexes every five minutes. It takes 105 minutes for flow cell A to complete three cycles around the system. By contrast, FIG. 55 shows a system with seven functional stations, numbered one through seven, and three non-functional stations (e.g. assuming a sequencing cycle requires only seven steps), numbered eight through ten, equally positioned around a carousel with ten positions for detachable flow cells, numbered A through 1. The table shows the progression of the ten flow cells through the ten stations for a system that indexes every five minutes. Because of the three non-functional stations, it takes 150 minutes for flow cell A to complete three cycles around the system. FIG. 56 shows yet another problematic situation where seven functional stations, numbered one through seven, and three non-functional stations, numbered eight through ten, are equally positioned around a carousel with ten positions for detachable flow cells—but where only seven flow cells, numbered A through G, populate the carousel (i.e. there are three open slots). The table shows the progression of flow cells through the ten stations for a system that indexes every five minutes. It takes 150 minutes for flow cell A to complete three cycles around the system. Because the system is a synchronous indexing system (and assuming there is no means for moving flow cells to different positions), the flow cells all spend five minutes indexing through each of the ten stations, even thought some are non-functional.

Figure 57:
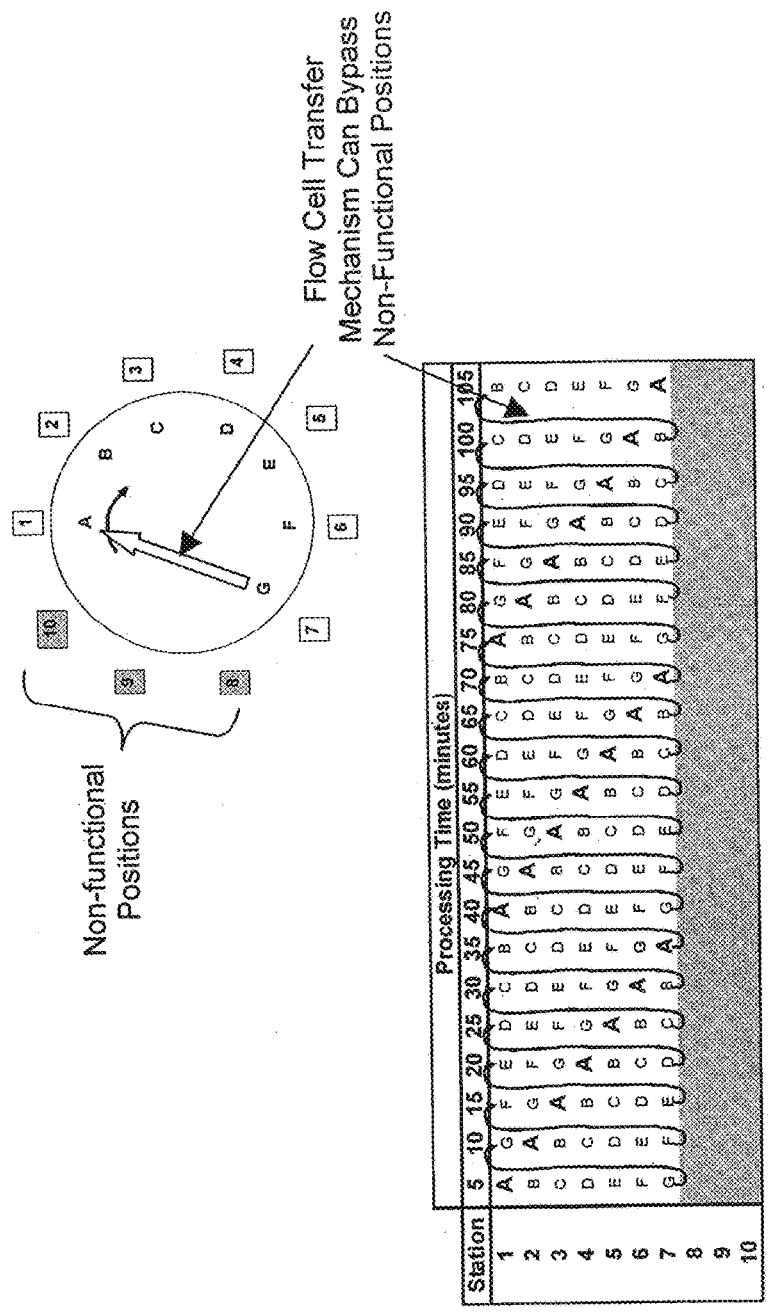
FIG. 57 shows a scheme whereby a system with open slots and non-functional stations can be optimized by movement of flow cells to different positions. An associated Table provides the overall time to complete sequencing cycles using this system.

Having now described the problem, the present invention contemplates in one embodiment a solution comprising a mechanism to bypass non-functional stations and/or open slots. FIG. 57 shows a system with seven functional stations, numbered one through seven, and three non-functional stations, numbered eight through ten, equally positioned around a carousel with ten positions for detachable flow cells. Only seven flow cells, numbered A through G, populate the carousel. The system is fitted with a mechanism (shown in more detail in FIG. 59) that can transfer flow cells from position 7 to any location on the carousel. The table shows the progression of flow cells through the ten stations for a system that indexes every five minutes. This is a solution to the problem, because the flow cell transfer mechanism can move flow cells that have completed a cycle at position 7 to a location on the carousel which will bring them to position 1 at the next cycle, thereby bypassing the non-functional positions. By moving a flow cell to a different position, it takes only 105 minutes for flow cell A to complete three cycles around the system.

Figure 58:
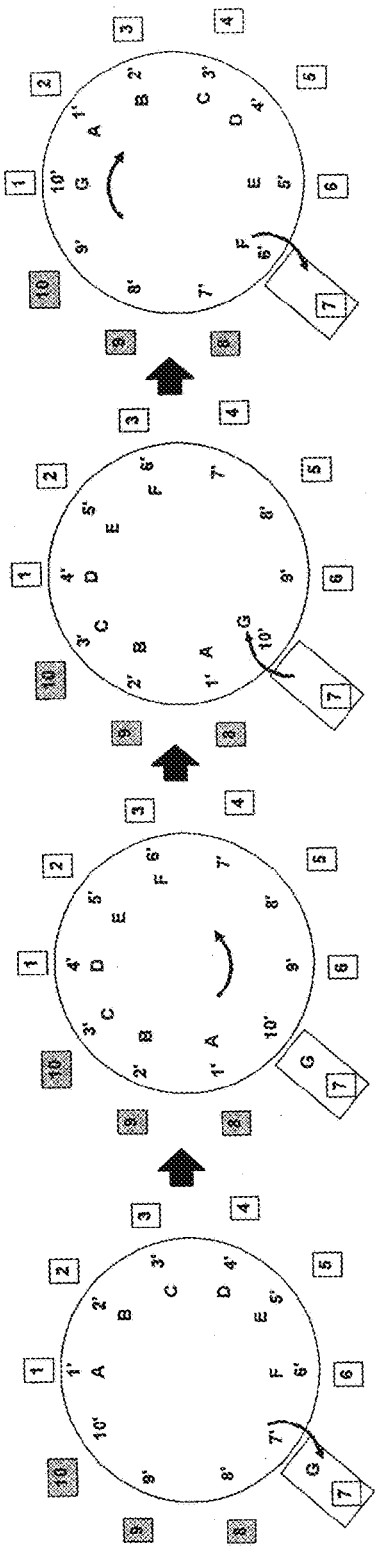
FIG. 58A-D shows one embodiment of a process whereby clockwise and counterclockwise movement of a carousel permits the repositioning of flow cells into positions for maximum efficiency.
Figure 59:
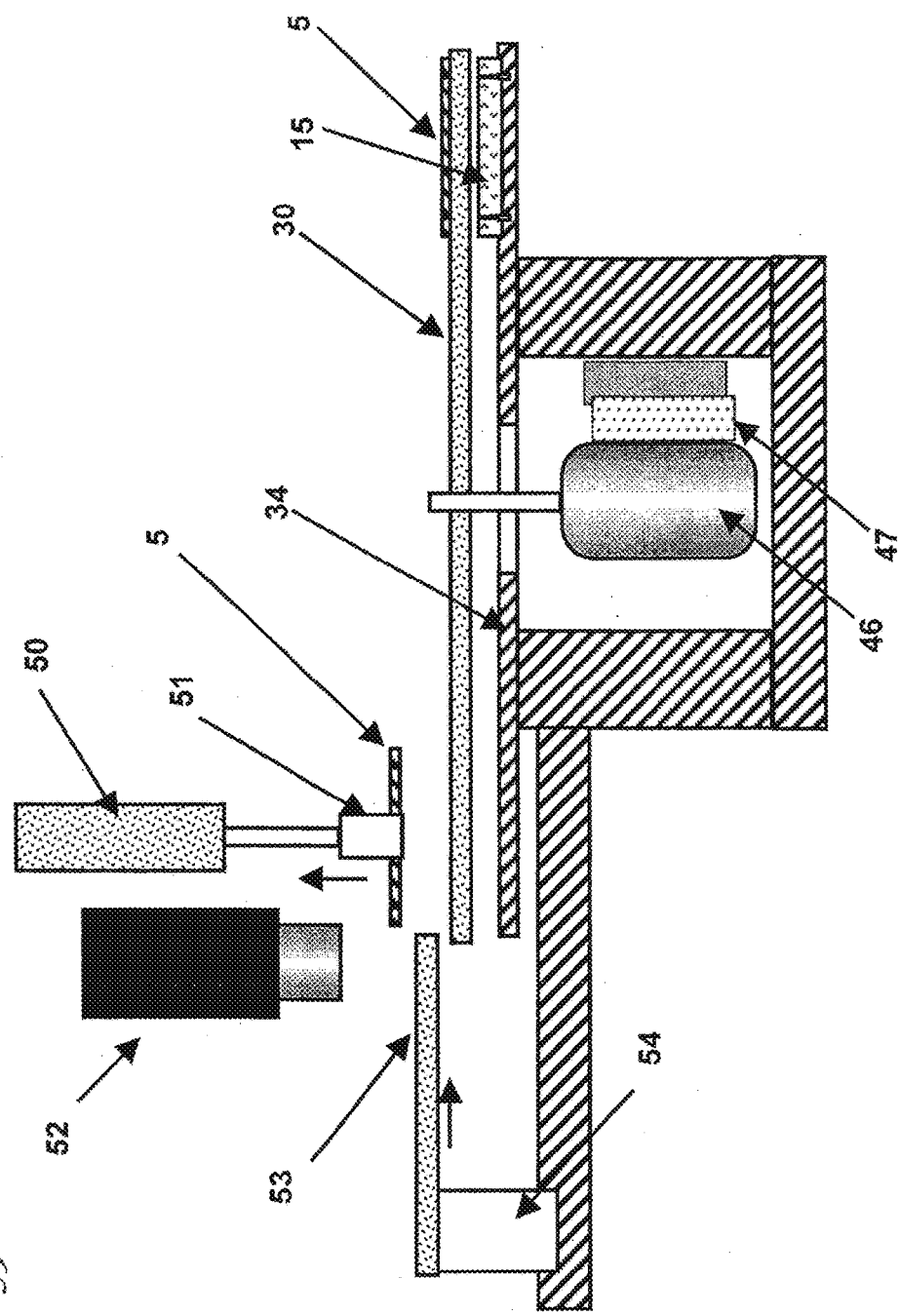
FIG. 59 shows one embodiment of the mechanics for off-loading flow cells from the carousel in a manner that will permit the process of FIG. 58A-D.
Figure 60:
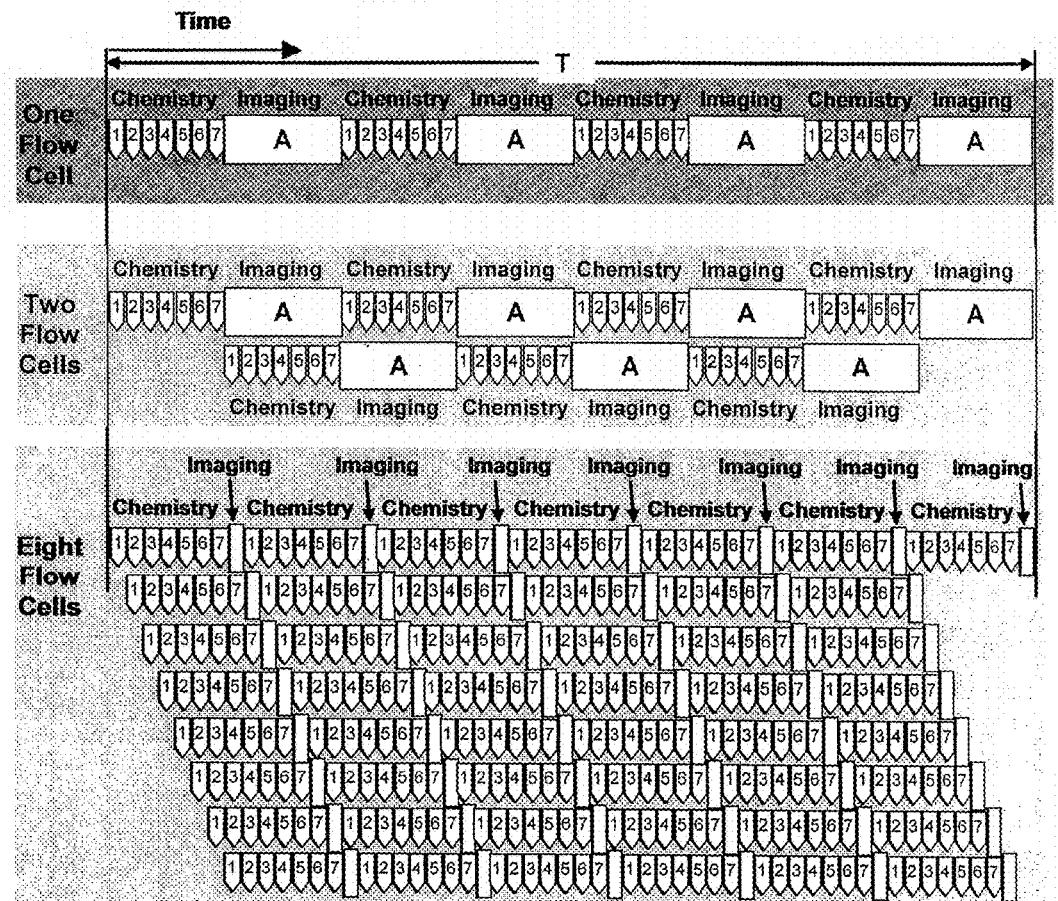
FIG. 60 is a schematic (with an associated table) that quantitatively compares throughput and cycle time for a single flow cell system, a dual flow cell system and an eight flow-cell system.
Figure 61:
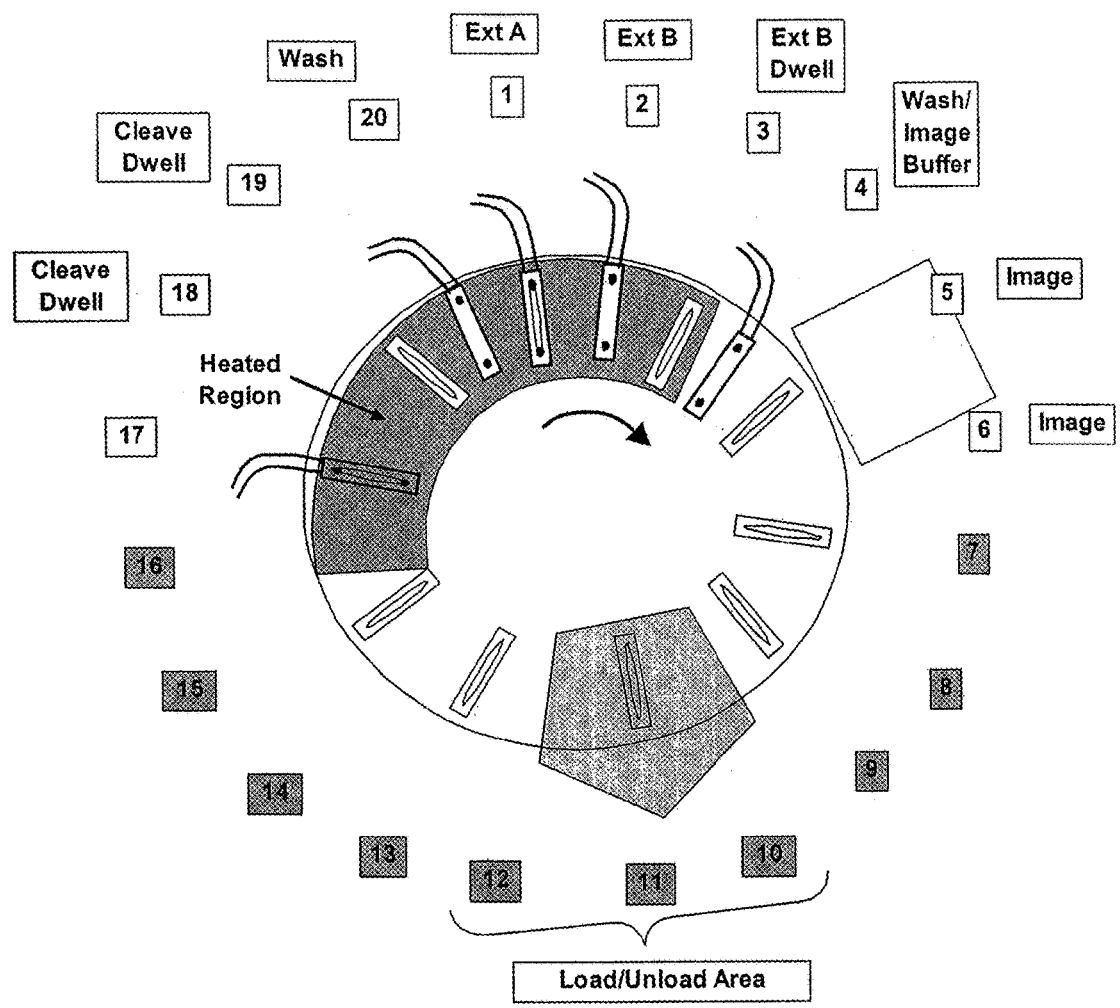
FIG. 61 is a schematic showing a representative system where stations are associated with sequencing steps, including some steps where there is heating.
Figure 62:
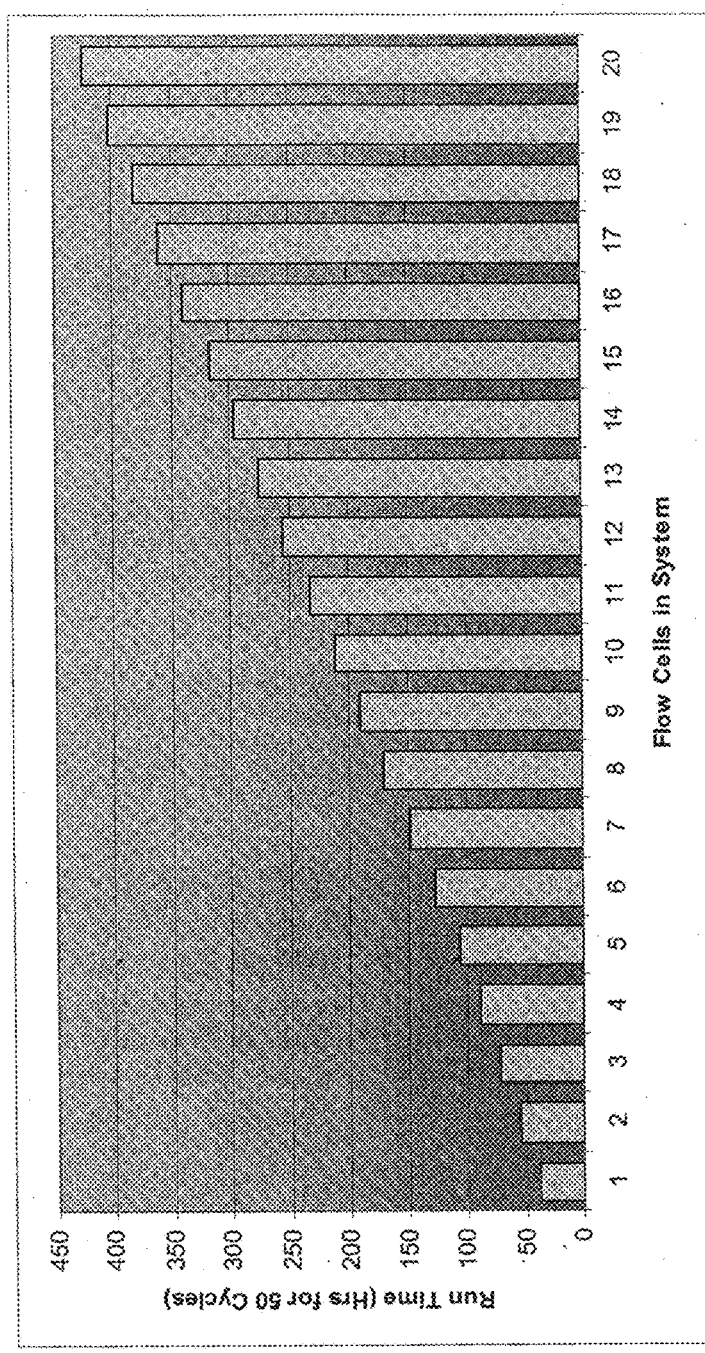
FIG. 62 is a bar graph showing the relationship of the number of flow cells to cycle time where the flow cells are small.

FIG. 58A-D shows one embodiment of how the system can bypass stations and/or open slots, utilizing both clockwise and counterclockwise motion of the carousel. FIG. 58A-D shows a sequencing system with seven functional stations (labeled 1 through 7) and three non-functional stations (labeled 8 through 10) equally spaced around a circular carousel. The system is configured to process flow cells on an under populated carousel as fast as possible as shown in FIG. 57, wherein non-functional stations may be bypassed. Under a normal indexing operation, the carousel turns clockwise one station, thereby advancing all the flow cells to the next station required for processing. One station, preferably the last functional station (number 7 in this case), is fitted with a device that can remove and replace flow cells from the carousel (e.g. off-load them onto a platform). In one embodiment, this is a detection station where flow cells are removed from the carousel and placed on a programmable positioning table so that they may be scanned by a detector, as shown in FIG. 59. In this case, the same mechanism that is used to place the flow cells on the station 7 positioning table also has the capability to replace the flow cell to any carousel position that is located at position 7. In FIG. 58a, each of the ten positions on the carousel where flow cells may be located is labeled 1' through 10'. In the figure, seven flow cells to be processed, labeled A through G, are located at corresponding carousel positions 1' through 7'. Three carousel positions, 8', 9' and 10', are empty. FIG. 58A shows flow cell G being removed from the carousel onto a remote positioning table for scanning of samples. Rather than a normal clockwise carousel indexing motion at the completion of the cycle, the carousel is moved counter clockwise so that position 10' is in front of station 7, FIG. 58b. The flow cell G is replaced onto the carousel at position 10', FIG. 58c. The carousel is then moved clockwise to the next indexing position so that each of the flow cells A through F are position to the next station in their sequence and flow cell G is positioned at station 1, bypassing all of the non-functional stations, FIG. 58d. FIG. 58A-D shows only one example of an underpopulated carousel. It should be understood that any number of flow cells on the carousel may be processed and moved in a similar manner.

FIG. 59 shows one embodiment of a detection station and the mechanics for moving flow cells. In this embodiment, the carousel (30) rotates the flow cell (5) in front of the detection station. The station comprises a vertical actuator (50) fitted with a gripper (51) that can grasp the flow cell (5) and lift it off the carousel (30). A programmable positioning table (53) is then positioned under the lifted flow cell (5) by a linear positioner (54). The positioner (54) is also used to position various parts of the flow cell under the detector (52) so high-magnification data may be generated across the entire desired area of the flow cell (5). By using the carousel motor (46) to position any location around the carousel (30) in front of the detection station, it is possible to replace/reposition the flow cell (5) to any location on the carousel.

In one embodiment, the sequencing by synthesis is carried out using reversibly terminating nucleotides and polymerase. The nucleotides comprise a protective group at their 3'-OH which prevents multiple incorporations and allows for accurate decoding of the sequence. Once incorporated the protective groups can be cleaved with high efficiency and specificity to allow subsequent nucleotide incorporations. The nucleotides may also comprise a detectable label which can be cleaved after the detection.

In one embodiment, the present invention contemplates a series of method steps, which an instrument for automated sequencing by synthesis may carry out. In one embodiment, the process is comprised of the following reagent reservoirs: 1) Extend A (reversibly terminated labeled nucleotides and polymerase); 2) Extend B (reversibly terminated unlabeled nucleotides and polymerase, but lacking labeled nucleotide analogues); 3) Wash solution 1 (e.g. in one embodiment comprising a detergent, such as polysorbate 20, in a citrate solution, such as saline sodium citrate); 4) Cleave solution; 5) Wash solution 2 (e.g. in one embodiment, comprising a detergent, such as polysorbate 20 in a buffer comprising tris(hydroxymethyl)aminomethane or "Tris"). Of course, the present invention is not limited to particular concentrations of reagents in these solutions (and other buffers and detergents can be employed). Nonetheless, in order to achieve high throughput rates, the incorporation reactions and the cleavage reactions are desired to be fast. In one embodiment, high reaction rates are achieved by increasing the concentration of reagents, agitation, pH or temperature (or the combination of all these factors). The incorporation rate in addition is dependent on the specific activity and processivity of the polymerase used. In one particular embodiment (which is provided by way of a non-limiting example), the reagents solutions have the following compositions and concentration ranges:
1) Extend A—reversibly terminated labeled (1 nM to 1 uM) and non-labeled nucleotides (1 uM to 100 uM) and a first polymerase (1-500 ug/ml)); 2) Extend B—reversibly terminated non-labeled nucleotides (1 uM to 100 uM) and a second polymerase (1-500 ug/ml)); 3) Wash solution 1 (3×SSC, 0.02% Tween 20); 4) Cleave solution (50-100 mM TCEP); 5) Wash solution 2 (100 mM Tris-HCl, 0.02% Tween 20, 10 mM KCl, 20 mM (NH2)2SO4. In one embodiment, the first polymerase incorporates labeled nucleotides better than the second polymerase, which incorporates unlabeled nucleotides more efficiently. Examples of commercially available polymerases that can be used include Therminator I-III. These polymerases are derived from *Thermococcus* sp. and carry mutations allowing for incorporation of modified nucleotides. Examples of these polymerases are listed in Table below:

| Therminator I | NEB cat. # M0261L | 9°N A485L (exo-) DNA Polymerase |
| Therminator II | NEB cat. # M0266L | 9°N A485L/Y409V (exo-) DNA Polymerase |
| Therminator III | NEB cat. # M0333L | 9°N L408S/Y409A/P410V (exo-) DNA Polymerase |

Other polymerases derived from 9 deg N parent polymerase or *Thermococcus* sp. could also be used. Other suitable polymerase families could conceivably be used after introducing mutation controlling the steric gate and enabling reversible terminators incorporation.

In one embodiment, the sequenceable DNA (preferably loaded on the chip or slide) is subjected to these solutions and compositions in the instrument, and the sequencing is performed using automated protocol. Again, it is not intended that the present invention be limited to a precise protocol or series of method steps. The order and number of steps can vary, as well as the time taken for each step. By way of a non-limiting example, in one embodiment, the instrument protocol comprises (and is configured as) as follows:

1. Extend A—0.5-5 minutes (delivery+agitation)
2. Extend B—1-20 minutes (delivery+agitation)
3. Wash 2—5-10 minutes (10-20× delivery and agitation followed by flow cell evacuation)
4. Image
5. Cleave A (or Cleave A and B)—1-5 minutes (delivery+agitation)
6. Wash 1—5-10 minutes (10-20× delivery and agitation followed by flow cell evacuation)
7. Wash 2—5-10 minutes (10-20× delivery and agitation followed by flow cell evacuation)
8. Go to step 1

The cycle may be repeated as desired and images may be taken and subsequently analyzed to decode the DNA sequence present at each location. As noted above, in one embodiment, one or more of these steps is associated with a "station" (having the requisite reagent or wash delivery elements) and flow cells are moved to each station in order to carry out the step of the sequencing protocol. Any one of these steps can be done at two stations if desired, i.e. a step taking a longer time can be completed over the course of two stations, each station doing a part (e.g. half of the step).

In one embodiment of the above indicated cycle, eight nucleotide analogues are employed: four (A, T, C, G) cleavably labeled and reversibly terminated; four (A, T, G, C) unlabeled but reversibly terminated. In one embodiment, the concentration of the labeled analogues is at a relatively low concentration [e.g. just enough to be incorporated into a substantial portion (e.g. so the label is visible and detected) of the plurality of primers, whether they be detached primers or self-priming hairpins on the template]. By contrast, the unlabeled analogues, in one embodiment, are employed in a relatively hip concentration (e.g. in order to drive the extensions to completion, and avoid primers, whether they be detached primers or self-priming hairpins, that lack incorporation of a first nucleotide analogue). It has been found empirically that the use of unlabeled nucleotides improves read lengths, and reduces lead and lag (discussed below).

One example of a currently optimized protocol is shown in the Table (below),

| Nucleotide | Labeled nucleotides [nM] | Un-labeled nucleotides [uM] |
|---|---|---|
| dCTP | 30 | 250 |
| dATP | 20 | 250 |
| dGTP | 30 | 250 |
| TTP | 30 | 250 | wherein un-labeled nucleotides are employed in ratios between 8.33 to 1 and 12.5 to 1 (relative to labeled nucleotides). In one embodiment, the labeling (i.e. incorporation) step uses Kapa RevTerm polymerase (from Kapa Biosystems, Woburn, Mass.) at 2 μg/ml and is performed at 55 deg C. for 1-2 minutes. This is followed by synchronization step where only non-labeled nucleotides are used at 25 μM concentration and a polymerase derived from 9 deg N (*Thermococcus* sp). at 25 μg/ml is used. This step is also carried out at 55 deg C. Thus, unlabeled nucleotide analogues can be employed together with labeled nucleotides, as well as in steps where no labeled nucleotides are employed.

B. Device

In one embodiment, the present invention contemplates using an optical system, for exciting and measuring fluorescence on or in samples comprising fluorescent materials (e.g., fluorescent labels, dyes or pigments). In a further embodiment, a device is used to detect fluorescent labels on nucleic acid. In another embodiment, the device comprises a fluorescent detection system and a flow cell for processing biomolecules (e.g., nucleic acid samples) arrayed on a "chip" or other surface (e.g., microscope slide, etc.). The flow cell(s) permit the user to perform biological reactions, including but not limited to, hybridization and sequencing of nucleic acids. Using a plurality of smaller flow cells moving to stations associated with steps (or partial steps) of the sequencing protocol permits the user to perform smaller sequencing jobs (100 megabases to 1 gigabases) without wasting reagent or waiting long times to get access to a shared machine.

It is not intended that the present invention be limited to particular light sources. By way of example only, the system can employ ultra-bright LEDs (such as those available from Philips Lumileds Lighting Co., San Jose, Calif.) of different colors to excite dyes attached to the arrayed nucleic acids. These LEDs are more cost effective and have a longer life than conventionally used gas or solid state lasers. Other non-lasing sources of lights such as incandescent or fluorescent lamps may also be used.

FIG. 1 shows a useful configuration of the LEDs, whereby the emitted light converges on a region or platform (e.g., suitable for positioning the flow cell or sample). However, linear arrays of LEDs can also be used.

It is not intended that the present invention be limited to particular light collection devices. By way of example only, the system may employ a high sensitivity CCD camera (such as those available from Roper Scientific, Inc., Photometric division, Tucson Ariz. or those available from Apogee Instruments, Roseville, Calif.) to image the fluorescent dyes and make measurements of their intensity. The CCD cameras may also be cooled to increase their sensitivity to low noise level signals. These may also be CMOS, vidicon or other types of electronic camera systems.

Since LED illumination light is not a collimated beam as from lasers, it is therefore an appropriate choice for imaging a larger area of many nucleic acid spots. To get sufficient light and therefore fluorescent signals over the larger area, the area seen by each pixel of the camera must be of sufficient size to allow enough fluorescent dye molecules to create a sufficient signal (for example, an Apogee U13 CCD available has 1.3 megapixels of 16 microns in size, while the Apogee U32 has 3.2 megapixels of 6.8 microns in size).

To increase capacity and efficiency, the present invention contemplates in one embodiment, a two flow cell system (e.g. while one chip in a first flow cell is undergoing one or more reaction steps, a second chip in a second flow cell is being scanned and imaged) with a single camera. In yet another embodiment of an imaging system, two flow cells and two cameras are employed.

Figure 2A:
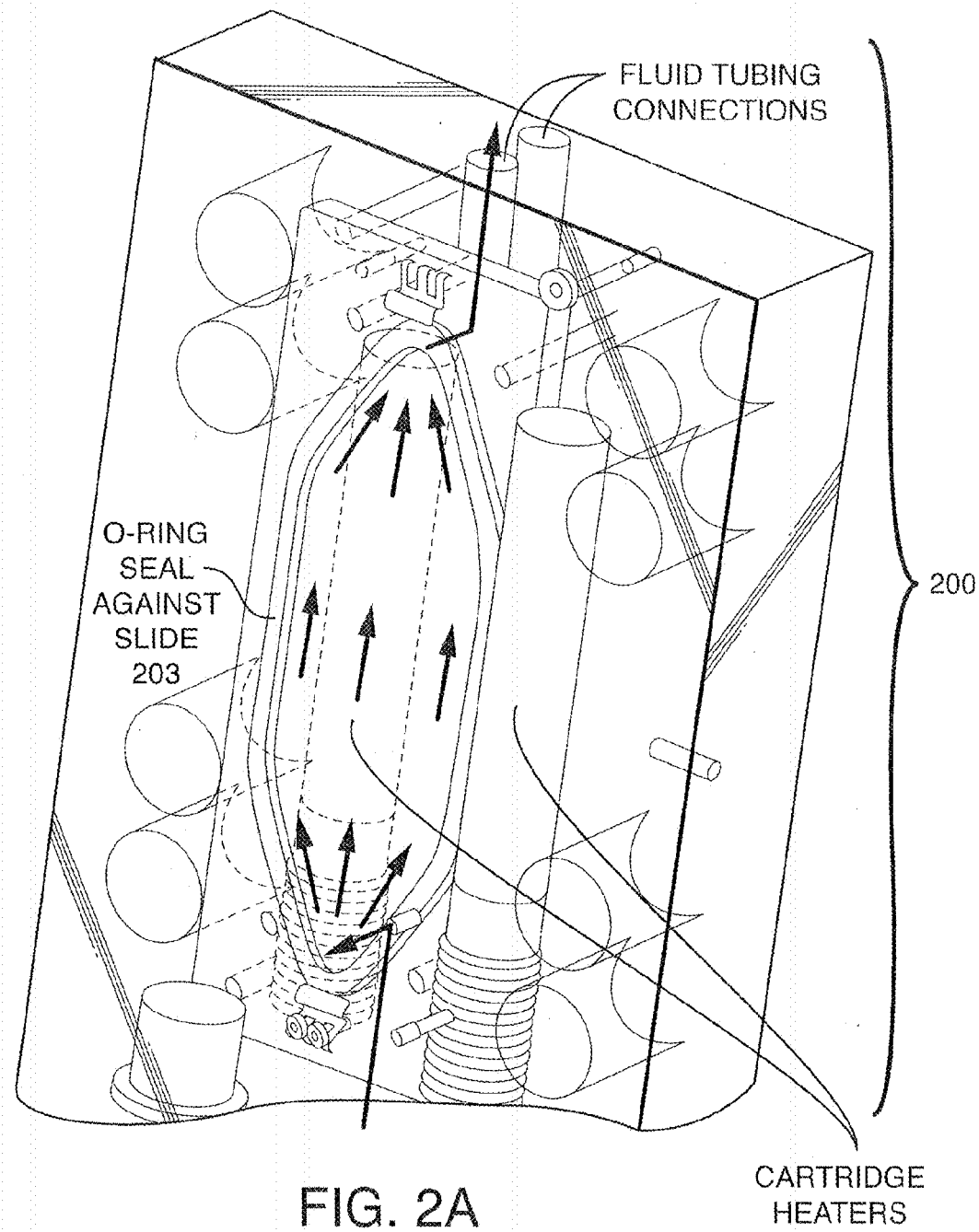
FIGS. 2A-2C schematically shows one embodiment of a flow cell (200).
Figure 2B:
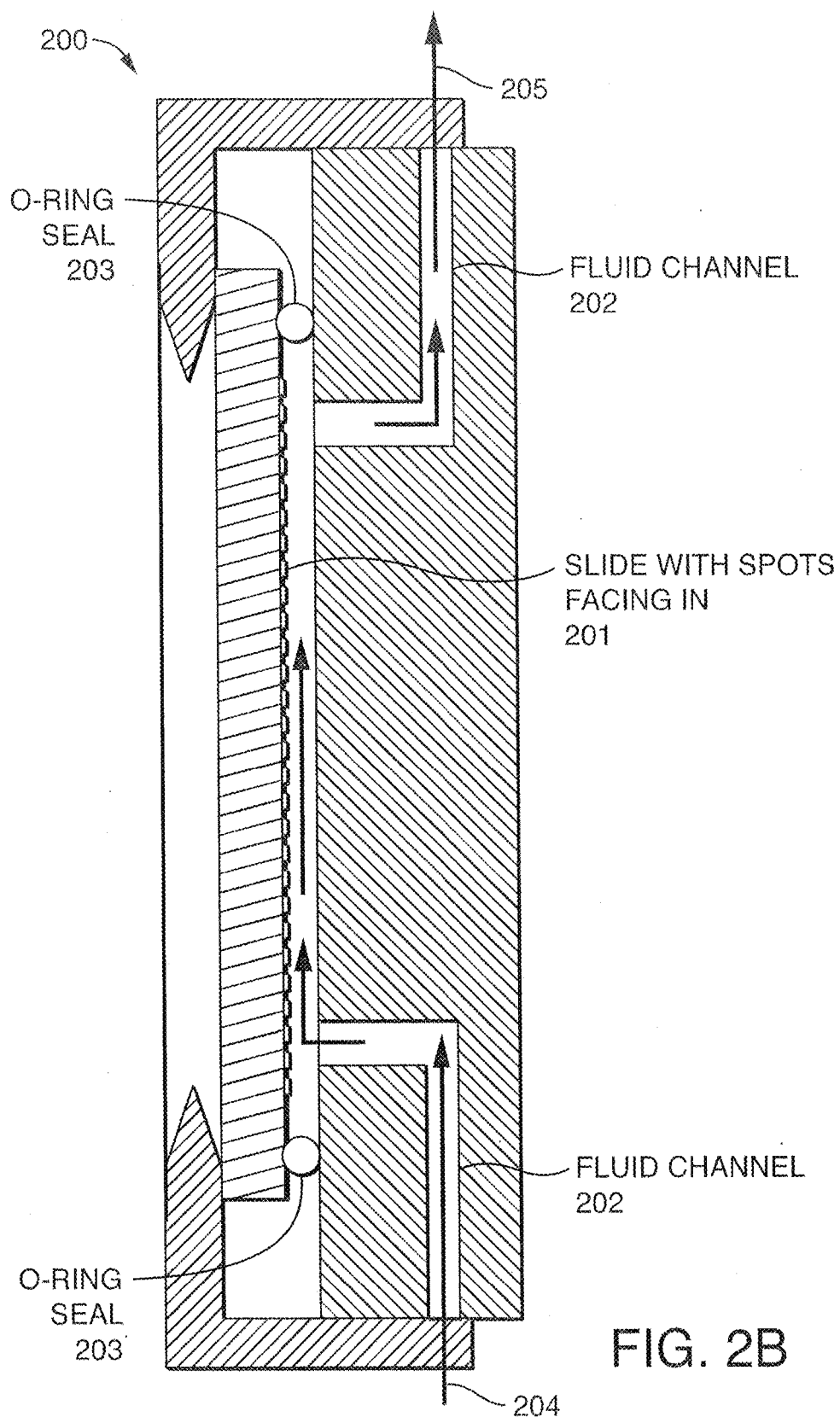
Figure 2C:
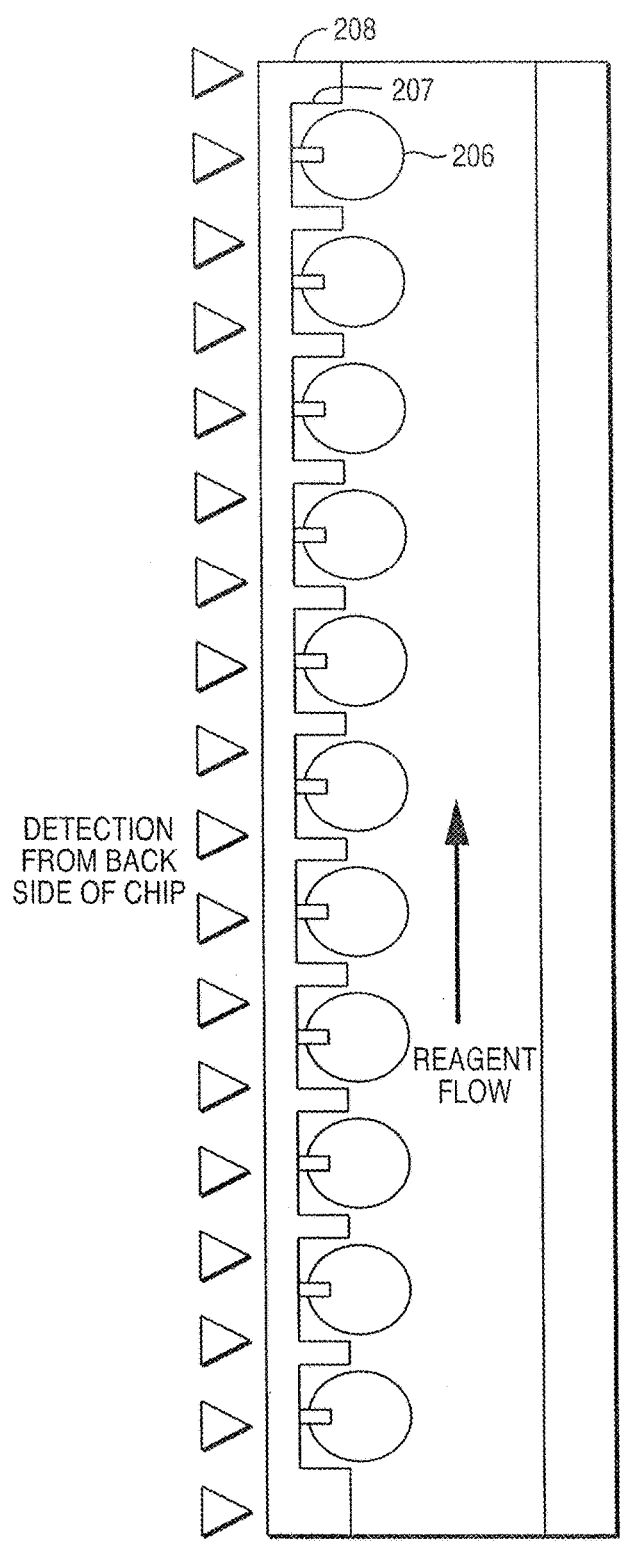
Figure 3A:
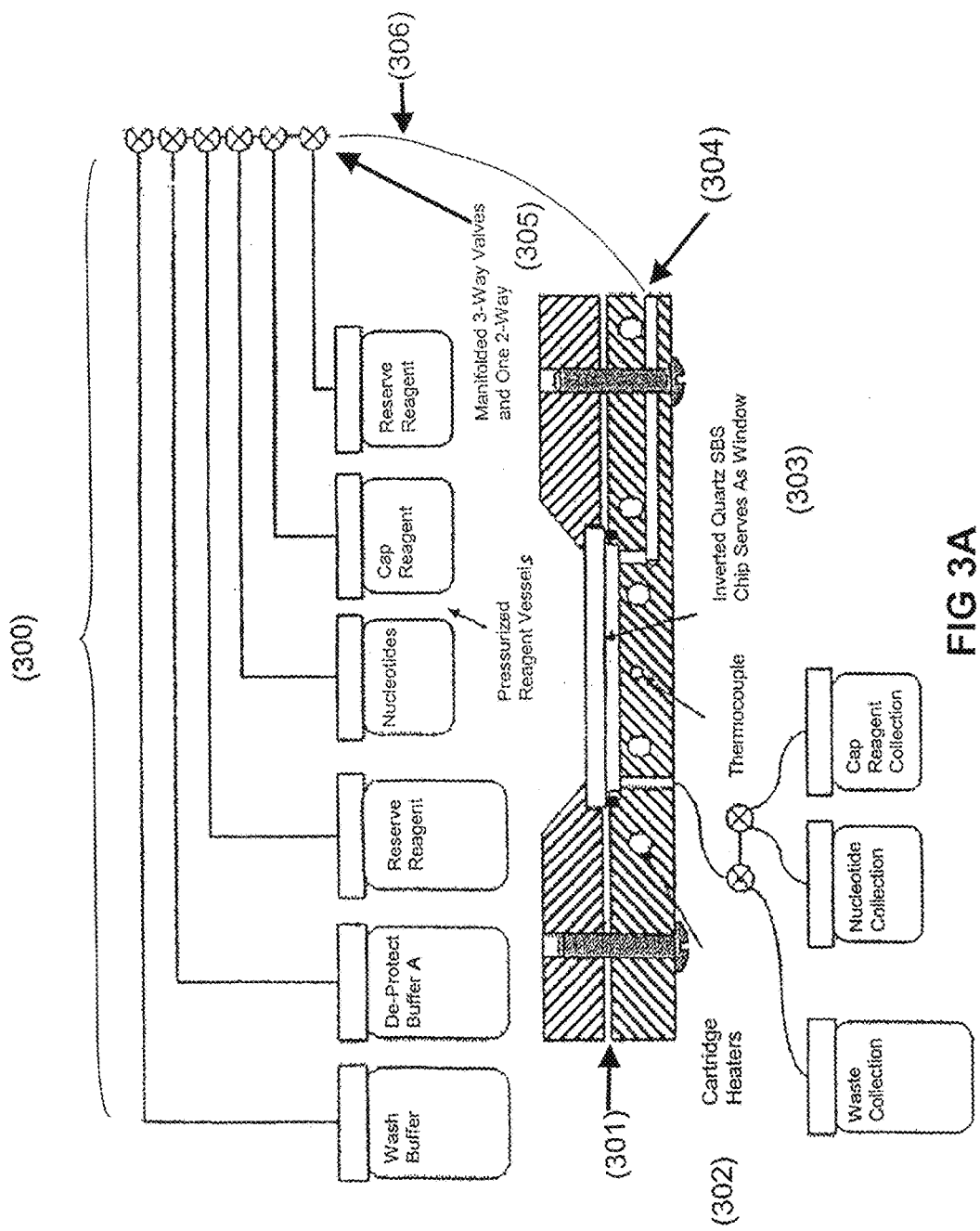
FIG. 3A schematically shows one embodiment of a fluidics system (300), comprising a variety of illustrative reagent and buffer reservoirs in communication (via tubing (306) or other channeling into a manifold comprising valves (305)) with one embodiment of a flow cell (comprising a side entrance port (301) and one or more heaters 302), wherein the array or chip (303) is inverted and the exit port (304) is on the bottom, thereby permitting the fluid channel to be drained at least in part by gravity so that waste can be readily collected into a reservoir.
Figure 3B:
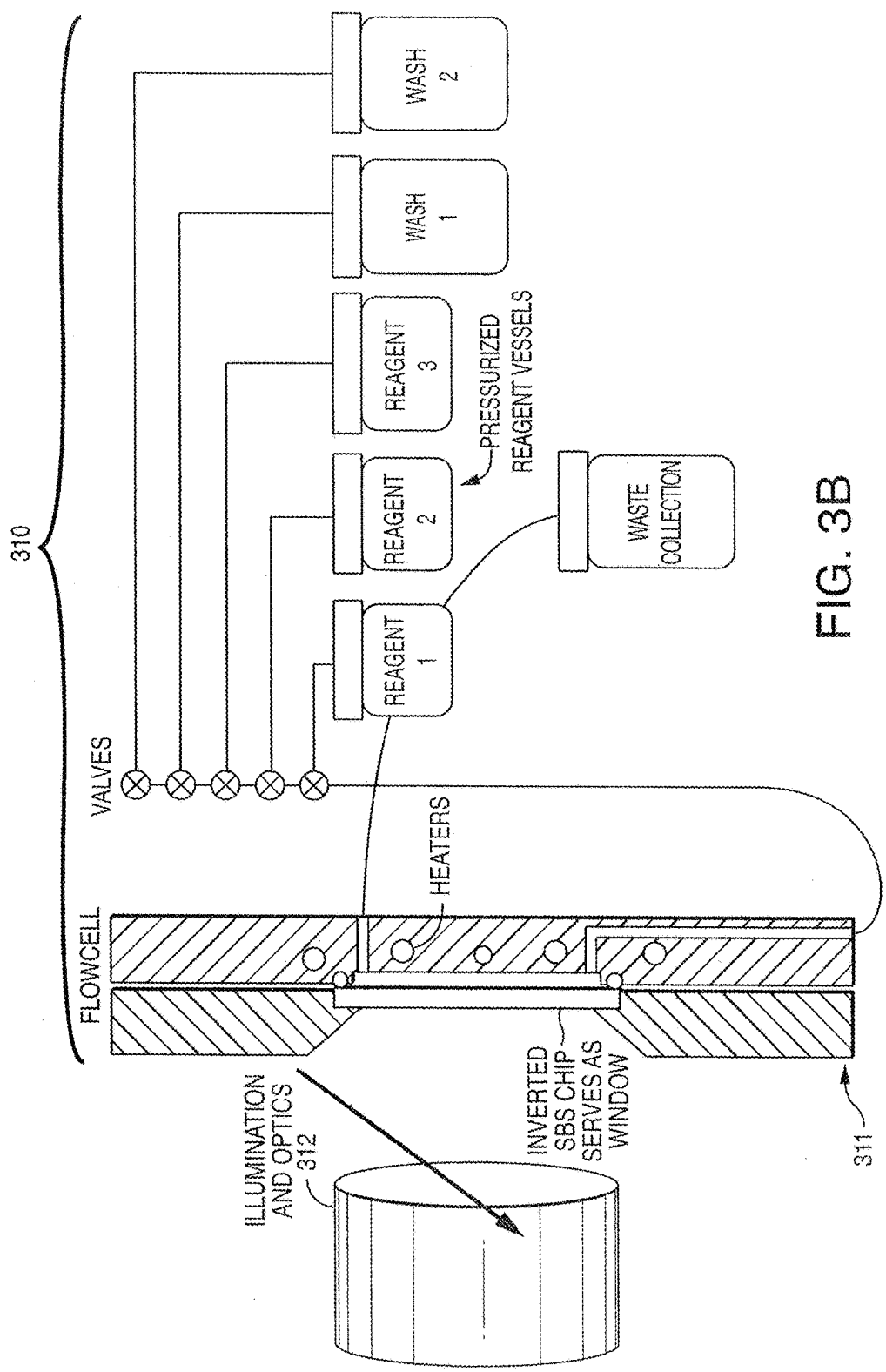
FIG. 3B shows another embodiment of the system (310), showing the flow cell (311) in relationship to the illumination and optics (312).
Figure 5:
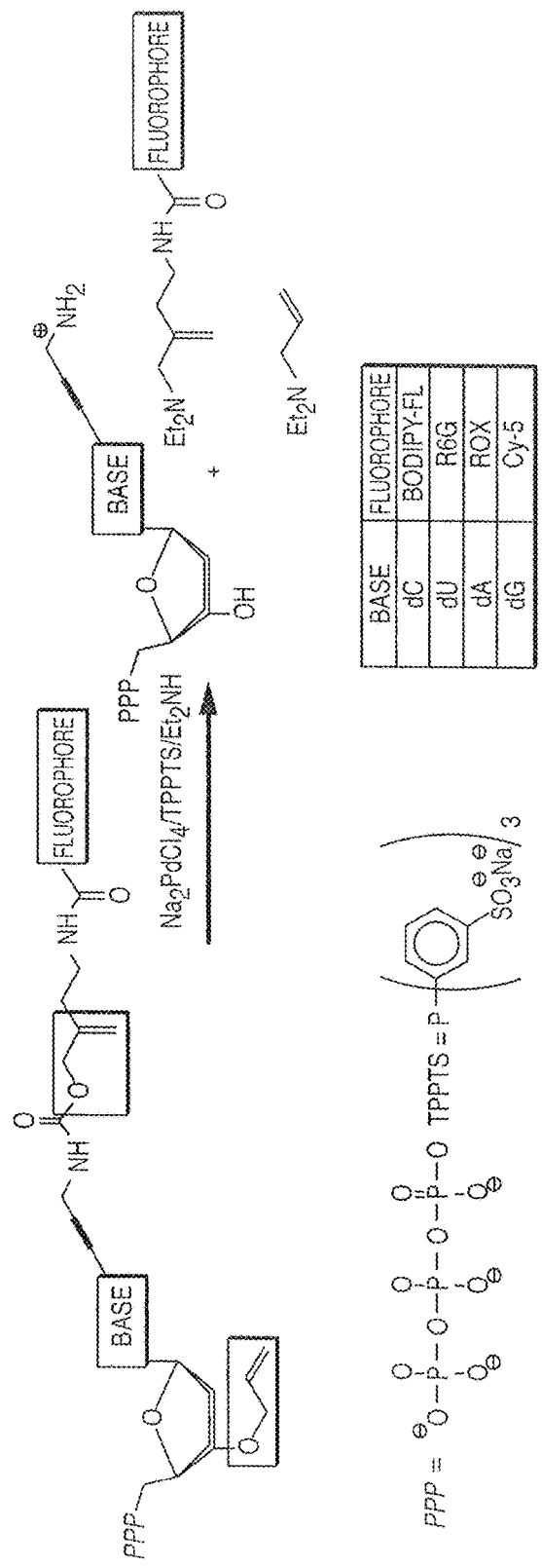
FIG. 5 shows a general structure of embodiments of cleavable fluorophore nucleotide conjugates with reversible terminator functionality. The 3'-OH group is reversibly blocked by an allyl ether function and the fluorophore is attached via a cleavable allyl carbamate linker (both shown in frames). After incorporation and signal readout, the fluorophore and the 3-O-allyl protective groups are cleaved by aqueous solution of Pd (0).

In one embodiment, the chip containing the array of nucleic acid spots is processed in a transparent flow cell incorporated within the instrument, which flows reagent past the spots and produces the signals required for sequencing (see FIGS. 2A and 2B). In a particular embodiment, the chip remains in the flow cell while it is imaged by the LED detector. The flow cell and associated reagents adds the nucleic acids, enzymes, buffers, etc. that are required to produce the fluorescent signals for each sequencing step, then the flow cell delivers the required reagents to remove the fluorescent signals in preparation for the next cycle. Measurement by the detector occurs between these two steps. In order for reactions to take place, the flow channels are configured to be of sufficient dimensions. For example, in one embodiment, the flow-cell fluid channel formed by the array and the flat surface of the flow cell are at least 0.1 mm in depth (more particularly 0.5 mm in depth) and the volume formed by the chip, the block and the seal is at least 100 microliters in volume (more particularly, between 100 and 700 microliters, and still more particularly, between 150 and 300 microliters, e.g. 200 microliters, in volume). Where a plurality of smaller flow cells is used, in one embodiment, the volume of reagents introduced into the flow cell is approximately 50 microliters or less, typically approximately 20 microliters.

In one embodiment, the flow cell is motionless (i.e., not moved during reactions or imaging). On the other hand, the flow cell can readily be mounted on a rotary or one or more linear stages, permitting movement. For example, in a two flow cell embodiment, the two flow cells may move up and down (or side to side) across the imaging system. Movement may be desired where additional processes are desired (e.g., where exposure to UV light is desired for photochemical reactions within the flow cell, such as removal of photocleavable fluorescent labels), when multiple flow cells share a single camera, or when the field of view of the detection system is smaller than the desired area to be measured on the flow cell. The detector system may also be moved instead of or in addition to the flow cell.

In a further embodiment, the flow cell is in fluid communication with a fluidics system (see illustrative system shown in FIG. 3A-B. In one embodiment, each bottle is pressurized with a small positive gas pressure. Opening the appropriate valve allows reagent to flow from the source bottle through the flow cell to the appropriate collection vessel(s). In one embodiment, the nucleotides and polymerase solutions are recovered in a separate collection bottle for re-use in a subsequent cycle. In one embodiment, hazardous waste is recovered in a separate collection bottle. The bottle and valve configuration allow the wash fluid to flush the entire valve train for the system as well as the flow cell. In one embodiment, the process steps comprise: 1) flushing the system with wash reagent, 2) introducing nucleotides (e.g. flowing a nucleotide cocktail) and polymerase, 3) flushing the system with wash reagent, 4) introducing de-blocking reagent (enzyme or compounds capable of removing protective groups in order to permit nucleic acid extension by a polymerase), 5) imaging, 6) introducing label removing reagent (enzyme or compounds capable of removing fluorescent labels), and 7) flushing the system with wash reagent. In one embodiment of the present invention, the steps described above can be achieved by moving a flow cell to different ports/locations.

In the embodiment with moving flow cells (described above), the fluid path from the source reagent bottles (or reservoirs) to the pump is intermittently broken by the disconnecting of the flow cells from the station (prior to the next movement). Were the fluid allowed to return to the reagent bottles, the fluid would need to be pumped back through the tubing prior to filling a flow cell, thereby taking more time. Therefore, in a preferred embodiment, a check (or other type of) valve may be used to assure that fluids to not flow out of the tubing back to the reagent bottles. This approach is also useful, given the precise volume may be unknown since a full bottle would start with the fluid level in the dip tube closer to the flow cell than a nearly empty bottle.

Having the reagent sources (e.g. reservoirs) below the flow cell serves as a backup strategy. In this regard, should the check valve as described above fail for any reason, then fluids in the tubing would flow back to the source bottles rather than out through the station ports and onto the bottom of the instrument.

It is also important, in the moving flow cell embodiment, that fluid may be maintained in the flow cell (when desired) after it is disconnected from the station ports and while it is being moved from one position ("station") to another. This can be achieved by a number of approaches. For example, this can be achieved with a flow cell design that does not allow fluid to entirely exit due to horizontal orientation, as well as due to small dimensions, which allows the viscosity of the fluids to help keep them stationary relative to the flow cell. Alternatively, this can be achieved with valving within the flow cell.

The mechanics of connecting and disconnecting flow cells at each station can be done in a number of ways. In a preferred embodiment, the present invention contemplates a reagent source (e.g. reservoir) on one port, and a pump on other side, automatically detachable from both connections prior to movement of the flow cell.

In one embodiment, the present invention contemplates systems, methods and instruments employing two cameras. As shown in FIG. 64C, each of the cameras is dedicated to measuring two of the four colors in the system. For example, while camera number 1 is measuring the blue and yellow channel, camera number 2 is measuring the green and red channels. In one embodiment, the cameras are used with 28× magnification. Where two 5 megapixel un-cooled CCD cameras are used, very high resolution lenses are preferred. A further advantage to using the pair of cameras is that the CCD chip is significantly smaller in the 5 megapixel camera (11 mm vs. 51 mm diagonal) as compared to higher pixel-count camera chips, which leads to greater uniformity of image illumination and less optical distortion at the image edges.

In one embodiment, more than one color is illuminated at a time. Most fluorescent microscopes that use epi-illumination (light follows the same path as the image through the objective) illuminate only one color at a time. By contrast, in a preferred embodiment (FIGS. 64A, 64B, and 64C) of the dual camera system, two different fluorescent dyes are measured simultaneously by the two cameras. In one embodiment, dichroic mirrors are used to split out the long wavelength light from the shorter wavelength light. FIGS. 64B and 64C show the filters, mirrors and optical path for one embodiment of a dual camera system.

In a preferred embodiment, LED (light emitting diode) illumination is used instead of the typical laser or incandescent white light illumination. Within just the past few years, breakthroughs in LED technologies have given rise to ultra-bright LED systems. For example, Luminus Devices (Billerica Mass.) makes LEDs that are nearly an order of magnitude brighter than those available just three years ago. They are available in blue, green and red (and an amber LED will be launched in early 2010). Spectra for these are close enough to the excitation spectra for the preferred four dyes (Alexa 488, Cy3, Texas Red and Cy5) used for labeling the nucleotide analogues.

LEDs are far superior to incandescent systems, since their lifetime is measured in tens of years rather than months. It used to be that conventional white light incandescent systems were able to put more light through an epi-illumination system than an LED based system. Now the opposite is true. Depending on the color, one is able to get 2 to 5 times the amount of light onto the nucleic acid sequencing chip as compared to a current white light system.

Figure 65A:
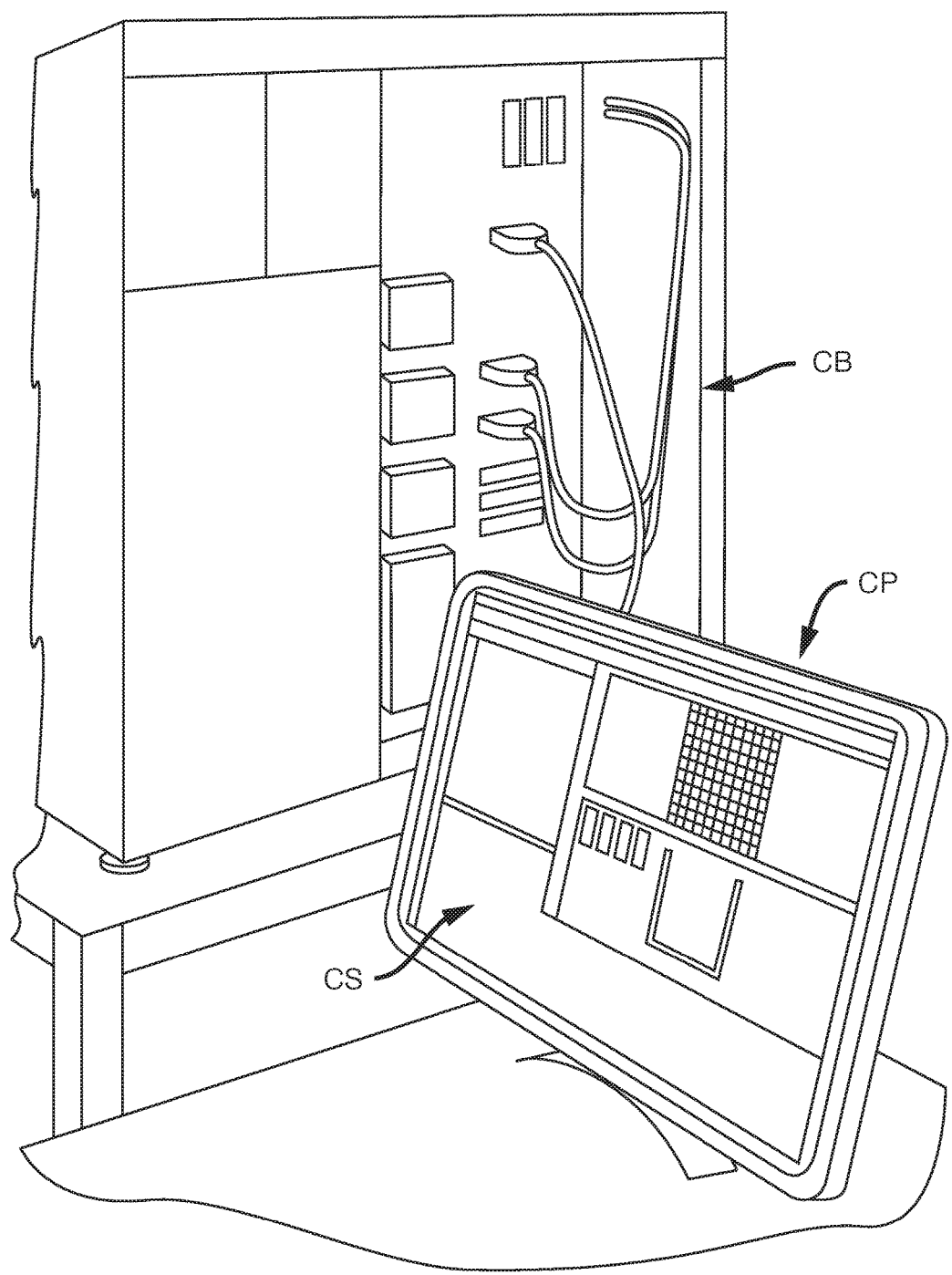
Figure 65B:
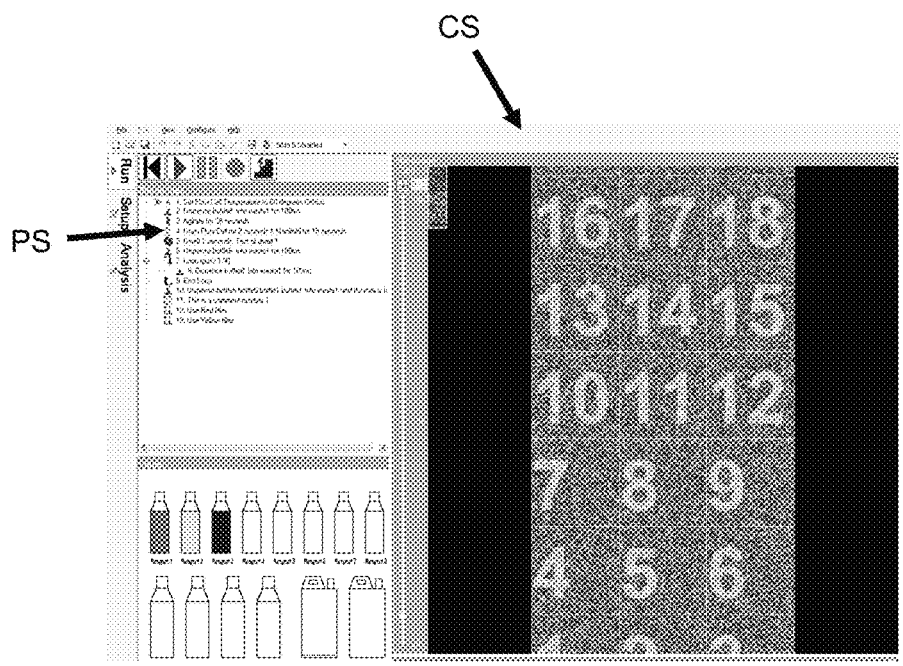
FIG. 65B a picture of a version of the software user interface that shows some steps in a protocol (PS) and some data (simulated) on a chip.
Figure 67:
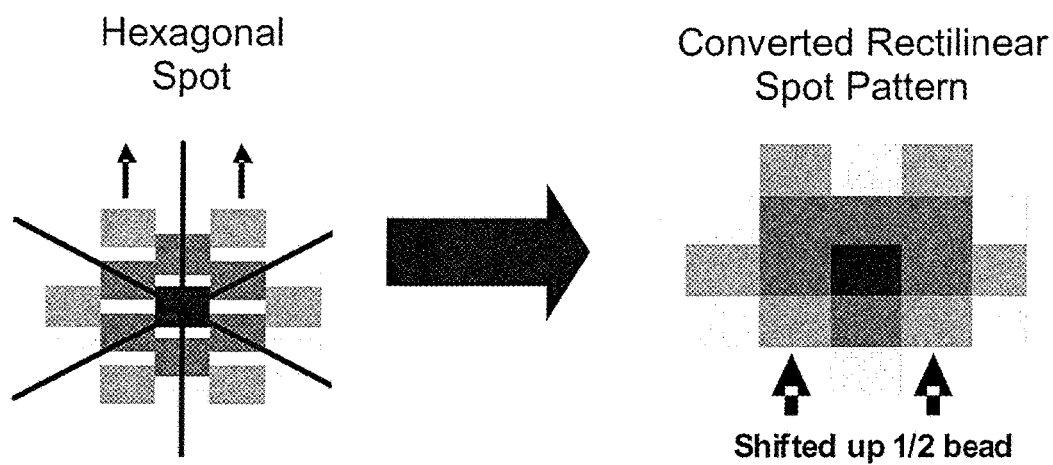
FIG. 67 shows a visual representation of a solution to the neighbor influence problem from spot data that is in hexagonal form. The data is first put into a rectilinear array by shifting the even vertical columns up by ½ of a pixel. A two-dimensional rectilinear matrix, whose elements represent the magnitude of each spot in the original image of the hexagonal array of spots, may be used.

The system can be made to include a user interface system. The Labview (National Instruments, Austin, Tex.) system is available and provides software for computer controlled systems. Galil Motion Control (Rocklin, Calif.) provides motion control systems that can be interfaced to control the instrument. FIG. 65A shows a control board (CB) of the system in communication with a computer screen (CS) which serves as a user interface, wherein the interface is in electronic communication with the computer processor (CP). FIG. 65B shows a closeup of the computer screen, allowing for the control over reagents and the sequencing protocol steps (PS).

C. Nucleotides

The invention's compositions and methods contemplate using nucleotide sequences that contain nucleotides. The terms "nucleotide" and "nucleic acid" and "nucleic acid" refer to constituents of nucleic acids (DNA and RNA) that contain a purine or pyrimidine base, such as adenine (A), guanine (G), cytosine (C), uracil (U), or thymine (T)), covalently linked to a sugar, such as D-ribose (in RNA) or D-2-deoxyribose (in DNA), with the addition of from one to three phosphate groups that are linked in series to each other and linked to the sugar. The term "nucleotide" includes native nucleotides and modified nucleotides.

FIG. 66A shows one embodiment of a modified nucleotide comprising an acyclic structure lacking the (deoxy)ribose furanose ring. FIG. 66B shows a modified nucleotide comprising the furanose ring. PG1 stands for protective group that is selectively removable and, and CL stands for cleavable linker, which is also selectively cleavable. Several particular embodiments of this invention are contemplated. In one embodiment these nucleotide compositions can be incorporated into the nucleic acid by nucleic acids modifying enzymes in a controlled fashion, for example to decode the identity of the bases encoded by the marker moiety M. Once the identity of the base has been decoded, then the marker moiety can be cleaved off and removed. The present invention contemplates using either or both in the sequencing protocol. Both can have a variety of different labels and protecting groups (as described herein).

"Native nucleotide" refers to a nucleotide occurring in nature, such as in the DNA and RNA of cells. In contrast, "modified nucleotide" refers to a nucleotide that has been modified by man, such as using chemical and/or molecular biological techniques compared to the native nucleotide. The terms also include nucleotide analogs attached to one or more probes to facilitate the determination of the incorporation of the corresponding nucleotide into the nucleotide sequence. In one embodiment, nucleotide analogues are synthesized by linking a unique label through a cleavable linker to the nucleotide base or analogue of the nucleotide base, such as to the 5-position of the pyrimidines (T, C and U) and to the 7-position of the purines (G and A), to use a small cleavable chemical moiety to cap the 3'-OH group of the deoxyribose or ribose to make it nonreactive, and to incorporate the nucleotide analogues into the growing nucleotide sequence strand as terminators, such as reversible terminators and irreversible terminators. Detection of the unique label will yield the sequence identity of the nucleotide. Upon removing the label and the 3'-OH capping group, the polymerase reaction will proceed to incorporate the next nucleotide analogue and detect the next base. Exemplary fluorescent moieties and fluorescent semiconductor crystals are described in Ju et al., U.S. Pat. No. 6,664,079, hereby incorporated by reference.

Other nucleotide analogs that contain markers, particularly cleavable markers, are also contemplated, such as those configured using allyl groups, azido groups, and the like, and which are further described below. The nucleotide compositions of the invention are particularly useful in massively parallel DNA Sequencing By Synthesis (SBS) approaches utilizing fluorophores as markers.

a. Allyl Analogs

Cleavable fluorescent nucleotides with photo-cleavable linkers having reversible terminator allyl groups have been described in Ruparel et al. (2005) Proc. Natl Acad. Sci. 102(17) 5932-7. Similar, fluorescent nucleotide conjugates have been described in Bi et al. (2006) J. Am. Chem. Soc. 128(8) 2542-3. In one embodiment, the invention contemplates using nucleotide analogs with cleavable markers conveniently configured with allyl groups. In a particular embodiment, the exposed amine groups of incorporated nucleotides are capped during sequencing. In other embodiments, the nucleotide derivatives comprise two or more allyl ethers and synthetic intermediates thereto.

Sample preparation and parallel sequencing steps are exemplified, but not limited, to those illustrated in FIGS. 4 A-B and 5. FIG. 4 A shows how one isolates and prepares the DNA prior to sequencing and FIG. 4 B shows the sequencing cycle. One isolates DNA from a biological source and shears it by a mechanical device to the desired average size. One end-repairs, A-tails, and circularizes the fragments using a dT-tailed linker about 100 nucleotides in length. The linker consists of two outward directed primer recognition sequences and an arbitrary sequence of about 100 bases between the priming sites. After ligation, one decomposes noncircular sequences by treatment with an endonuclease. One dilutes the circular DNA fragments to prepare them for bead-based emulsion PCR using a biotinylated forward primer and a bead-attached reverse primer carrying an azido group on its 5'-end. One performs emulsion PCR. An aqueous mix containing all the necessary components for PCR plus primer-bound beads and template DNA are stirred together with an oil/detergent mix to create microemulsions. The aqueous compartments contain an average of less than one template molecule and less than one bead. The microemulsions are temperature-cycled as in a conventional PCR. If a DNA template and bead are present together in a single aqueous compartment, the bead-bound oligonucleotides act as primers for amplification. One breaks the emulsion and subjects the mixture to an enrichment step by using streptavidin coated magnetic beads. One denatures the nucleic acid immobilized on the beads generating single stranded amplicons to which a self-priming hairpin moiety is then ligated.

The beads are then arrayed on a chip surface and the sequencing by synthesis reactions are performed. Each cycle comprises steps that are used to read out the DNA sequence (See FIG. 4, B). One subjects the array segment to the fluorescent nucleotide conjugate with a hydroxyl-protecting group on the 3' end. One scans the array and the fluorescent output of each of the fluorescent markers and measures the output for each position. One exposes the array to conditions for cleavage of the fluorescent marker and the hydroxyl-protecting group. The entire process is repeated with another set of nucleotide bases unit the sequence of each position is determined. As the sequence data is generated, one collects the sequence information and aligns the reference sequences for diagnosis. One may use computer software and a database of previously known mutations and corresponding sequences to correlate them to the sequence with known mutations.

The PCR approach described above ensures that instead of sequencing of the entire pool of templates, one performs clonal or digital sequencing, resulting in much higher sensitivity for detection of mutations. For example, if a spontaneous mutation is present at only 5% of the population and the remaining 95% of the gene copies are wild types it is difficult to detect the mutated DNA using a conventional pool sequencing approach because of insufficient sensitivity. In the applicants' approach, one dilutes the input sample so that each PCR emulsion bubble contains at most a single template, which is then subjected to sequencing. If one performs this process on 1,000 unique clones, then one on average detects mutant sequences (present in 5% of amplicons) in 50 reactions and wild type sequence in 95% of the reactions.

b. Azido Analogs

Nucleotide analogs that contain cleavable markers configured using azido groups are also useful in the invention's methods and compositions. The nucleotide analogs are exemplified by

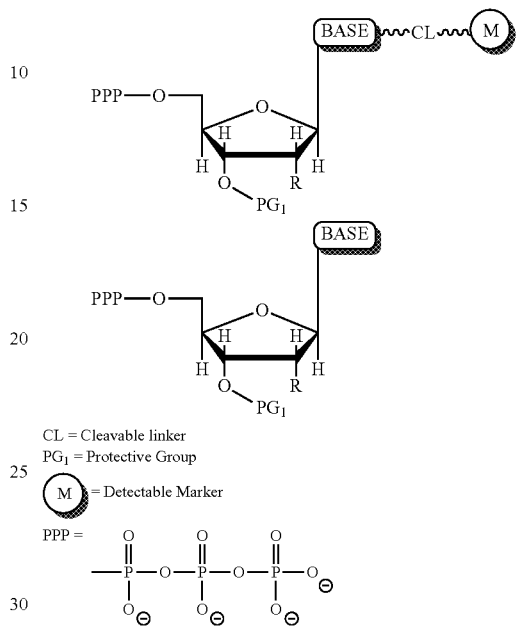

CL = Cleavable linker
PG₁ = Protective Group
M = Detectable Marker

PPP =

$$-\overset{O}{\underset{O_{\ominus}}{\overset{\|}{P}}}-O-\overset{O}{\underset{O_{\ominus}}{\overset{\|}{P}}}-O-\overset{O}{\underset{O_{\ominus}}{\overset{\|}{P}}}-O_{\ominus}$$

nucleotide compositions of the above general structure (and the structures in FIG. 66 A-B), where PG1 stands for protective group that is selectively removable and, and CL stands for cleavable linker, which is also selectively cleavable, and R is selected from the group of H, OH, F, $NH_2$. Several particular embodiments of this invention are contemplated. In one embodiment these nucleotide compositions can be incorporated into the nucleic acid by nucleic acids modifying enzymes in a controlled fashion to decode the identity of the bases encoded by the marker moiety M. Once the identity of the base has been decoded, then the marker moiety can be cleaved off and removed. This invention contemplates the use of the cleavable linkers based on the "trimethyl lock" mechanism or the "1,6-rearrangement" mechanism. The 3'-O-protective groups, which act as reversible terminators, can also be cleaved off to enable addition of the next nucleotide. This invention contemplates the use, of azidomethyl, methylaminoxy, disulfide and allyl groups as reversible 3'-OH terminators.

Methods for synthesizing exemplary nucleotide analogs that contain cleavable markers configured using azido groups are described in Examples 2-11 and shown in FIGS. 20-26.

The invention contemplates the use of the cleavable linkers based on the "trimethyl lock" mechanism or the "1,6-rearrangement" mechanism. The 3'-O-protective groups which act as reversible terminators can also be cleaved off to enable addition of the next nucleotide. The invention contemplates the use of azidomethyl, aminooxy, methylaminoxy and allyl groups as reversible 3'-OH terminators.

i. Cleavable Linkers (Cl)

Cleavable linkers are exemplified by trimethyl lock based linkers and 1,6-rearrangement linkers as further described below.

1. Trimethyl Lock Based Linkers

Cleavable linkers are the linkers linking the marker molecule M to the base and these can be selectively cleaved using specific cleaving agents. Specifically, this invention contemplates the use of a "trimethyl lock" structure as the cleavage mechanism. These structures are well known in the chemical arts and have been used before in controlled drug release applications. The general structures of cleavable trimethyl lock based linker utilized in particular embodiments of the present invention are shown below:

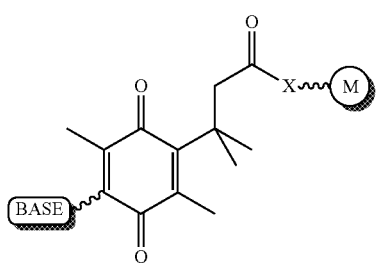

The above shows exemplary embodiment A where BASE is selected from any ribo- or deoxyribo-nucleobases: adenosine, cytidine, guanosine, thymidine and analogs, M is a detectable marker, and X is a divalent group selected from NH, O, S.

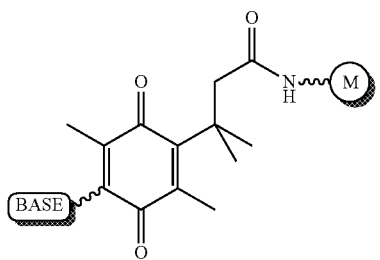

The above shows exemplary embodiment B where BASE is selected from any ribo- or deoxyribo-nucleobases: adenosine, cytidine, guanosine, thymidine and analogs, M is a detectable marker, and X is NH.

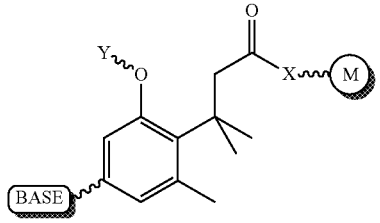

The above shows exemplary embodiment C where BASE is selected from any ribo- or deoxyribo-nucleobases: adenosine, cytidine, guanosine, thymidine and analogs, M is a detectable marker, and X is a divalent group selected from NH, O, S, and Y is a selectively removable protective group.

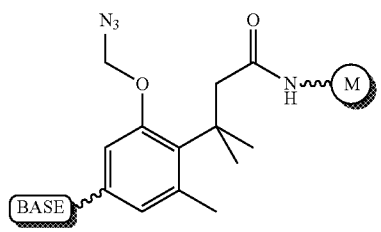

The above shows exemplary embodiment D where BASE is selected from any ribo- or deoxyribo-nucleobases: adenosine, cytidine, guanosine, thymidine and analogs, M is a detectable marker, X is NH, and Y is an azidomethyl group.

Figure 6:
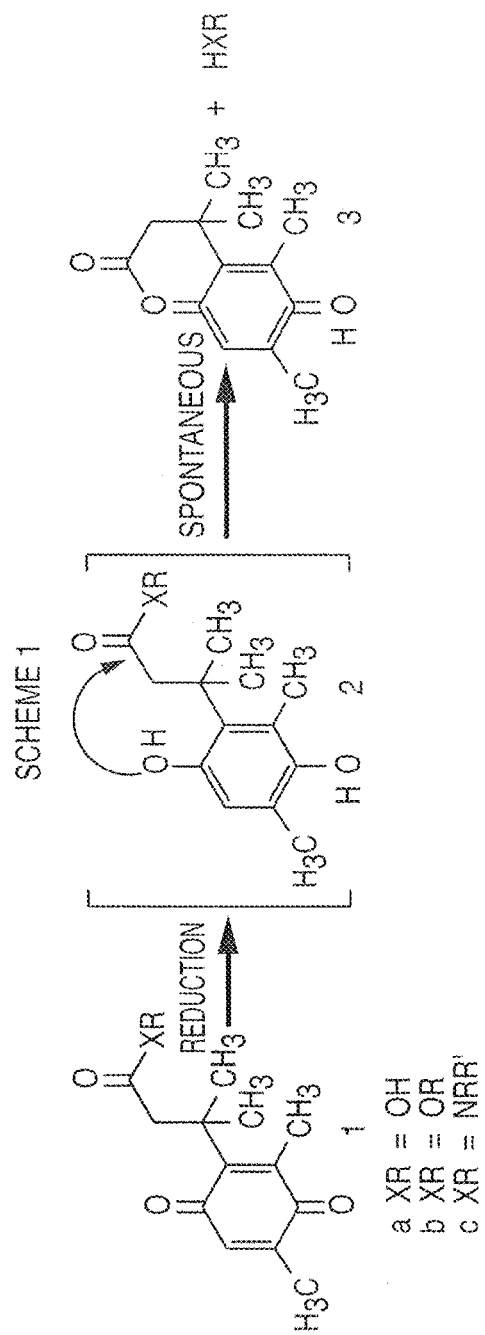
FIG. 6 shows a cleavage mechanism for trimethyl look based compounds.

The cleavage mechanism for the trimethyl lock based compounds is shown schematically in FIG. 6. This phenomenon has been previously described in the chemical literature and used as for basic research studies (Borchardt and Cohen (1972). J. Am. Chem. Soc. 94(26): 9166-9174, Wang et al. (1996) Bioorg. Chem. 24: 39-49), as caging agents for controlled drug delivery (Wang et at (1997). J. Org. Chem. 62(5): 1363-1367) and as protective groups in organic synthesis (Wang et al (1995). J. Org. Chem. 60(3): 539-543).

The linkers in the present invention leverage the ability of the trimethyl lock system to create cleavably linked nucleotides.

2. 1,6-Rearrangement Linkers

The invention contemplates another category of cleavable linkers linking the detectable marker moiety to the nucleotide that are based on 1,6 quinone methide rearrangement mechanism (Carl at al. (1981). J. Med. Chem. 24(5):479-480; Duimstra et at (2005). J. Am. Chem. Soc. 127(37): 12847-12855). These structures are well known in the chemical arts and they have been used before for the controlled drug release applications and for chemical synthesis (Azoulay et al. (2006) Bioorganic & Medicinal Chemistry Letters 16(12): 3147-3149; Murata et al. (2006) Tetrahedron Letters 47(13): 2147-2150). The general structures of cleavable 1,6 rearrangement mechanism based linker utilized in some embodiments of the present invention are shown below:

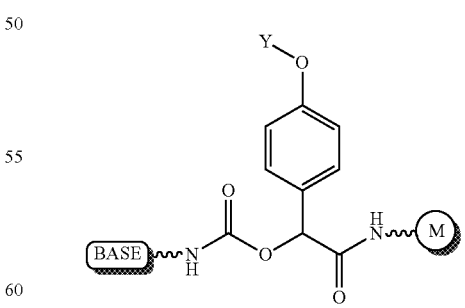

The above shows exemplary embodiment E, where BASE is selected from any ribo- or deoxyribo-nucleobases: adenosine, cytidine, guanosine, thymidine and analogs, M is a detectable marker and Y is a selectively removable protective group.

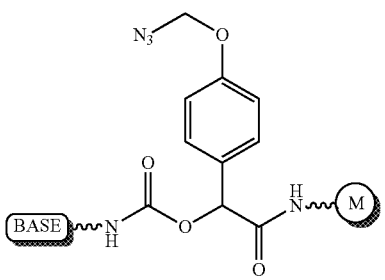

The above shows exemplary embodiment F, where BASE is selected from any ribo- or deoxyribo-nucleobases: adenosine, cytidine, guanosine, thymidine and analogs, M is a detectable marker.

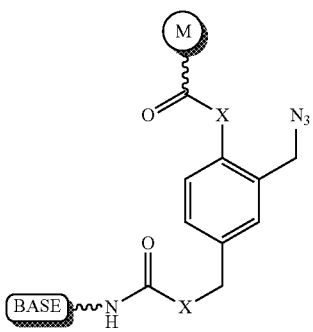

The above shows exemplary embodiment G where BASE is selected from any ribo- or deoxyribo-nucleobases: adenosine, cytidine, guanosine, thymidine and analogs, M is a detectable marker, and X is a divalent group selected from the following: NH, O, S.

Figure 7:
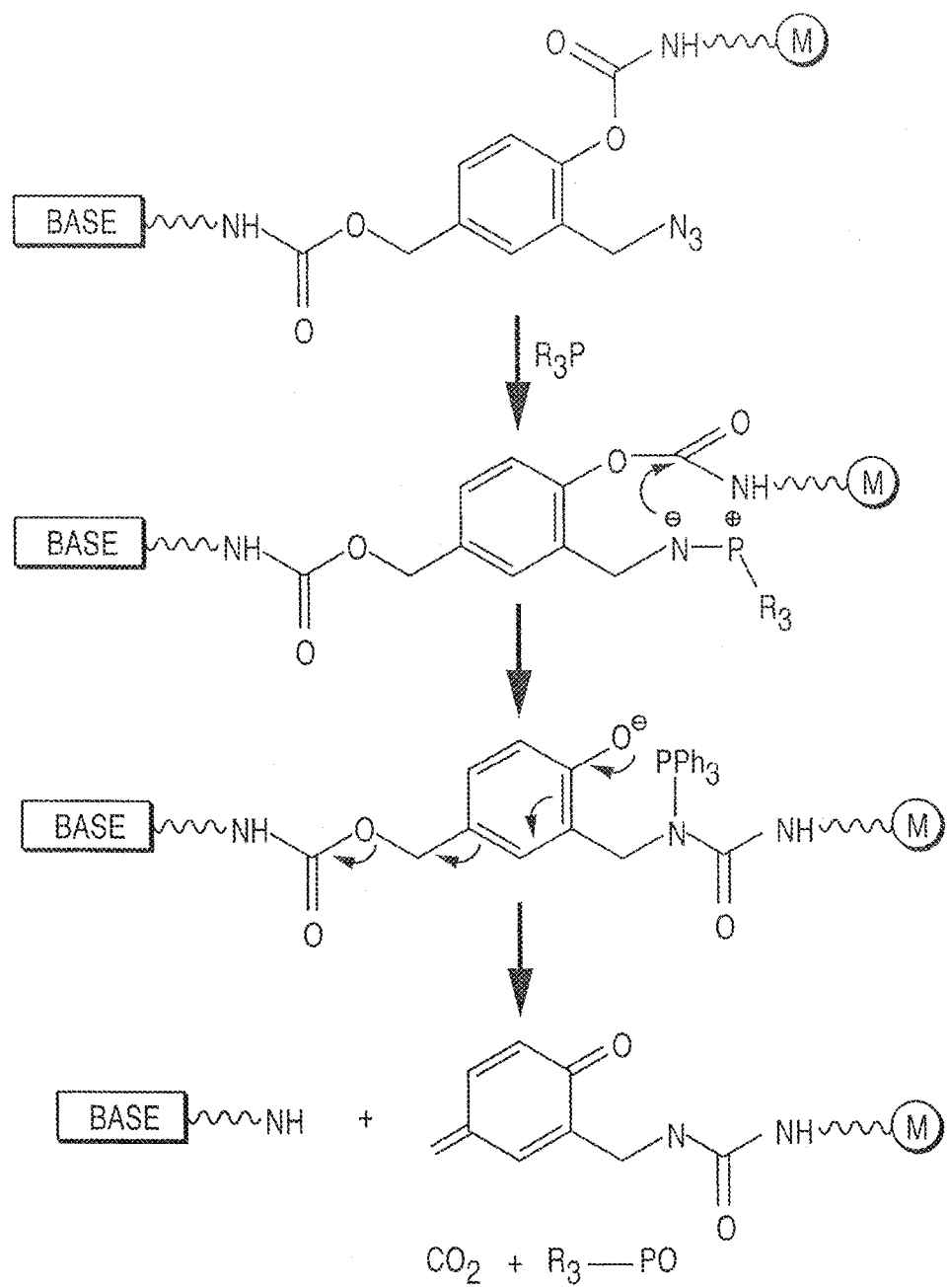
FIG. 7 shows a cleavage mechanism for 1,6-rearrangement based compounds.

FIG. 7 shows an exemplary cleavage mechanism for the cleavable linker described in the following exemplary embodiment G.

A)

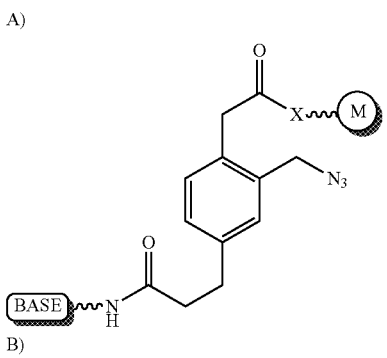

B)

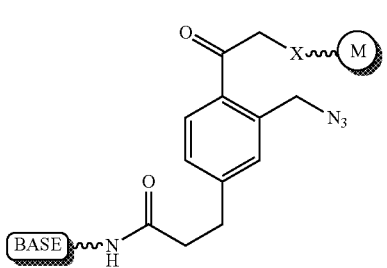

The above shows exemplary embodiment H where BASE is selected from any ribo- or deoxyribo-nucleobases: adenosine, cytidine, guanosine, thymidine and analogs, M is a detectable marker, and X is a divalent group selected from the following: NH, O, S. The cleavage is driven here by the reducing agent and nucleophilic attack of the resulting amino group on the carbonyl followed by cyclization. This mechanism has been used before for the development of protective groups for applications in the carbohydrate and nucleoside chemistry (Wada et al. (2001). Tetrahedron Letters 42(6): 1069-1072; Xu et al. (2002) Carbohydrate Research 337(2): 87-91).

The cleavable linker attachment to the base moiety can be achieved in variety of ways that are well known in the art. Among these is the use of linkers based on 1) propargylamino nucleosides, 2) aminoallyl nucleosides, 3) propargylhydroxy nucleosides, and 4) hydroxymethyl nucleotides as described in co-pending application Ser. No. 61/171,975, hereby incorporated by reference.

A variety of cleavable linkers can be used in this invention and are described in the literature. The linkers may be cleavable chemically, cleavable by light or by other physical means. WO99/57321 describes the use of nucleotides comprising fluorophores linked to the nucleotide by chemically or photochemically cleavable linker moieties (Olejnik et al., Proc. Natl. Acad. Sci., 92:7590-7594 (1995). For example, the linkers could contain disulfide bonds (Mitra, R. D., Shendure, 3, Olejnik, J., Edyta-Krzymanska-Olejnik, and Church, G. M. (2003) Anal Biochem. 320(1):55-65) cleavable under reducing conditions (or contain cis-diol linkages cleavable by periodate (WO/53812). The linkers could also be cleavable by enzymes (WO 01/92284). Other types of acid or base, oxidative or reducing agent cleavable linkers are also contemplated as will be recognized by the skilled in the art. Examples of such linkers are described in the literature (Greene et al., Protective Groups In Organic Synthesis, Second Edition, John Wiley & Sons, (1991). One particularly useful cleavable linker contemplated by this invention is the linker comprising the substituted azidomethyl ether (WO2004/018493). Another preferred class of cleavable linkers comprise hydrocarbyldithiomethyl groups as described in the U.S. Pat. No. 7,279,563, hereby incorporated by reference.

ii. Protective Groups (PG1)

The invention contemplates nucleotide compositions comprising the following protective groups (PG1) that reside on the 3'-OH groups of the nucleotides: 1) 3'-O-Azidomethyl ethers, 2) 3'-O-disulfide, 3) 3'-O-methylaminoxy, and 4) 3'-O-ally.

With respect to the 3'-O-Azidomethyl ethers, exemplary protective groups that reside on the 3'-OH groups of the nucleotides that are within the scope of this invention are 3'-O-azidomethyl groups. These groups can be removed using mild reducing agents, such as Tris(2-carboxyethyl)phosphine (TCEP).

With respect to the 3'-O-disulfide group, the 3'-O-disulfide group can be removed under mild oxidative conditions, for example using in using mild reducing agents, such as Tris(2-carboxy-ethyl)phosphine (TCEP).

With respect to the 3'-O-methylaminoxy group, the 3'-O-methylaminoxy (3'-O—CH2-NH2) group can be removed under mild oxidative conditions, for example using in situ generated nitrous acid (such as from sodium nitrite).

As to the 3'-O-allyl group, this protective group can be removed using a variety of reducing agents, including transition metal complexes (Pd, Rh).

In one embodiment, a 3'-O—CH2-SSSS—R (3'-O-(Alkyl-tetrasulfanyl-methyloxy) group is also contemplated. The synthesis of these derivatives has been established and is described in the art (Tetrahedron, Vol. 61, Issue 4, 2005, 965-970) These protective groups can be removed using variety of reducing agents and is cleaved into the corresponding 3'-OH derivative, for example by using tris(carboxyethyl)phosphine (TCEP) (Int. J. of Mass Spectrometry, Volume 209, Issue 1, 24 Aug. 2001, Pages 47-55).

c. 3-O-Protected Nucleosides and Nucleotides

The invention contemplates compositions comprising compounds of the following general

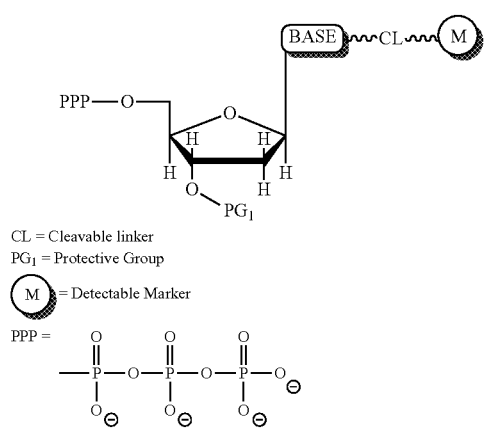

CL = Cleavable linker
PG$_1$ = Protective Group
M = Detectable Marker
PPP =

PG1 stands for protective group that is selectively removable and, and CL stands for cleavable linker, which is also selectively cleavable. In one embodiment these nucleotide compositions can be incorporated into the nucleic acid by nucleic acids modifying enzymes in a controlled fashion for example to decode the identity of the bases encoded by the marker moiety M. Once the identity of the base has been decoded, then the marker moiety can be cleaved off and removed. In one embodiment, the invention contemplates the use of cleavable protection for 3'-OH in nucleotides for reversible terminators for SBS.

Figure 28:
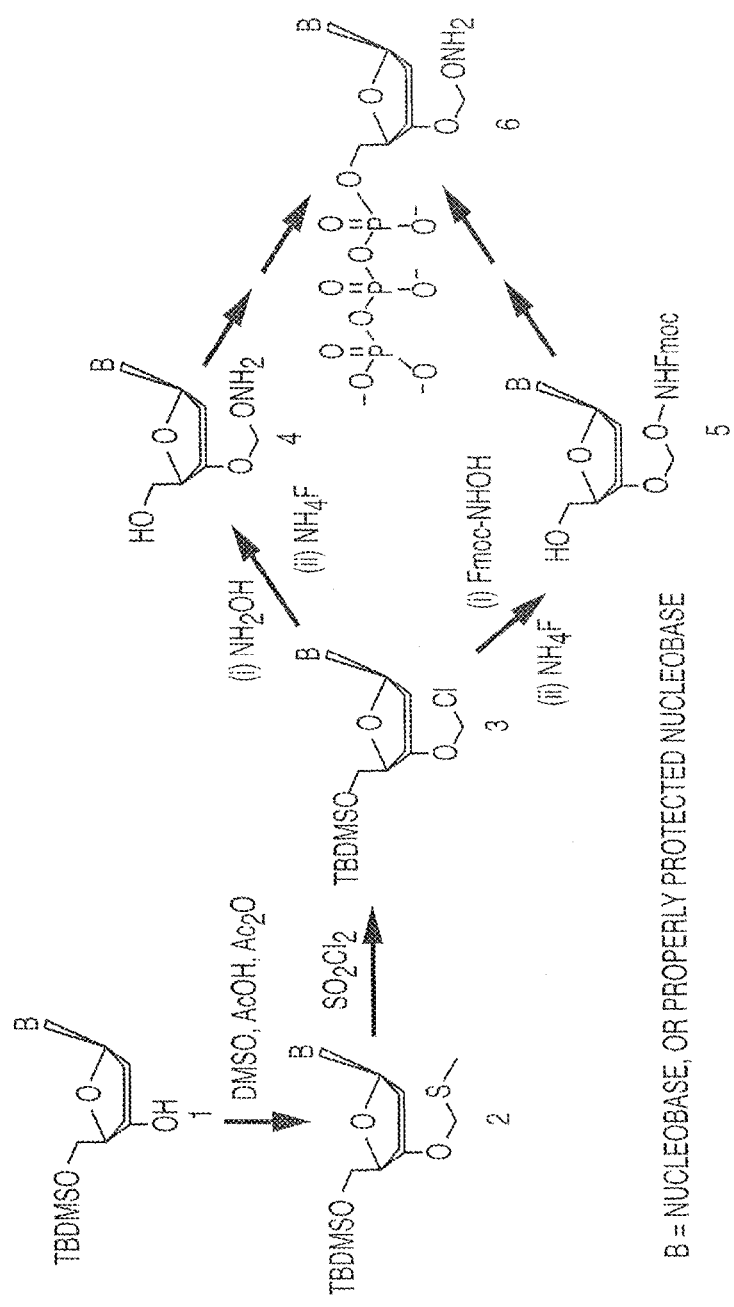
FIG. 28 shows an exemplary general synthetic pathway to install 3'-O amino hemiacetal group ($—CH_2ONH_2$) and conversion to nucleotides.
Figure 29:
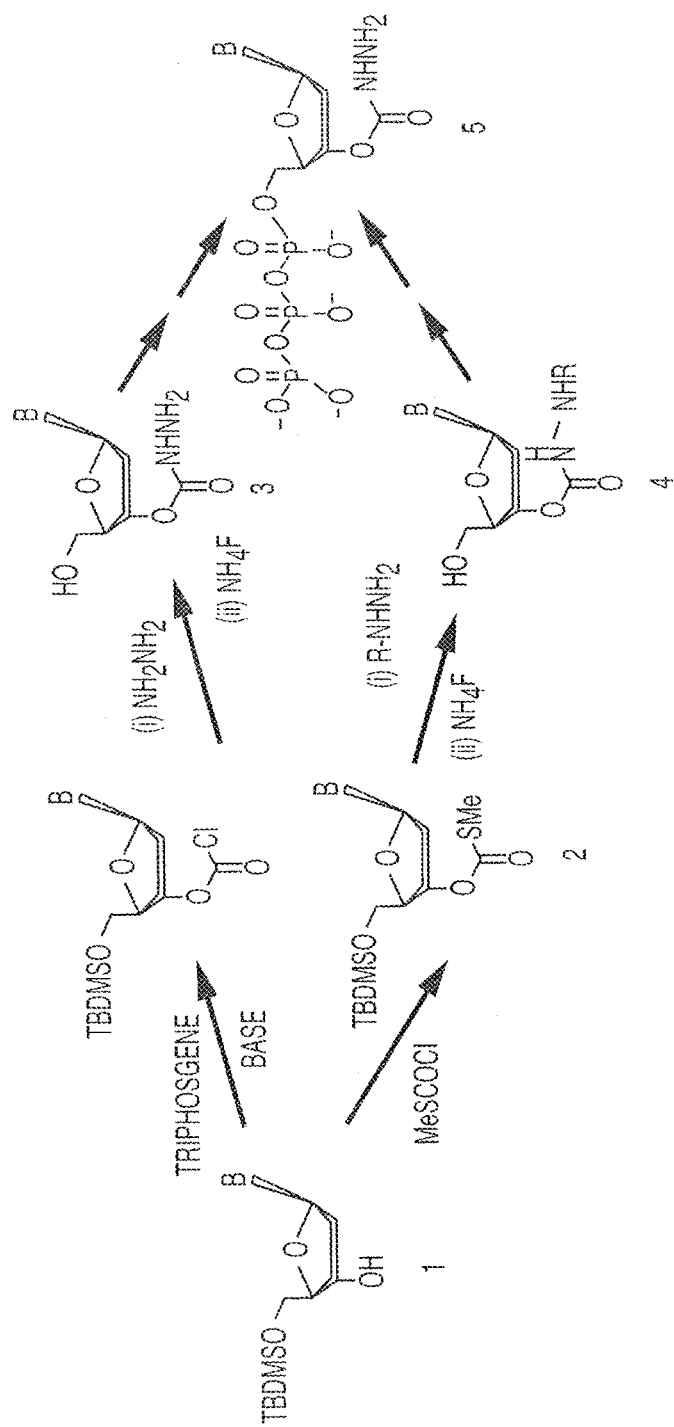
FIG. 29 shows an exemplary synthetic pathway to prepare 3'-O carbazate ($—CH_2ONH_2$) nucleotide analogues
Figure 30:
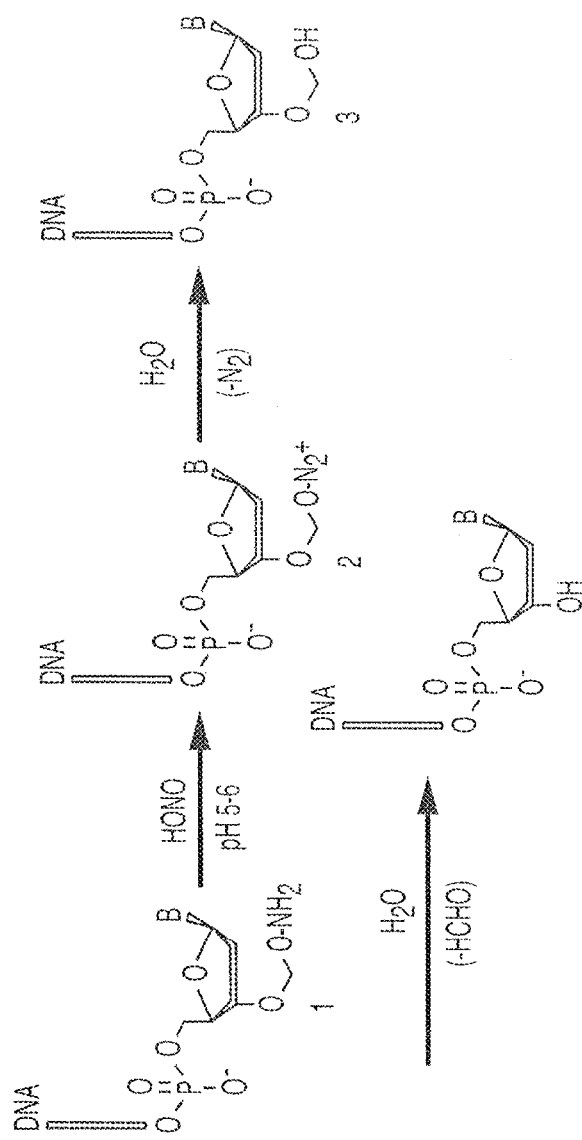
FIG. 30 shows an exemplary mechanism of 3'-O amino hemiacetal ($—CH_2ONH_2$) nucleotides deprotection reaction to generate free 3'-OH group.
Figure 31:
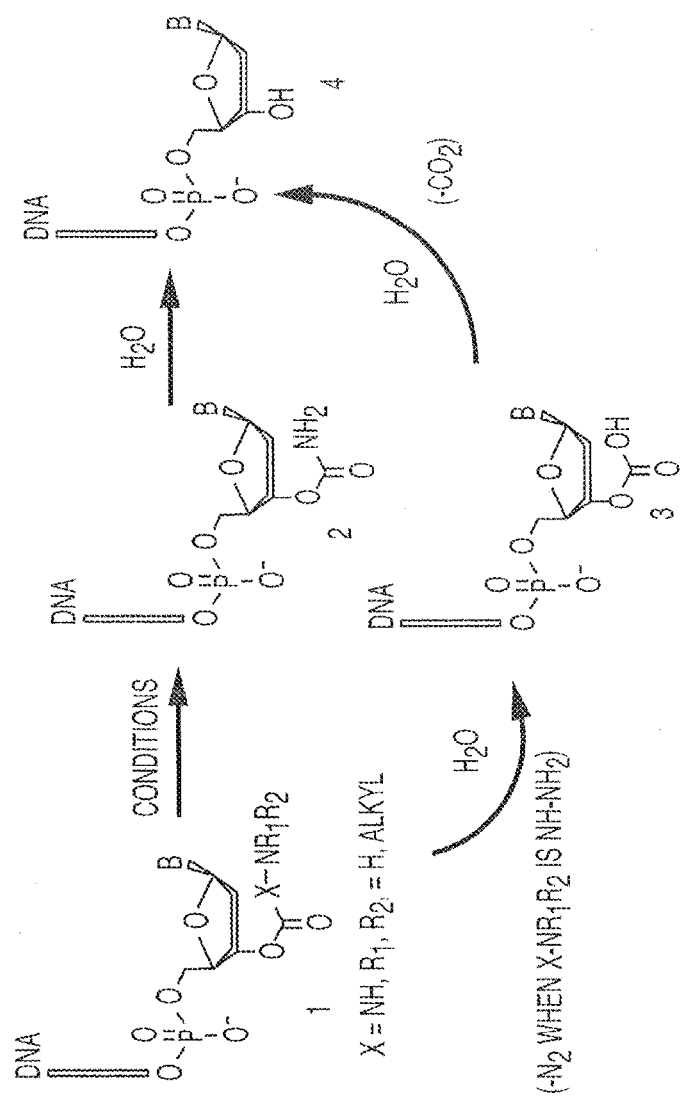
FIG. 31 shows an exemplary mechanism of 3'-O-carbazate ($—C(O)NHNH_2$) nucleotides deprotection. The reaction may be fast due to higher entropy contribution of the leaving molecular nitrogen and carbon dioxide gas.

Examples of PG1 protective groups are shown in FIG. 27. As an illustration, the synthesis of one of the embodiments in such classes of nucleotide-3'-O—(CH$_2$ONH$_2$)-dNTPs is presented in FIG. 28. Briefly, the protected 3'-methylthiomethyl nucleoside (I) upon treatment with SO$_2$Cl$_2$ produce activated product (2) which after reaction with hydroxylamine or its N-Fmoc protected compound install aminoxy group. The later compounds can be triphosphorylated to result in nucleotides. Other compounds and exemplary synthesis pathways within the scope of the invention are shown in FIGS. 29-31.

The nucleotide analogs compositions shown in FIG. 66A comprise the acyclic structure lacking the (deoxy)ribose furanose ring. These nucleotide analogs have been described (Gardner, A. F. and Jack, W. E. (2002) Nucl. Acids Res., 30, 605-613) and can be incorporated with high efficiency into the DNA by archeon and Taq DNA polymerases. These analogs compared to regular deoxyribose and ribose analogs lack the furanose ring and are easier to synthesize. The same Archeon polymerase's mutants are also known to incorporate a variety of terminating nucleotides (Gardner, A. F. and Jack, W. E. (1999) Nucl. Acids Res., 27, 2545-2555). In addition this invention contemplates the use of other suitable nucleotide analogs that have the ability to form the correct pairing with the nucleic acid molecules and are incorporated by enzyme or by chemical means. Examples of these include, but are not limited to 2',3'-Dideoxy-3'-thionucleotides and their reversibly 3'-protected forms (Organic Letters, 2007, Vol. 9, No. 6, 1161-1163), Glycerol Nucleoside Triphosphates (Organic Letters 2006, Vol. 8, No. 23, 5345-5347) α-L-Threofuranosyl nucleoside triphosphates (Am. Am. Chem. Soc. 2003, 125, 856-857).

D. Reducing Lead and Lag

Figure 35:
FIG. 35 provides examples of chemical structures of the reversibly terminating nucleotides used in sequencing. These examples include: 3'-azidomethyl nucleotides, 3'-O-aminoxy nucleotides, 3'-O-allyl nucleotides; and disulfide nucleotides.
Figure 36:
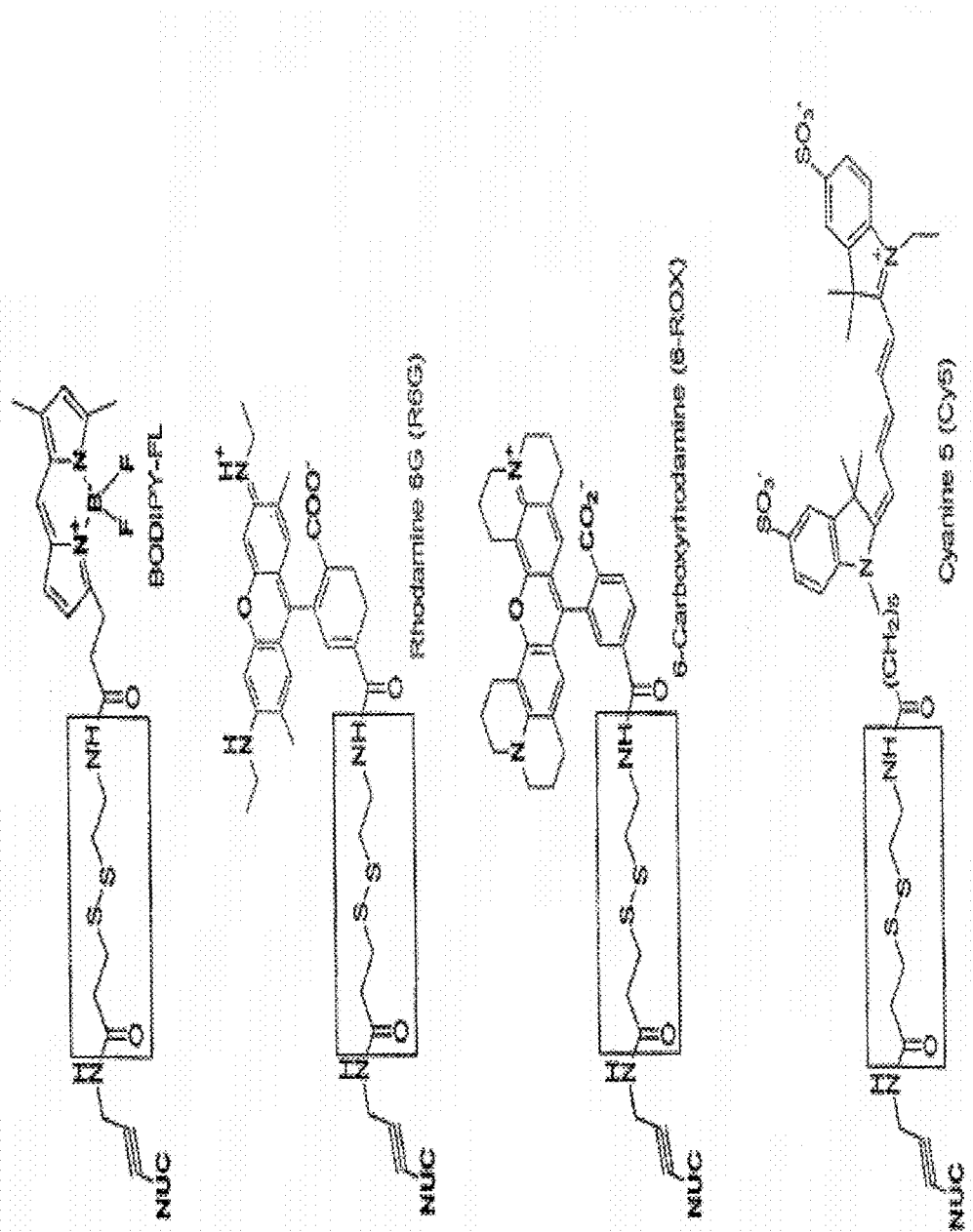
FIG. 36 provides examples of dyes conjugated to reversibly terminating nucleotides via a cleavable linker.

The cleaving agent is designed to cleave the 3'-OH or the dye attached to the nucleotide or both the 3'-OH and the dye. A variety of chemistries may be used for these attachments. FIG. 35 shows various possible chemistries for the 3'-OH group. FIG. 36 shows disulfide linkers for attaching the dye. Importantly, for any particular nucleotide, the chemistries may be same or may be different. For example, in one embodiment, the 3'-OH group can carry an azidomethyl ether and yet the dye can be attached via an azido linker. In another embodiment, however, the 3'-OH group can carry an azidomethyl ether and yet the dye can be attached via a disulfide linker. Both the azidomethyl ether and the disulfide linker are cleavable by TCEP (Tris-carboxyethyl)phosphine, although the disulfide linker cleaves much faster than the 3'-O-azidomethyl ether. In one embodiment, two cleavage steps are contemplated. In the case of disulfide cleavable linker and azidomethyl ether combination, a two-step cleavage could be used and is advantageous. Lower concentrations of the cleaving reagents can be used to achieve 2-step cleavage. This has an advantage of being able to better wash out the cleaving reagents after the cleavage is complete and, in this way, reduce any potential lead problems. This may also result in lower concentration of cleaving agent scavengers used in the extension steps. The cleaving agent scavengers need to be compatible with the polymerase and as such the working concentration may be limited. In the case of disulfide cleavable linker and azidomethyl ether combination, CLEAVE A could be any reagent that can cleave efficiently the disulfide bridge. In one embodiment, the use of simple thiols at low concentration is contemplated. For example, cysteamine, beta mercaptoethanol, dithiothreitiol, reduced glutathione could all be used at low concentration (1-2 mM) to achieve complete disulfide bridge cleavage. CLEAVE B would comprise, in one embodiment, a reducing agent capable of reducing azido group and resulting in self elimination and conversion of the aminomethyl ether to the hydroxyl group. This could be achieved by using variety of reducing agents, for example solutions of boroydrides, phosphines etc. (Chem Rev vol. 88, 297 (1988). One example of the cleaving agent is TCEP (Tris-carboxyethyl)phosphine which could be used in this case at a lower concentration, e.g., 10 mM. In another embodiment, the cleavage of the disulfide bridge is achieved using TCEP (Tris-carboxyethyl)phosphine at 1 mM concentration and at pH 5.5-6.0, while the cleavage of azidomethyl ether is achieved by using TCEP (Tris-carboxyethyl)phosphine at 10 mM an at pH 8-9.

In the case of one step cleavage, the cleaving agent is used at relatively high concentration (50-100 mM) to achieve fast and efficient cleavage at both locations. It is important for the sequencing process to remove any traces of cleaving agent in the wash steps, as these traces could interact with the Extend A and B solution (see the discussion of these solutions above) in the next cycle and create native nucleotides. This is highly undesirable as this leads to sequence dephasing (lead and lag) and limits useful read lengths.

One approach might be to increase the number of washes. However, it has been found empirically that increased washing cycles after cleavage step have only minimal effect on the sequencing performance unless very high numbers of washes are used (see Example 14). Such an approach would slow down the process considerably.

The present invention, in one embodiment, contemplates a different approach to solving the problem. In one embodiment, the present invention contemplates novel compositions to be used in one or more of the solutions employed in the sequencing by synthesis method (or in a new, additional separate solution) that reduce, minimize and/or inhibit the cleaving agent and the "pre-cleaving" effect. In one embodiment, a cleavage agent "scavenger" is contemplated. The cleavage agent scavenger is designed to react with any leftover cleaving reagent remaining in the flow cell or the fluidics (e.g. tubing) by inefficient or incomplete washing. In one preferred embodiment, the scavenger agent is added to the wash solution directly after the cleave step. In another embodiment the scavenger is added to the Extend A solution. In yet another embodiment the scavenger agent is added to Extend B solution. The scavenger requirements are as follows: I) solubility, 2) fast and specific reaction with the cleaving agent. In the embodiments where the scavenger is added to Extend A or B solution, there is the additional requirement of lack of inhibition of polymerase reaction and lack of reactivity with functional groups on the nucleotides, dyes or polymerase.

Figure 37:
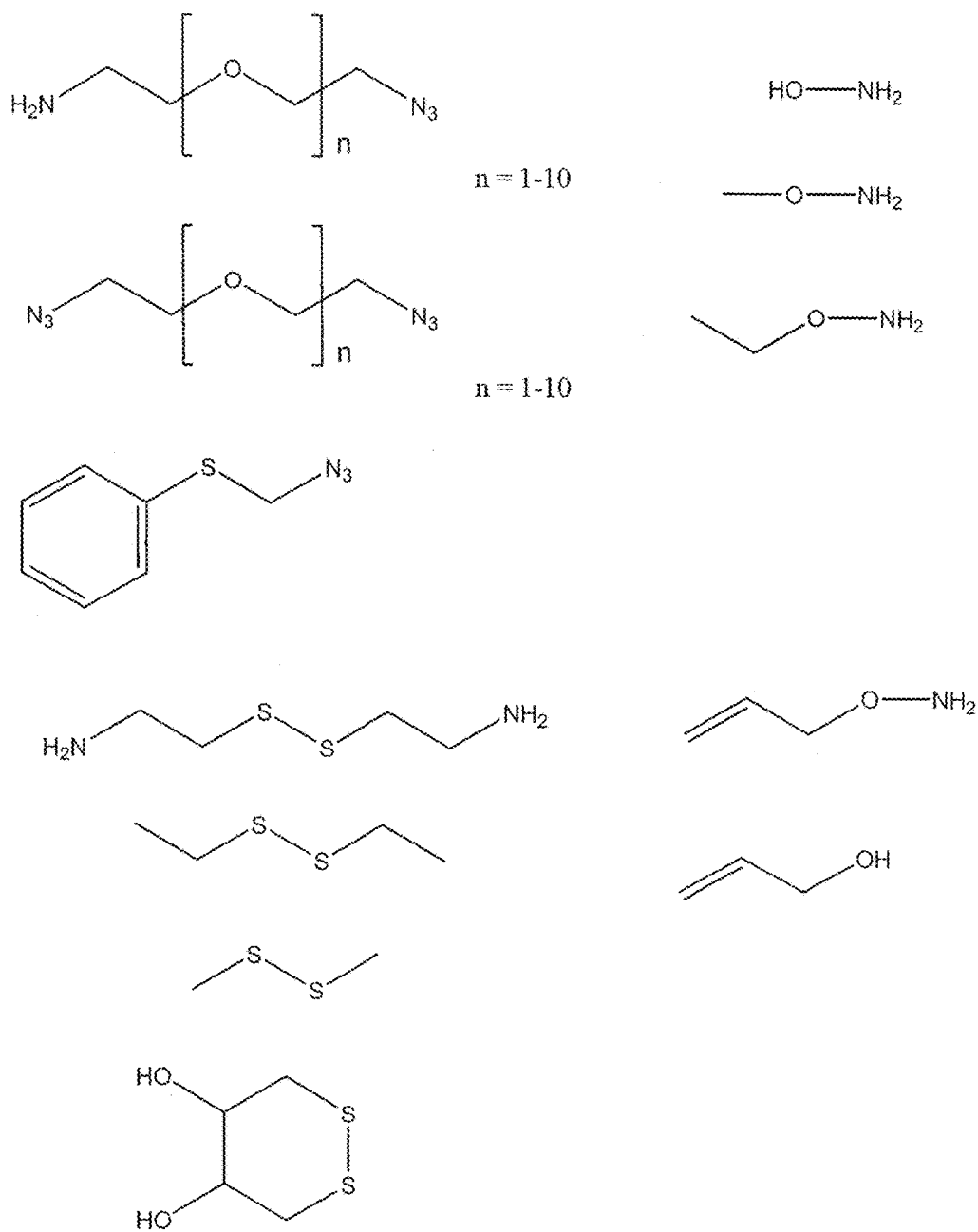
FIG. 37 provides examples of compounds useful as cleaving agent "scavengers."

In one particular embodiment the scavenger agent mimicks the structure of the protective group present on the 3'-OH location of the nucleotide. In another embodiment, the scavenger mimicks only the reactivity of the protective group. For example, in case of 3'-O-azidomethyl nucleotides scavenger compounds could comprise azidomethyl, azidoethyl ethers or disulfide compounds. In case of 3'-O—NH2 nucleotides the scavengers could be any aminoxy compounds, such as hydroxylamine. In case of 3'-O-allyl nucleotides the scavengers could be any allyl ether or disulfide compounds. FIG. 37 provides examples of cleaving agent "scavengers." It has been found empirically (see Example 15), that the use of such compounds improves base calling accuracy, without the need for additional wash steps (and in particular, without the need for high numbers of wash cycles).

E. Dephasing

Many next-generation DNA sequencing systems read the sequence of millions of different single-stranded DNA fragments in parallel by using a polymerase enzyme to incorporate fluorescently labeled DNA nucleotides into the complementary strand one cycle at a time. However, incorporation errors can shift the phase of some of the templates, so base read outs may lead ahead or lag behind the cycle number. The invention provides a model and methods to account for incorporation errors and show how the model may be inverted to correct this dephasing and extend read lengths.

Although fluorescence-based, single-molecule sequencing on a chip has been demonstrated, it is very sensitive to polymerase incorporation errors. This may be reduced and therefore reliability of sequence read out may be increased if each spot on a chip is an ensemble of identical template molecules. Polymerase errors (such as the incorporation of the wrong complementary nucleotide or no incorporation at all) are inevitable, but infrequent. Therefore, the superposition of all of the fluorescent signals from template molecules within an ensemble will primarily be from the correct nucleotide. As the number of cycles gets large, however, certain errors can accumulate within an ensemble and contribute to possible miscalling of the correct nucleotide.

For our analysis, we assume that a set of reversibly terminated and cleavably labeled nucleotides with four different dye colors (one for each nucleotide type: A, C, G and T) are used for sequence read out. The methods described herein may also be applied to other types of SBS processes such as pyrosequencing. If the SBS process works without mis-incorporations, then for each cycle only a single nucleotide type is incorporated into every strand in an ensemble. During a read out phase, the color of each ensemble is measured, then during a cleavage phase, the terminator and dyes are cleaved off and the chip is ready for the next cycle. Thus, the position of the base being read out on every template on the chip is synchronized with the cycle number.

Figure 8:
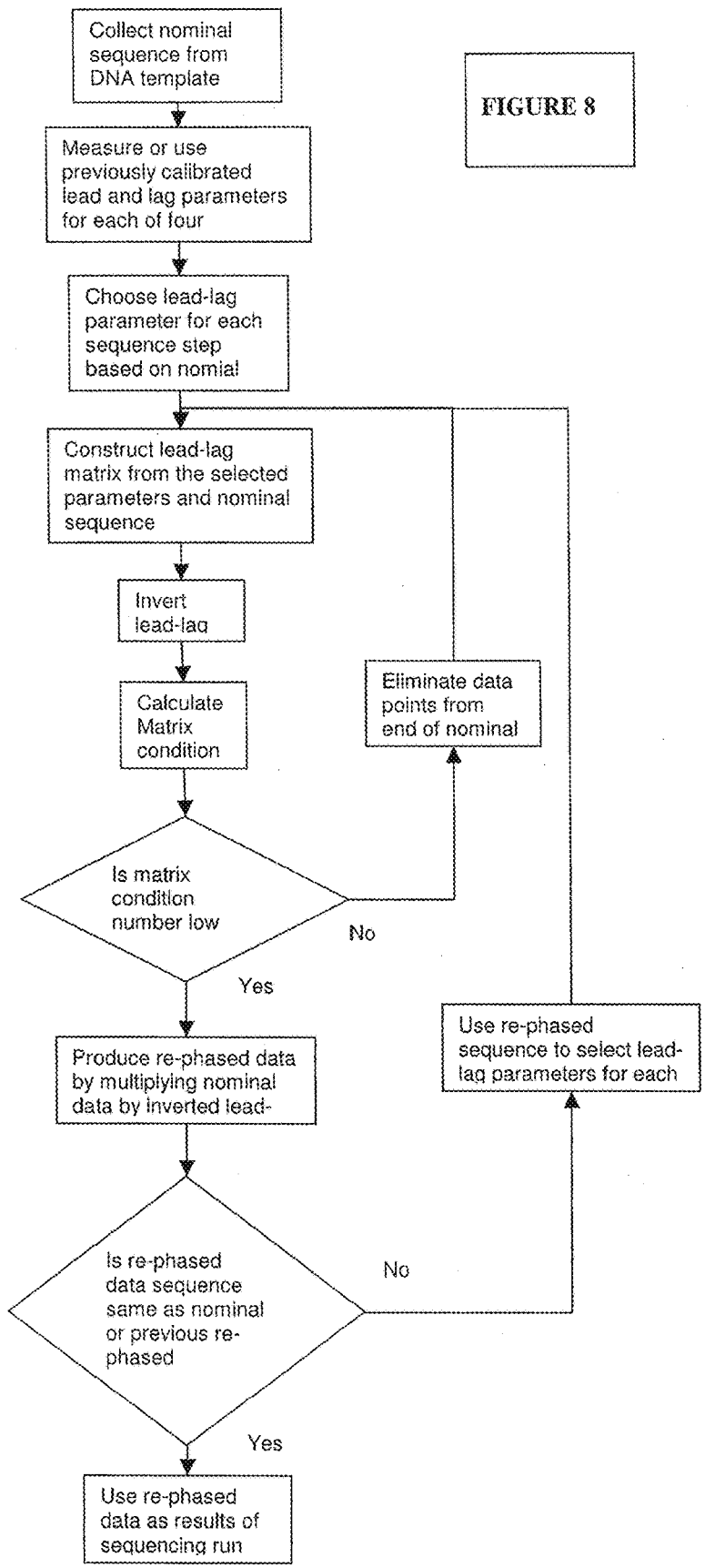
FIG. 8 is a schematic flow chart for re-phasing.
Figure 9A:
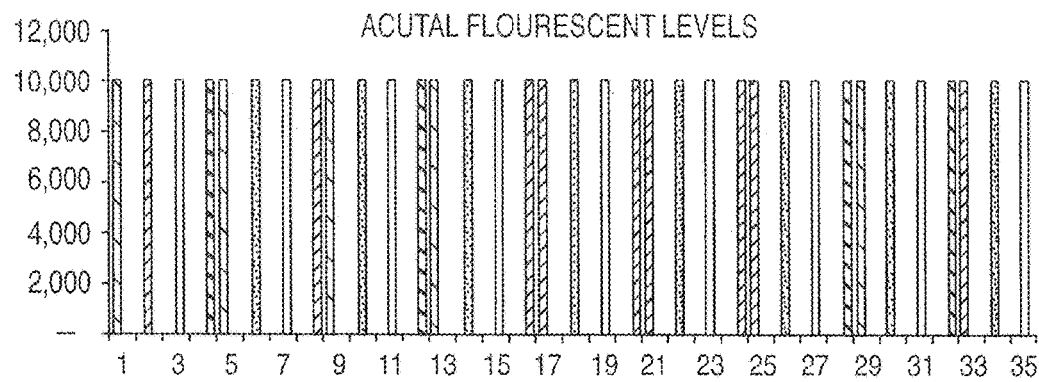
FIGS. 9A-B show simulated data showing sequence lead due to incorporation of small amounts of non-terminated nucleotides mixed with the reversibly terminated nucleotides.
Figure 9B:
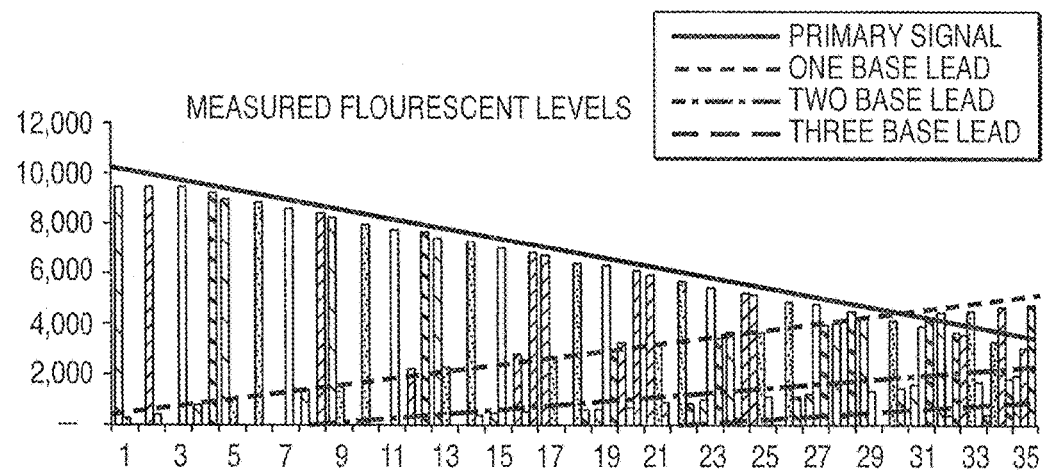

Because of impurities, limited polymerase efficiencies and other errors, some of the templates within an ensemble may get out of phase with the cycle number. For example, the base that is incorporated in the $i^{th}$ cycle may be complementary to the $i-1^{st}$ position or the $i+1^{st}$ position in the template rather than the expected $i^{th}$ position. The invention's methods provide computational re-phasing of the dephased data. FIG. 8 is a schematic flow chart for re-phasing. Additional data demonstrating the efficacy of the invention's methods is discussed below, including FIGS. 9 A-B-19 and Example 11 (FIGS. 33 A-B-34 A-B).

a. Sequence Lead

Polymerases that have an increased capacity for incorporating 3' reversibly terminated nucleotide analogs continue to have a preference for incorporating native nucleotides. This means that even though nucleotide analogs may be extremely pure, any residual nucleotides with 3'-OH (non-terminated) will be incorporated at a much higher rate and therefore appear to be more prevalent. The incorporation of non-terminated nucleotides has the effect of skipping a base, as a second incorporation (the next base) will occur in the same cycle. Thus, the fluorescent measurement for that template will exhibit the dye from the following base rather than the expected base at that cycle number. Since that template now exhibits a "lead," it will continue to do so, even if all future nucleotides are reversibly terminated. This effect is cumulative and shown in simulated data in FIG. 9 A-B for a non-terminated nucleotide incorporation rate of 2% as compared to the terminated nucleotide analog rate and a repeated 35 base sequence of ACTGACTGACTG . . . . Here we make the assumption that each of the nucleotides has the same non-terminated incorporation rate thereby allowing us to use a linear model. Again, the actual nucleotide purity may well be better than say 99.5%, but the apparent non-terminated incorporation rate may be 2% depending on the polymerase. In the example in FIG. 9 A-B, the model tells us the amount of signal due to the sequence lead effect. In cycle 20, the model calculates that we have 60% of the signal from the primary base at the 20th position (red), 32.4% of the signal from the base at the 21st position (blue), 6.7% of the signal from the base at the 22nd position (green), 0.8% of the signal from the base at the 23rd position (yellow), and 0.07% of the signal from the base at the 24th position (red). An interesting observation is that with the lead effect, the primary base signal (actual base at that cycle) does not have a 100% signal as some templates are already "reading out" subsequent bases on that strand. Thus at the end of a run, we can "look forward" and shift back the lead signals and correct the primary signals. We denote the contributions at the $i^{th}$ cycle as $R_{0Lead,1}$, $R_{+1Lead,1}$, $R_{+2Lead,1}$, $R_{+3Lead,1}$, etc. for the ratio between the reduced signal for the $i^{th}$ base to the actual $i^{th}$ base population, the ratio contribution to the $i^{th}$ base signal from the $i+1^{st}$ base, the ratio contribution to the $i^{th}$ base signal from the $i+2^{nd}$ base, etc.

Because the amount of lead changes with each cycle, there will be a different set of ratios for each cycle.

b. Sequence Lag

Figure 10:
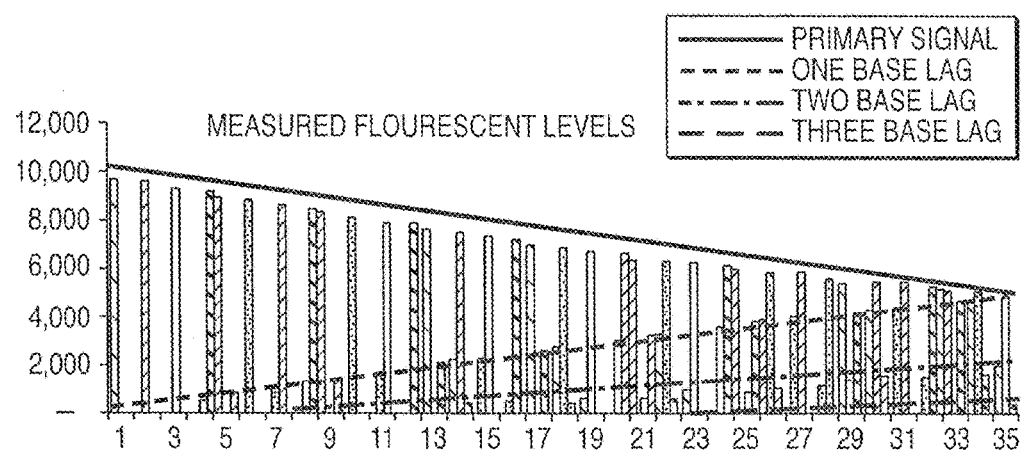
FIG. 10 shows simulated data showing sequence lag due to finite incorporation efficiency.

We developed a model for de-phasing due to sequence lag. This is caused by limited incorporation efficiency where some small percentage of the templates do not get a base incorporated in the cycle. FIG. 10 shows simulated data for a 98% incorporation efficiency for the same template sequence as in FIG. 9A-B. We denote the contributions at the $i^{th}$ cycle as $R_{0Lag,1}$, $R_{-1Lag,1}$, $R_{-2Lag,1}$, $R_{-3Lag,1}$, etc., for the ratio between the reduced signal for the $i^{th}$ base to the actual $i^{th}$ base population, the ratio contribution to the $i^{th}$ base signal from the $i-1^{st}$ base, the ratio contribution to the $i^{th}$ base signal from the $i-2^{nd}$ base, etc.

c. Nucleotide Incorporation Events

As discussed above, every time there is an available site for the polymerase to incorporate a nucleotide on a template, there are three possible outcomes: First, no nucleotide is incorporated—Event No-I. If no nucleotide is incorporated due for example to polymerase inefficiency, then the site remains available for the next cycle. We term this a "lag" event as it has the effect of causing a readout in the next cycle that will be from the position behind or lagging the cycle number. Second, a reversibly terminated nucleotide is incorporated—Event T-I. If as expected, a reversibly terminated nucleotide is incorporated, then the nucleotide readout is in synchrony with the cycle number. In the next cycle, the next consecutive template nucleotide position will be available for incorporation. Third, a non-terminated (native) nucleotide is incorporated—Event N-I. If a non-terminated nucleotide is incorporated, then during that same cycle, there is a second opportunity for another nucleotide to be incorporated at the subsequent position in the template strand. We term this a "lead" event as it has the effect of causing a readout of a nucleotide that is at a position that is ahead of or leading the cycle number. This second incorporation event is subject to the same three possible outcomes (No-I, T-I or N-I); thus, N-I events are recursive.

We will use the variable $G_i$ to represent the rate at which a lag occurs at template position i and similarly $D_i$ for the lead rate at position i. The analysis assumes that these rates may vary from position to position depending on the identity of the nucleotide that is to be incorporated, but we have assumed that all incorporation events for a particular nucleotide have the same lag and lead rates, even if the incorporation is not the first one in a cycle (it follows an NJ event). The fluorescent signal that will be generated from an incorporation event at a template location i is proportional to $(1-G_i-D_i)$, so at every $i^{th}$ incorporation event, the three types of events (No-I, T-I and N-I) will occur at the following rates: Event No-I at rate $G_i$, Event T-I at rate $(1-G_i-D_i)$, and Event N-I at rate D.

d. Signals Produced in Each Cycle

Figure 11:
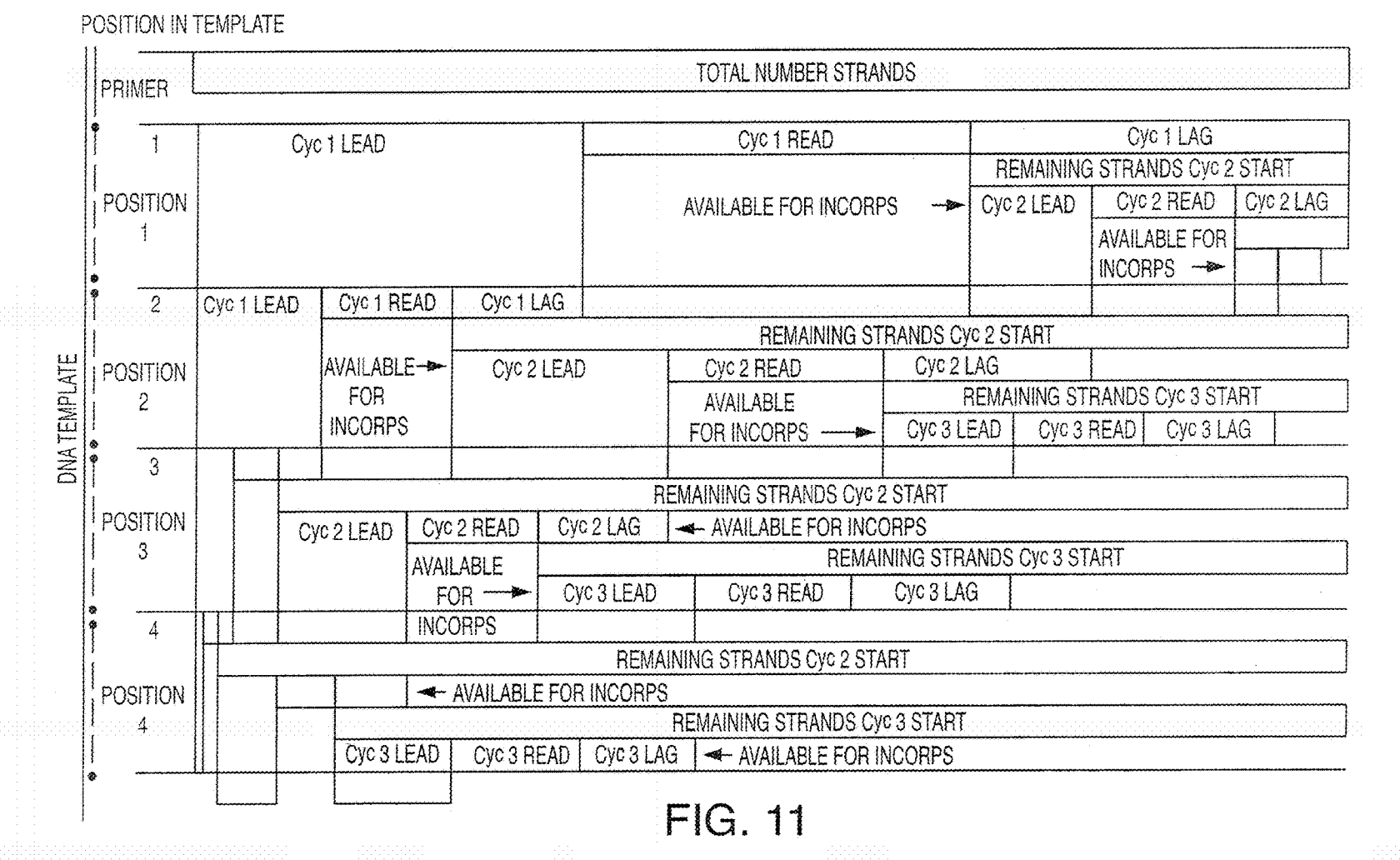

Although there are only three potential outcomes from an incorporation event, all of the combined events from multiple cycles in a template can be fairly complex. FIG. 11 may be used to better visualize the sequence of extension events. For simplicity, only 4 templates positions and only 3 cycles are illustrated in FIG. 11. The numbered regions in the vertical direction along the left edge indicate the nucleotide position along the strand. The horizontal direction symbolizes the relative number of strands in an ensemble that undergo events No-I, T-I or N-I (lag, readout or lead). The various events for cycle 1 in the sequence process are shown in shades of blue, events for cycle 2 are shown in red and events in cycle 3 are shown in green.

For clarity in FIG. 11, we have designated each of the three possible events (No-I, T-I and N-I) to occur at the same rate for every cycle. In an actual system, the lead and lag rate are both likely to be much smaller values. The chart is easier to understand if it is viewed one color at a time. The blue regions represent events that occur during the first cycle. At position 1 of the template, the entire ensemble of templates are available for extensions, thus (light blue) undergo a lag (no incorporation), (medium blue) are read out and (dark blue) undergo a lead. The portion of templates that experienced a lag (light blue) during the first cycle, remain available during the second cycle for incorporations. The portion of the templates that experienced a readout (medium blue) comprises the signal that is read during cycle 1 at position 1. This portion will progress in synchrony and allow incorporations to occur at position 2 during the second cycle. The portion of the templates that experienced a lead at position 1 will have a second incorporation event during cycle 1 at the second position of the template. This incorporation again will be split equally into the three possible events. A portion of the templates will remain unextended (lag), a portion will generate a signal (readout) and a portion will undergo a lead and produce a third set of incorporation events at position 3. This process will continue during cycle 1. Although lead events may continue down the entire length of the template during cycle 1, in practical terms, the effects after about 4 lead events are negligible.

Figure 12:
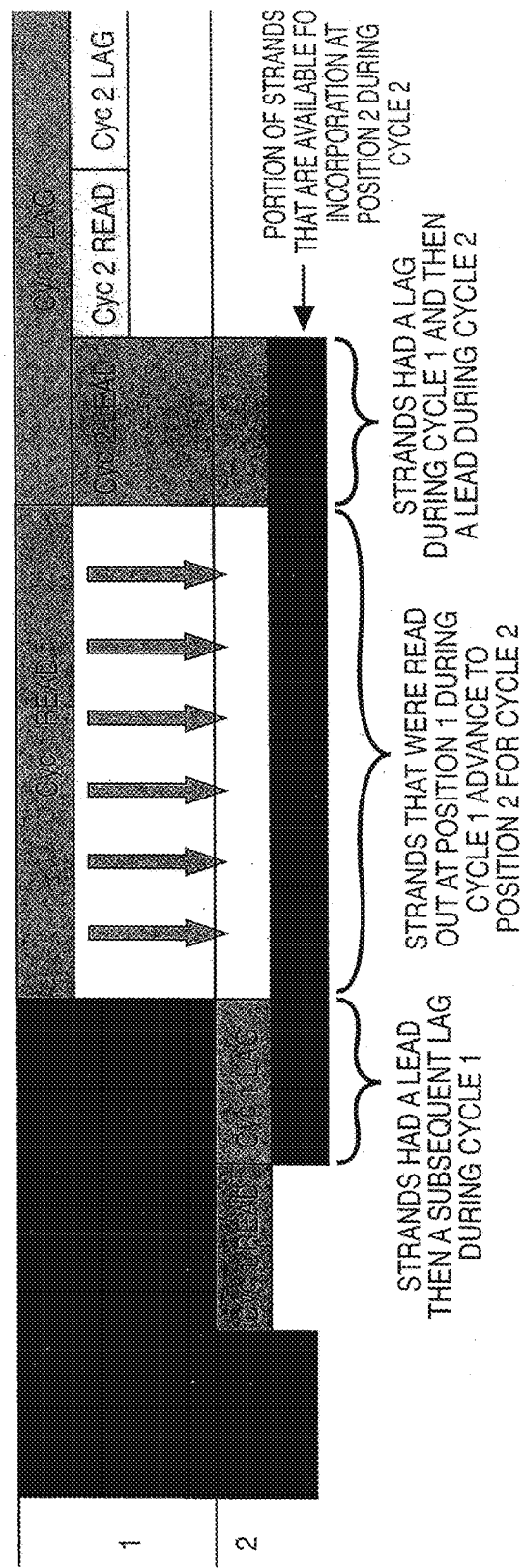
FIG. 12 is a chart of an exemplary sequence of extension events.

In cycle 2 (red colors), the only strands that are available to be extended at position 2 are those for which one of three events occurred (see FIG. 12): (1) strands that were read out at position 1 during cycle 1, (2) strands that experienced both a lead at position 1 and a lag at position 2 during cycle 1, and (3) strands that experienced a lag at position 1 during cycle 1 along with a subsequent lead at position 1 during cycle 2. A portion of these strands will also experience a cycle 2 lead to the third position, however, since they have "caught up" to the other strands with available sites at the second position, they are lumped together with them and further leads are considered as portions of the combined population.

Similar events occur at each template position during cycle 2. The events of cycle 3 (green shades) follow very similar patterns to those described for cycle 2.

e. Mathematical Models of Dephasing and Rephasing

We may derive general equations that describe all the incorporation events at each position and for each cycle. If we denote the relative magnitude (out of 1) of the number of strands that remain unincorporated for position i at the end of a cycle j as $R_{i,j}$, and the number of strands that are available for incorporation in the next cycle as $A_{i,j}$ then $$R_{i,j} = R_{i,j-1} - A_{i,j-1}(1-G_i) \quad (1)$$

and $$A_{i,j} = R_{i,j} - R_{i-1,j} + A_{i-1,j}D_{i-1} \quad (2)$$

Figure 13:
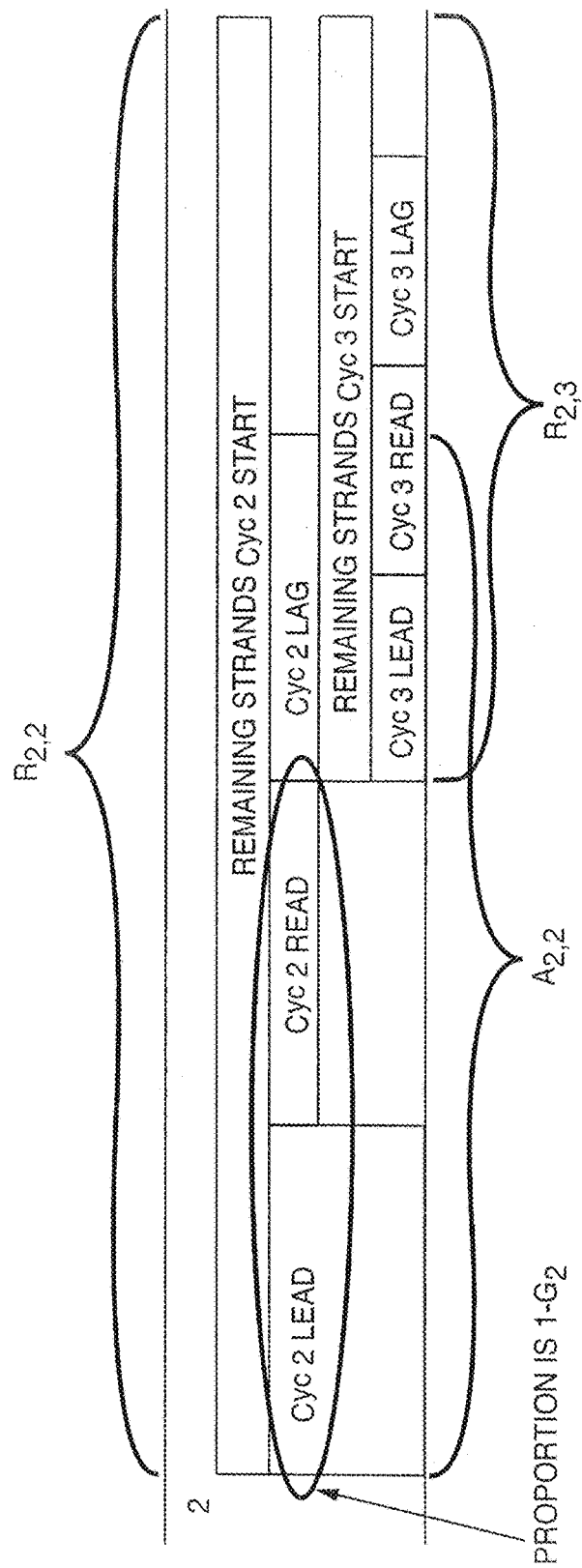
FIG. 13 shows a first portion of the chart of FIG. 11.

To explain the derivation of Equation 1, we use the example in FIG. 13, which shows a portion of the chart from FIG. 11. Only cycles 2 and 3 are shown for position 2. $R_{2,3}$ is comprised of $R_{2,2}$ minus a portion $(1-G_2)$ of $A_{2,2}$.

Figure 14:
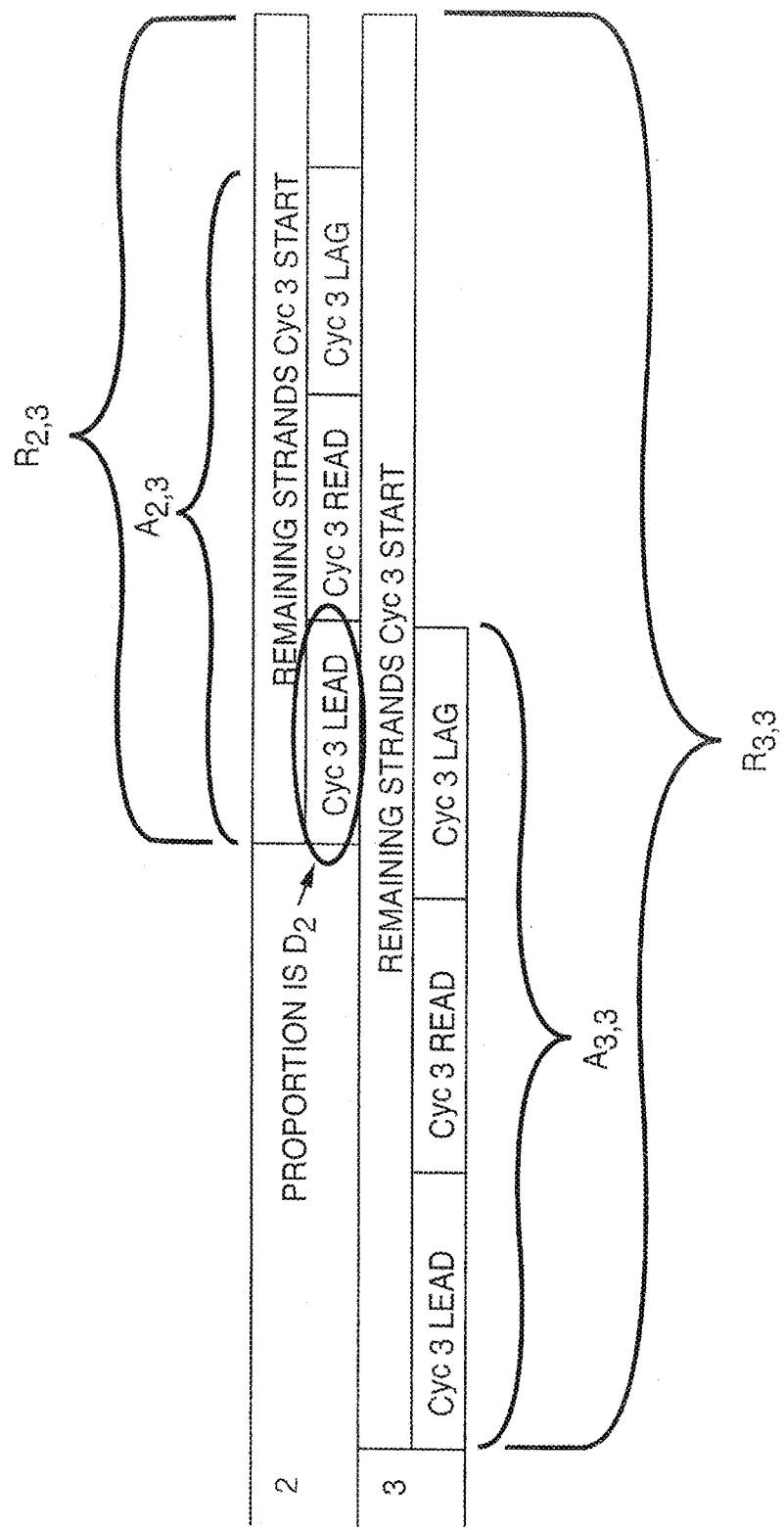
FIG. 14 shows a second portion of the chart of FIG. 11.

To explain the derivation of Equation 2, we use the example in FIG. 14, which shows a portion of the chart from FIG. 11. Only cycle 3 is shown for positions 2 and 3. $A_{3,3}$ is comprised of $R_{3,3}$ minus $R_{2,3}$ plus the lead portion $(D_2)$ of $A_{2,3}$.

It should be noted that for any particular cycle and position, the number of available strands, $A_{i,j}$, is generally fewer than the number of remaining strands, $R_{i,j}$, since some templates at the particular position are still lagging and unavailable, but may "catch up" in future cycles.

The signal that is produced, $S_{i,j}$, at the $i^{th}$ position at the end of the $j^{th}$ cycle comes from the proportion of the strands that are available, $A_{i,j}$, that undergo event T-I $$S_{i,j} = A_{i,j}(1 - D_i - G_i) \quad (3).$$

In one embodiment, the model is used to apply the lead-lag compensation based on calibration of parameters, before or during the test, and to provide an initial estimate of the base identity at each location as determined during the sequencing run. In a particular embodiment, $G_i$ and $D_i$ for each nucleotide may be pre-calibrated or measured during the sequencing procedure. In general, the model is constructed with lag parameters that are applied to each cycle and lead parameters that are recursively applied to each cycle.

In a particular embodiment, the lead-lag matrix is formulated after an initial draft sequence is measured. This allows application of the proper set of $G_i$ and $D_i$ parameters to each cycle based on the nucleotides identified at each position in the draft sequence. In a further embodiment, the re-phasing of data is iterated using the result of one re-phasing calculation to select an updated set of $G_i$ and $D_i$ parameters for the next iteration.

f. Simulated Dephased Sequencing Data

Figure 15:
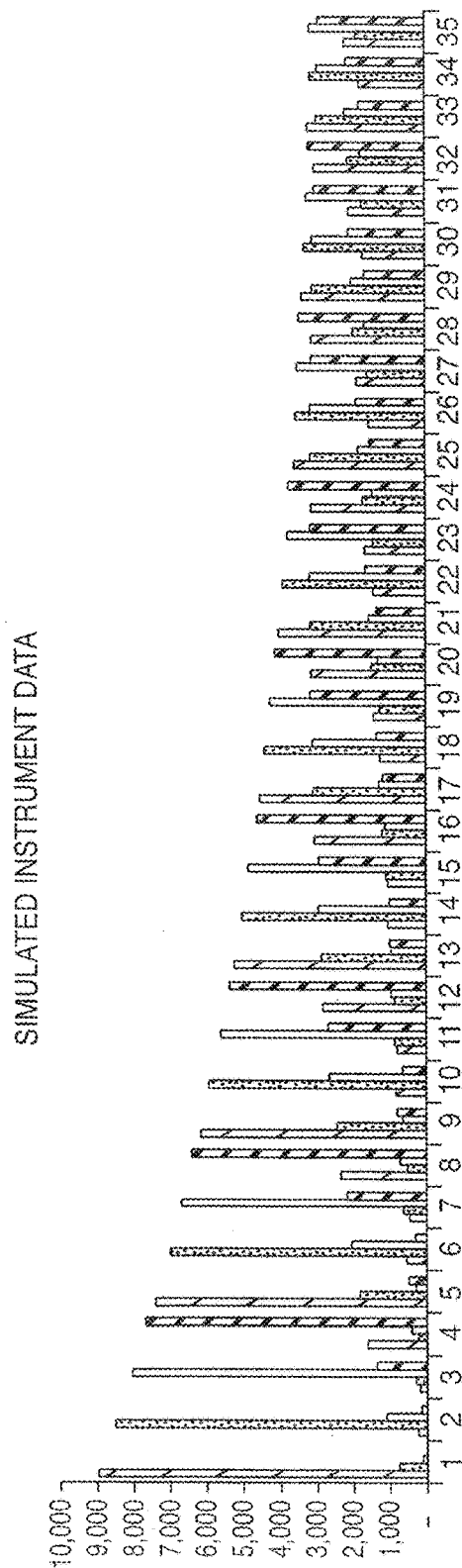
FIG. 15 shows data generated from the iterative application of equations 1-3 using parameters in Table 1.

We may use the relationships derived in the previous section to generate sequence data that simulate the signals that might occur when portions of every incorporation undergo a lead and a lag. As an example, we use the lead and lag factors below and generate simulated sequence data assuming the maximum signal from the template is 10,000 counts and the template has a 35 base repeating sequence of AGCTAGCTAGCT. FIG. 15 shows data generated from the iterative application of equations 1-3 using the parameters in Table 1.

TABLE 1

Lead Factors and Lag Factors for Nucleotides

|  | A | G | C | T |
|---|---|---|---|---|
| Lead Factors | 4.10% | 4.20% | 4.30% | 4.40% |
| Lag Factors | 1.10% | 1.20% | 1.30% | 1.40% |

FIG. 15 shows that with the presence of a lead and lag component, there is a cumulative effect that reduces the signal from the expected nucleotide at a particular cycle and "spreads" some of the signal forwards and backwards. As the number of cycles increases, it becomes more and more difficult to directly read the correct base from the graph, thereby limiting the effective read length of the template.

g. Re-Phasing Sequencing Data

Data herein (Example 11, FIGS. 33A-B-34A-B) demonstrate that applying the methods and the below described equations of the invention, exemplary 16-base and 25-base nucleotide sequences were sequenced with high fidelity. The high quality of the data, particularly in the last several bases in FIG. 34A-B, demonstrates that the read length will not be limited by signal decline. Thus, it is contemplated that the invention's methods are applicable to sequences containing at least 16 nucleotides, at least 25 nucleotides, at least 35 nucleotides, at least 50 nucleotides, at least 100 nucleotides, at least 1,000 nucleotides, and at least 10,000 nucleotides. Further description of the equations used to re-phase sequencing data is described as follows.

We constructed a matrix equation that describes a model for the reduced measured signal, $I_{Mi}$, from the lead and lag effect in the $i^{th}$ cycle from the original template populations, $I_{Ai}$, for all cycles, i=1 to N. Here each of the intensity matrices ($[I_{Ai}]$ and $[I_{Mi}]$) have N rows (one for each cycle) and four columns (one for each color).

$$\begin{bmatrix} I_{M1} \\ I_{M2} \\ \vdots \\ I_{MM} \end{bmatrix} = K_{Lead/Lag} \begin{bmatrix} I_{A1} \\ I_{A2} \\ \vdots \\ I_{AN} \end{bmatrix}, \quad (4)$$

where the lead/lag matrix, $K_{Lead/Lag}$, is a square N×N matrix of the following form:

$$K_{Lead/Lag} = \begin{bmatrix} R_{Lag/Lead,1} & R_{+1Lead,1} & R_{+2Lead,1} & R_{+3Lead,1} & \cdots & R_{+(N-1)Lead,1} \\ R_{-1Lag,2} & R_{Lag/Lead,2} & R_{+1Lead,2} & R_{+2Lead,2} & \cdots & R_{+(N-2)Lead,2} \\ R_{-2Lag,3} & R_{-1Lag,3} & R_{Lag/Lead,3} & R_{+1Lead,3} & \cdots & R_{+(N-3)Lead,3} \\ R_{-3Lag,4} & R_{-2Lag,4} & R_{-1Lag,4} & R_{Lag/Lead,4} & \cdots & R_{+(N-4)Lead,4} \\ \vdots & \vdots & \vdots & \vdots & \ddots & \vdots \\ R_{-(N-1)Lag,N} & R_{-(N-2)Lag,N} & R_{-(N-3)Lag,N} & R_{-(N-4)Lag,N} & \cdots & R_{Lag/Lead,N} \end{bmatrix} \quad (5)$$

The diagonal terms, $R_{Lag/Lead,i}$, in the $K_{Lead/Lag}$ matrix above is the fractional remaining signal in the $i^{th}$ cycle from the $i^{th}$ position of the templates after all of the leads and lags to that point. Each of the terms in the upper triangular portion of the matrix, $R_{+kLead,i}$, is the fractional contribution to the signal in the $i^{th}$ cycle from k positions forward of the $i^{th}$ position. Each of the terms in the lower triangular portion of the matrix, $R_{-kLag,i}$, is the fractional contribution to the signal in the $i^{th}$ cycle from k positions before the $i^{th}$ position. In most systems, the terms with k greater than about 4 (5 positions or more away from the position corresponding to the cycle number) are negligible. The diagonal terms are close to 1 for the earlier cycles and do not drop below about 0.25 for the later cycles. Thus, this matrix is invertable.

In order to compensate for both sequence leads and lags, we solved for $[I_{Ai}]$ in Equation 4 by taking the inverse, $K_{Lead/Lag}^{-1}$, of $K_{Lead/Lag}$ (Equation 5) to get an estimate of the actual template population $[I_{Ai}]$:

$$\begin{bmatrix} I_{A1} \\ I_{A2} \\ \vdots \\ I_{AN} \end{bmatrix} = K_{Lead/Lag}^{-1} \begin{bmatrix} I_{M1} \\ I_{M2} \\ \vdots \\ I_{MN} \end{bmatrix}. \quad (6)$$

When the lead rates for all the nucleotides are identical and the lag rates for all of the nucleotides are identical, then the lead/lag matrix, $K_{Lead/Lag}$, does not depend on the sequence. This makes Equation 6 linear and the inverse of the matrix is deterministic. In this case the inverse of the lead/lag model gives the correction matrix, $K_{Lead/Lag}^{-1}$, which is applied just once at the end of a run and takes into account all of the signals from the first to the last base.

If on the other hand the lead and lag factors vary from one nucleotide to the next, then the lead/lag matrix, $K_{Lead/Lag}$, depends on the actual sequence (solution of $[I_{Ai}]$ in Equation 6) and the problem is non linear. In other words, we need to determine an estimate for the true value of the intensities of each base in the sequence when the governing equations depend on this solution.

To solve the non-linear problem, one can estimate a solution and iterate until the solutions converge. We may use the raw out-of-phase sequence data to make an initial estimate of the sequence by taking the maximum value at each cycle, using this information to determine the lead and lag rates for each position, construct a lead/lag matrix ($K_{Lead/Lag}$), take the inverse of that matrix and solve for the corrected, re-phased sequence. We can then use the new sequence to make a new estimate of the lead/lag matrix, etc. As long as the various lead and nd lag factors are fairly close to one another, this method should converge in about two or three iterations.

h. Additional Factors

The above method is a very powerful way of "cleaning up" sequence data that has been dephased due to the lead and lag phenomena. The matrix condition number determines when matrix manipulations will be sensitive to small numerical variations. When the logarithm base 10 of the matrix condition is less than the number of significant digits of the data comprising the matrix, then the matrix is well behaved. A large condition number (where its logarithm base 10 is greater than the number of significant digits of the data) means the matrix is ill-conditioned or sensitive to the numerical inaccuracies inherent in the data. A good assumption for the type of data that is generated by fluorescent-based sequencing systems is that there are less than two significant digits in the data and the matrix condition number should therefore be less than about 20 in order to avoid ill-conditioned matrices.

Figure 16A:
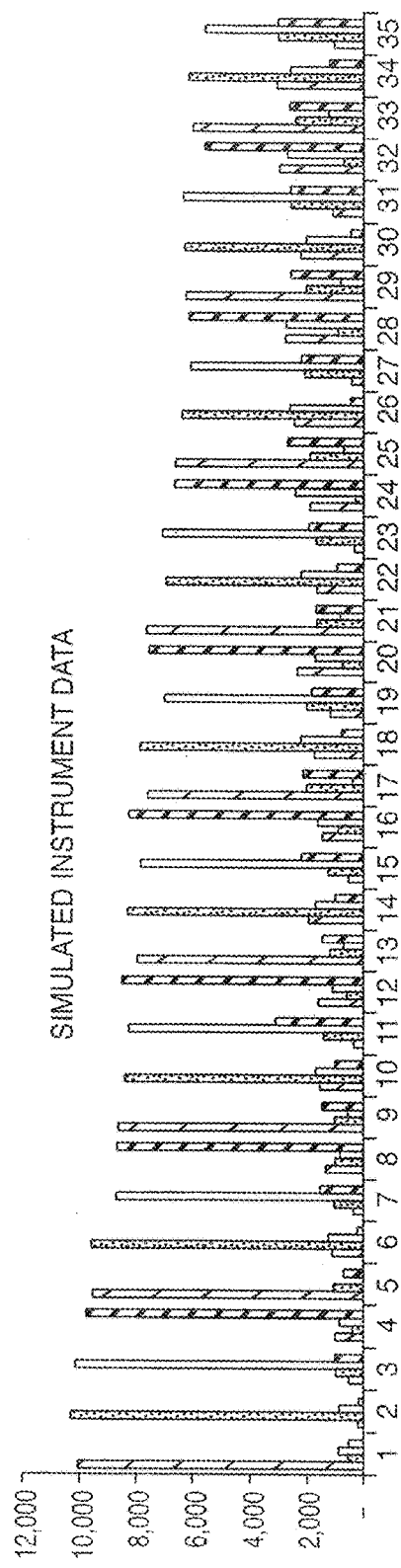
FIG. 16A shows simulated base read data with 10% noise added and lead and lag factors of 1% each.
Figure 16B:
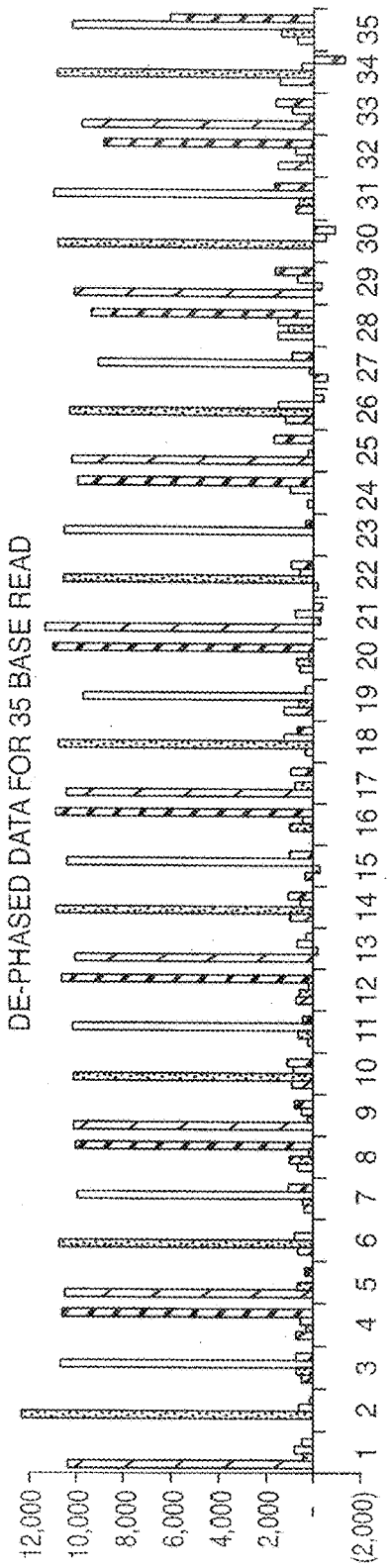
FIG. 16B shows reconstructed data with the lead and lag removed.
Figure 17A:
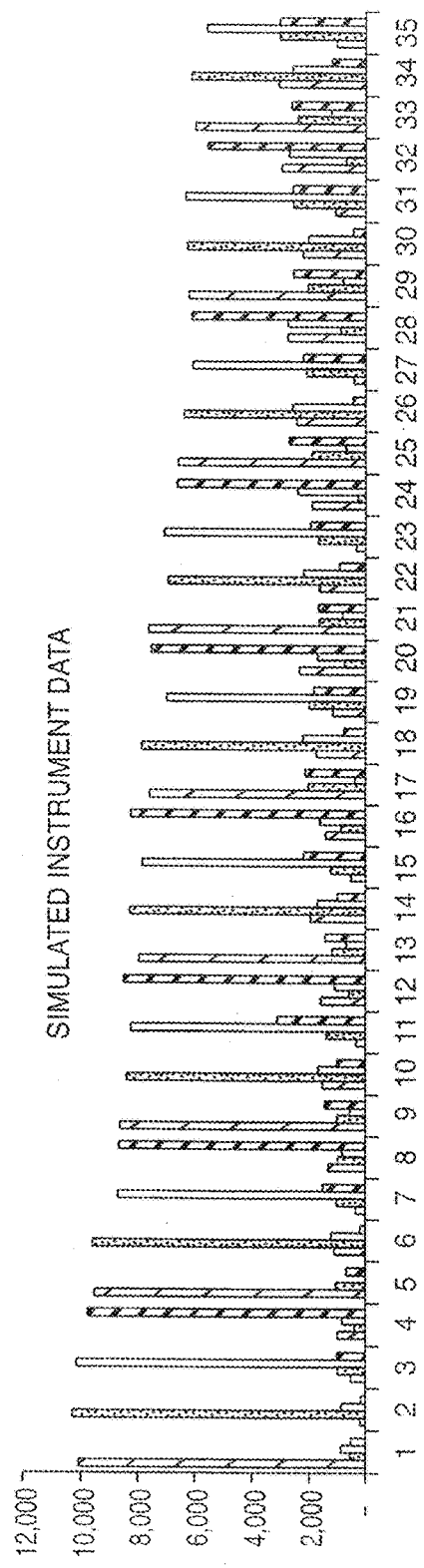
FIG. 17A shows simulated base read data with 10% noise added and lead and lag factors of 1.75% each.
Figure 18:
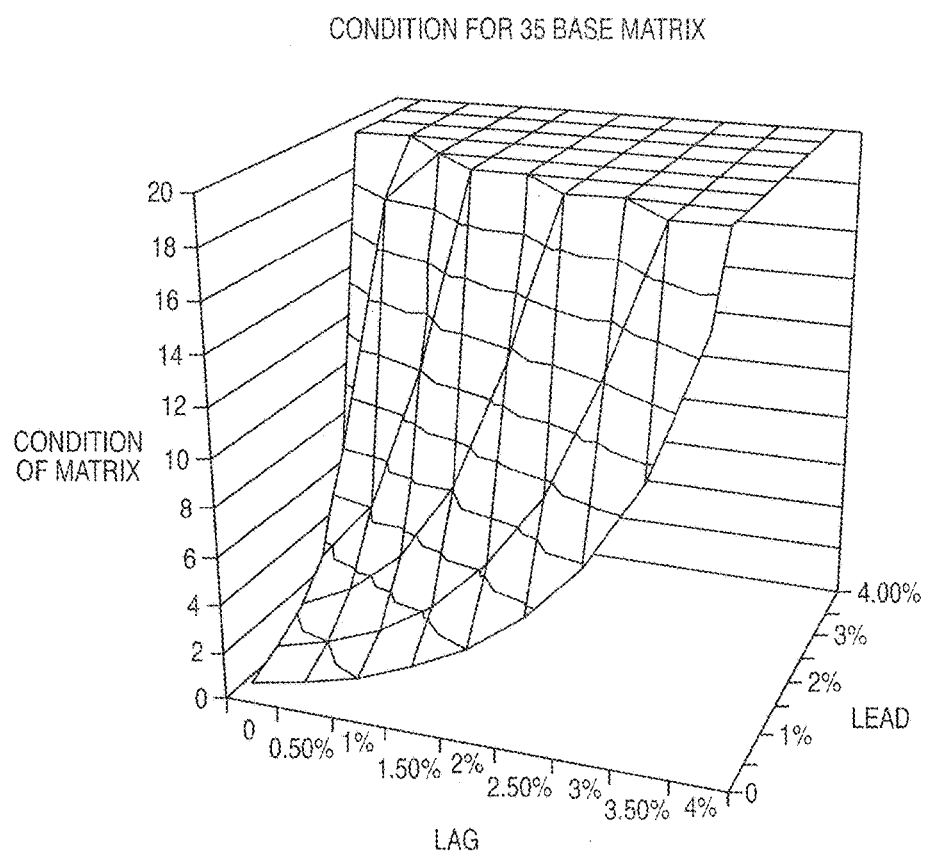
FIG. 18 shows lead/lag matrix conditions for various lead and lag parameters for a 35 base read. In one embodiment, a condition number below 20 produces accurate reconstruction.

FIG. 16A shows a simulated 35 base read data with 10% noise added and lead and lag factors of 1% each. FIG. 16B shows an accurate lead/lag compensation reconstruction using the inverse lead/lag matrix, $K^{-}_{Lead/Lag}$. The condition number for this lead/lag matrix is 5. FIG. 17A shows the same exemplary 35 base sequence with 10% noise and a lead and lag factor of 1.75% each and FIG. 17I shows the reconstruction. Here, the condition number is 550 and reconstruction is poor. FIG. 18 plots the matrix condition numbers below 20 (where matrices will be well-conditioned) for 35 base lead/lag matrices with various values of lead and lag. Because the lead/lag matrix is calculated independent of the DNA sequence in a template for the case where nucleotides all have equal lead ratios and equal lag ratios, we are able to determine our ability to accurately call bases without consideration of the A, C, T, and G content of the templates.

Even if a 35 base lead/lag matrix is ill-conditioned ad produces poor reconstruction, smaller matrices from a portion of the same data may still be well behaved. For example, FIG. 17C shows the reconstruction of the first 18 bases for a lead and lag of 1.75% each (same conditions that produced the poor reconstruction for the 35 base read). Here the 18×18 lead/lag matrix has a condition number of 3.7. The matrix becomes ill-conditioning when cumulative contributions from the lead or lag or both generate signals that are on the order of the signal from the true base (where the position equals the cycle number).

Figure 19:
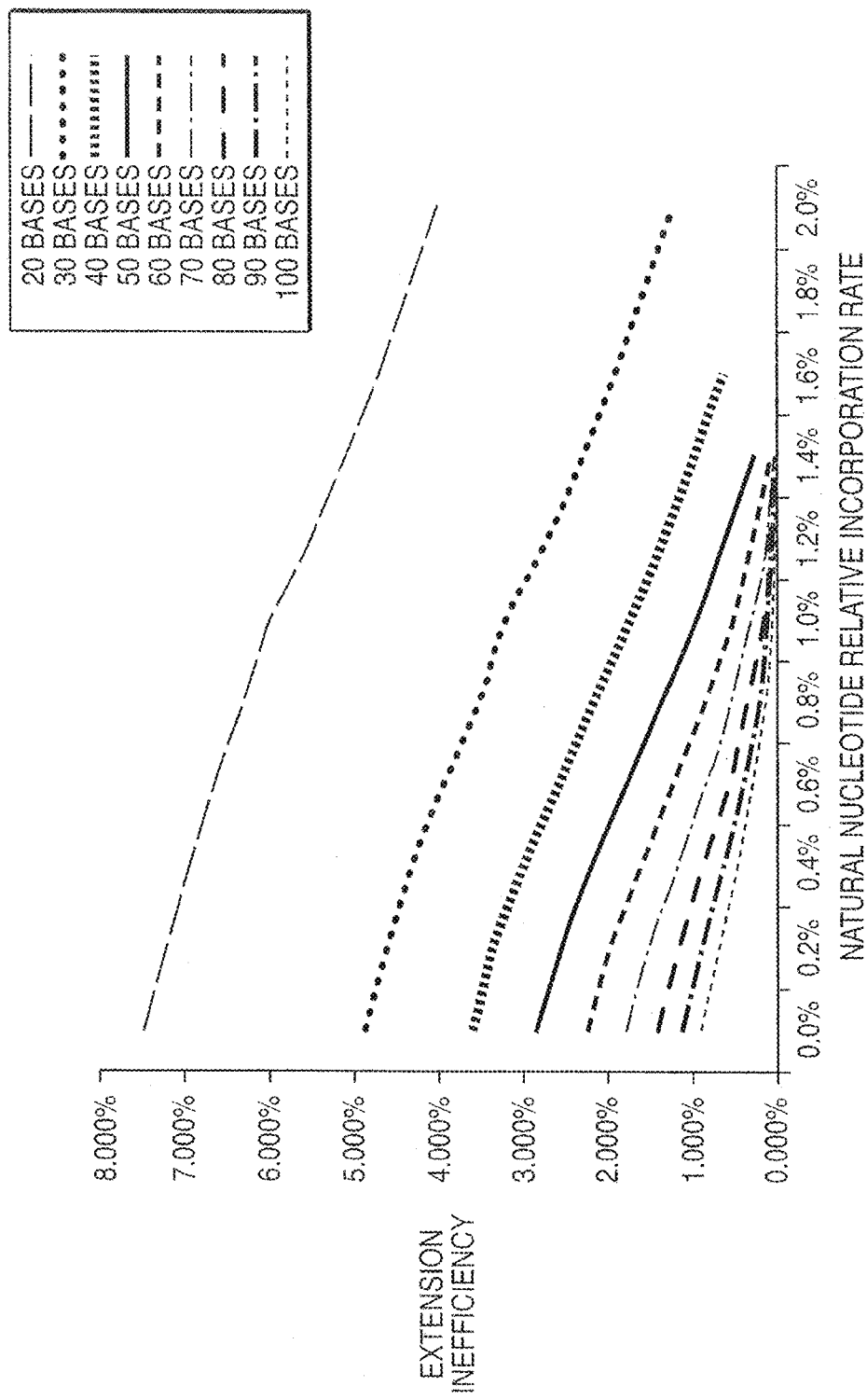
FIG. 19 shows exemplary read length for various values of lead and lag.

The above shows that changing the read length can provide an accurate reconstruction of earlier portions of the data. Thus, we can plot the lead and lag factors that will cause matrices of different sizes (read lengths) to have a condition number of 20 (the point where matrices become too ill-conditioned for precise reconstruction). For example, if a 23×23 matrix produces a condition number of 20, then we would restrict the read length to a maximum of 23 as reconstruction using the 24th base (as well as any additional bases) would likely create a matrix that is too ill-conditioned to accurately reconstruct the data. FIG. 19 shows the read lengths for various lead and lag factors. This plot provides a method for predicting the read length obtainable from a sequencing system based on two factors: the purity of the nucleotides (major contributor to the lead) and the polymerase incorporation efficiency (major contributor to the lag). This result also shows that if both the lead and lag factors are below about 0.5%, this results in reconstruction of a 100-base read.

Another way of producing more precise reconstructions when the matrix condition number is too large, is to approximate the lead/lag matrix by the product of two or more matrices with smaller lead and lag values. For example, the $K_{Lead/Lag}^{-1}$ of Equation 6 may be approximated by the product of two identical matrices, $K_{0.5Lead/0.5Lag}^{-1}$, each corresponding to leads and lags having half the values of the actually leads and lags.

$$K^{-1}_{Lead/Lag} = K^{-1}_{0.5Lead/0.5Lag} K^{-1}_{0.5Lead/0.5Lag} \qquad (7).$$

Figure 17B:
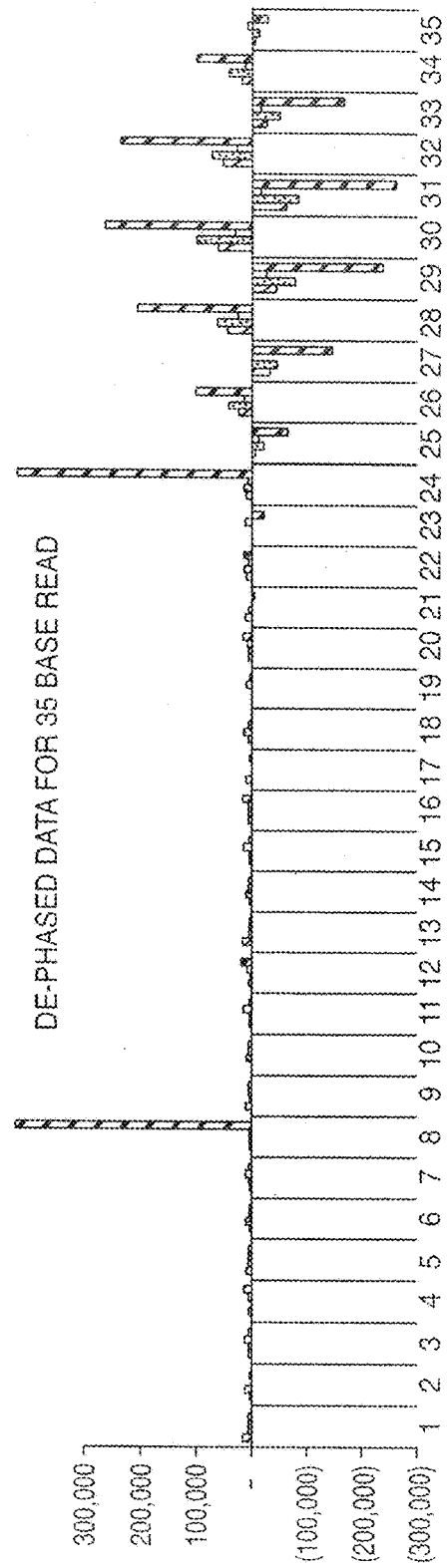
FIG. 17B shows that attempted reconstruction is poor as the lead/lag matrix is ill-conditioned, and FIG. 17C) shows reconstructed data with the lead and lag removed for only the first 18 bases. The 18-base lead/lag matrix is relatively well behaved and a more precise reconstruction may be performed.
Figure 17C:
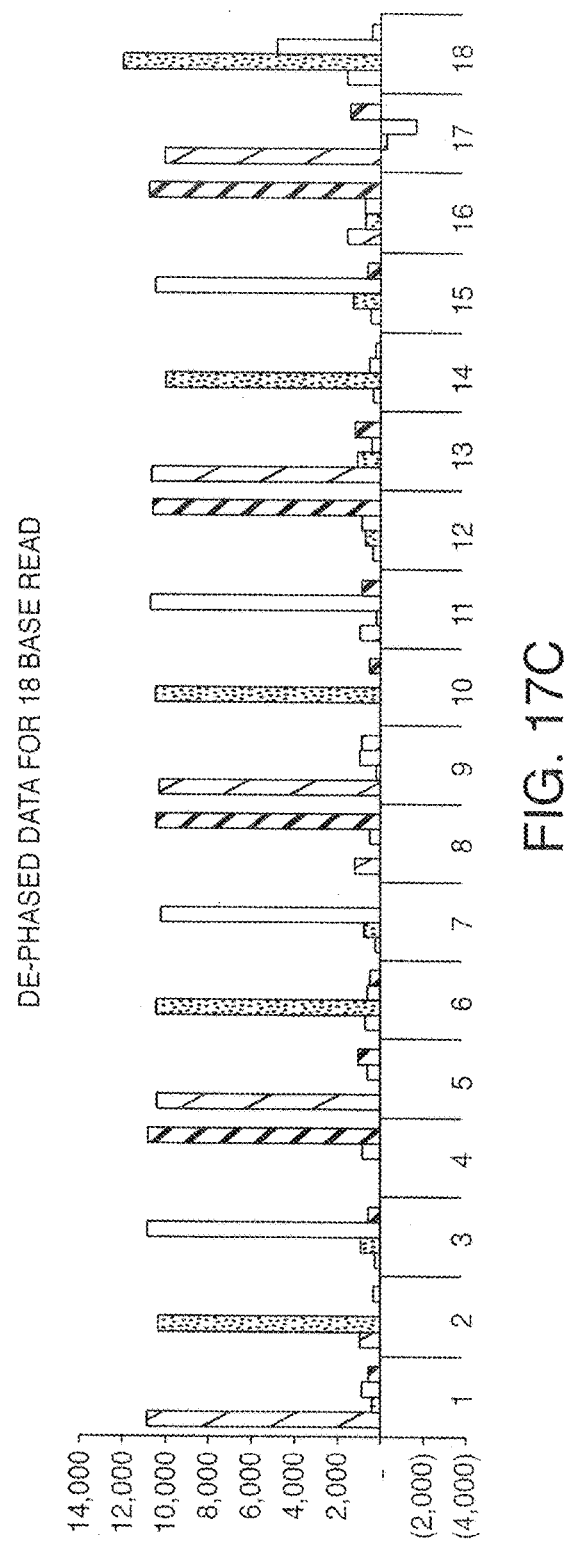
Figure 17D:
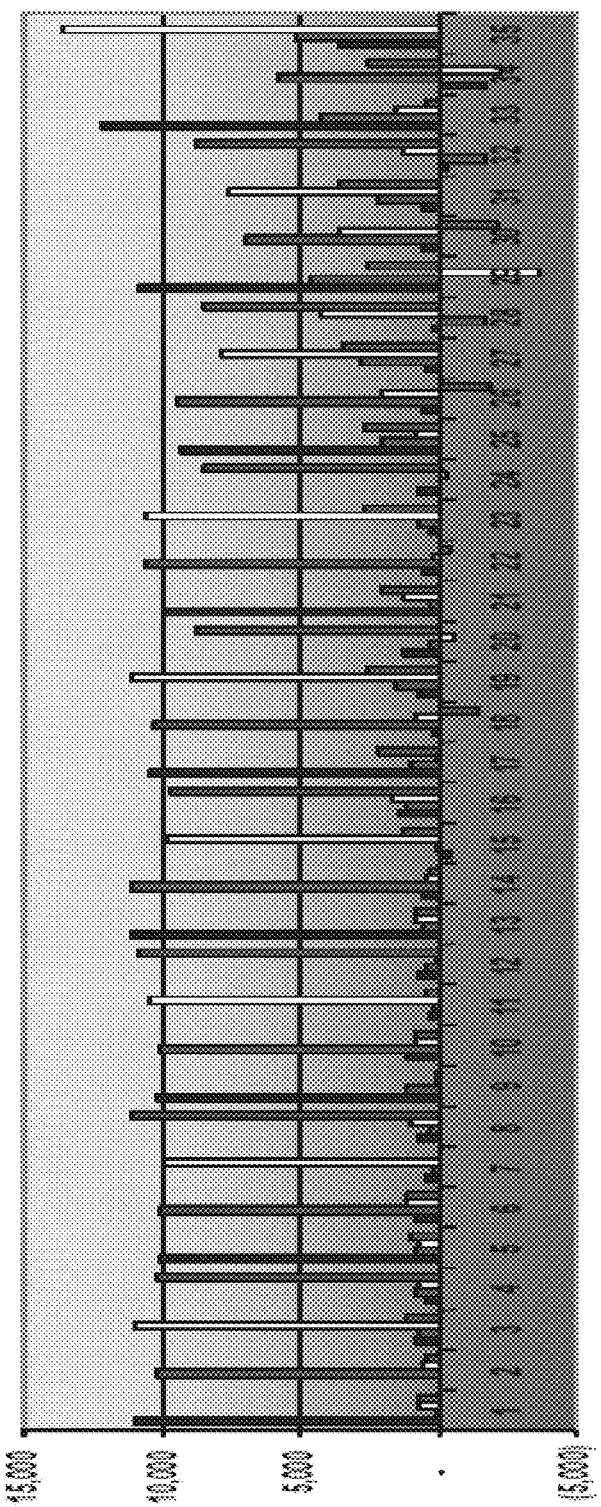

FIG. 17D shows the same reconstruction as FIG. 17B, but with Equation 7 being used for the value of $K_{Lead/Lag}^{-1}$ of Equation 6. Reconstruction using multiple smaller-lead/lag-value matrices gives nearly identical reconstruction of well-conditioned systems as the nominal $K_{Lead/Lag}^{-1}$ matrix. For certain ill-conditioned systems, the method may produce stable reconstructions where the nominal $K_{Lead/Lag}^{-1}$ matrix will not; however, they are likely to be less precise than reconstructions in well-conditioned systems.

Although this example describes the matrix approximation using the product of two identical matrices with half the lead and lag values, any number of matrices in the product and any combination of lead lag values may be used as long as the values produce well-conditioned matrices.

F. Field Flattening

In one embodiment, when a chip of uniform dye concentration is imaged, it may be desirable that all of the pixels in the resultant image have nearly the same intensity, with variations reflecting only the relatively small distribution inherent in the camera's optical system. In practice, however, the inventors have found that variations in illumination and filter response produce a significant spatially correlated pattern in an image. The inventors have also found that the pattern is highly reproducible and has a linear response to changes in dye concentration and camera exposure. These conditions lead to the following algorithm for removing this spatial correlation between pixel intensity and location of the pixel on the solid substrate.

First, for each machine and each filter, we image the pattern of a spatially uniform fluorescence on a dyed microscope slide. Second, the image is smoothed using a low-pass filter. In the resultant smoothed image, M, we choose an origin point, $M_{x0,y0}$. The choice of the point is fairly arbitrary but it is selected from a region in which the smoothed images of all of the filters have low intensity gradients to minimize the impact of changes in the system. Third, the intensity of each pixel at a point in a raw image ($R_{x,y}$) is replaced by its field-flattening value, $F_{x,y}$, where, $F_{x,y}=R_{x,y} M_{x0,y0}/M_{x,y}$ and $M_{x,y}$ is the value of the model image at the same spatial location as the raw image pixel. The resultant "Field Flattened" image, F, has intensities that are now solely dependent on the camera exposure and dye concentration, and do not have any correlation with the spatial location of the pixel in the image.

The invention's algorithms and equations for field flattening are distinguished from those described by, for example Eltoukhy et al. (2006), since the algorithms of Eltoukhy et al. relate to signal noise that is uncorrelated to system parameters (e.g., uneven light source). In contrast, the signal noise that is corrected by the invention's methods is correlated to the signal's position across the solid substrate. In one embodiment, each pixel is corrected (i.e., field flattened) based on a previously calibrated baseline intensity at that pixel position and a scaling factor based on for example a longer exposure time.

G. Spot Location in the Array

In one embodiment, the present invention contemplates a processing step (preferably in a series of processing steps as discussed above) for locating the spots in the array. In one embodiment, the spot locating image processing algorithm uses the fact that the spots on the chip are in a regular hexagonal pattern along vertical columns and diagonal rows. To find the columns of spots, image pixel values are summed along the vertical direction. This results in a one-dimensional set of data that resembles a sinusoidal pattern. The peaks of the pattern are measured and used to determine the period and phase of the pattern. There are then used to guide a search to determine a set of equations for vertical lines that approximately bisect each of the spots in a column. The result is a set of equations for parallel lines (slope, intercept and spacing) at regular spacing. A number of these lines are then probed to establish a second sinusoidal-like pattern of intensities along the lines. These are then used to determine the period, angle and phase of the diagonal lines that bisect each of the spots. These second set of lines are at a 60 degree angle from the vertical lines. The intersection of the diagonal set of lines and the vertical set of lines give an estimate for the subpixel locations of each of the spot centers.

H. Image Sharpening

In one embodiment, the present invention contemplates a processing step (preferably in a series of processing steps as discussed above) to sharpen the image of the spots on the array. This is particularly useful if chips are constructed with tightly packed spots. In such a case, it might be beneficial to run the images through a sharpening filter in order to reduce the amount of blur or spread for each of the spots. This will reduce the amount of light energy blooming into adjacent spots. Similarly, if the optics for the system cannot sufficiently resolve spots on the chip, then the application of a sharpening filter may also help to precisely analyze the images. A number of sharpening algorithms may be used to narrow the spread of the spots. One embodiment uses a Wiener filter (as described, for example, in The Image Processing Handbook, by John C. Russ, Published by CRC Press, 2006, ISBN 0849372542, 9780849372544, 817 pages) to make the diameter of the spots smaller and remove light energy from adjacent spots.

I. Spot Brightness Determination

In one embodiment, the present invention contemplates a processing step (preferably in a series of processing steps as discussed above) to determine spot brightness. In one embodiment, the pixels that surround each of the subpixel locations of the spots are summed to determine an estimate for the spot brightness. The local set of pixels that is selected depends on both the diameter of the spots and the location within the pixel of the subpixel center location. For example, if the subpixel location is close to the top of the pixel that contains the center, then more pixels above the pixel that contains the center are counted than pixels below the pixel containing the center.

In one embodiment, the above method for making spot brightness measurements is repeated independently for each of the four different color channels (four separate images) and the sharpening and neighbor influence (see below) correction calculations are applied, then the color crosstalk correction is applied (see below). In one embodiment, the result of the color crosstalk calculation produces a list of four values (one for each dye color) for each spot in the images that may be used to call the base for that sequencing cycle.

J. Neighbor Influence Elimination

In addition to each of the spots expanding beyond its physical bounds, the light from one spot (bead) may illuminate an adjacent spot and make it appear to have more of the color of its neighbors. This might happen because light being emitted from one bead make impinge on an adjacent bead, be reflected within the bead and then remitted from that bead. This neighbor influence may be eliminated by, in one embodiment, constructing an influence or "spreading" matrix, then applying the inverse of this matrix to the data. To formulate the solution to the neighbor influence problem from spot data that is in hexagonal form, it is convenient to first put the data into a rectilinear array. This is done by shifting the even vertical columns up by ½ of a pixel as shown below. Thus, a two-dimensional rectilinear matrix, whose elements represent the magnitude of each spot in the original image of the hexagonal array of spots, may be used. To further facilitate matrix manipulations, the rectilinear spot matrix may be made into a spot vector by stacking the columns from the two-dimensional matrix under one another to form a one dimensional array or vector. In other words, the second column is appended to the bottom of the first, the third to the bottom of the second, etc., thereby generating a $1 \times N^2$ vector formed from an $N \times N$ spot matrix.

In one embodiment, a "spreading matrix" is next formed that represents the magnitude of the influence from a spot to neighboring spots. In a general formulation, a central spot may be thought of as influencing the nearest six neighbors surrounding the central spot by a fraction, A, of the central spot brightness, the next nearest neighbors by a smaller fraction, B, etc. If the central spot is very bright, then its neighbors may appear to be emitting their own light of the same color as the central spot, even if they actually generate none of their own light in that color. The spreading matrix is formulated such that if it is applied to an ideal image of single element spots (each spot is an idealized point and does not extend beyond one element of the matrix), then the resultant matrix will have spots that have been spread across several elements due to the neighbor influence phenomenon. Thus, the spreading matrix is a model for the influence of any spot in the image to any other spot in the image.

For hexagonal arrayed spots that have been make into a one-dimensional vector with dimensions $N^2 \times 1$ (in other words, a concatenation of all the columns of the matrix), the spreading matrix, S, may be formulated as a $N^2 \times N^2$ matrix. An example 25×25 spreading matrix corresponding to a 5×5 spot image that has the three levels of neighbor influence (A for the closest 6 neighbors, B for the next closest 6 and C for the third closest 6) is shown below.

```
1 A C 0 0 A A B 0 0 B C 0 0 0 0 0 0 0 0 0 0 0 0 0
A 1 A C 0 B A A B 0 C B C 0 0 0 0 0 0 0 0 0 0 0 0
C A 1 A C 0 B A A B 0 C B C 0 0 0 0 0 0 0 0 0 0 0
0 C A 1 A 0 0 B A A 0 0 C B C 0 0 0 0 0 0 0 0 0 0
0 0 C A 1 0 0 0 B A 0 0 0 C B 0 0 0 0 0 0 0 0 0 0
A B 0 0 0 1 A C 0 0 A B 0 0 0 B C 0 0 0 0 0 0 0 0
A A B 0 0 A 1 A C 0 A A B 0 0 C B C 0 0 0 0 0 0 0
B A A B 0 C A 1 A C B A A B 0 0 C B C 0 0 0 0 0 0
0 B A A B 0 C A 1 A 0 B A A B 0 0 C B C 0 0 0 0 0
0 0 B A A 0 0 C A 1 0 0 B A A 0 0 0 C B 0 0 0 0 0
B C 0 0 0 A A B 0 0 1 A C 0 0 A A B 0 0 B C 0 0 0
C B C 0 0 B A A B 0 A 1 A C 0 B A A B 0 C B C 0 0
0 C B C 0 0 B A A B C A 1 A C 0 B A A B 0 C B C 0
0 0 C B C 0 0 B A A 0 C A 1 A 0 0 B A A 0 0 C B C
0 0 0 C B 0 0 0 B A 0 0 C A 1 0 0 0 B A 0 0 0 C B
0 0 0 0 0 B C 0 0 0 A B 0 0 0 1 A C 0 0 A B 0 0 0
0 0 0 0 0 C B C 0 0 A A B 0 0 A 1 A C 0 A A B 0 0
0 0 0 0 0 0 C B C 0 B A A B 0 C A 1 A C B A A B 0
0 0 0 0 0 0 0 C B C 0 B A A B 0 C A 1 A 0 B A A B
0 0 0 0 0 0 0 0 C B 0 0 B A A 0 0 C A 1 0 0 B A A
0 0 0 0 0 0 0 0 0 0 B C 0 0 0 A A B 0 0 1 A C 0 0
0 0 0 0 0 0 0 0 0 0 C B C 0 0 B A A B 0 A 1 A C 0
0 0 0 0 0 0 0 0 0 0 0 C B C 0 0 B A A B C A 1 A C
0 0 0 0 0 0 0 0 0 0 0 0 C B C 0 0 B A A 0 C A 1 A
0 0 0 0 0 0 0 0 0 0 0 0 0 C B 0 0 0 B A 0 0 C A 1
```

If the spreading matrix, S, is inverted, $S^{-1}$, it may be used to eliminate the neighbor influence modeled by the spreading matrix. If we multiply the measured spot matrix (in the form of a vector), $v_{spot}$, by the inverse of the spreading matrix, $S^{-1}$, we can generate an estimate for the spot matrix with the neighbor influence removed, $v_{uninfluenced}$ $$v_{uninfluenced} = S^{-1} v_{spot}$$

The method described above for removing the neighbor influence can generate sizable spreading matrices on the order of $N^4$ and therefore may be computationally intensive for typical images. Since the influence of spots that are relatively far from the spot of interest have relatively negligible influence, it is possible to reduce the size of the spreading matrices used for the calculation and perform the calculation on smaller subsections of the image at a time. This can significantly reduce the computational complexity and computer memory requirements for the calculation. It should be understood that the methods set forth above may be generalized in algorithms that are more efficient or operate on smaller portions of the image.

K. Spectral Crosstalk Calibration

In one embodiment, it may be desirable to correct the data to account for color crosstalk. This may be done using methods known in the art (e.g., U.S. Pat. No. 7,209,836 incorporated by reference) as well as methods disclosed herein (see Example 10, FIG. 32 A-B). For example, a four-color fluorescent detection system (for detection of the exemplary colors blue, green, yellow and red) has one detector channel for each of the four different color dyes. However, because the dyes have fairly broad spectra, there is some detection of dyes in adjacent color channels. For example, when exciting only a green dye, a signal is visible in the yellow channel as well as the green channel. If this spectral crosstalk is calibrated, it may be removed from subsequent measurements even if the dyes are mixed in unknown quantities. To determine actual fluorescent intensities for the four colors, A, B, C and D from measured detector outputs, $M_A$, $M_B$, $M_C$, $M_D$ in corresponding channels, one needs to know all of the spectral crosstalk factors: $R_{AB}$, $R_{BA}$, $R_{BC}$, $R_{CB}$, $R_{CD}$, and $R_{DC}$. For example, $R_{AB}$ is the ratio between the portion of the signal in the A channel coming from the B dye and the actual intensity of the B dye. If for instance $R_{AB}$ is 20%, then the A channel will have an additional signal equal to 0.2 times the actual B dye intensity in the B channel. Thus for channel B, the observed measurement, $M_B$, is the direct measurement of B and the two contributions from the adjacent channels (if any): $M_B = B + R_{BA}A + R_{BC}C$ (6). For the four channels, this may be written in matrix form:

$$\begin{bmatrix} M_A \\ M_B \\ M_C \\ M_D \end{bmatrix} = K \begin{bmatrix} A \\ B \\ C \\ D \end{bmatrix} \qquad (7)$$

where $$K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix}.$$

Each of the six spectral crosstalk factors may be determined through an experiment with pure dyes. We want to solve for the actual fluorescent signals, A, B, C and D given the detector measurements, $M_A$, $M_B$, $M_C$, $M_D$. Thus, we want to solve the above matrix Equation (7). This is equation (8):

$$\begin{bmatrix} A \\ B \\ C \\ D \\ \cdots \end{bmatrix} = K^{-1} \begin{bmatrix} M_A \\ M_B \\ M_C \\ M_D \\ \cdots \end{bmatrix}$$

where $K^{-1}$ is the inverse of matrix K. Although the inverse of matrix K may be written out in terms of the six spectral crosstalk factors, it is somewhat complex and is best performed by plugging in the numbers and letting the computer take the inverse. The results are discussed in Example 10 which demonstrate that a base in the sequence would have been miscalled were the spectral crosstalk calibration not performed.

Any multicolor sequencing by synthesis device may be calibrated using the above equations and the resultant spectral crosstalk matrix may be used in all four color measurements from the device. In one embodiment, if we also include information on the relative magnitude of each of the four colors, then we can also correct for differences in perceived dye brightness from one channel to the next. Multiplying the matrix K by a diagonal matrix, whose diagonal terms are the relative brightness for each dye, produces a new matrix K whose inverse will automatically scale the dyes to be consistent with one another.

K. Base Calls

As discussed above, at each sequencing by synthesis cycle, the signals that are observed in the four color channels are used to both determine the most likely base at that cycle (base call) and to determine a quality score for the base call. Because of a number of factors, it may not always be the case that the brightest color in the raw data indicates the most likely base. Thus, it may be desirable to correct for at least one, and more particularly all, of the following phenomena that were discussed supra: field flattening, spectral crosstalk, sequence lead and sequence lag. After the correction factors (field flattening, spectral crosstalk and/or lead-lag compensation) have been applied, a base is called based on the maximum signal between the four channels. The output of the base calls may be a file similar to a FASTA format. In one embodiment, this file is also accompanied by a quality score file.

To optimize the alignment and assembly of the data into contigs, it is desirable to have a precise quality score associated with each base call. A quality file may be generated that encodes quality scores for each cycle. Preserving the information for all four bases is also desirable to allow the sequence alignment software to examine several likely calls instead of only the one with the highest signal.

M. Software Appendices A-C

The below software Appendices A, B and C (copyright Intelligent Bio-Systems, Inc., 34 Bear Hill Road, Waltham, Mass. 02451) provide source code for implementing the present invention. Appendix A is a source code for correcting a raw image using a flat map calibration image, as exemplified by the code under FlattenImageInArray and AdjustRawValue. Appendix B is a source code for applying the inverse cross-talk array to four filter images. In particular, the FindBeadIntensities method calls ProcessOneBead to apply the spectral crosstalk correction matrix. Appendix C is a source code for creating a flat map calibration image. In one embodiment, this is a process that uses a combination of automated and manual steps. The automated steps are exemplified by the emoveSpikesWithSlope and LocalSmoothing methods. The manual steps are exemplified by ImageJ to replace spikes in the calibration image with smoothed data. The manual and automated steps may be carried out in any order. In a particular embodiment, the manual steps are carried out before the automated steps.

EXPERIMENTAL

The following examples serve to illustrate certain exemplary embodiments and aspects of the present invention and are not to be construed as limiting the scope thereof.

Example 1

Materials and Methods

The following is a brief description of the exemplary materials and methods used in the following Examples. All solvents and reagents were reagent grades, purchased commercially and used without further purification. Protected nucleosides 5'-O-(tert-butyldimethylsilyl)-2'-deoxythymidine, $N^4$-benzoyl-5'-O-tert-butyldimethylsilyl-2'-deoxycytidine, $N^6$-Benzoyl-5'-O-tert-butyldimethylsilyl-2'-deoxyadenosine, $N^2$-isobutyryl-5'-O-(tert-butyldimethylsilyl)-2'-deoxyguanosine were purchased from CNH Technologies, Inc. All other chemicals were purchased from Sigma-Aldrich.

Example 2

Synthesis of 3'O-Azidomethyl Nucleotides

Figure 20:
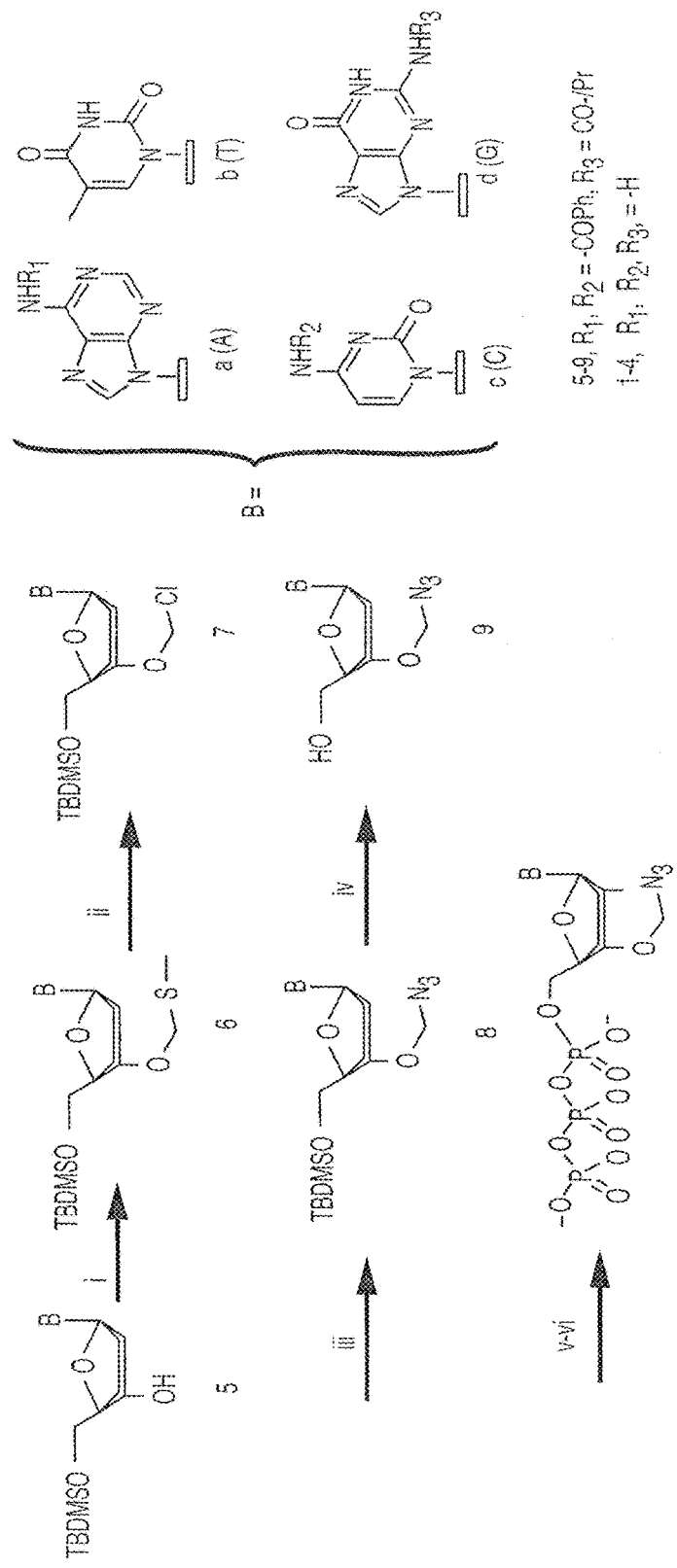
FIG. 20 shows synthesis of 3'-O-azidomethyl-dNTPs where the steps denote treatment with (i) DMSO, AcOH, $Ac_2O$, 48 h; (ii) $SO_2Cl_2$, dry $CH_2Cl_2$, 1-2 h; (iii) $NaN_3$ in DMF, 3 h; (iv) $NH_4F$ in MeOH, 16-20 h; (v) $(MeO)_3PO$, $POC_3$ then $(t-Bu_3NH)_4P_2O_7$, TEAB, 1 h; vi) $NH_4OH$.

The synthesis of 3'-O-azidomethyl-dNPTs is described in FIG. 20. Briefly, reaction of 5'-O-TBDMS-2'-deoxynucleosides (5) with a mixture of DMSO, acetic acid, and acetic anhydride installed the 3'-O-methylthiomethyl group (3'-O-MTM, 6), which upon treatment with $SO_2Cl_2$ converted to activated 3'-O—$CH_2$Cl (7). The latter can be monitored in TLC as 3'-OH (5) after dissolving in wet organic solvent due to fast hydrolysis of the —$CH_2$Cl group. The 3'-O—$CH_2$Cl-2'-deoxynucleoside (7) is then treated with $NaN_3$ in dry DMF without purification to convert to 3'-O—$CH_2N_3$ (8). 3'-O-azidomethyl-2'-deoxynucleosides of A, T, and C (9a-9c) were obtained in good yield after deprotection of the 5'-O-TBDMS group as described in the FIG. 20. Similar synthesis route for guanosine (G, 9d), lead only very low yield (>10%) due to formation of a number of side reaction products. To circumvent this, a new method was introduced for the synthesis of guanosine analog (14) which is described in the FIG. 21, which involved protection of the $O^6$— group by diphenycarbamoyl group. After protection of this particular group, the intermediate (12-14) became less polar, making easier to purify, and lead good overall yield in the azidomethyl group installation step.

Example 3

Synthesis of $N^6$-benzoyl-3'-O-(azidomethyl)-dA (9a)

The following describes exemplary synthesis steps for compounds shown in FIG. 20.

A. Synthesis of $N^6$-Benzoyl-3'-O-(methylthiomethyl)-5'-O-(tert-butyldimethylsilyl)-2'-deoxyadenosine (6a)

3.0 g $N^6$-Benzoyl-5'-O-tert-butyldimethylsilyl-2'-deoxyadenosine (5a) (6.38 mmol) was dissolved in a mixture consisting of 11.96 mL DMSO, 5.46 mL acetic acid, and 17.55 mL acetic anhydride and stirred at room temperature for 48 h. The reaction mixture was then neutralized treating with a sufficient amount of saturated $NaHCO_3$ solution and extracted with $CH_2Cl_2$ (3×100 mL). The combined organic extract was then washed with a saturated $NaHCO_3$ solution (100 mL), dried over $Na_2SO_4$, and concentrated under vacuum. The resultant yellowish oil was then purified on silica gel column (Hex: EtOAc/1:1 to 1:4) to obtain the product $N^6$-benzoyl-3'-O-(methylthiomethyl)-5'-O-(tert-butyldimethylsilyl)-2'-deoxyadenosine (6a) as white powder in 71% yield (2.4 g, $R_1$ 0.6, EtOAc: hex/7:3). HR-MS: obs. m/z 530.2273, calcd. for $C_{25}H_{36}O_4N_5SiS$ 530.2257 $[M+H]^-$. $^1$H-NMR ($CDCl_3$): $\delta_H$ 9.00 (s, 1H), 8.83 (s, 1H), 8.35 (s, 1H), 8.05 (d, J=7.6 Hz, 2H), 7.62 (m, 1H), 7.55 (m, 2H), 6.55 (t, J=7.19 Hz, 1H), 4.73 (m, 2H), 4.68 (m, 1H), 4.24 (m, 1H), 3.88 (dd, J=11.19, 3.19 Hz, 1H), 2.74-2.66 (m, 2H), 2.35 (s, 3H), 0.94 (s, 9H) and 0.13 (s, 6H) ppm.

B. Synthesis of $N^6$-benzoyl-3'-O-(azidomethyl)-2'-deoxyadenosine (9a)

To 0.4 g $N^6$-benzoyl-3'-O-(methythiomethyl)-5'-O-(tert-butyldimethylsilyl)-2'-deoxyadenosine (0.76 mmol) dissolved in 7 mL dry $CH_2Cl_2$ was treated with 0.4 mL cyclohexene and 155 µL $SO_2Cl_2$ (1.91 mmol) at 0° C. for 2 h. During this time the starting material completely converted to 7a which was shown by disappearance of the starting material and appearance of 3'-OH analog (5a) in TlC (EtOAC:Hex/7:3, $R_f$~0.3; the 3-$CH_2Cl$ (7a) could not detected in TLC due to decomposition in TLC plate to 5a). Then solvent was removed by rotary evaporation and kept about 10 minutes in high vacuum pump. Then dissolved in 5 mL dry DMF and treated with 400 mg $NaN_3$ (6.6 mmol) at room temperature for 3 h. Then the reaction mixture was partitioned in $H_2O/CH_2Cl_2$, the combined organic part was dried over $Na_2SO_4$ and concentrated by rotary evaporation. The crude sample was then dissolved in 5 mL MeOH and treated with 300 mg $NH_4F$ (8.1 mmol) more than 38 h. Then MeOH was removed by rotary evaporation. After partioning in $H_2O/EtOAc$, the combined organic part was dried over $Na_2SO_4$, concentrated, and purified by silica gel column chromatography (100% EtOAc to 98:2, EtOAc/MeOH) resulting 150 mg of 9a as white powder (48% yield in three steps). HR-MS: Obs. m/z 411.1530, calcd for $C_{18}H_{19}O_4N_8$ 411.1529 $[M+H]^+$. $^1$H-NMR ($CDC_3$): $\delta_H$ 8.84 (brs, 1H), 8.70 (brs, 1H), 8.08 (m, 1H), 7.76-7.54 (m, 5H), 6.47 (t, J=5.6 Hz, 1), 4.83 (m, 2H), 4.78 (m, 1H), 4.39 (m, 1H), 4.09 (d, J=12.78 Hz, $H_5$', 1H), 3.88 (d, J=12.78 Hz, $H_5$", 1H), 3.09 (m, $H_2$', 1H), and 2.65 (m, $H_2$", 1H) ppm.

Example 4

Synthesis of 3'-O-azidomethyl-dT (9b)

The following describes exemplary synthesis steps for compounds shown in FIG. 20.

A. Preparation of 3'-O-(methylthiomethyl)-5'-O-(tert-butyldimethylsilyl)-2'-deoxythymidine (6b)

2.0 g 5'-O-(tert-butyldimethylsilyl)-2'-deoxythymidine (5b) (5.6 mmol) was dissolved in a mixture consisting of 10.5 mL DMSO, 4.8 mL acetic acid, and 15.4 mL acetic anhydride and stirred for 48 h at room temperature. The mixture was then quenched by treating with a saturated $NaHCO_3$ solution and extracted with EtOAc (3×100 mL). The combined organic extract was then washed with a saturated solution of $NaHCO_3$ and dried over $Na_2SO_4$, concentrated under vacuum, and finally purified by silica gel column chromatography (Hex: EtOAc/7:3 to 1:1). The 3'-O-(methylthiomethyl)-5'-O-(tert-butyldimethylsilyl)-2'-deoxythymidine (6b) was obtained as white powder in 75% yield (1.75 g, $R_f$=0.6, hex:EtOAc/1:1). HR-MS: Obs. m/z 417.1890, cald. for $C_{18}H_{33}N_2O_5SSi$ 417.1879 $[M+H]^+$. $^1$H-NMR ($CDCl_3$): $\delta_H$ 8.16 (s, 1H), 7.48 (s, 1H), 6.28 (m, 1H), 4.62 (m, 2H), 4.46 (m, 1H), 4.10 (m, 1H), 3.78-3.90 (m, 2), 2.39 (m, 1H), 2.14, 2.14 (s, 3H), 1.97 (m, 1H), 1.92 (s, 3H), 0.93 (s, 9H), and 0.13 (s, 3H) ppm.

B. Preparation of 3'-O-(azidomethyl)-2'-deoxythymidine (9b)

To 1.095 g 3'-O-(methylthiomethyl)-5'-O-(tert-butyldimethylsilyl)-2'-deoxythymidine (6b) (2.6 mmol) dissolved in 10 mL dry $CH_2Cl_2$ were added 1.33 mL cyclohexene and 284 µL $SO_2Cl_2$ (3.5 mmol) at 0° C. and stirred at the ice-cold temperature for 1.5 h. Then the flask temperature was brought to room temperature and transferred to a round bottom flask. The volatiles were removed by rotary evaporation followed by high vacuum pump. Then the crude sample was dissolved in 5 mL dry DMF and 926 mg $NaN_3$ (15.4 mmol) was added to it and stirred for 3 h at room temperature. The crude sample was dispersed in 50 mL distilled water and extracted with $CH_2Cl_2$ (3×50 mL), the organic extracts were combined and dried over $Na_2SO_4$ and concentrated by rotary evaporation. The crude sample was then dissolved in MeOH (5 mL) and treated with $NH_4F$ (600 mg, 16.2 mmol) for 24 h at room temperature. Then reaction mixture was concentrated and partitioned between $H_2O$/$CH_2Cl_2$ and the combined organic extract was dried over $Na_2SO_4$, concentrated, and purified the product by silica gel column chromatography using Hex: EtOAc/1:1 to 2:5 resulting the final product (9b) as white powders (550 mg, 71% yield in three steps, $R_f$=0.3, Hex: EtOAc/1:1.5). HR-MS: Observed m/z 298.1146, calcd for $C_{11}H_{16}O_5N_5$ 298.1151 $[M+H]^+$. $^1$H-NMR ($CDC_3$): $\delta_H$ 8.30 (brs, 1H), 7.40 (s, 1H), 6.14 (t, J=6.8 Hz, 1H), 4.79-4.70 (m, 2H), 4.50 (m, 1H), 4.16 (m, 1H), 4.01-3.84 (m, 2H), 2.45 (m, 2H) and 1.95 (s, 3H) ppm.

Example 5

Synthesis of N⁴-Benzoyl-3'-O-(azidomethyl)-dC (9c)

The following describes exemplary synthesis steps for compounds shown in FIG. 20.

A. Preparation of N⁴-Benzoyl-3'-O-(methylthiomethyl)-5'-O-(tert-butyldimethylsilyl)-2'-deoxycytidine (6c)

3.5 g 3-benzoyl-5-O-tert-butyldimethylsilyl-2'-deoxycytidine (5c) (7.65 mmol) was dissolved in a mixture consisting of 14.7 mL DMSO, 6.7 mL acetic acid, and 21.59 mL acetic anhydride and stirred for 48 h at room temperature. During this period of time, a complete conversion to product was observed by TLC($R_f$=0.4, EtOAc:hex/10:1). The mixture was then neutralized with a saturated NaHCO₃ solution and extracted with $CH_2Cl_2$ (3×100 mL). The combined organic extract was then washed with saturated solution of NaHCO₃ and dried over $Na_2SO_4$, and concentrated under vacuum. The product was then purified by silica gel column chromatography (EtOAc:hex/2:1 to 9:1) to obtain N⁴-benzoyl-3'-O-(ethylthiomethyl)-5'-O-(tert-butyldimethylsilyl)-2'-deoxycytidine (6c) as white powder in 73% yield (2.9 g, $R_f$=0.6, EtOAc:hex/9:1). HR-MS: obs. m/z 506.2134, cald. for $C_{24}H_{36}O_5N_3SiS$ [M+H]⁺. 506.2145. ¹H-NMR (CDCl₃): $\delta_H$ 8.43 (d, J=7.1 Hz, 1H), 7.93 (m, 2H), 7.64 (m, 1H), 7.54 (m, 3H), 6.30 (m, 1H), 4.62 & 4.70 (2×d, J=11.59 Hz, 2H), 4.50 (m, 1H), 4.19 (m, 1H), 3.84 & 3.99 (2×dd, J=11.59 & 2.79 Hz, 2H), 2.72 (m, 1H), 2.21 (m, 1H), 2.14 (s, 3H), 0.99 (s, 9H), and 0.16 (s, 6H) ppm.

B. Preparation of N⁴-Benzoyl-3'-O-(azidomethyl)-2'-deoxycytidine (9e). To 0.5580 g N⁴-benzoyl-3'-O-(methylthiomethyl)-5'-O-(tert-butyldimethylsilyl)-2'-deoxycytidine (6c)

(1.04 mmol) dissolved in 8 mL dry $CH_2Cl_2$ were added 0.56 mL cyclohaxene and 220 μL $SO_2Cl_2$ (27 mmol) at 0° C. and stirred at the ice-cold temperature for 1 h. During this time, the starting material converted to the chlorinated product as shown by the 3'-OH (5c) compound in the TLC. The volatiles were then removed under vacuum and resuspended in dry DMF (5 mL) and treated with NaN₃ (400 mg, 6.6 mmol) and stirred for 2 h at room temperature. The sample was then partitioned between water and $CH_2Cl_2$ and the organic extracts were combined and dried over $Na_2SO_4$ and concentrated under vacuum. The crude sample was then dissolved in MeOH (5 mL) and treated with NH₄F (600 mg, 16.2 mmol) for 20 h at room temperature. Then solvent was removed under vacuum and extracted with $CH_2Cl_2$ and the organic extract was then dried over $Na_2SO_4$ and concentrated under vacuum. The sample was then purified by silica gel column chromatography (Hex:EtOAc 1:4 to 1:10), and the product (9e) was obtained as white powdery substance (~200 mg, 50% yield in three steps, $R_f$=0.5, EtOAc:Hex/5:0.5). HR-MS: Obs. m/z 387.1408, calcd for $C_{17}H_{19}O_5N_6$ 387.1417 [M+H]⁺. ¹H-NMR (CDC₃): $\delta_H$ 8.30 (d, J=7.2 Hz, 1H), 7.93 (d, J=7.50 Hz, 1H), 7.66-7.51 (m, 5H), 6.18 (t, J=6.4 Hz, 1H), 4.81-468 (m, 2H), 4.52 (m, 1H), 4.25 (m, 1H), 4.08-3.88 (m, 2H), 2.69 (m, 1H), and 2.50 (m, 2H) ppm.

Example 6

Synthesis of N²-isobutyryl-O⁶-diphenylcarbamoyl-3'-O-azidomethyl-dG (14)

Figure 21:
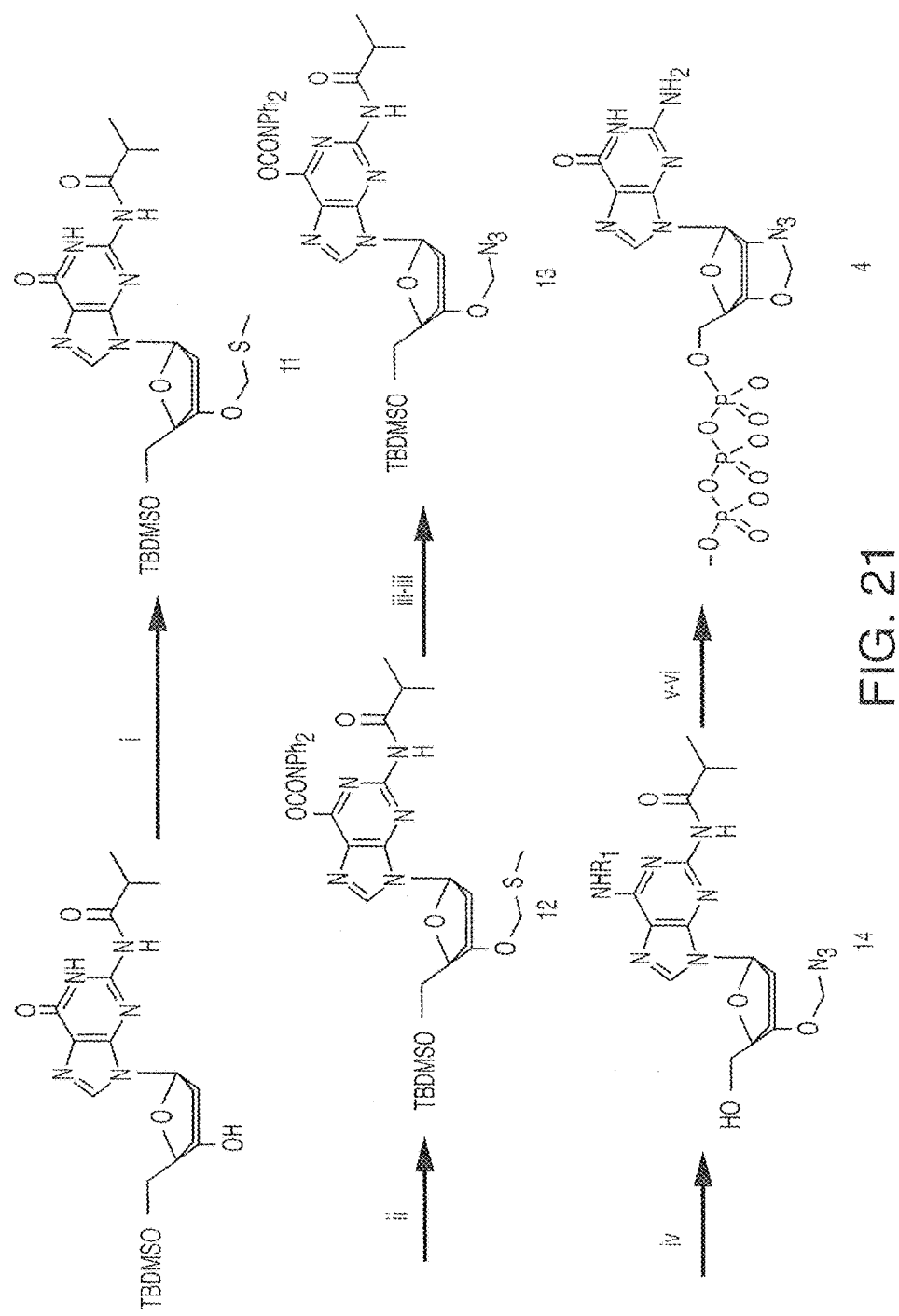
FIG. 21 shows synthesis of 3-O-azidomethyl-dGTP where the steps denote treatment with (i) DMSO, AcOH, $Ac_2O$, 48 h; (ii) $Ph_2NCOCl$, DIEA, Pyridine 3 h; (iii) $SO_2Cl_2$, dry $CH_2Cl_2$, 1-2 h; (iii) $NaN_3$ in DMF, 3 h; (iv) $NH_4F$ in MeOH, 24 h; (v) $(MeO)_3PO$, $POCl_3$ then $(t-Bu_3NH)_3P_2O_7H$, TEAB, 1 h; (vi) $NH_4OH$.
Figure 22A:
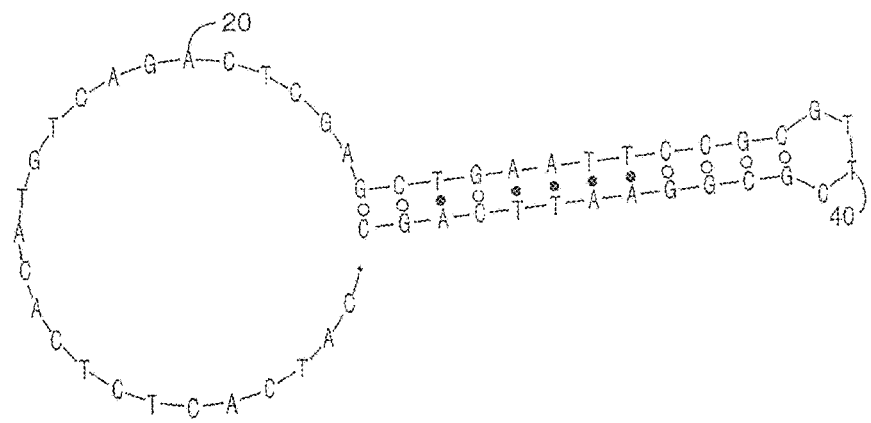
FIGS. 22A-D show synthetic DNA templates (FIGS. 22A, 22B, 22C and 22D) used in exemplary sequencing experiments.
Figure 22B:
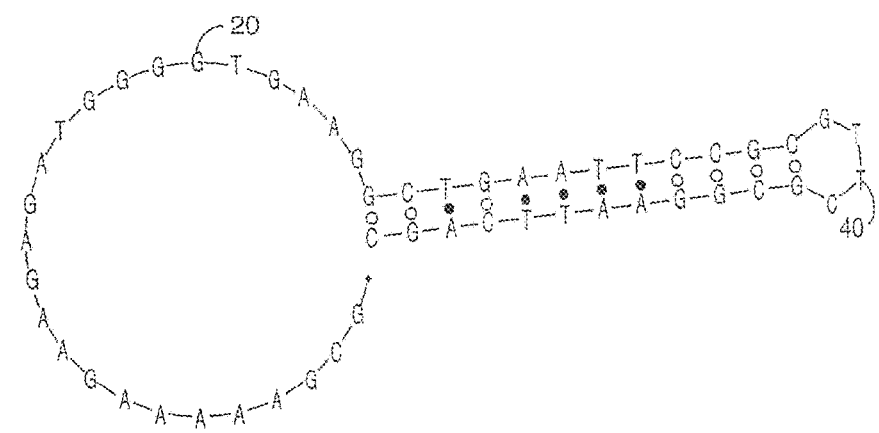
Figure 22C:
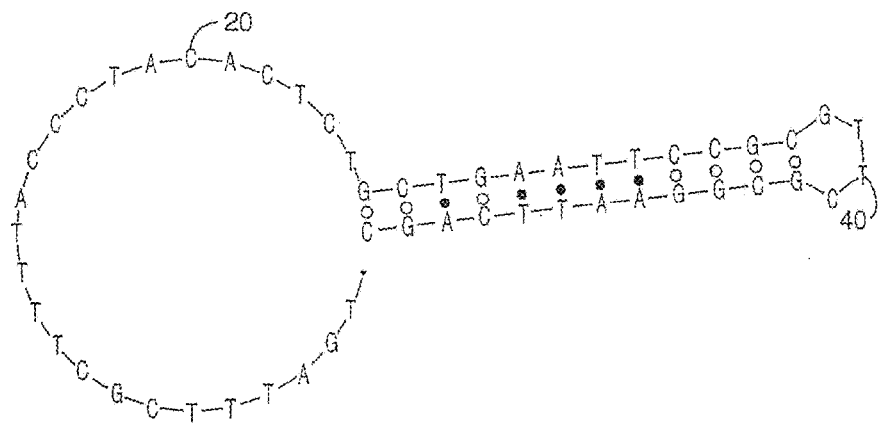
Figure 22D:
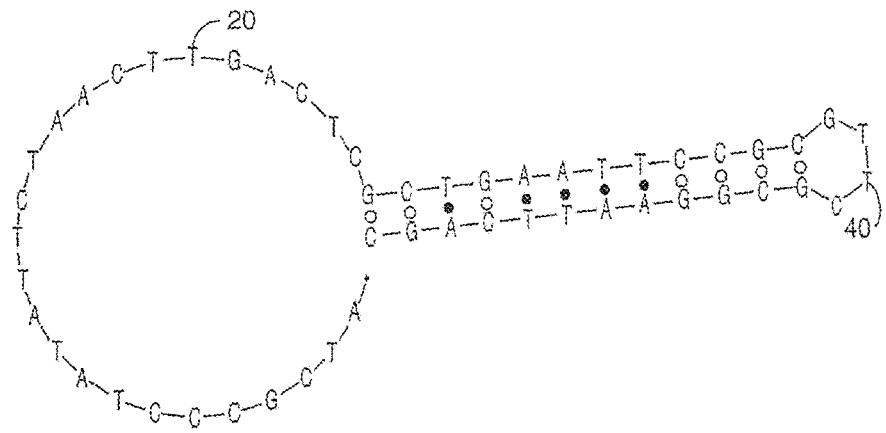
Figure 23A:
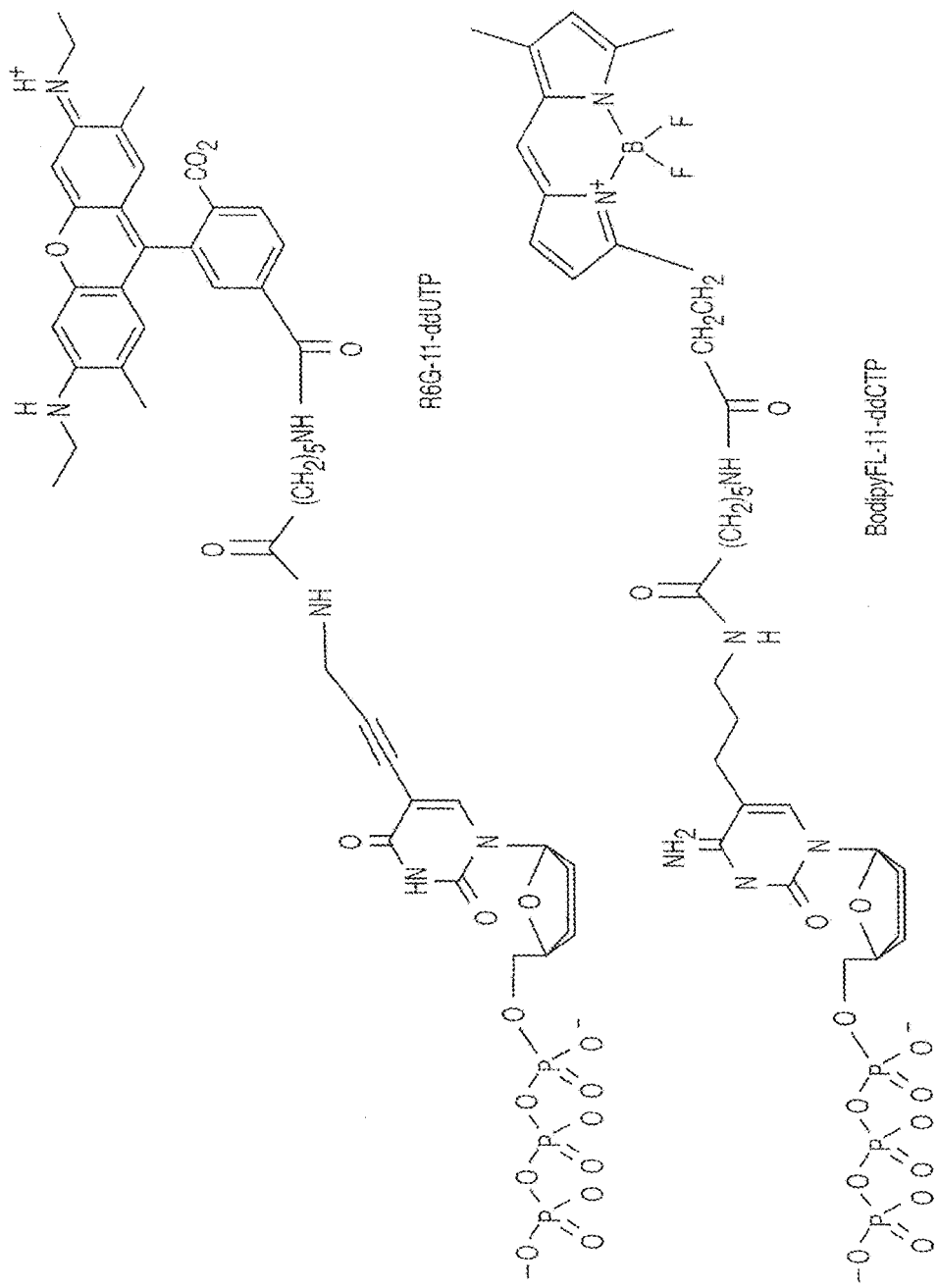
FIGS. 23A-B show the structures of exemplary labeled 2,3'-dideoxynucleotides (FIGS. 23A and 23B) used in the sequencing by synthesis
Figure 23B:
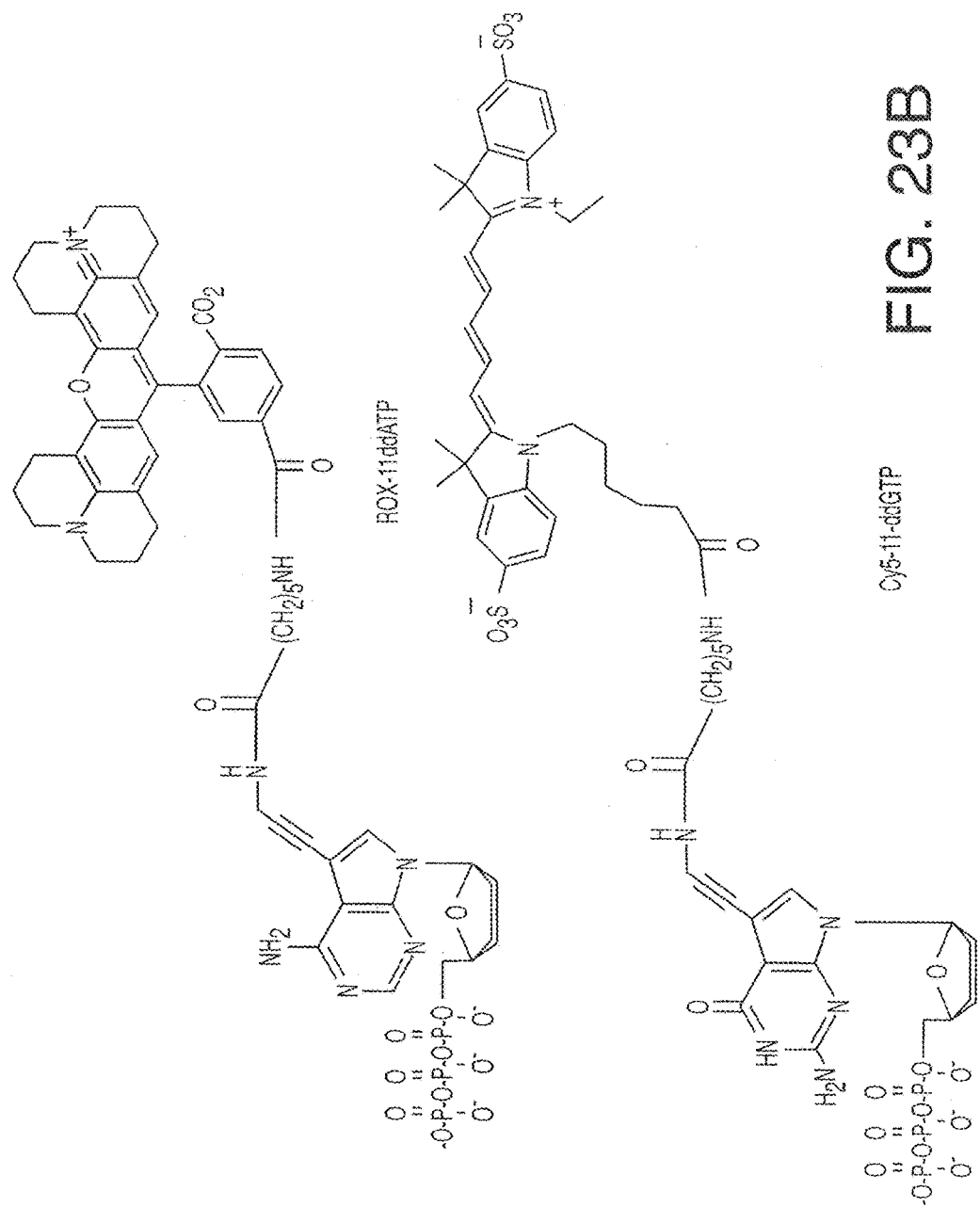

The following describes exemplary synthesis steps for compounds shown in FIG. 21.

A. Preparation of N²-isobutyryl-3'-O-(methylthiomethyl)-5'-O-(tert-butyldimethylsilyl)-2'-deoxyguanosine (11)

5 g of N²-isobutyryl-5'-O-(tert-butyldimethylsilyl)-2'-deoxyguanosine (11.0 mmol) dissolved in 21 mL dry DMSO was treated with 10 mL acetic acid and 32 mL acetic anhydride, and stirred for 48 h at room temperature. The crude reaction mixture was then neutralized by adding a $K_2CO_3$ solution, and extracted with ethyl acetate (100×3 mL). The combined organic extract was then washed with saturated NaHCO₃ solution, dried over $Na_2SO_4$ and concentrated under vacuum. Then reaction mixture was purified by a silica gel column chromatography resulting the product 11 as white powder (3.9 g, 69% yield; $R_f$=0.35, $CH_2Cl_2$:MeOH/20:1). HR-MS: Obs. m/z 512.2344 cald. for $C_{22}H_{38}O_5N_5SiS$ 512.2363 [M+H]⁺. ¹H-NMR (CDCl₃): $\delta_H$ 12.0 (s, 1H), 8.95 (brs, 1H), 8.09 (s, 1H), 6.24 (t, J=6.8 Hz, 1H), 4.73 (m, 2H), 4.66 (m, 1H), 4.16 (m, 1H), 3.81 (m, 2H), 2.76 (m, 1H), 2.59 (m, 1H), 2.54 (m, 1H), 2.21 (s, 3H), 1.29 (m, 6H), 0.91 (a, 9H), and 0.10 (s, 64) ppm.

B. Synthesis of N²-isobutyryl-O⁶-diphenylcarbamoyl-3'-O-(methylthiomethyl)-5'-O-(tert-butyldimethylsilyl)-2'-deoxyguanosine (12)

To 1.0 g N²-isobutyryl-3'-O-(methylthimethyl)-5'-O-(tert-butyldimethylsilyl)-2'-deoxyguanosine (11, 1.95 mmol) dissolved in 22 mL dry pyridine were added diphenylcarbamoyl chloride (0.677 g, 2.92 mmol) and 1.02 mL N,N-diisopropylethylamine, and stirred at room temperature for 3 h under nitrogen atmosphere. The reaction mixture became dark red during this time. The solvent was removed under high vacuum, and product was then purified by silica gel column chromatography using EtOAc:hex/1:1 to 7:3 as mobile phase. The product 12 was isolated as yellowish powder (1.09 g, ~80% yield; $R_f$=0.7, EtOAc:hex (1:1)). HR-MS: Obs. m/z 707.3068 calcd. for $C_{35}H_{47}O_6N_6SiS$ 707.3047 [M+H]⁺. ¹H-NMR (CDCl₃): $\delta_H$ 8.25 (s, 1H), 7.94 (brs, 1H), 7.47-7.37 (m, 10H), 6.42 (m, 1), 4.75 (m, 2H), 4.71 (m, 1H), 4.18 (m, 1H), 3.88-3.70 (m, 2H), 2.80 (m, 1H), 2.60 (m, 1H), 2.19 (s, 3H), 1.30 (d, J=7.2 Hz, 6H), 0.93 (s, 9H) and 0.14 (s, 6H) ppm.

C. Preparation of N²-isobutyryl-O⁶-diphenylcarbamoyl-3'-O-azidomethyl-2'-deoxyguanosine (14)

To 786 mg 12 (1.1 mmol) dissolved in 8 mL dry $CH_2Cl_2$ was treated with 0.56 mL cyclohexene and 180 μL $SO_2Cl_2$ (2.2 mmol) at 0° C. and stirred for 1.5 h at the same temperature. The solvent was then removed by rotary evaporation, and further dried under high vacuum for 10 minutes. The crude product was then dissolved in 5 mL dry DIM and reacted with 600 mg NaN₃ (10 mmol) at 0 aC and stirred at room temperature for 3 h. Reaction mixture was then partitioned $H_2O/CH_2Cl_2$, the combined organic extract was then dried over $Na_2SO_4$, and concentrated by rotary evaporation. The crude was then dissolved in 5 mL dry MeOH, treated with 500 mg NH₄F (13.5 mmol) at room temperature for more than 24 h. Then MeOH solvent was removed by rotary evaporation, and partitioned ($H_2O/CH_2Cl_2$). The combined organic part was dried over $Na_2SO_4$ and concentrated by rotary evaporation and purified by silica gel column chromatography resulting pure product of 14 as white powder (230 mg, ~36% yield in three steps; hex:EtOAc 1:1 to 1:5, ($R_f$=~0.3, Hex:EtOAc/1:4). HR-MS: Obs. m/z 588.2343, calcd for $C_{28}H_{30}O_6N_9$ 588.2319 [M+H]$^+$. $^1$H-NMR (DFM-$d_6$): $\delta_H$ 8.64 (brs, 1H), 7.48-7.34 (m, 10H), 6.36 (t, J=7.0 Hz), 4.93 (m, 2H), 4.76 (m, 1H), 4.04 (m, 1H), 3.57 (m, 1H), 3.34 (m, 2H), 2.97 (m, 1H), 2.81 (m, 1H), and 1.10 (m, 6H).

Example 7

General Method for the Preparation of 3'-O-Azidomethyl-Dntps

The protected 3'-O-azidomethyl nucleoside (0.3 mmol) and proton sponge (75.8 mg; 0.35 mmol) were dried in a vacuum desiccator over $P_2O_5$ overnight before dissolving in trimethyl phosphate (0.60 mL). Then freshly distilled $POCl_3$ (33 μL, 0.35 mmol) was added drop-wise at 0° C. and the mixture was stirred at 0° C. for 2 h. Subsequently, a well-vortexed mixture of tributylammonium pyrophosphate (552 mg) and tributylamine (0.55 mL; 2.31 mmol) in anhydrous DMF (2.33 mL) was added in one portion at room temperature and stirred for 30 min. Triethyl ammonium bicarbonate solution (TEAB) (0.1 M, 15 mL, pH 8.0) was then added and the mixture was stirred for 1 h at room temperature. Then 15 mL of $NH_4OH$ was added and stirred overnight at room temperature. The resulting mixture was concentrated in vacuo and the residue was diluted with 5 mL of water. The crude mixture was then purified with anion exchange chromatography on DEAE-Sephadex A-25 at 4° C. using a gradient of TEAB (pH 8.0; 0.1-1.0 M). Further purification by RP HPLC to give corresponding target as colorless syrup:

Example 8

3'-O-Azidomethyl Nucleotides Cleavage

The 3'-O-azidomethyl group cleavage can be accomplished with a variety of reducing agents such as phosphines. The cleavage agents that are particularly desirable are those that are soluble in aqueous media and do not cause any damage to the DNA. One particularly desirable agent is tri(carboethoxy)phosphine (TCEP).

The 3'O-azidomethyl nucleotides can be separated from native nucleotides using RP HPLC. In the next experiment, the kinetics of the 3'-O-azidomethyl TTP cleavage was studied. For this purpose, a 1 mM solution of nucleotide was prepared in water and mixed with 50 mM solution of TCEP/400 mM of Tris at pH 8.0 and incubated at 55 deg C. for various periods of time. After the incubation, the reaction was stopped by mixing with 4 M NaOAc at pH=4.3 and an aliquot of reaction mixture (0.5 nmole of nucleotide) was injected and separated on the RP HPLC column. The integrated peak area was then plotted against time.

Example 9

Sequencing by Synthesis Using 3'-O-Azidomethyl Nucleotides

We established conditions for sequencing by synthesis on the surface using 3'-O-azidomethyl nucleotides. For this purpose we used variants of the 9 deg N polymerase that were developed specifically to incorporate 3'-O-azidomethyl nucleotides. For these sequencing experiments we were using synthetic DNA templates that encompass self priming moieties. Examples of these DNA templates and their secondary structures are shown in FIG. 22A-D.

These oligonucleotides carry a 5'-amino modification through which they are attached to assay surface. The surface constitutes any surface that is bio-compatible, has low fluorescent background and has functional groups on the surface which can be used to covalently attach the DNA. In the described case, pre-activated Codelink (from GE Healthcare) slides were used for this purpose. The solution of the oligonucleotides (50 uM) for spotting was prepared in 150 mM phosphate/bicarbonate spotting buffer (pH=7.5). The arrays were then spotted and incubated in the humid chamber at 25 deg C. overnight. After the incubation, the arrays were blocked by washing in the 1×TBST/2% BSA buffer, rinsed with nuclease free water and dried.

The sequencing was performed in a chambered slide (Grace Biolabs). In the experiment, each well was subjected to different number of cycles using the mixture of 3'-O-azidomethyl nucleotides with each extension cycle followed by a cleavage cycle. Extension cycle consisted of incubating the well with the solution containing: 3'-O-azidomethyl nucleotide mix—75 uM, 9 deg N polymerase mutant—250 ug/ml, 10 mM KCl, 10 mM (NH4)2SO4, 20 mM Tris-HCl, 4 mM MnSO4, 0.1% Triton-X-100, 0.1% acetylated BSA, pH 8.8. The incubation was carried out at 65 deg C. for 20 minutes. After the incubation the wells were washed with Thermopol II buffer 3× and then subjected to cleavage with TCEP (100 mM) in 400 mM Tris-HCl (pH=8.5) at 65 deg C. for 15 minutes. After the cleavage the wells were washed with the extension reaction buffer (3×) and subjected to the next extension reaction. The wells were read out with final readout mixture consisting of: 2,3'-dideoxynucleotide mix (labeled)—2 μM, Therminator II polymerase—250 μg/ml, 10 mM KC, 10 mM (NH4)2SO4, 20 mM Tris-HCl, 2 mM MnSO4, 0.1% Triton-X-10. The structures of these nucleotides are presented in FIG. 23 A-B. After labeling cycle the slide was washed with wash/block buffer (5×SSC, 0.1% Tween, 2% BSA), rinsed with water and dried before imaging. Each well was imaged using a prototype sequencing instrument and bases were then called based on the relative intensity of the observed signal. The result of the experiment is presented in FIG. 24 A-D.

Example 10

Synthesis of 2'-Fluoro, 3'-O-Azidomethyl Nucleotides

Figure 25:
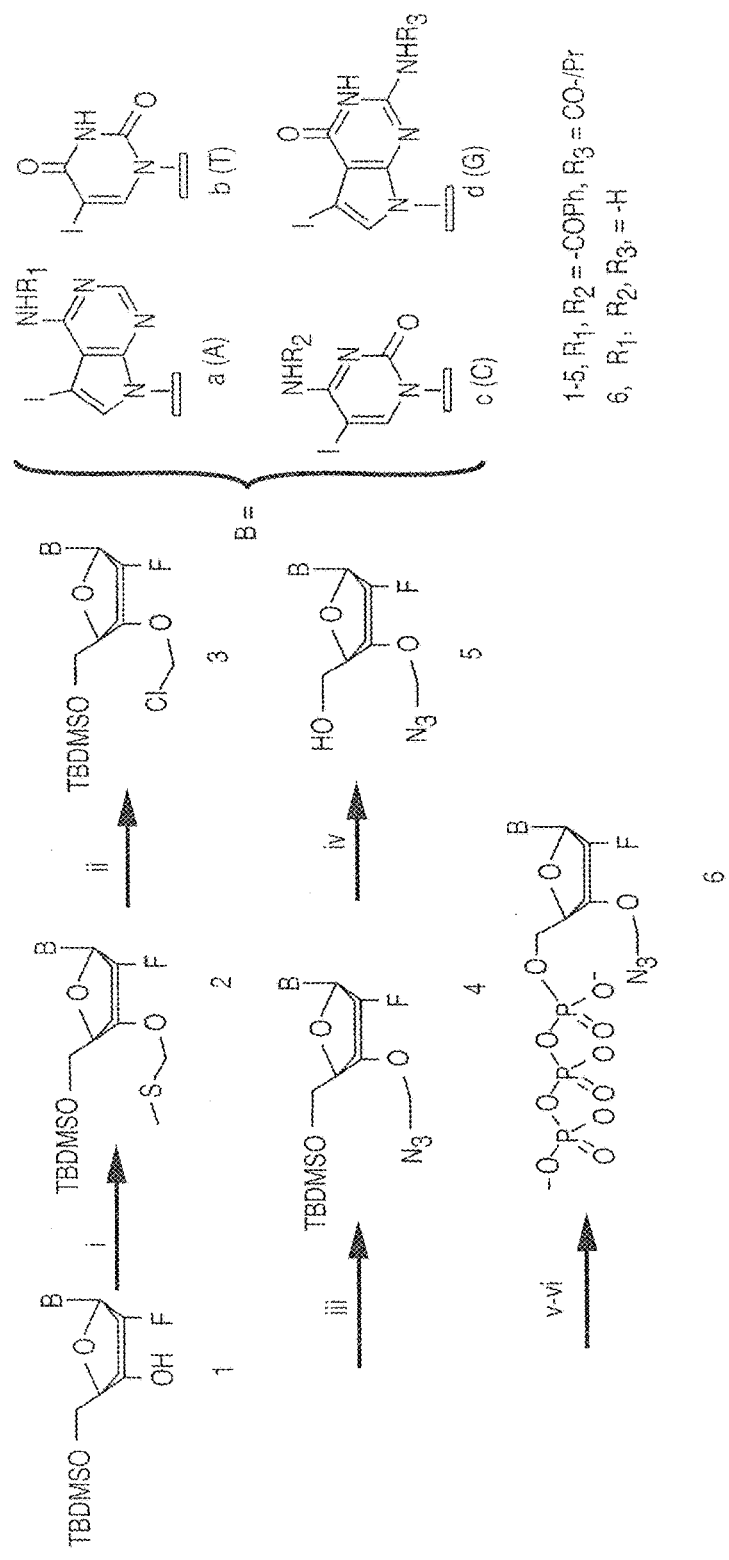
FIG. 25 shows synthesis steps for 2'-fluoro-3'-O-azidomethyl-dNTPs, where the steps comprise the following exemplary conditions (i) DMSO, AcOH, $Ac_2O$, 48 h; (ii) $SO_2Cl_2$, dry $CH_2Cl_2$, 1-2 h; (iii) $NaN_3$ in DMF, 3 h; (iv) $NH_4F$ in MeOH, 16-20 h; (v) $(MeO)_3PO$, $POCl_3$ then $(t-Bu_3NH)_4P_2O_7$, TEAB, 1 h; vi) $NH_4OH$.

The synthesis of 2'-fluoro-3'-O-azidomethyl-dNTPs is described in FIG. 25. Briefly, reaction of 5'-O-TBDMS-2'-fluoro-2'-deoxynucleosides (1) with a mixture of DMSO, acetic acid, and acetic anhydride installed the 3'-O-methylthiomethyl group (3'-O-MTM, 2), which upon treatment with $SO_2Cl_2$ converted to activated 3'-O—$CH_2Cl$ (3). The 2'-fluoro-3'-O—$CH_2Cl$-2'-deoxynucleoside (3) is then treated with $NaN_3$ in dry DMF without purification to convert the 3'-O—$CH_2Cl$ to 3'-O—$CH_2N_3$(4). 2'-fluoro-3'-O-azidomethyl-2'-deoxynucleosides of A, T, and C (5a-5c) can be obtained in good yield after deprotection of the 5'-O-TBDMS group as described in FIG. 25. In case of 2'-fluoro-3'-O-azidomethyl-2'-deoxybuanosine (0, 5d), the $O^6$— group is protected by diphenycarbamoyl group to increase yield. Finally, the respective nucleosides are phosphorylated using phosphorous oxychloride followed by tetrabutylammonium pyrophosphate in the presence of proton sponge (1,8-dimethylaminonaphthalene) and converted to their respective triphosphates (6).

Example 11

Synthesis of 2'-Fluoro, 3'-O-Azidomethyl Propargylamino Nucleotides

Figure 26:
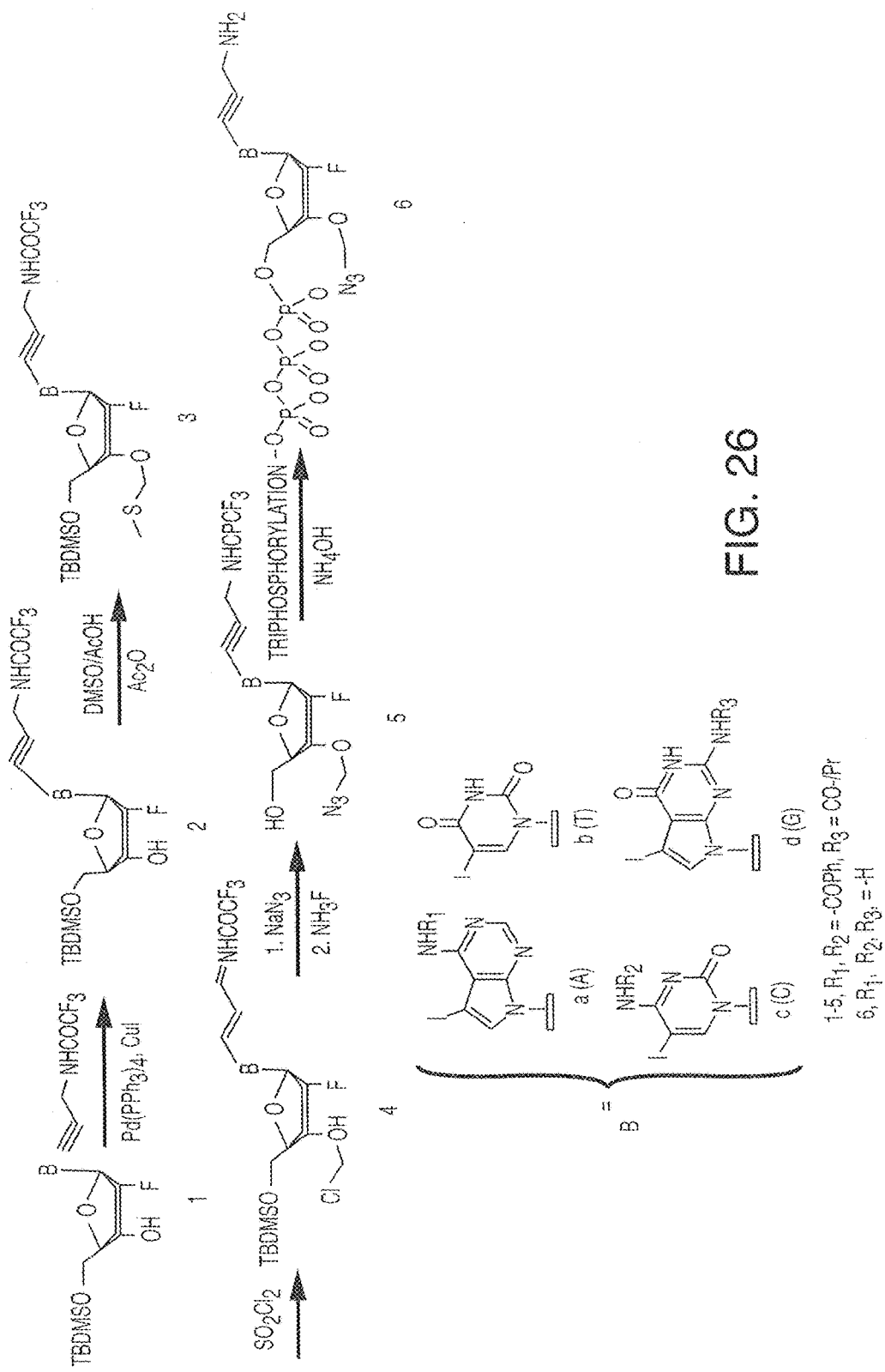
FIG. 26 shows synthesis steps for 2'-fluoro-3'-O-azidomethyl-(propargylamino)-dNTP synthesis.

Synthesis of 2'-fluoro-3'-O-azidomethyl-(propargylamino)-dNTPs is described in FIG. 26. Briefly, reaction of 5'-O-TBDMS-2'-fluoro-(5/7-iodo*)-2'-deoxynucleosides (1) with a mixture of N-trifluoroacetyl-propargylamine, tetrakis (triphenylphosphine) palladium (0) and CuI resulted in the formation of 5/7-propargylamido substituted nucleosides (2). In the next step the mixture of DMSO, acetic acid, and acetic anhydride installed the 3'-O-methylthiomethyl group (3'-O-MTM, 3), which upon treatment with $SO_2Cl_2$ converted to activated 3'-O—$CH_2Cl$ (4). The 2'-fluoro-3'-O—$CH_2Cl$-5/7-propargylamido-2'-deoxynucleosides (4) were then treated with $NaN_3$ in dry DMF without purification to convert the 3'-O—$CH_2Cl$ to 3'-O—$CH_2N_3$. (5) 2'-fluoro-3'-O-azidomethyl-(propargylamino)-2'-deoxynucleosides of A, T, and C (5a-5c) can be obtained in good yield after deprotection of the 5'-O-TBDMS group as described in FIG. 26. In case of 2'-fluoro-3'-O-azidomethyl-2'-deoxybuanosine (C, 5d), the $O^6$— group is protected by diphenycarbamoyl group to increase yield. *5-iodo, 2'-fluoro-2'-deoxy purines and 7-iodo-7-deaza-2'-fluoro-2'-deoxy pyrimidines were used as starting material. The synthesis of these compounds is well known to those skilled in the art.

Example 12

Spectral Crosstalk Calibration

Figure 32A:
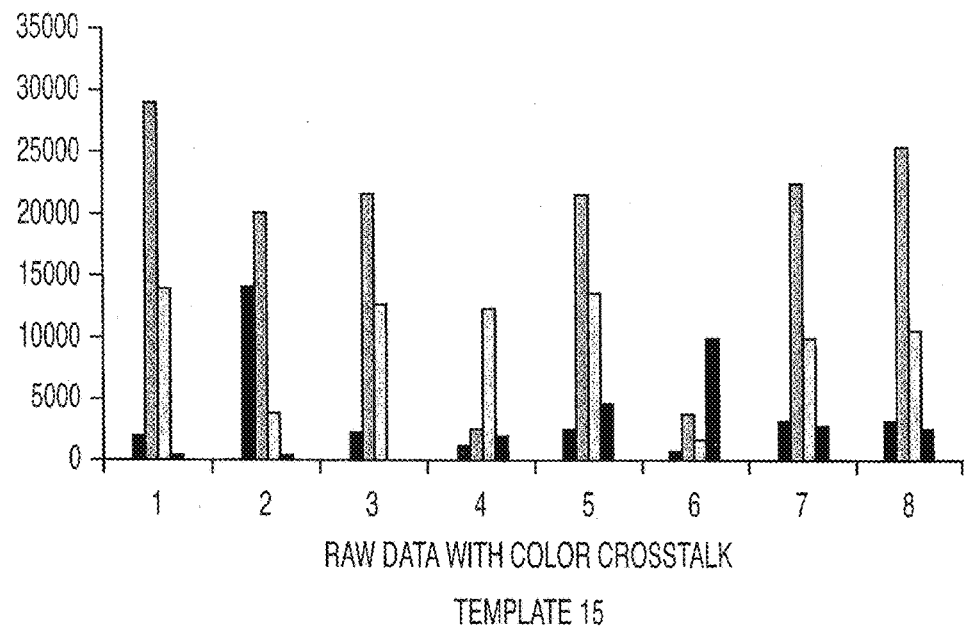
FIGS. 32A-B show sequencing by synthesis probe intensity in four channels (blue, green, yellow, and red) for a spot on a chip.
Figure 32B:
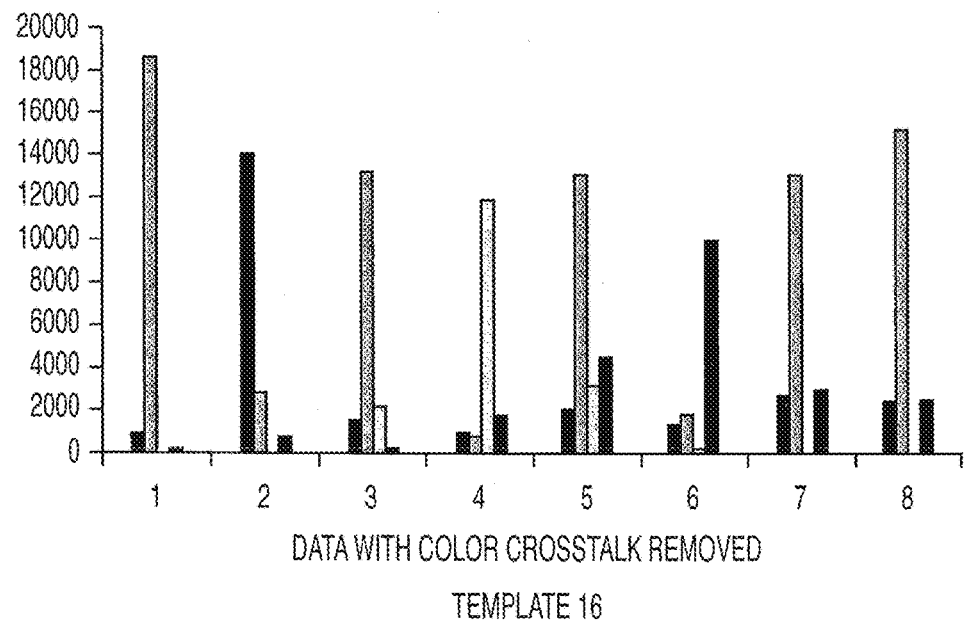

We calibrated the four color detection system of the above described exemplary SBS device using a chip spotted with four separate dyes, one in each of four spots. We then made measurements of the chip in all four channels, calculated the spectral crosstalk factors and constructed the K and $K^{-1}$ matrices. FIG. 32 A-B shows the effect of applying the spectral crosstalk calibration matrix K-1 to raw sequencing data. The data demonstrates that the second base in the sequence would be miscalled as green were the spectral crosstalk calibration not performed.

Example 13

Re-Phasing Sequencing by Synthesis Data

Figure 33A:
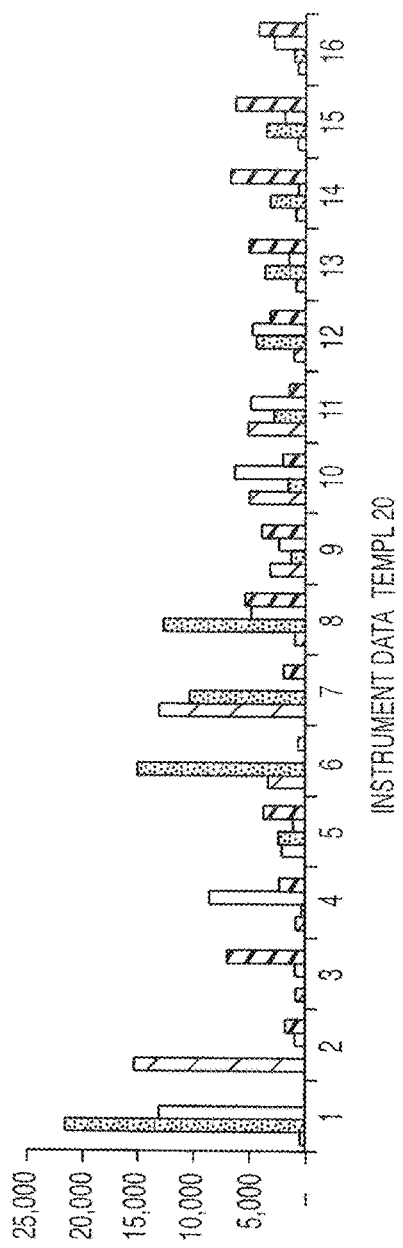
FIG. 33A shows 16-base-long sequence data.
Figure 33B:
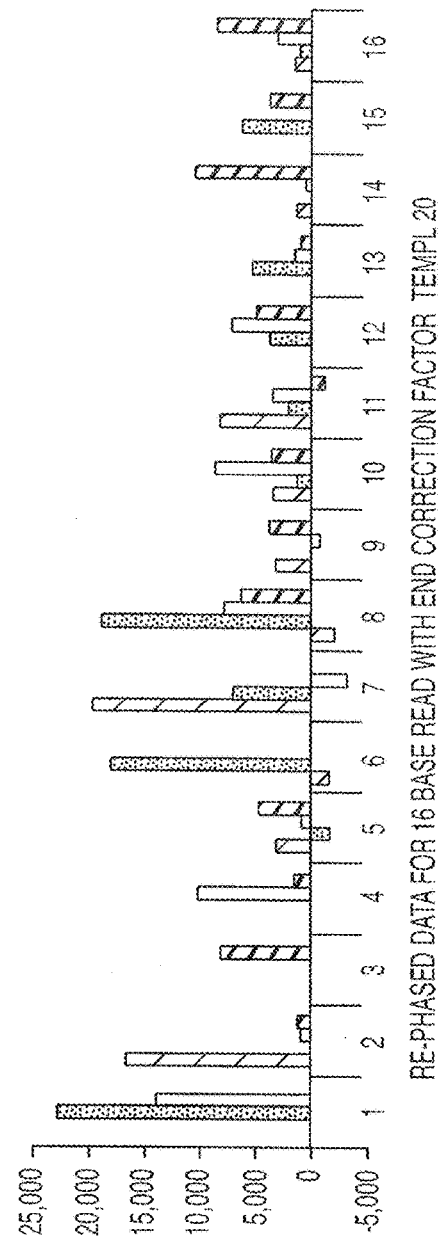
FIG. 33B shows the same data after applying the lead/lag compensation algorithm.
Figure 34A:
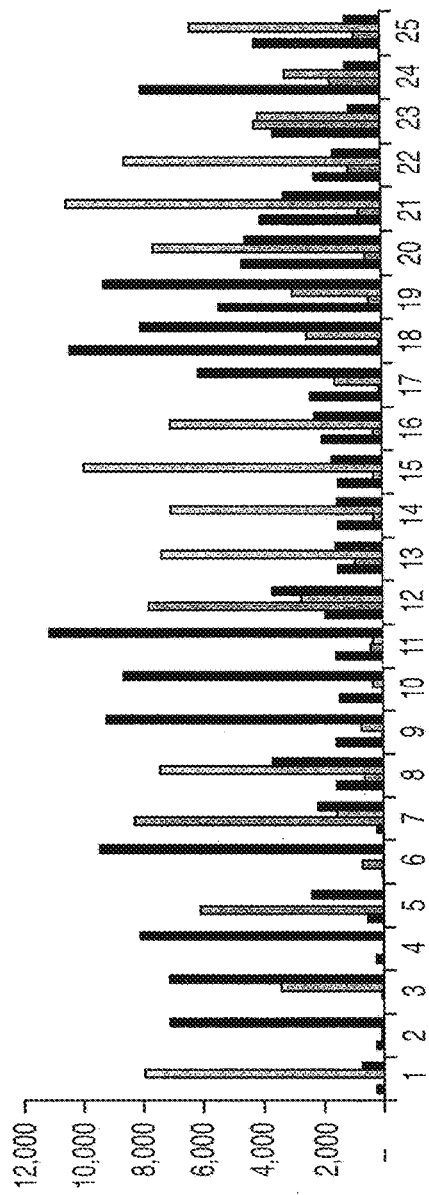
FIG. 34A shows 25-base-long sequence data and FIG. 34B shows the same data after applying the lead/lag compensation algorithm.
Figure 34B:
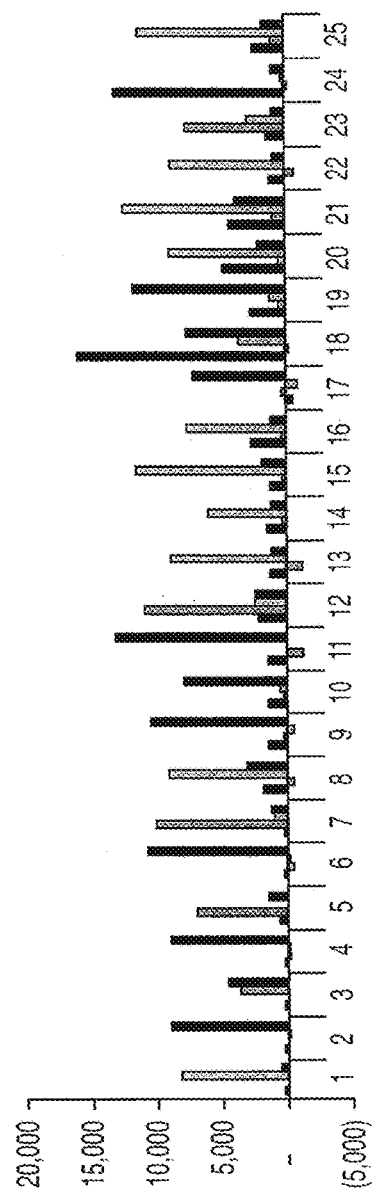

As discussed above, dephasing of sequence data is cumulative and can potentially be significant with longer read lengths. We applied the lead/lag compensation described above to both a 16-base and 25-base sequences containing an AGCT repeat. The results are shown in FIGS. 33A-B and 34A-B. FIG. 33A shows the original data captured by the fluorescent detection system and FIG. 33B shows the data after being multiplied by the lead/lag compensation matrix with a lead parameter of 4.5% and a lag parameter of 1%. The relatively high lead parameter was probably due to native nucleotide contamination in the polymerase preparation. FIG. 33 A-B illustrates how the compensation helps to correct miscalls. For example, bases at locations 11, 13 and 15 would be a miscall in the original dephased data, but are correctly called (as are all the other bases) in the rephased data. For the 25-base read in FIG. 34 A-B, the lead and lag parameters were 1.2% and 1.5% respectively. Although the lead and lag for this sample were not large enough to create miscalls in the original data (FIG. 34A), the lead/lag correction does make the correct base a stronger signal compared to the other colors (FIG. 34B). While in both corrected sequences (FIGS. 33B and 34B), the matrix multiplication produces some negative values, these are probably due to noise, and may be ignored as long as they are small values. FIG. 34 A-B shows that we were able to generate data with high fidelity out to 25 bases.

Example 14

Sequencing by Synthesis Data: Extra Washing

In this example, additional washing was done in an attempt to completely remove the cleaving agent prior to the next cycle in sequencing by synthesis. Interestingly, increased washing cycles after cleavage step have only minimal effect on the sequencing performance, as illustrated in the Table below.

| | Rephased Data | | | | | |
|---|---|---|---|---|---|---|
| | 25 nt Templates | | 35 nt Templates | | All Templates % Correct | |
| Washes | Lead | Lag | Lead | Lag | Calls | Qa* |
| 24 | 2.56% | 1.69% | 1.75% | 1.12% | 92.0% | 0.822 |
| 48 | 1.55% | 2.32% | 1.20% | 1.80% | 96.0% | 0.862 |
| 100 | 1.40% | 2.80% | 0.95% | 1.65% | 95.5% | 0.826 |

*Qa = Intensity of the correct base signal/intensity of the second highest signal The metric used to measure the dephasing process is the lead percentage derived empirically to compensate for the lead observed in the run. Only at very high wash cycles (i.e. too many washes to be practical) can one improve the base calling accuracy.

Example 15

Sequencing by Synthesis Data: Using a Scavenger

In this example, scavengers were used in an attempt to inhibit any remaining cleaving agent prior to the next cycle in sequencing by synthesis. As noted above, such compounds can be included in the solutions used for sequencing by synthesis (or in a separate additional solution if desired). In this example, the suitable operating concentration for the scavenger in the Extend A/B solutions was explored. Two different scavengers were used.

A. Cystamine Scavenger

3'-O-azidomethyl nucleotides labeled with dyes on a cleavable disulfide linker were used. A range of scavenger concentrations were tested to determine which concentration is acceptable by the polymerase. The table below shows lead and lag values, and percentage of correct calls for the 3'-O-azidomethy/disulfide chemistry in the absence and in the presence of a first scavenger (cystamine @ 1 mM).

| | AVG Lead [%] | AVG Lag [%] | Correct calls [%] |
|---|---|---|---|
| NO SCAVENGER | 2.0 | 3.1 | 93.7 |
| CYSTAMINE SCAVENGER | 1.1 | 1.9 | 98.7 |

Figure 38:
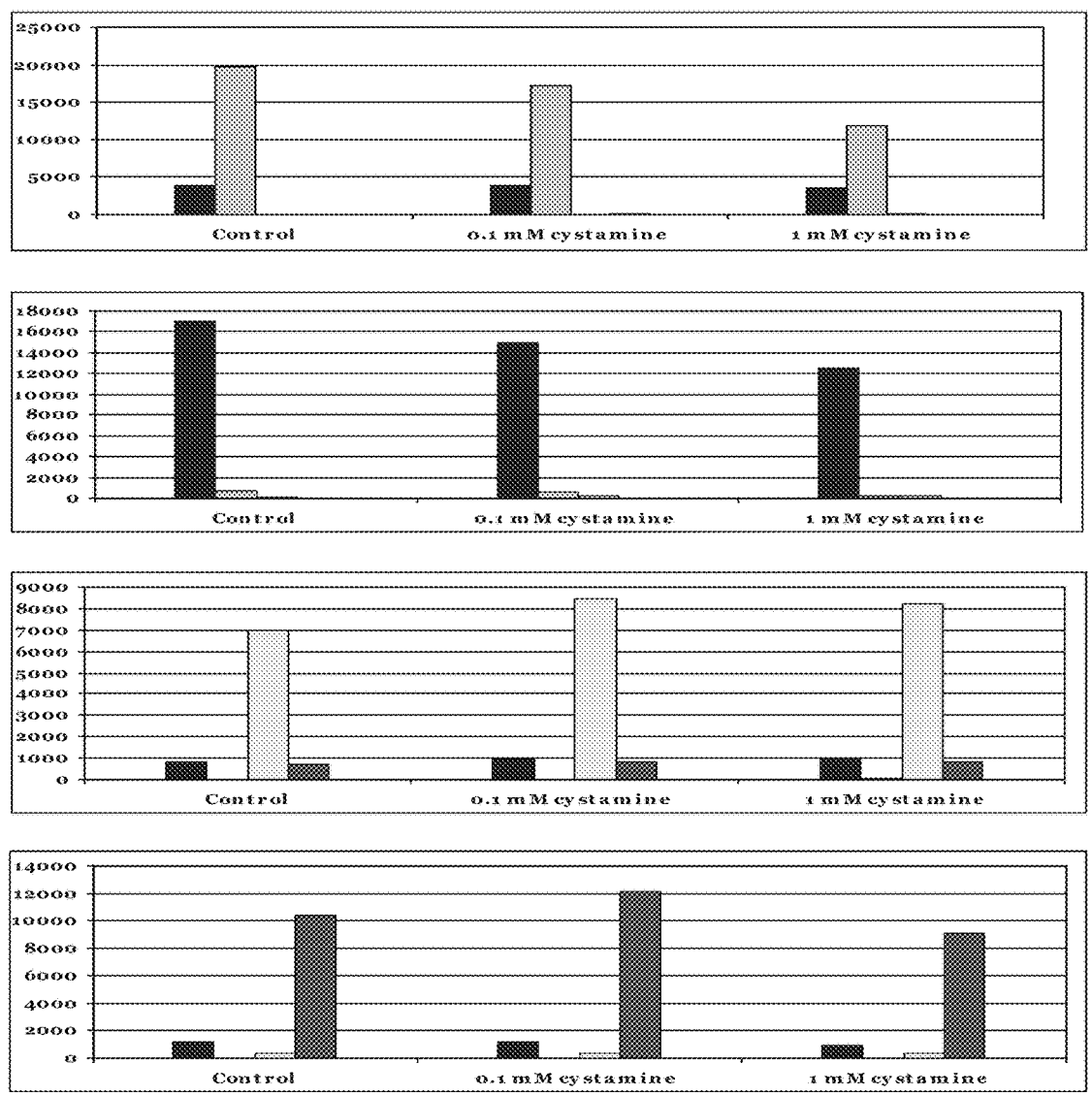
FIG. 38 shows detection of incorporated nucleotides in an extension reaction done in the presence of a first scavenger (cystamine).

It is clear from the data in the table that the use of a scavenger can improve the accuracy of base calling and reduce lead and lag. Importantly, extension reactions performed in the absence and in the presence of this disulfide based scavenger, cystamine, showed the additive does not significantly interfere with the extension reaction (FIG. 38).

B. ATA Scavenger

Figure 39:
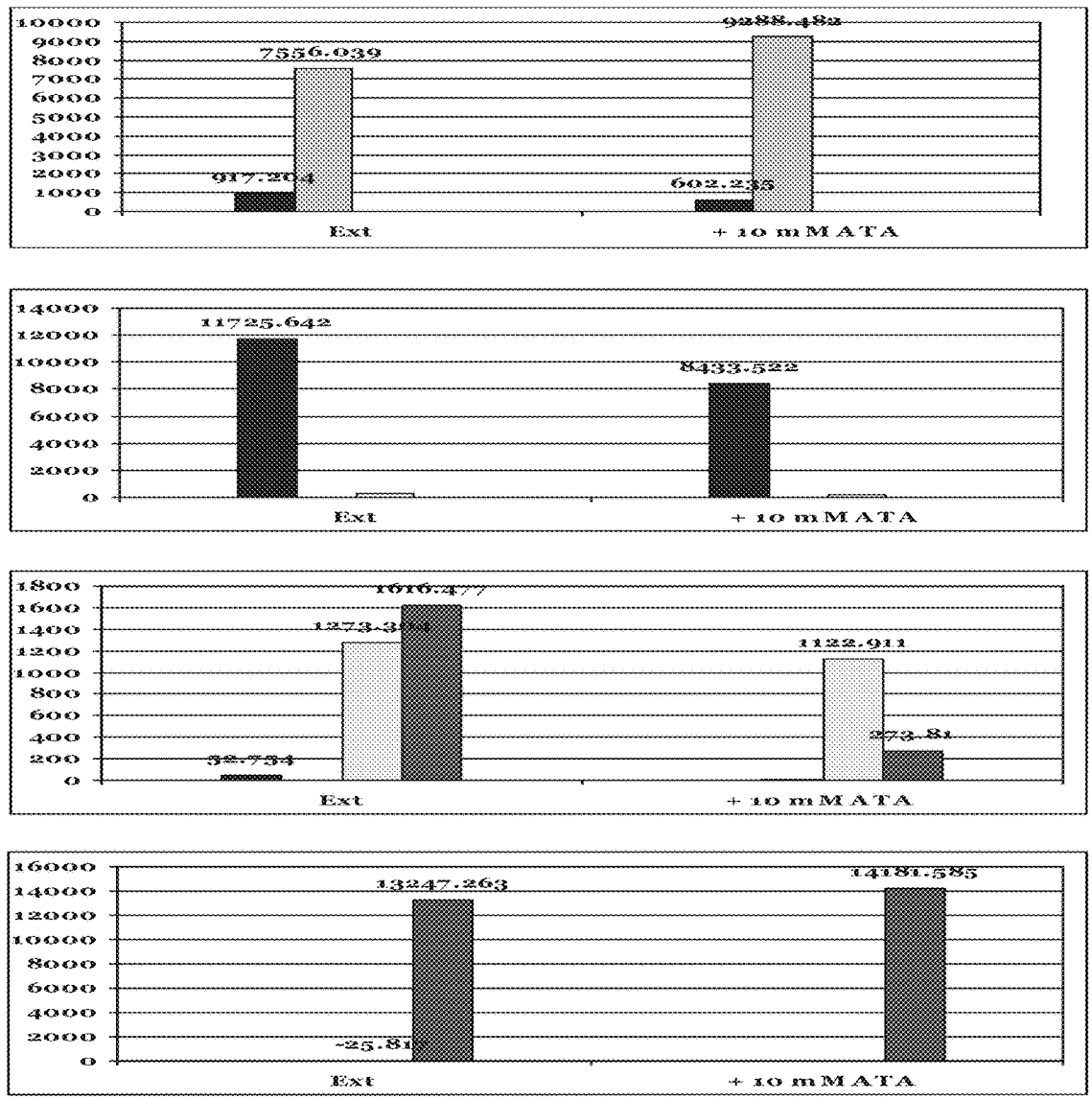
FIG. 39 shows detection of incorporated nucleotides in an extension reaction done in the presence of a second scavenger (ATA).

A second scavenger was also tested, i.e. the azido based scavenger, ATA: (11-Azido-3,6,9-trioxaundecan-1-amine). Extension reactions performed in the absence and in the presence of this azido based scavenger. Nucleotides with 3'-O-azidomethyl groups and with azido based cleavable linkers were used. The results (FIG. 39) show that the additive does not significantly interfere with the extension reaction.

Example 16

Synthesis of Disulfide-Dye Labeled 3'-O-Azidomethyl Nucleotide

Figure 40:
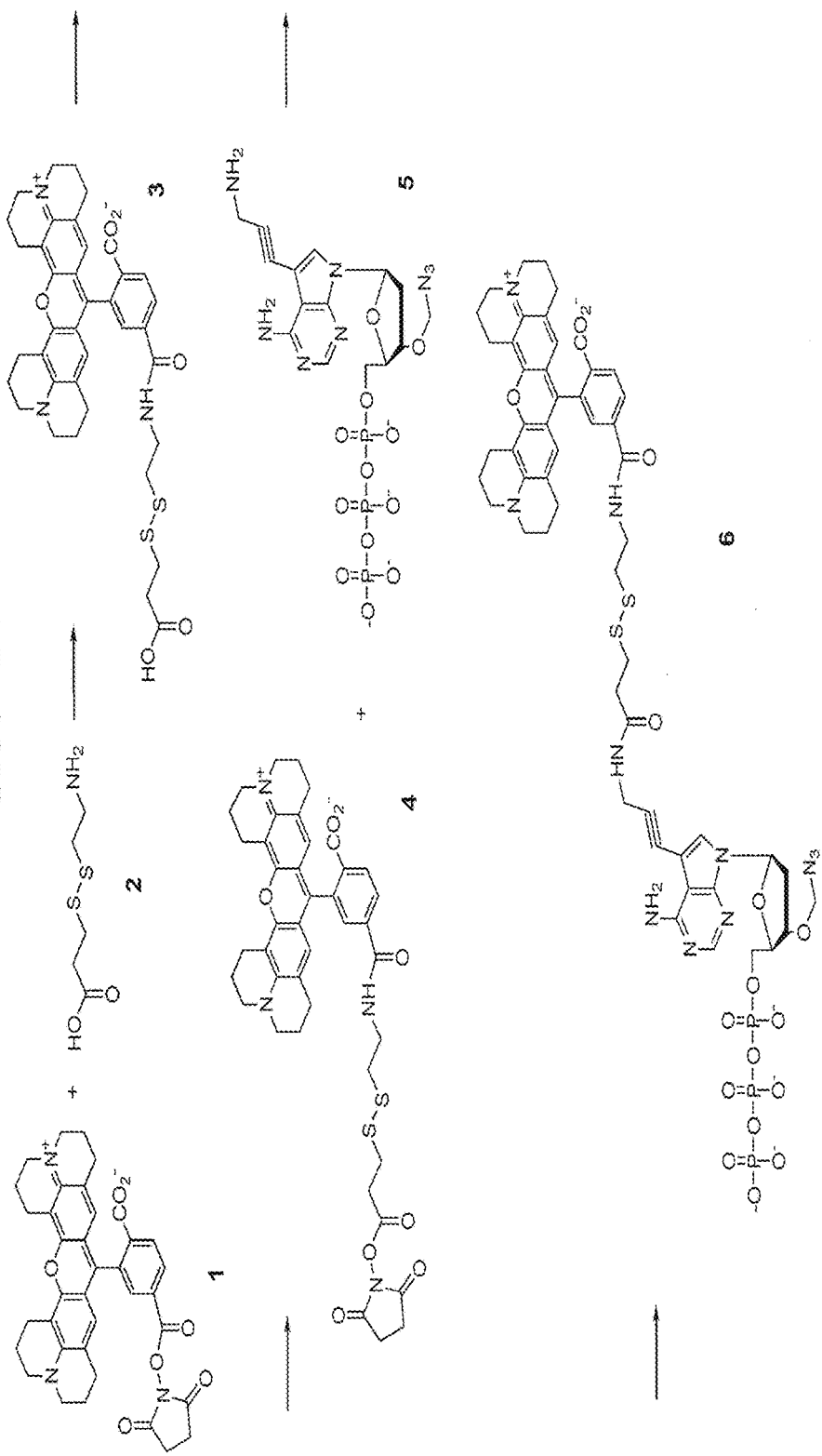
FIG. 40 is a schematic showing one embodiment for the synthesis of 3'-O-azidomethyl, 7-propargylamido-[3-((2-amidoethyl)dithio) propionamido]-6-carboxy-X-rhodanine deoxyadenosine triphosphate.

In this example, a method is described for synthesizing a nucleotide analogue containing an azidomethyl group on the 3"-OH and a label attached via a disulfide linker (which is cleavable). The scheme is shown in FIG. 40. Preparation of the linker buffer solution: 11 mg of 3-((2-aminoethyl)dithio) propionic acid hydrochloride (Prod #22101 from Pierce Biotech company, 2) was dissolved in 100 µl of 0.1 M sodium bicarbonate and 900 µl of acetonitrile, 14 µl of triethylamine was added. To a solution of 6-carboxy-X-rhodamine, succinimidyl ester (6-ROX SE, cat. #C6126, Invitrogen, 1) (158 µl L, 25 mM, 3.96 µmol) in DMF was added the above linker solution (500 µl, 50 mM, 25.0 µmol). The reaction mixture was stirred overnight at room temperature and then 800 µl of TEAB buffer (50 mM, pH 8) was added. The mixture was purified by HPLC and concentrated to give 0.51 µmol of product 3. HPLC method: A, 50 mM triethylammonium bicarbonate (TEAB) buffer, pH=8.0; B, acetonitrile and eluted with a linear gradient of 0-70% B over 35 minutes and at a flow rate of 2 ml/min. The column used was NoaPak C18, 8×100 mm. Retention time for product is 20.5 min. Retention time for hydrolysis of starting material is 18.2 min.

To the above linker-dye conjugate product 3 (0.51 µmol) in 300 µl of DMF was added a solution of 2,6-dimethylaminopyridine (DMAP) (25 mM, 31 µl, 0.77 µmol) and a solution of N,N'-disuccinimidyl carbonate (DSC) (25 mM, 31 µl, 0.77 µmol). The reaction mixture was stirred for one hour at room temperature. 7-propargylamino, 3'-O-azidomethyl-dATP 5 (1.5 µmol) was dissolved in 300 µl of water and 40 µl of tri-n-butylamine was added. All solvents were removed under vacuum and the residue dissolved in 300 µl of DMF. This solution was then added to the activated linker-dye conjugate 4 and the mixture was stirred overnight. The reaction mixture was diluted with 800 µl of TEAB buffer (50 mM, pH 8), purified by HPLC and concentrated. 198 nmol of product 6 was obtained (Retention time for product is 18.5 min).

Example 17

Hot Embossing: Millions to Billions of Beads on Slides or Chips

In one embodiment, the present invention contemplates such microspheres or beads disposed at high density into microwells or indentations on a surface. It is not intended that the present invention be limited by the nature of the surface or the method of fabrication. Nonetheless, in one embodiment, the present invention contemplates methods of fabrication to generate beads on slides at high density.

Figures 41A, 41B, 41C, 41D:
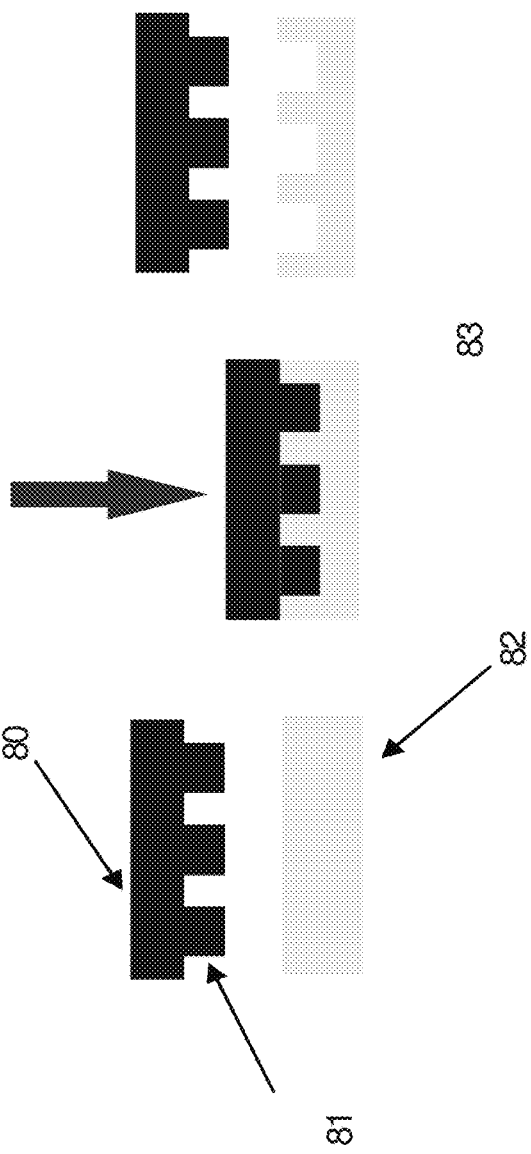
FIG. 41A-D is a schematic showing one embodiment of a hot embossing technique for making slide (or chips) with indentations (which can receive millions to billions of microbeads comprising nucleic acid).

In one preferred embodiment, the method relies on the use of a hot embossing technique as schematically shown in FIG. 41 A-D. Briefly, the process employs a stamp (80) having projections (81) that will create desired features (83) of desired dimensions when pressed into the polymer (82). The pressing step (B) is typically done with heat and pressure. Thereafter, the stamp is removed and the polymer is cooled (step C). Finally (step D), microspheres (84) containing biomolecules (85) are loaded into the microwells (86). In another embodiment, the method relies on the use of injection molding technique.

It is not intended that the present invention be limited by the nature of the polymer used in performing the hot embossing or molding process. A variety of polymers can be used including but not limited to: PMMA (polymethyl methacrylate), COP (cycloolefine polymer), and COC (cycloolefine copolymer). In the case of polymers that lack natural functional groups on the surface these groups can be grafted on the surface by performing ozonation, oxidation, corona discharge treatment, surface plasma or UV treatment or combination thereof. These fabrication methods allow one to generate substrates with varying features/wells density. Using standard size microscope slides casted out of PMMA or COP polymers one can create wells with 20 um, 5 um, and 1 um diameters. The slides with approximately 5 um features (e.g. between 4.8 um and 5.3 um) contain about 40 million microwells per slide, while the 1 um feature slide contains about 1 billion features per slide. With the biomolecule-containing microspheres deposited within the microwells, a single slide with such features permits a variety of high throughput, robust assays (e.g. sequencing by synthesis, hybridization, etc.). Nucleic acid fragments representing a large portion of a genome (e.g. human genome) or even an entire genome can be placed on a single slide or handful of slides, and then assayed sequentially or simultaneously.

Example 18

Sequencing: Changing the Spacer Arm Groups or Charge

Figure 42:
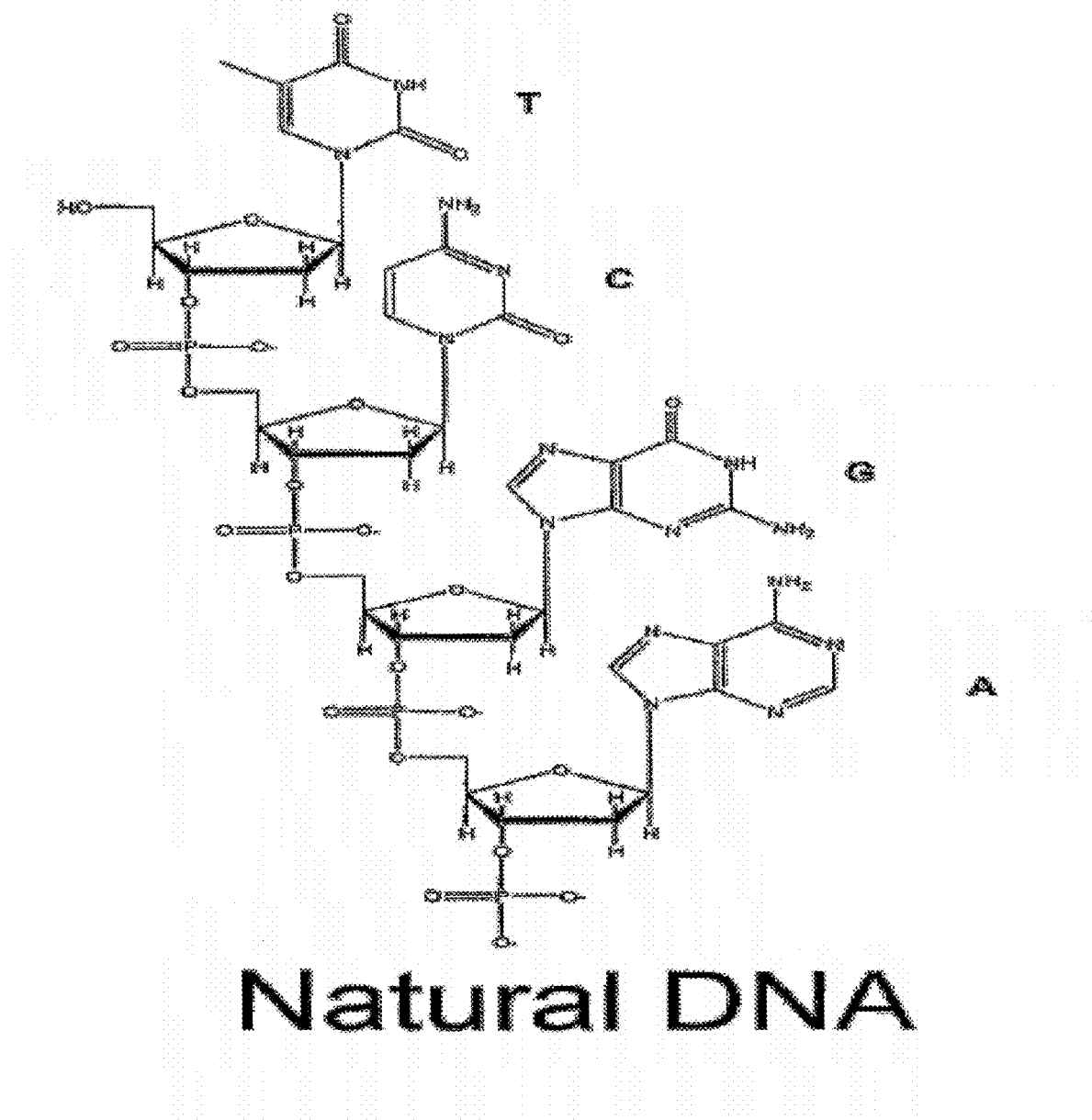
FIG. 42 is a schematic comparing the structure of natural DNA with DNA that was labeled with cleavable terminating nucleotides and then the label was removed. In this particular schematic, the example shows propargylamino derivatives.
Figure 42:
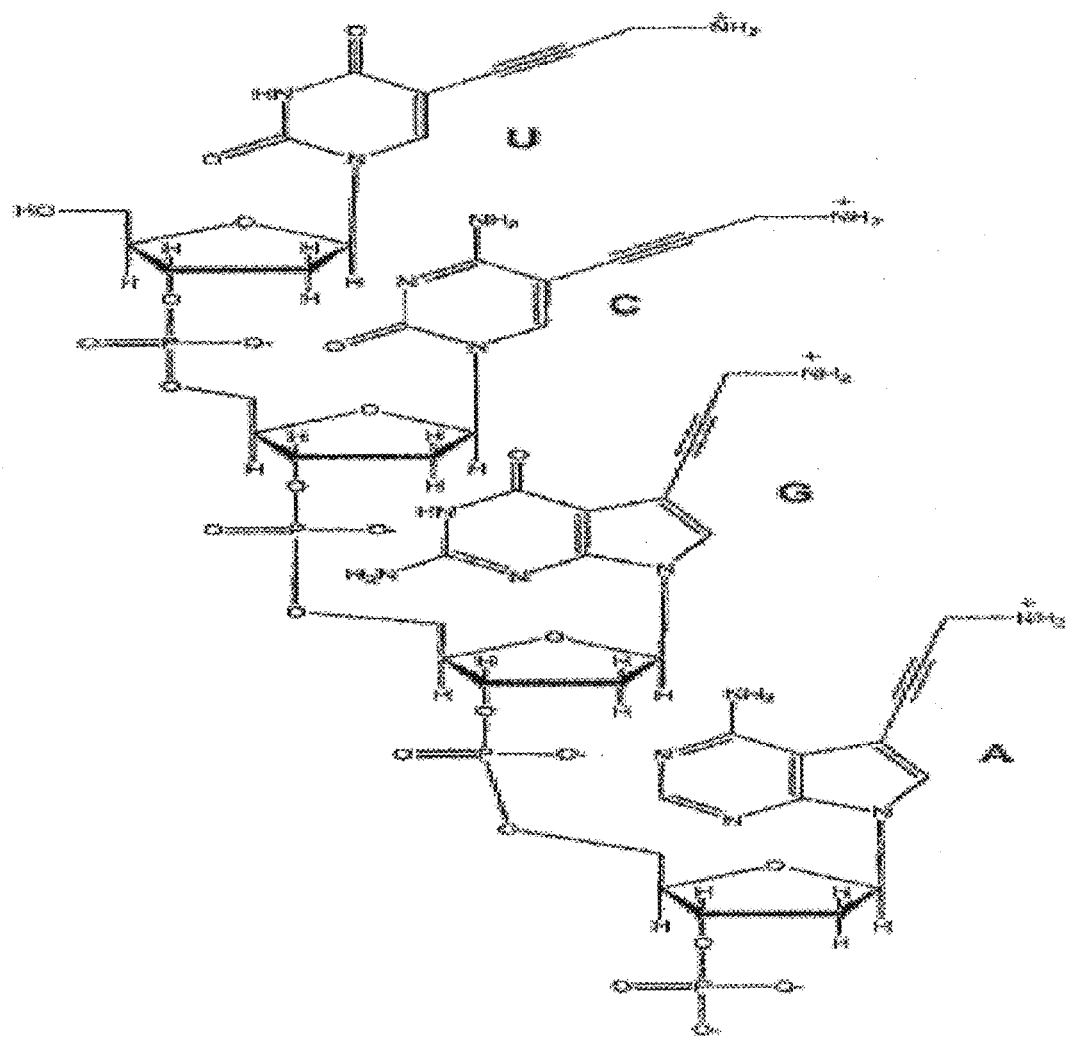

When performing sequencing by synthesis process one needs to use labeled nucleotides to be able to read the signal. In most cases these labeled nucleotides after cleavage result in structures that is not of the native nucleotide. For example, if one uses only labeled nucleotides the DNA structure after cleavage of the dye looks like one shown in FIG. 42 (right side). As can be seen, the spacer arm used to attach the dye to the base still remains attached.

Figure 43:
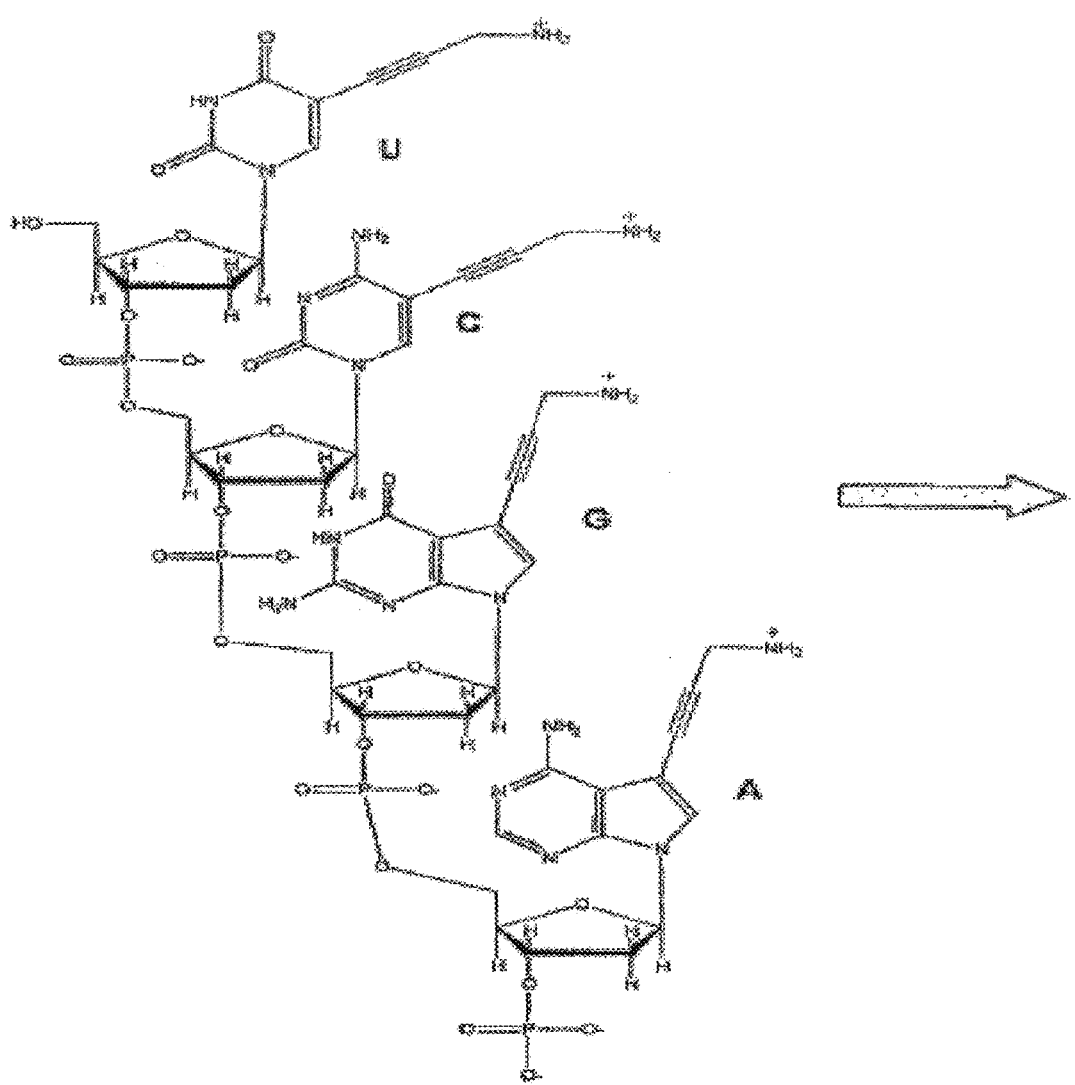
FIG. 43 is a schematic showing a capping step to neutralize the reactive groups after dye cleavage. For amines, one example that could be used is acetylation (such as acetic acid NHS ester); for the thiols (SH) N-methyl-maleimide or iodoacetamide can be used.
Figure 43:
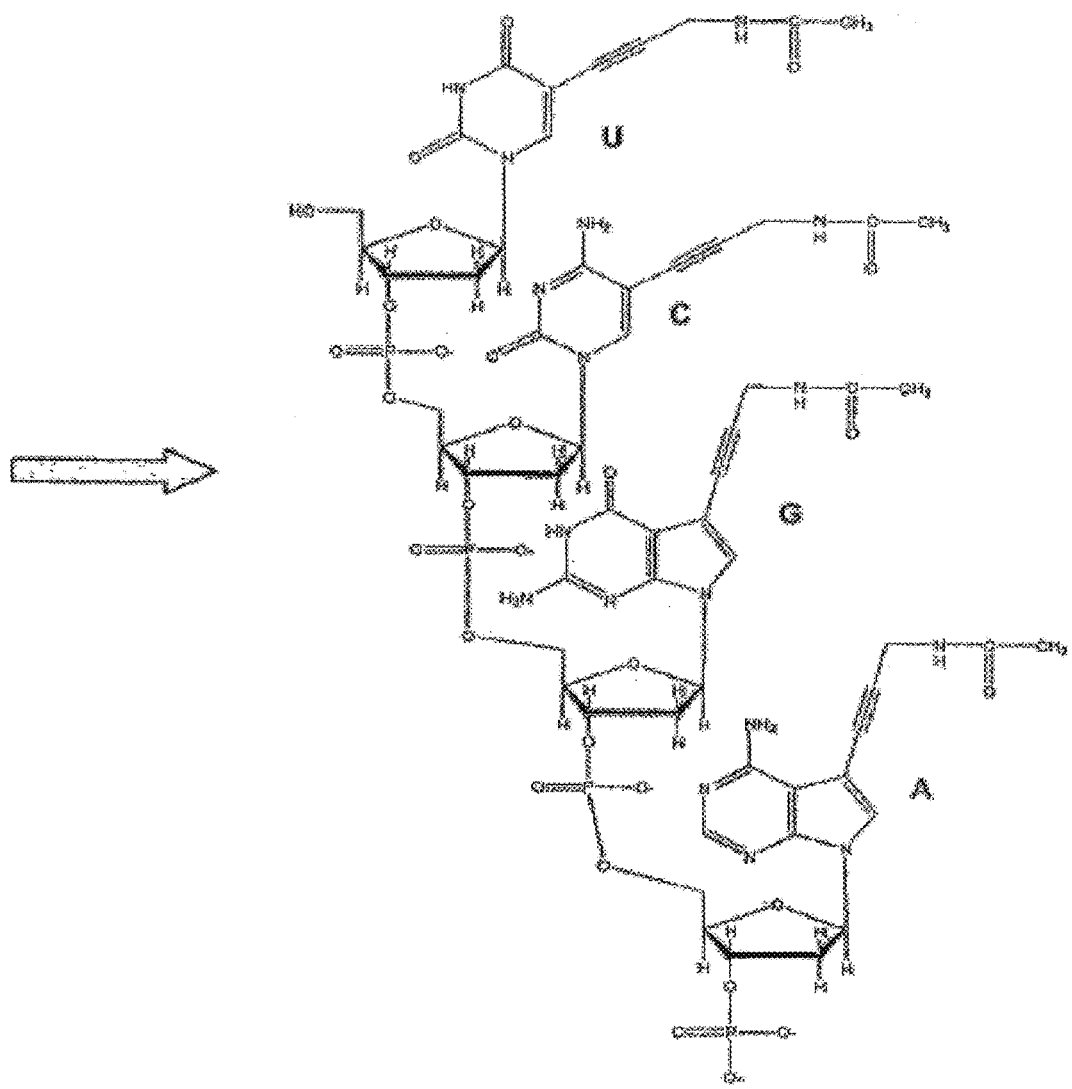
Figure 44:
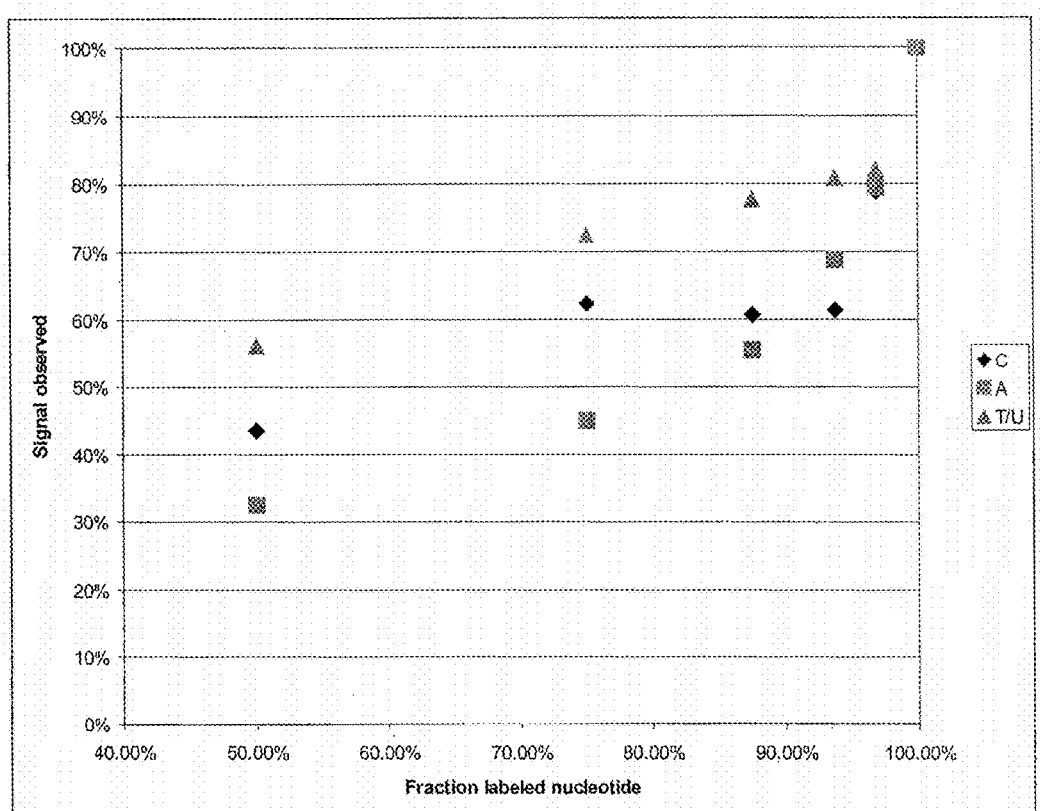
FIG. 44 shows the fluorescence signal from incorporated nucleotide analogues observed as a function of the composition of the extension mixture. In this case labeled nucleotides (3'-O-allyl) were supplemented with up to 1 equivalent of non-labeled terminators (also 3'-O-allyl). The extension was performed and the resulting signal measured. The response is different for different nucleotides tested and is a function of polymerase bias.
Figure 45A:
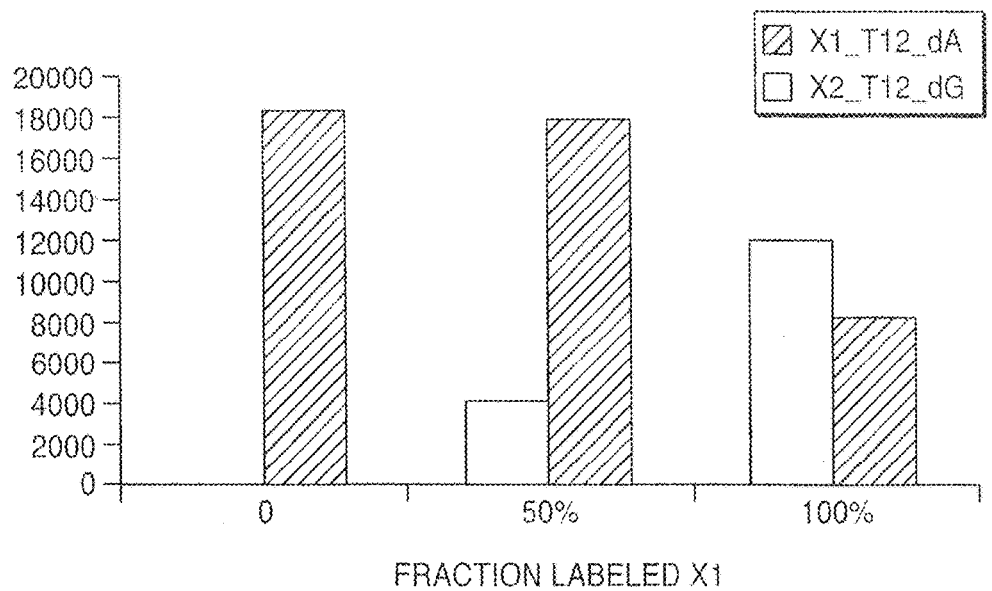
FIGS. 45A-D show the results for two subsequent extensions performed on 4 different DNA template (FIG. 45A, 45B, 45C, 45D). For extension 1, various amounts of labeled reversible terminating nucleotides were used (0, 50% and 100%). After cleavage, second extension was performed and the resulting signals were measured (bars on the right in each set). As can be seen the use of 100% labeled nucleotides in cycle 1 reduces the signal in subsequent cycle to by 50% compared to non-labeled reversible terminators.
Figure 45B:
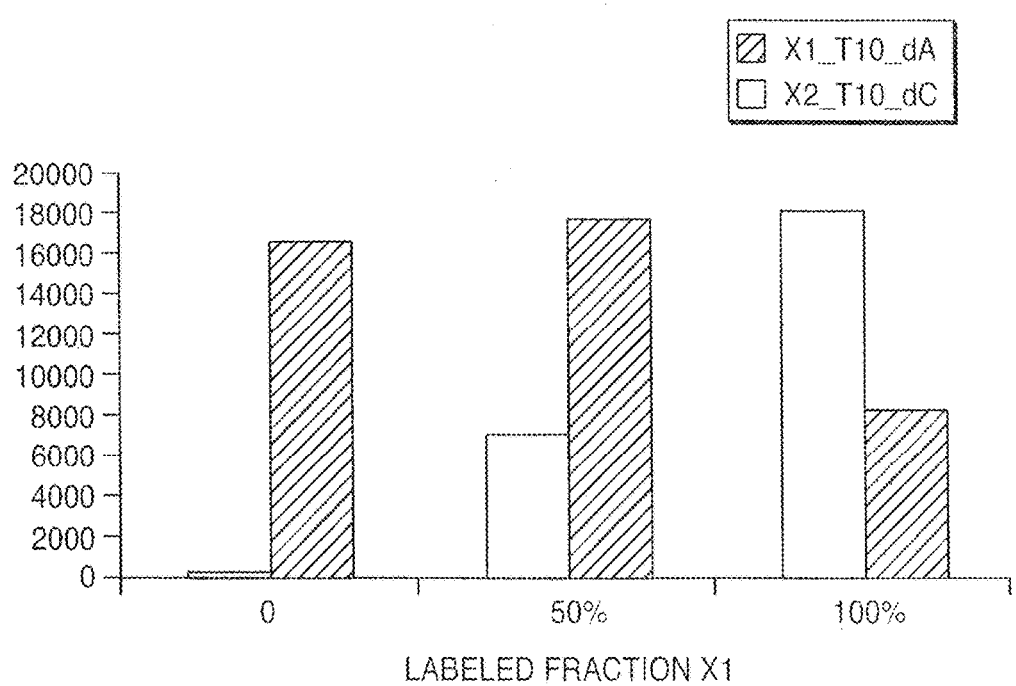
Figure 45C:
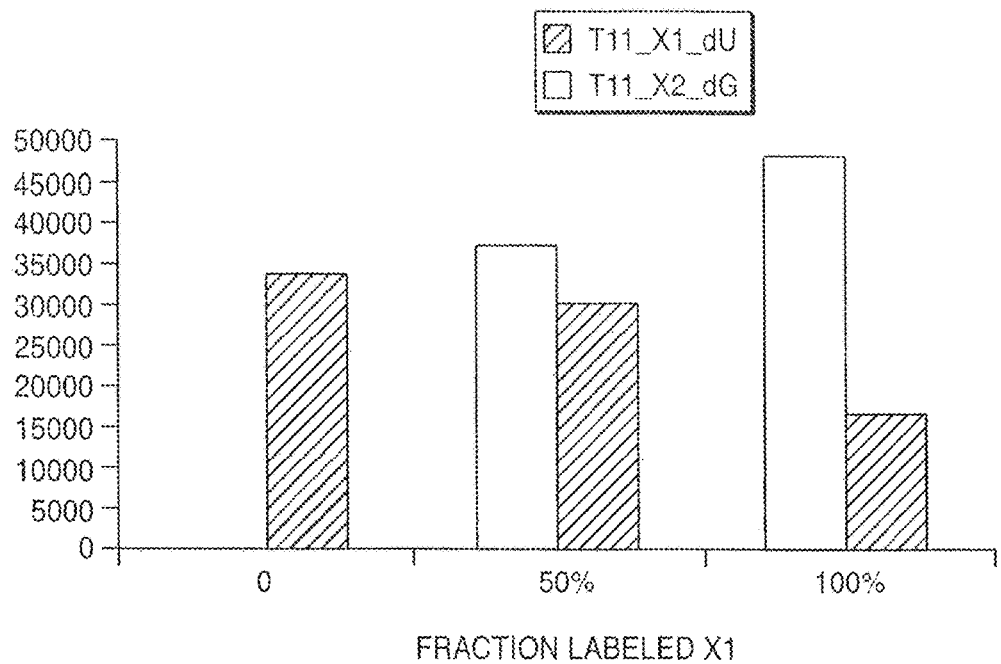
Figure 45D:
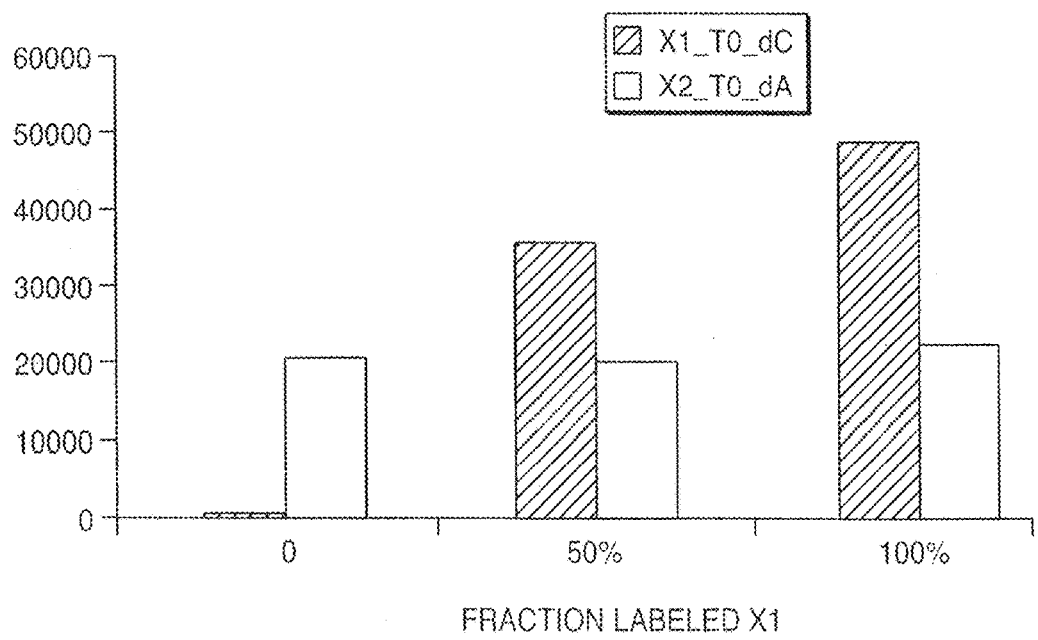

In some cases the spacer also carries a charge, such as for example when propargylamino nucleotides are used. In the case of disulfide bonds what remains after cleavage is the spacer arm with thiol (SH) group attached. The presence of these spacers and groups may affect the ability of the sequencing polymerases to incorporate the subsequent nucleotide. One approach to minimize or eliminate this undesirable effect is to change the reactivity of the spacer arm groups or their charge by performing a chemical "capping" step, where specific reagent is added to react only with groups on the spacer arm. This is shown schematically in FIG. 43.

Example 19

Sequencing by Synthesis Data: Using Labeled and Unlabeled Nucleotides

As noted previously, the presence of the linkers, spacers and groups on nucleotides may affect the ability of the sequencing polymerases to incorporate the subsequent nucleotide. One approach to minimize or eliminate this undesirable effect is to reduce the amount of labeled nucleotides incorporated in the template. Reducing the amount of labeled nucleotides that are incorporated can be accomplished by reducing the concentration of labeled nucleotides in the extension solution, and/or mixing labeled nucleotides (reversible terminators) with non-labeled reversibly terminating nucleotides. In contrast to labeled nucleotides, non-labeled reversible terminator nucleotides after cleavage convert to native nucleotide.

The effect of reducing the concentration of labeled nucleotides can be best observed by measuring the ability of polymerase to incorporate the subsequent nucleotides efficiently and with high fidelity. This is shown in FIGS. 44, 45A-D and 46.

Figure 47:
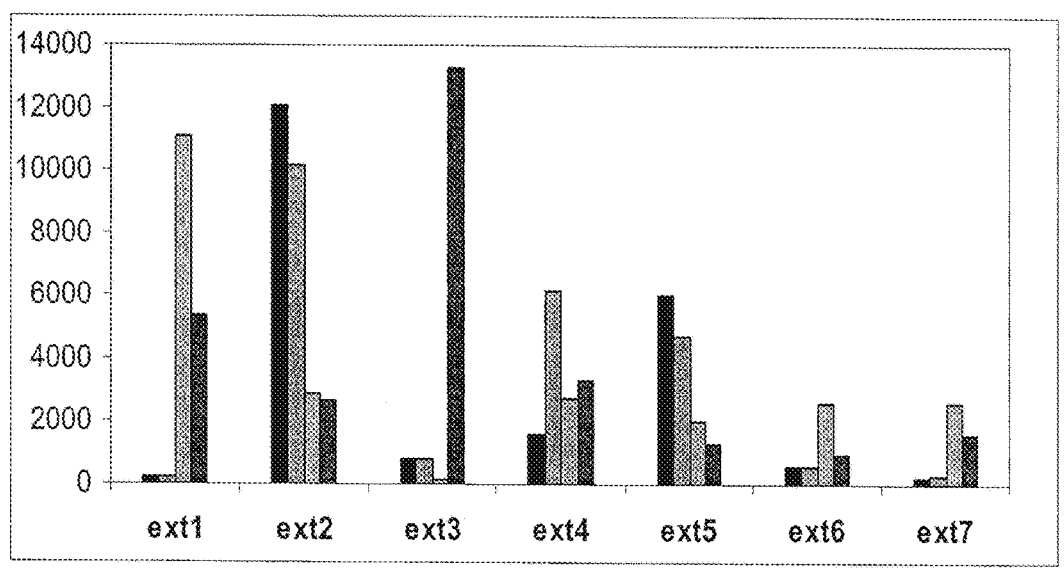
FIG. 47 shows the signal decline observed using labeled nucleotides in sequencing.
Figure 48C:
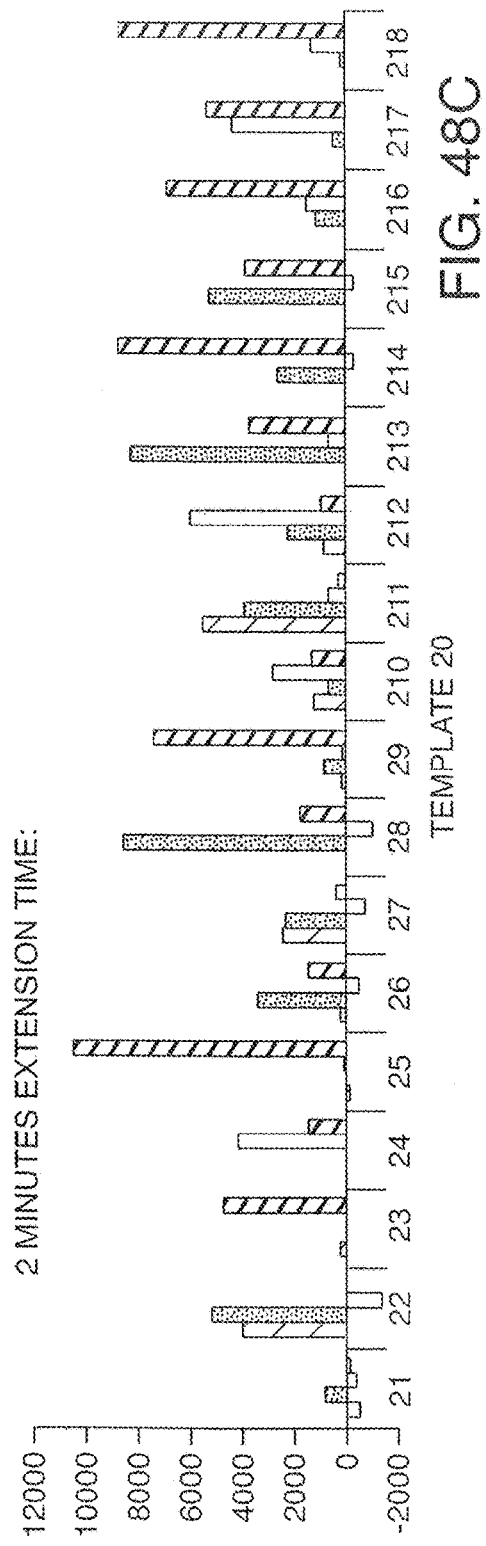
Figure 48D:
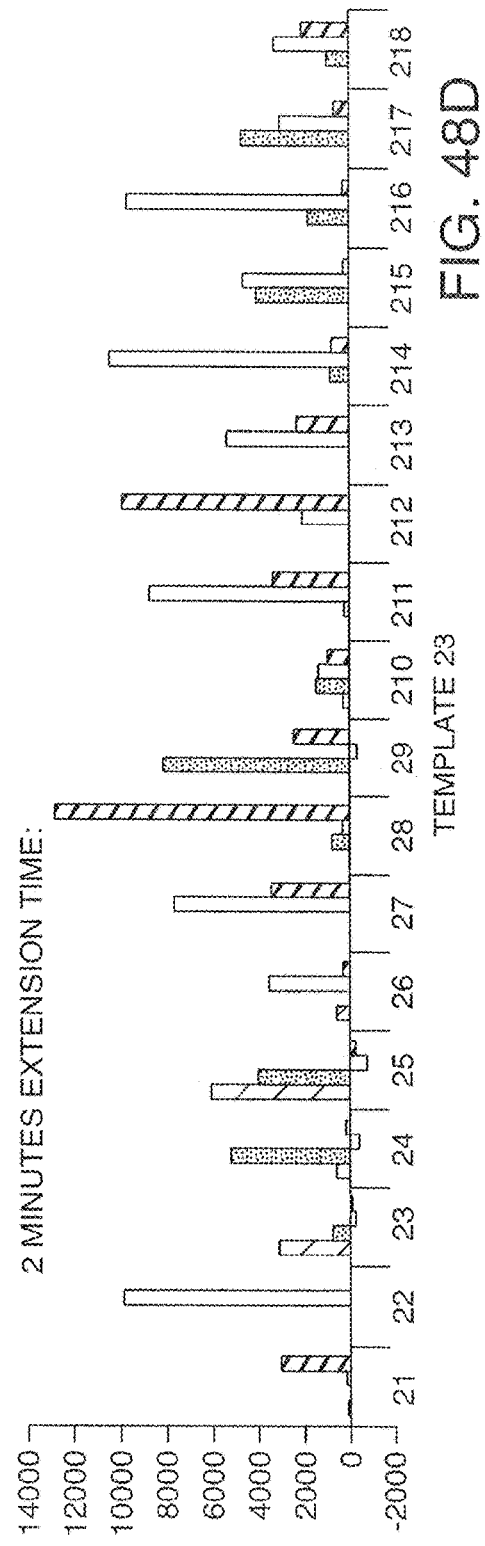
Figure 49K:
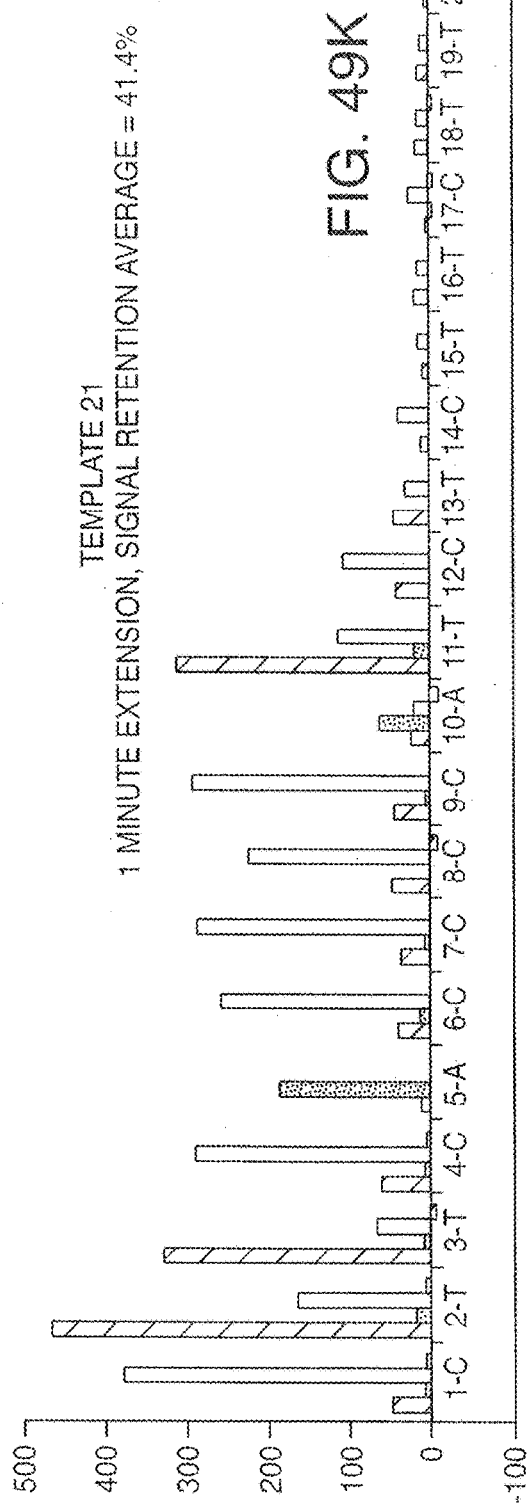
Figure 49L:
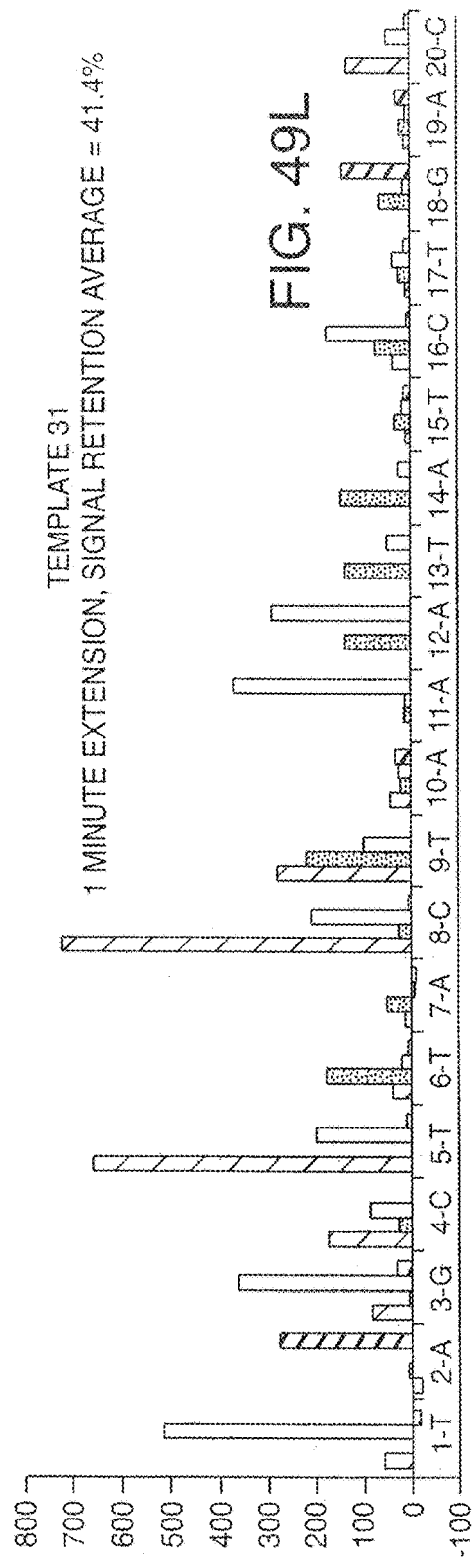

When the amount of labeled nucleotides is reduced, this results in reduction of fluorescent signal as shown in FIG. 47 (where only labeled nucleotides are used in successive extention reactions). In principle only the amount of signal necessary to decode the nucleotide is required. In addition to changing the ratio of labeled and unlabeled nucleotides and optimizing it for particular polymerase, one can also adjust the time of extension (e.g. reduce extension times down to 1-2 minutes) to gain even better control on the signal/incorporation ratio of labeled nucleotides. This is shown in FIGS. 48A-D and 49A-P where additional performance improvement is achieved upon reducing extension time (to 2 minutes and 1 minute, respectively).

All publications and patents mentioned in the above specification are herein incorporated by reference. Various modifications and variations of the described methods and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

---

The invention claimed is:

1. An automated nucleic acid sequencing system, comprising:
   a) flow cells comprising nucleic acid to be sequenced, said flow cells mounted on
   b) a moveable support controlled by a
   c) software user interface, said support configured to move flow cells to
   c) reagent delivery stations, each reagent delivery station in fluidic communication with
   d) reagent reservoirs configured to supply extension reagents including fluorescent nucleotide analogues,
   e) an imaging platform configured to detect said fluorescent nucleotide analogues, and
   f) a transfer means configured for moving at least one of said flow cells from said moveable support to said imaging platform.

2. The system of claim 1, wherein said imaging platform is associated with a camera, said camera positioned for imaging one or more flow cells.

3. The system of claim 2, wherein said imaging platform is configured for x/y movement and said imaging platform is positioned under said camera.

4. The system of claim 1, wherein said system is contained within the housing of an instrument, said software user interface mounted on said housing, said software user interface in communication with a programmable processor.

5. The system of claim 1, wherein said moveable support is a carousel.

6. The system of claim 1, further comprising an actuator configured for raising said moveable support so as to disconnect said flow cells from said stations.

* * * * *

UNITED STATES PATENT AND TRADEMARK OFFICE
CERTIFICATE OF CORRECTION

PATENT NO. : 10,222,349 B2
APPLICATION NO. : 15/656307
DATED : March 5, 2019
INVENTOR(S) : Steven Gordon et al.

It is certified that error appears in the above-identified patent and that said Letters Patent is hereby corrected as shown below:

On the Title Page

Item (63), in Column 1, under "Related U.S. Application Data", Line 11-12, delete "which is a continuation of application No. 12/020,284" and insert -- and a continuation-in-part of application No. 12/020,284 --, therefor.

Signed and Sealed this
Thirtieth Day of December, 2025

John A. Squires
*Director of the United States Patent and Trademark Office*